US007335469B2

(12) United States Patent
Gelb et al.

(10) Patent No.: US 7,335,469 B2
(45) Date of Patent: Feb. 26, 2008

(54) METHODS FOR DIAGNOSING NOONAN SYNDROME

(75) Inventors: Bruce D. Gelb, Dobbs Ferry, NY (US); Marco Tartaglia, New York, NY (US)

(73) Assignee: Mt. Sinai School of Medicine of New York University, New York City, NY (US)

( * ) Notice: Subject to any disclaimer, the term of this patent is extended or adjusted under 35 U.S.C. 154(b) by 343 days.

(21) Appl. No.: 10/262,552

(22) Filed: Oct. 1, 2002

(65) Prior Publication Data

US 2003/0125289 A1    Jul. 3, 2003

Related U.S. Application Data

(60) Provisional application No. 60/326,532, filed on Oct. 1, 2001.

(51) Int. Cl.
*C12Q 1/68* (2006.01)
*C07H 21/02* (2006.01)
*C07H 21/04* (2006.01)

(52) U.S. Cl. ................... 435/6; 536/23.1; 536/23.5; 536/24.31

(58) Field of Classification Search ............... None
See application file for complete search history.

(56) References Cited

U.S. PATENT DOCUMENTS

| 5,536,636 A | 7/1996 | Freeman, Jr. et al. |
| 5,589,375 A | 12/1996 | Ullrich et al. |
| 6,156,551 A | 12/2000 | Neel et al. |

FOREIGN PATENT DOCUMENTS

| WO | WO-99/23493 A1 | 5/1999 |
| WO | WO 99/52942 | * 10/1999 |

OTHER PUBLICATIONS

Hacker et al. (Gut, 1997, vol. 40, pp. 623-627).*
Pennisi et al. , Science, 281 (5384):1787-1789.*
Tartaglia et al. American Journal of Human Genetics. 2006. 78: 279-290.*
Kontaridis et al. Journal of Biological Chemistry. 2006. 281: 6785-6792.*
Tartaglia, Marco, et al., "*PTPN11* Mutations in Noonan Syndrome: Molecular Spectrum, Genotype-Phenotype Correlation, and Phenotypic Heterogeneity", Am. J. Hum. Genet., 2002, vol. 70, pp. 1555-1563.
Tartaglia, Marco, et al., "Mutations in *PTPN11*, encoding the protein tyrosine phosphatase SHP-2, cause Noonan syndrome", Nature Genetics, Dec. 2001, vol. 29, pp. 465-468.
Kosaki, Kenjiro, et al., "*PTPN11* (Protein-Tyrosine Phosphatase, Nonreceptor-Type 11) Mutations in Seven Japanese Patients with Noonan Syndrome", The Journal of Clinical Endocrinology & Metabolism, 2002, vol. 87, No. 8, pp. 3529-3533.

Maheshwari, M., et al., "*PTPN11* Mutations in Noonan Syndrome Type I: Detection of Recurrent Mutations in Exons 3 and 13", Human Mutation, 2002, vol. 20, pp. 298-304.
Crosby, A.H., et al., "Genomic organisation of the PPP1CC gene located within the Noonan syndrome critical interval", American Journal of Human Genetics, Oct. 1999, vol. 65, No. 4, pp. A185.
Adachi, Masaaki, et al., "Molecular cloning of a novel protein-tyrosine phosphatase SH-PTP3 with sequence similarity to the *src*-homology region 2", Federation of European Biochemical Societies Letters, Dec. 1992, vol. 314, No. 3, pp. 335-339.
Ahmad, Sultan, et al., "A widely expressed human protein-tyrosine phosphatase containing *src* homology 2 domains", Proc. Natl. Acad. Sci. USA, Mar. 1993, vol. 90, pp. 2197-2201.
Ion et al., "Detailed mapping, mutation analysis, and intragenic polymorphism identification in candidate Noonan syndrome genes MYL2, DCN, EPS8 and RPL6", J. Med. Genet. 2000, 37,884-886.
Saxton et al. "The SH2 tyrosine phosphatase Shp2 is required for mammalian limb development", Nature Genetics, Apr. 2000, 24, 420-423.
Bridget L. Craddock et al., "Phosphoinositide 3-Kinase-dependent Regulation of Interleukin-3 induced Proliferation", *The American Society for Biochemistry and Molecular Biology, Inc.*, vol. 276, No. 26, Issue of Jun. 29, 24274-24283 (2001).
Cheng-Kui Qu et al., "Genetic evidence that Shp-2 tyrosine phosphatase is a signal enhancer of the epidermal growth factor receptor in mammals", *Proc. Natl. Acad. Sci. USA*, vol. 96, 8528-8533 (Jul. 1999).
David Van Vactor et al., "Genetic analysis of protein tyrosine phosphatases", *Genetics & Development* 8:112-126 (1998).
Experimental Cell Research, "Shp-2 Tyrosine Phosphatase: Signaling One Cell or Many", Academic Press, 1999, 253, 47-54.
Hong Xu et al., "Multiple Effector Domains within SNT1 Coordinate ERK Activation and Neuronal Differentiation of PC12 Cells", *The American Society for Biochemistry and Molecular Biology, Inc.*, vol. 276, No. 16, Issue of Apr. 20, 13049-13056 (2001).
Hum Genet, "Protein-tyrosine phosphatase SH-PTP2 (PTPN11) is localized to 2q24.1-24.3", *Springer-Verlag*, 96:609-615 (1995).
Jess M. Cunnick et al., "Requirement of SHP2 Binding to Grb2-associated Binder-1 for Mitogen-activated Protein Kinase Activation in Response to Lysophosphatidic Acid and Epidermal Growth Factor", *The American Society for Biochemistry and Molecular Biology, Inc.*, vol. 275, No. 18, Issue of May 5, 13842-13848 (2000).

(Continued)

*Primary Examiner*—Carla Myers
(74) *Attorney, Agent, or Firm*—Gary M. Myles; Darby & Darby, P.C.

(57) ABSTRACT

Diagnostic and therapeutic applications for Noonan Syndrome are described. The diagnostic and therapeutic applications are based on certain mutations in the protein tyrosine phosphatase gene PTPN11 and its expression product, PTPN11, as well as mutations in other components in a PTPN11 signal transduction pathway promoting an increased signaling flux. Also described are nucleotide sequences, amino acid sequences, probes, and primers related to PTPN11 and PTPN11 variants, and cells expressing such variants.

10 Claims, 12 Drawing Sheets

OTHER PUBLICATIONS

JT Lee Jr. et al., "The Raf/MEK/ERK signal transduction cascade as a target for chemotherapeutic intervention in Leukemia", Nature Publishing Group 486-507 (2002).

Marco Tartaglia et al., "Mutations in PTPN11, encoding the protein tyrosine phosphatase SHP-2, cause Noonan syndrome", Nature Publishing Group, vol. 29, 465-468 (Dec. 2001).

Marco Tartaglia et al., "PTPN11 Mutations in Noonan Syndrome: Molecular Spectrum, Genotype-Phenotype Correlation, and Phenotypic Heterogeneity", Am. J. Hum. Genet.,70:1555-1563 (2002).

"Noonan Syndrome; NS1", 1-14 (Sep. 27, 2002); http://www.ncbi.nlm.nih.gov/htbin-post/Om_im/dismim?163950.

Robert M. Freeman, Jr. et al., "Identification of a human src homology 2-containing protein-tryrosine-phosphatase: A putative homolog of Drosophila corkscrew", Proc. Natl. Acad. Sci. USA, vol. 89, 11239-11243 Cell Biology (Dec. 1992).

Sultan Ahmad et al., "A widely expressed human protein-tyrosine phosphatase containing src homology 2 domains", Proc. Natl. Acad. Sci. USA, vol. 90, 2197-2201(Mar. 1993).

Allanson, "Noonan syndrome", Journal of Medical Genetics 1987, 24, 9-13.

Attie, "Genetic studies in idiopathic short stature", Current Opinionin Pediatrics 2000, 12:400-404.

Bastien, "Cloning, Expression and Mutational Nalaysis of SH-PTP2, Human Protein-Tyrosine Phosphatase", vol. 196, No. 1, Oct. 15, 1993; pp. 124-133.

Bennett, "Multiple Requirements for SHPTPf2 in Epidermal Growth Factor-Mediated Cell Cycle Progression", Molecular and Cellular Biology, Mar. 1996, p. 1189-1202.

Bertola, "Are Noonan Syndrome and Noonan-Like/Multiple Giant Cell Lesion Syndrome Distinct Entities?", American Journal of Medical Genetics 98:230-234 (2001).

Brady, "Further Delineation of the Critical Region for Noonan Syndrome on the Long Arm of Chromosome 12", European Journal of Human Genetics, 1997; 5:336-337.

Burch, "Cardiologic Abnormalities in Noonan Syndrome: Phenotypic Diagnosis and Echocardiographic Assessment of 118 Patients", the American College of Cardiology, vol. 22, No. 4, Oct. 1993: 1189-92.

Chen, "Mice mutant for Egfr and Shp2 have defective cardiac semilunar valvulogenesis", Nature Genetics, vol. 24, Mar. 2000, 296-299.

Gorlin, "Syndrome Identification", The national Foundation-March of Dimes, 1974, vol. II, No. 14-17.

Cohen, Jr., "Noonan-Like/Multiple Giant Cell Lesion Syndrome", American Journal of Medical Genetics 40:159-166 (1991).

Digilio, "Grouping of Multiple-Lentigines/LEOPARD and Noonan Syndromes on the PTPN11 Gene", Am. J. Hum. Genet. 71:389-394, 2002.

Duncan, "A Comprehensive Scoring System for Evaluating Noonan Syndrome", Amer. J. of Med. Gene. 10:37-50 (1981).

Alizon, "Spatial constraints on the recognition of phosphoproteins by the tandem SH2 domains of the phosphatase SH-PTP2", Nature—vol. 379—Jan. 18, 1996 p. 277-280.

Harder, "Characterization and kinetic analysis of the intracellular domain of human protein tyrosine phosphatase β (HPTP β) using synthetic phosphopeptides", Biochem J. (1994) 298, 395-401 (printed in Great Britain).

Hof, "Crystal Structure of the Tyrosine Phosphatase SHP-2", Cell, Vo. 92, 441-450, Feb. 20, 1998, Copyright 1998 by Cell Press.

Huyer, "The specificity of the N-Terminal SH2 Domain of SHP-2 Is Modified by a Single Point Mutation", Biochemistry 1998, 37, 2741-2747.

Jamieson, "Mapping a gene for Noonan syndrome to the long arm of chromosome 12", Nature Genetics vol. 8, Dec. 1994, 357-360.

Lee, Jr., "The Raf/MEK/ERK signal transduction cascade as a target for chemotherapeutic intervention in leukemia", Leukemia (2002) 16, 486-507.

Lee, "Crystal structures of peptide complexes of the amino-terminal SH2 domain of the Syptyrosine phosphatase", Current Biology Ltd ISSN 0969-2126, Structure 1994, vol. 2, No. 5. 423-438.

Legius, "PTPN11 mutations in LEOPARD syndrome", J. Med Genet 2002, 39:571-574.

Legius, "Fine mapping of Noonan/cardio-facio cutaneous syndrome in a large family", European Journal of Human Genetics (1998) 32-37.

Maroun, "The Tyrosine Phosphatase SHP-2 Is Required for Sustained Activation of Extracellular Signal-Regulated Kinease and Epthelial Morphogenesis Downstream from the Met Receptor Tyrosine Kinease", Molecular and Cellular Biology, No. 2000, p. 8513-8525.

Mendez, "Noonan Syndrome: A Review" American Journal of Medical Genetics 21:493-506 (1985), Publication Jun. 1, 1983.

Noonan, "Hypertelorism With Turner Phenotype, A New Syndrome With Associated Congenial Heart Disease", Amer. J. Dis. Child, vol. 116, Oct. 1968 373-380.

Noonan, "Noonan Syndrome—An Update and Review for the Primary Pediatrician", Clinical Pediatrics, Sep. 1994 548-555.

O'Reilly, "Activated Mutants of SHP-2 Preferentially Induce Elongation of Xenopus Animal Caps, Molecular and Cellular Biology", Jan. 2000, vol. 20, No. 1, p. 299-311.

Pathak, "Sodium Stibogluconate Is a Potent Inhibitor of Protein Tyrosine Phosphatases and Augments Cytokine Responses in Hemopoietic Cell Lines", The American Associate of Immunologists, Copyright 2001, p. 3391-3397.

Qu, "Genetic evidence that Shp-2 tyrosine phosphatase is a signal enhancer of the epidermal growth factor receptor in mammals", Proc. Natl. Acad. Sci. USA, vol. 96, pp. 8528-8533, Jul. 1999, Developmental Biology.

Saxton, "Abnormal mesoderm patterning in mouse embryos mutant for the SH2 tyrosine phosphatase Shp-2", The EMBO Journal. vol. 16, No. 9 pp. 2352-2364, 1997.

Schaeper, "Coupling of Gab 1 to c-Met, Grb2, and Shp2 mediates Biological Responses", The Journal of Cell Biology, vol. 149, No. 7, Jun. 26, 2000 1419-1432.

Shapiro, "Distribution of Left Ventricular Hypertrophy in Hypertrophic Cardiomyopathy: a Two-Dimensional Echocardiographic Study", JACC, vol. 2, No. 3, Sep. 1983: 437-44.

Burch, "A clinical study of Noonan Syndrome, Archives of Disease in Childhood 1992"; p. 178-183.

Snellen, "Pulmonic Stenosis", Supplement V to Circulation, vols. XXXVII and XXXVIII, Jul. 1968, V-93-V-101.

Stein-Gerlach, "Molecules in focus SHP-2, SH2-containing protein tyrosine phosphatase -2", The International Journal of Biochemistry & Cell Biology 1997, p. 559-566.

Burgt, "Clinical and Molecular Studies in a Large Dutch Family With Noonan Syndrome", American Journal of Medical Genetics 53:187-191 (1994).

Burgt, "Genetic Heterogeneity in Noonan Syndrome", American Journal of Medical Genetics 94:46-51 (2000).

Xiao, "Denaturing High-Performance Liquid Chromatography: A Review", Human Mutation 17:439-474 (2001).

Vactor, "Genetic Analysis of Protein Tyrosine Phosphatases", Current opinion in Genetics & Development, 1998; p. 112-126.

You, "Shp-2 Tyrosine Phosphatase Functions as a Negative Regulator of the Interferon-Stimulated Jak/STAT Pathway", Molecular and Cellular Biology, Mar. 1999, vol. 19, No. 3, p. 2416-2424.

You, "Modulation of the Nuclear Factor kB Pathway by Shp-2 Tyrosine Phosphatase in Mediating the Induction of Interleukin (IL)-6 or Tumor Necrosis Factor", J. Exp. Med, vol. 193, No. 1, Jan. 2001 101-109.

* cited by examiner

SEQUENCE LISTING

<160> NUMBER OF SEQ ID NOS: 35

<210> SEQ ID NO 1
<211> LENGTH: 1782
<212> TYPE: DNA
<213> ORGANISM: Homo sapiens
<220> FEATURE:
<221> NAME/KEY: CDS
<222> LOCATION: (1)..(1779)
<223> OTHER INFORMATION:

<400> SEQUENCE: 1

```
atg aca tcg cgg aga tgg ttt cac cca aat atc act ggt gtg gag gca      48
Met Thr Ser Arg Arg Trp Phe His Pro Asn Ile Thr Gly Val Glu Ala
1               5                   10                  15 gaa aac cta ctg ttg aca aga gga gtt gat ggc agt ttt ttg gca agg      96
Glu Asn Leu Leu Leu Thr Arg Gly Val Asp Gly Ser Phe Leu Ala Arg
                20                  25                  30 cct agt aaa agt aac cct gga gac ttc aca ctt tcc gtt aga aga aat     144
Pro Ser Lys Ser Asn Pro Gly Asp Phe Thr Leu Ser Val Arg Arg Asn
            35                  40                  45 gga gct gtc acc cac atc aag att cag aac act ggt gat tac tat gac     192
Gly Ala Val Thr His Ile Lys Ile Gln Asn Thr Gly Asp Tyr Tyr Asp
        50                  55                  60 ctg tat gga ggg gag aaa ttt gcc act ttg gct gag ttg gtc cag tat     240
Leu Tyr Gly Gly Glu Lys Phe Ala Thr Leu Ala Glu Leu Val Gln Tyr
65                  70                  75                  80 tac atg gaa cat cac ggg caa tta aaa gag aag aat gga gat gtc att     288
Tyr Met Glu His His Gly Gln Leu Lys Glu Lys Asn Gly Asp Val Ile
                85                  90                  95 gag ctt aaa tat cct ctg aac tgt gca gat cct acc tct gaa agg tgg     336
Glu Leu Lys Tyr Pro Leu Asn Cys Ala Asp Pro Thr Ser Glu Arg Trp
                100                 105                 110 ttt cat gga cat ctc tct ggg aaa gaa gca gag aaa tta tta act gaa     384
Phe His Gly His Leu Ser Gly Lys Glu Ala Glu Lys Leu Leu Thr Glu
            115                 120                 125 aaa gga aaa cat ggt agt ttt ctt gta cga gag agc cag agc cac cct     432
Lys Gly Lys His Gly Ser Phe Leu Val Arg Glu Ser Gln Ser His Pro
        130                 135                 140 gga gat ttt gtt ctt tct gtg cgc act ggt gat gac aaa ggg gag agc     480
Gly Asp Phe Val Leu Ser Val Arg Thr Gly Asp Asp Lys Gly Glu Ser
145                 150                 155                 160 aat gac ggc aag tct aaa gtg acc cat gtt atg att cgc tgt cag gaa     528
Asn Asp Gly Lys Ser Lys Val Thr His Val Met Ile Arg Cys Gln Glu
                165                 170                 175 ctg aaa tac gac gtt ggt gga gga gaa cgg ttt gat tct ttg aca gat     576
Leu Lys Tyr Asp Val Gly Gly Gly Glu Arg Phe Asp Ser Leu Thr Asp
                180                 185                 190
```

```
ctt gtg gaa cat tat aag aag aat cct atg gtg gaa aca ttg ggt aca        624
Leu Val Glu His Tyr Lys Lys Asn Pro Met Val Glu Thr Leu Gly Thr
        195                 200                 205 gta cta caa ctc aag cag ccc ctt aac acg act cgt ata aat gct gct        672
Val Leu Gln Leu Lys Gln Pro Leu Asn Thr Thr Arg Ile Asn Ala Ala
210                 215                 220 gaa ata gaa agc aga gtt cga gaa cta agc aaa tta gct gag acc aca        720
Glu Ile Glu Ser Arg Val Arg Glu Leu Ser Lys Leu Ala Glu Thr Thr
225                 230                 235                 240 gat aaa gtc aaa caa ggc ttt tgg gaa gaa ttt gag aca cta caa caa        768
Asp Lys Val Lys Gln Gly Phe Trp Glu Glu Phe Glu Thr Leu Gln Gln
            245                 250                 255 cag gag tgc aaa ctt ctc tac agc cga aaa gag ggt caa agg caa gaa        816
Gln Glu Cys Lys Leu Leu Tyr Ser Arg Lys Glu Gly Gln Arg Gln Glu
        260                 265                 270 aac aaa aac aaa aat aga tat aaa aac atc ctg ccc ttt gat cat acc        864
Asn Lys Asn Lys Asn Arg Tyr Lys Asn Ile Leu Pro Phe Asp His Thr
    275                 280                 285 agg gtt gtc cta cac gat ggt gat ccc aat gag cct gtt tca gat tac        912
Arg Val Val Leu His Asp Gly Asp Pro Asn Glu Pro Val Ser Asp Tyr
290                 295                 300 atc aat gca aat atc atc atg cct gaa ttt gaa acc aag tgc aac aat        960
Ile Asn Ala Asn Ile Ile Met Pro Glu Phe Glu Thr Lys Cys Asn Asn
305                 310                 315                 320 tca aag ccc aaa aag agt tac att gcc aca caa ggc tgc ctg caa aac       1008
Ser Lys Pro Lys Lys Ser Tyr Ile Ala Thr Gln Gly Cys Leu Gln Asn
            325                 330                 335 acg gtg aat gac ttt tgg cgg atg gtg ttc caa gaa aac tcc cga gtg       1056
Thr Val Asn Asp Phe Trp Arg Met Val Phe Gln Glu Asn Ser Arg Val
        340                 345                 350 att gtc atg aca acg aaa gaa gtg gag aga gga aag agt aaa tgt gtc       1104
Ile Val Met Thr Thr Lys Glu Val Glu Arg Gly Lys Ser Lys Cys Val
    355                 360                 365 aaa tac tgg cct gat gag tat gct cta aaa gaa tat ggc gtc atg cgt       1152
Lys Tyr Trp Pro Asp Glu Tyr Ala Leu Lys Glu Tyr Gly Val Met Arg
370                 375                 380 gtt agg aac gtc aaa gaa agc gcc gct cat gac tat acg cta aga gaa       1200
Val Arg Asn Val Lys Glu Ser Ala Ala His Asp Tyr Thr Leu Arg Glu
385                 390                 395                 400 ctt aaa ctt tca aag gtt gga caa ggg aat acg gag aga acg gtc tgg       1248
Leu Lys Leu Ser Lys Val Gly Gln Gly Asn Thr Glu Arg Thr Val Trp
            405                 410                 415 caa tac cac ttt cgg acc tgg ccg gac cac ggc gtg ccc agc gac cct       1296
Gln Tyr His Phe Arg Thr Trp Pro Asp His Gly Val Pro Ser Asp Pro
        420                 425                 430 ggg ggc gtg ctg gac ttc ctg gag gag gtg cac cat aag cag gag agc       1344
Gly Gly Val Leu Asp Phe Leu Glu Glu Val His His Lys Gln Glu Ser
    435                 440                 445 atc atg gat gca ggg ccg gtc gtg gtg cac tgc agt gct gga att ggc       1392
Ile Met Asp Ala Gly Pro Val Val Val His Cys Ser Ala Gly Ile Gly
450                 455                 460 cgg aca ggg acg ttc att gtg att gat att ctt att gac atc atc aga       1440
Arg Thr Gly Thr Phe Ile Val Ile Asp Ile Leu Ile Asp Ile Ile Arg
465                 470                 475                 480 gag aaa ggt gtt gac tgc gat att gac gtt ccc aaa acc atc cag atg       1488
Glu Lys Gly Val Asp Cys Asp Ile Asp Val Pro Lys Thr Ile Gln Met
            485                 490                 495 gtg cgg tct cag agg tca ggg atg gtc cag aca gaa gca cag tac cga       1536
Val Arg Ser Gln Arg Ser Gly Met Val Gln Thr Glu Ala Gln Tyr Arg
        500                 505                 510
```

```
ttt atc tat atg gcg gtc cag cat tat att gaa aca cta cag cgc agg      1584
Phe Ile Tyr Met Ala Val Gln His Tyr Ile Glu Thr Leu Gln Arg Arg
    515                 520                 525 att gaa gaa gag cag aaa agg aag agg aaa ggg cac gaa tat aca aat      1632
Ile Glu Glu Glu Gln Lys Arg Lys Arg Lys Gly His Glu Tyr Thr Asn
530                 535                 540 att aag tat cct cta gcg gac cag acg agt gga gat cag agc cct ctc      1680
Ile Lys Tyr Pro Leu Ala Asp Gln Thr Ser Gly Asp Gln Ser Pro Leu
545                 550                 555                 560 ccg cct tgt act cca acg cca ccc tgt gca gaa atg aga gaa gac agt      1728
Pro Pro Cys Thr Pro Thr Pro Pro Cys Ala Glu Met Arg Glu Asp Ser
                565                 570                 575 gct aga gtc tat gaa aac gtg ggc ctg atg caa cag cag aaa agt ttc      1776
Ala Arg Val Tyr Glu Asn Val Gly Leu Met Gln Gln Gln Lys Ser Phe
            580                 585                 590 aga tga                                                              1782
Arg
```

<210> SEQ ID NO 2
<211> LENGTH: 593
<212> TYPE: PRT
<213> ORGANISM: Homo sapiens

<400> SEQUENCE: 2

```
Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255
```

```
Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
    370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
        435                 440                 445

Ile Met Asp Ala Gly Pro Val Val His Cys Ser Ala Gly Ile Gly
    450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
        515                 520                 525

Ile Glu Glu Glu Gln Lys Arg Lys Arg Lys Gly His Glu Tyr Thr Asn
    530                 535                 540

Ile Lys Tyr Pro Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
                565                 570                 575

Ala Arg Val Tyr Glu Asn Val Gly Leu Met Gln Gln Lys Ser Phe
            580                 585                 590

Arg

<210> SEQ ID NO 3
<211> LENGTH: 22
<212> TYPE: DNA
<213> ORGANISM: Artificial Sequence
<220> FEATURE:
<223> OTHER INFORMATION: Exon 1 - forward PCR primer

<400> SEQUENCE: 3
gctgacggga agcaggaagt gg                                          22
```

```
<210> SEQ ID NO 4
<211> LENGTH: 20
<212> TYPE: DNA
<213> ORGANISM: Artificial Sequence
<220> FEATURE:
<223> OTHER INFORMATION: Exon 1 - reverse PCR primer

<400> SEQUENCE: 4
ctggcacccg tggttccctc                                                   20

<210> SEQ ID NO 5
<211> LENGTH: 24
<212> TYPE: DNA
<213> ORGANISM: Artificial Sequence
<220> FEATURE:
<223> OTHER INFORMATION: Exon 2 - forward PCR primer

<400> SEQUENCE: 5
actgaatccc aggtctctac caag                                              24

<210> SEQ ID NO 6
<211> LENGTH: 22
<212> TYPE: DNA
<213> ORGANISM: Artificial Sequence
<220> FEATURE:
<223> OTHER INFORMATION: Exon 2 - reverse PCR primer

<400> SEQUENCE: 6
cagcaagcta tccaagcatg gt                                                22

<210> SEQ ID NO 7
<211> LENGTH: 22
<212> TYPE: DNA
<213> ORGANISM: Artificial Sequence
<220> FEATURE:
<223> OTHER INFORMATION: Exon 3 - forward PCR primer

<400> SEQUENCE: 7
cgacgtggaa gatgagatct ga                                                22

<210> SEQ ID NO 8
<211> LENGTH: 23
<212> TYPE: DNA
<213> ORGANISM: Artificial Sequence
<220> FEATURE:
<223> OTHER INFORMATION: Exon 3 - reverse PCR primer

<400> SEQUENCE: 8
cagtcacaag cctttggagt cag                                               23

<210> SEQ ID NO 9
<211> LENGTH: 25
<212> TYPE: DNA
<213> ORGANISM: Artificial Sequence
<220> FEATURE:
<223> OTHER INFORMATION: Exon 4 - forward PCR primer

<400> SEQUENCE: 9
gattgatcaa tcccttggag gaatg                                             25

<210> SEQ ID NO 10
<211> LENGTH: 21
<212> TYPE: DNA
<213> ORGANISM: Artificial Sequence
<220> FEATURE:
<223> OTHER INFORMATION: Exon 4 - reverse PCR primer
```

```
<400> SEQUENCE: 10
gtcaccagac ccaacgtggt g                                              21

<210> SEQ ID NO 11
<211> LENGTH: 24
<212> TYPE: DNA
<213> ORGANISM: Artificial Sequence
<220> FEATURE:
<223> OTHER INFORMATION: Exon 5 - forward PCR primer

<400> SEQUENCE: 11
ctgcagtgaa catgagagtg cttg                                           24

<210> SEQ ID NO 12
<211> LENGTH: 23
<212> TYPE: DNA
<213> ORGANISM: Artificial Sequence
<220> FEATURE:
<223> OTHER INFORMATION: Exon 5 - reverse PCR primer

<400> SEQUENCE: 12
gttgaagctg caatgggtac atg                                            23

<210> SEQ ID NO 13
<211> LENGTH: 21
<212> TYPE: DNA
<213> ORGANISM: Artificial Sequence
<220> FEATURE:
<223> OTHER INFORMATION: Exon 6 - forward PCR primer

<400> SEQUENCE: 13
tgcattaaca ccgttttctg t                                              21

<210> SEQ ID NO 14
<211> LENGTH: 23
<212> TYPE: DNA
<213> ORGANISM: Artificial Sequence
<220> FEATURE:
<223> OTHER INFORMATION: Exon 6 - reverse PCR primer

<400> SEQUENCE: 14
gtcagtttca agtctctcag gtc                                            23

<210> SEQ ID NO 15
<211> LENGTH: 23
<212> TYPE: DNA
<213> ORGANISM: Artificial Sequence
<220> FEATURE:
<223> OTHER INFORMATION: Exon 7 - forward PCR primer

<400> SEQUENCE: 15
gaacatttcc taggatgaat tcc                                            23

<210> SEQ ID NO 16
<211> LENGTH: 22
<212> TYPE: DNA
<213> ORGANISM: Artificial Sequence
<220> FEATURE:
<223> OTHER INFORMATION: Exon 7 - reverse PCR primer

<400> SEQUENCE: 16
ggtacagagg tgctaggaat ca                                             22

<210> SEQ ID NO 17
<211> LENGTH: 24
```

```
<212> TYPE: DNA
<213> ORGANISM: Artificial Sequence
<220> FEATURE:
<223> OTHER INFORMATION: Exon 8 - forward PCR primer

<400> SEQUENCE: 17
gacatcaggc agtgttcacg ttac                                          24

<210> SEQ ID NO 18
<211> LENGTH: 24
<212> TYPE: DNA
<213> ORGANISM: Artificial Sequence
<220> FEATURE:
<223> OTHER INFORMATION: Exon 8 - reverse PCR primer

<400> SEQUENCE: 18
ccttaaagtt actttcagga catg                                          24

<210> SEQ ID NO 19
<211> LENGTH: 22
<212> TYPE: DNA
<213> ORGANISM: Artificial Sequence
<220> FEATURE:
<223> OTHER INFORMATION: Exon 9 - foward PCR primer

<400> SEQUENCE: 19
gtaagctttg cttttcacag tg                                            22

<210> SEQ ID NO 20
<211> LENGTH: 25
<212> TYPE: DNA
<213> ORGANISM: Artificial Sequence
<220> FEATURE:
<223> OTHER INFORMATION: Exon 9 - reverse PCR primer

<400> SEQUENCE: 20
ctaaacatgg ccaatctgac atgtc                                         25

<210> SEQ ID NO 21
<211> LENGTH: 26
<212> TYPE: DNA
<213> ORGANISM: Artificial Sequence
<220> FEATURE:
<223> OTHER INFORMATION: Exon 10 - forward PCR primer

<400> SEQUENCE: 21
gcaagacttg aacatttgtt tgttgc                                        26

<210> SEQ ID NO 22
<211> LENGTH: 24
<212> TYPE: DNA
<213> ORGANISM: Artificial Sequence
<220> FEATURE:
<223> OTHER INFORMATION: Exon 10 - reverse PCR primer

<400> SEQUENCE: 22
gaccctgaat tcctacacac catc                                          24

<210> SEQ ID NO 23
<211> LENGTH: 24
<212> TYPE: DNA
<213> ORGANISM: Artificial Sequence
<220> FEATURE:
<223> OTHER INFORMATION: Exon 11 - forward PCR primer

<400> SEQUENCE: 23
```

```
caaaaggaga cgagttctgg gaac                                        24
```

<210> SEQ ID NO 24
<211> LENGTH: 24
<212> TYPE: DNA
<213> ORGANISM: Artificial Sequence
<220> FEATURE:
<223> OTHER INFORMATION: Exon 11 - reverse PCR primer

<400> SEQUENCE: 24

```
gcagttgctc tatgcctcaa acag                                        24
```

<210> SEQ ID NO 25
<211> LENGTH: 24
<212> TYPE: DNA
<213> ORGANISM: Artificial Sequence
<220> FEATURE:
<223> OTHER INFORMATION: Exon 12 - forward PCR primer

<400> SEQUENCE: 25

```
gctccaaaga gtagacattg tttc                                        24
```

<210> SEQ ID NO 26
<211> LENGTH: 22
<212> TYPE: DNA
<213> ORGANISM: Artificial Sequence
<220> FEATURE:
<223> OTHER INFORMATION: Exon 12 - reverse PCR primer

<400> SEQUENCE: 26

```
gactgttttc gtgagcactt tc                                          22
```

<210> SEQ ID NO 27
<211> LENGTH: 22
<212> TYPE: DNA
<213> ORGANISM: Artificial Sequence
<220> FEATURE:
<223> OTHER INFORMATION: Exon 13 - forward PCR primer

<400> SEQUENCE: 27

```
caacactgta gccattgcaa ca                                          22
```

<210> SEQ ID NO 28
<211> LENGTH: 22
<212> TYPE: DNA
<213> ORGANISM: Artificial Sequence
<220> FEATURE:
<223> OTHER INFORMATION: Exon 13 - reverse PCR primer

<400> SEQUENCE: 28

```
cgtatccaag aggcctagca ag                                          22
```

<210> SEQ ID NO 29
<211> LENGTH: 21
<212> TYPE: DNA
<213> ORGANISM: Artificial Sequence
<220> FEATURE:
<223> OTHER INFORMATION: Exon 14 - forward PCR primer

<400> SEQUENCE: 29

```
accattgtcc ctcacatgtg c                                           21
```

<210> SEQ ID NO 30
<211> LENGTH: 24
<212> TYPE: DNA
<213> ORGANISM: Artificial Sequence

```
<220> FEATURE:
<223> OTHER INFORMATION: Exon 14 - reverse PCR primer

<400> SEQUENCE: 30
cagtgaaagg catgtgctac aaac                                          24

<210> SEQ ID NO 31
<211> LENGTH: 22
<212> TYPE: DNA
<213> ORGANISM: Artificial Sequence
<220> FEATURE:
<223> OTHER INFORMATION: Exon 15 - forward PCR primer

<400> SEQUENCE: 31
caggtcctag gcacaggaac tg                                            22

<210> SEQ ID NO 32
<211> LENGTH: 21
<212> TYPE: DNA
<213> ORGANISM: Artificial Sequence
<220> FEATURE:
<223> OTHER INFORMATION: Exon 15 - reverse PCR primer

<400> SEQUENCE: 32
acattcccaa attgcttgcc t                                             21

<210> SEQ ID NO 33
<211> LENGTH: 300000
<212> TYPE: DNA
<213> ORGANISM: Homo sapiens
<220> FEATURE:
<221> NAME/KEY: misc_feature
<222> LOCATION: (1)..(300000)
<223> OTHER INFORMATION: where n may be a or g or c or t/u,
      unknown or other

<400> SEQUENCE: 33
gaattaaaga gagtccataa catatatgaa ataaaggccc cgggaacaga ctttggagac     60
atttttgggt tttaacagac atttcagtct tatattcata ttccaggcag atacacagtt    120
aagtagtttg agggccaaat tacaaagcat ggcactaatt tcatcagttt gagaatggat    180
aattgttttt gctccaaagg cccaaattca tctgaacaca ttaactcaat acttttacac    240
tgcaatggcc ttgtggttct agggtacttg tcaacaggga gtgtagagga gaactaagct    300
ggaagatcta gcaacccttt taatcaacaa ggaagaaaat gctgtgacaa cttctatgca    360
tggagtaact tgtgaaaggg agtgaacagg ggtctgatgt cctacaagtg aaaggagggt    420
cattctgaat agaaggagtg agctgacagg cctggtaagg tggctccacc tcaacaaaag    480
cccccagggc aaatgttttt ctgggattac agttagtact tggacctgtg aggactgcaa    540
gttcattttc ttttctagga agcgattatg actgaatacc ataccttcac caagtctttc    600
ggccaaccag ttcctaagac actacggctg ccatatccca gtgtgttgcc tccatattca    660
gcaaccttcc tactgtttgt gttaggcccc gcatatatca ccaacttcaa aacagaaaat    720
atactgttag actgtaaaag aaaaacaaaa acaacatcta caaataaaaa ggctgcaaaa    780
acatttgttt aaaatacaat tataaccagg cattggtgtc attatagtat aactaatatt    840
tcccgatttt tttaggtata actgatacta gtttggatgc aatcagtcat tggtatttac    900
agggaagcca cagagtaata acaattctta ataaaagaa gtatacttttt tatattacca    960 cactttaatt ggcttgggga cctcacatta aatagttata ctcagttatt gtacatcaat   1020 attttgaaa tagctatttt aatgctaatt aataacaaat aactcattaa taacagtttg   1080
```

```
gccccttaag tcctccccaa aattaataaa gtgagcaaat acagatggaa atatggttat      1140
atctaacaca acaacaaaat aaaagcacca aaaaaaatca atgaataaat aagaattttt      1200
aaaaatgcaa caaattgaaa ataagccata tattcttagg atgttgctta atggtataaa      1260
aagaaaatga tacaaatttg ggccagaaag ggggctgctg cttcttgggt cagttttcat      1320
gtatcaatat ttctctaatt catttataac cagctggctg actttctaat cggcagaaga      1380
aacatttata gctcatttgg cattcaaaga cttccatagg aaaaataaag ctctggcttc      1440
tgtaaatacc aaaccctgtc ttctaatgtg cgctctgact gcttctcact gcatctaagt      1500
tcagatttag tagctctatc ttcagccctg aatgcttatt atttcgtgat ttcttaccct      1560
ttggggcctt ttgctgacac cagccaggga ccactggaaa agtaaatgta cttttatcca      1620
tgtagtaagc ctctttgtgc ttcaccattt aacactaatg tctactgcag gcataagtta      1680
gcgcatattg gaaatgcaaa atacagtttt taaggagaaa acaaaacgac accaactaaa      1740
atggcagcct ctcccatttc tatattaaaa gtcacttcac ctgaacctgg gaaatggggg      1800
tagccaatgc caggagctat gaattacggt ggactgatgc taggagagat atgtttctga      1860
aaggcctact aaagatcatc tcatatattt tcttgcttcc agctaaggtg agttttgaag      1920
acaaggcttt ggggacacct gggaatcttc actatcctaa aagataatgg ggaagaggat      1980
tctataactt gcccagaaat gtgtttcacc atctcatagt atatacagtt aagaagtcct      2040
ttatttttaa cctaaaaacc tccccggata gaattttttt aaaagtcagc ctcagaagtc      2100
agaatcccct gctaggattt aagcccattt gccctcacac agttcacagg ggagagagaa      2160
aacagatcac taagaagcta cataaaaata gtatgcacga agctattaga taatcctcca      2220
actgttcttt catatgttac atatttcatt agcctttccc cctaagacca catgacaggt      2280
tacaattcaa caattctaag tagaagaaaa tgcttcaacc cctaagatgc ttcctttcgt      2340
tcataactgt taagccacca ggttggaaac tactcttcct caaaaaaaga acaaatgttt      2400
aaataaatat aaaccagatc ctagcacctc tgaaacccct ctaaaaagcc accttttccc      2460
aaaagataca tgaagagccc caagaattgg gcagtgagac cttctagat gaatggacat       2520 cacacatctg gggtaacttc aagcacggag ggagggcagg gggtaagcag aatgaaaagg      2580
aacatttcct tcctctcata tatctaagca cctgaaagct tacaaagtac actttcaaca      2640
tatcattaaa acattgttct tagactgcag aggtggtgtt tctttaactc cctcaatcac      2700 taccccttcaa agataagaac tttatcttag gaaagttctc cttagagata tctgcagaca      2760
gaaatcagtc aagaatggtg accagcagca aagaaaaata agaagcatct aagaatcagc      2820
ttactcgagg tggaaccaat agtaacccag ttcttactta ctttgtcata gtcatattgc      2880
gaagagcatc tgctatcaaa tctaaggtac aggcagcgag ctcctgggat atggaccgtt      2940
tctttaaatt tatagttgtc tctgacgggg tggactgttt ccacagtctt tccagcagcc      3000 catgggcag gaatctttaa accagtgaga atcctggct cttccttctc ttctaacatt       3060
ctaaacagaa aaagagaaag tgatttagct tagcagccaa ggaaaggaaa acaatgtaa      3120 acattaaatt gctcttaat tttccacagc atgcagtatg ataacactga ggcttttaaa      3180
tgcttgatat cagtggcaat cagaaacatt ttaaaaattc ctacatttaa gggttttttc      3240
tttccttgtt gtcagatatt atacttgctt ttttttttct ttttgcctt tttccaggac      3300 aagaagcaga gatatatttt cattttccc tctttttttc aagggcgaag cccagttgat      3360
atccaagaga agacctgatc aattctcatt taaaggtact cagaaaaaaa aaaaagatac      3420
```

```
tgtaaaggat ctttaagatt ggccactttg caaatcccac agggttagca tcctgtaaac    3480
atttccttt  gttgatatct acatgacaat tgttgaaaac tccaggagtc tacatagcta    3540
cttttcacca taattttac  taaagaaagg tgccttcaaa ggttctctta cctactgtaa    3600
ttgaactctc aaggacgaca tggagcctga ggttgtggaa tacaaactcc taagacttaa    3660
acttagttac catggaattc tcttattctt tcaactccga agcttgagct gcaaagcctt    3720
actgtccaat atggtagcta ctagtcacat gtggccattt caattaaatt gaatttaaat    3780
gaaataaaat ttaaaattca gctcctcagt cacattagct atattgcagg tgctaaataa    3840
ctacctgtgg ctatggaact agacagcaca gatagaagtt ttcatcactg cgaaaagctc    3900
aattccatag cctgctgctc tagagaaacc caggaaatct ttttaaaga  cagctttaat    3960
gcaacataac tgacataata aattgcacat atttaaaaca tacaacttga taagtttgga    4020
catttgttat accattaagt ttccttcttc ctctttgtaa ccactccatt tctctgccag    4080
gtgatcactt atttgctgtc tgtcactaga gattagtttg cattttctag agttttatag    4140
tatgtggctt ctttcactca gggttaagta ttttgagatt atataaacat tgttgtatat    4200
aacaaaagtt cattccttt  tattgctgat tagagtccat tgtatgacta tatcacaatt    4260
tgcttatcca ttcacttact gatggacgtt tatgttgttt ccagttttgg gctcttctaa    4320
ccaaaactgt tacgaacctt aatgtcaaag ctttgtaaga acctatgctt tcttttcttg    4380
tgtgaatacc taaaagtgaa atagttgggt catacaatag gtgtatgttt aactttttaa    4440
gaaacagccg gcagggtgtg gtggctcacg cctgtaatcc cagcactttg ggaggctgag    4500
gtgggcggat catgaggtca ggagttcaaa accagcctgg ccaacacagt gagacctcgt    4560
ctctactaaa aaatacaaaa attagctggg tgtggtggcg tacgcctgta atcctagcta    4620
ctcatgaggc tgagacagga gaattgcttg aacccaggag gtggaggttg cagtgagctg    4680
agattgcgcc actgcactcc agcctgggtg acagaacaag gctccatctc agaaaaaaaa    4740
aaaaaagaaa cagccaaact gcctgccaaa gtcataatat tttacatccc cactattagc    4800
atatgagaat ttcagatcaa ttttgaacta atctcttgat ccatggggaa atttatgcta    4860
accagttgct ataaatctac aaagcaatgc tacagttatc taaaattttc attctgaagt    4920
cttttttcttt tcacagctag ataatccttg ctaaaaatca ttttcataaa aggagtacta    4980
cgctttcacc caaagaaaac aagaaaaggg ttcctgcaag gaagcagcat tcattacctc    5040
tcatcaggga acagcctgca cttctggtct ggtgcaccac acggggaaca gcccacctca    5100
gcaaaaaccg gacactgggt tttaagcagc aacgccgtct gaaacacaaa accatcatta    5160
tgtcttccag ggctactgtc agttatctga atggtatgac agccaaactt agaggtctct    5220
cttaaatcat ctttttacaa tcctagtctg ctctccttca ttaagaaatg ctgtgctact    5280
tagaccactt aacattattt tacttaatgc tgtaatggaa tgcatcattt atattagcta    5340
ctattagctg gcaaggactc aggagacaaa ctataatggt aggttttggg tagcattgta    5400
tattagcatt tttatagctg atcagccatg aacacttgct aaaaggttgc agttagtaat    5460
ttagtcaaac aaataaaatg ttttcccta  ttatttattt ttatgacatg atattttct     5520
tcattccatc attatttccc ttggtttctg aaaggcagga ttatgtttat tctgtcttca    5580
gtgaaagcaa acagccatcc tgtgaagcag gttggccaaa aagcagttca ctttggcaca    5640
ccaaggatca tacctggctg gtatagagta ccagctgcac tagctgaggc atcagggcat    5700
ccgccatgat cagagtctgt aaatttggat gcatcaagga ggtcagtaac actggaagaa    5760
ggtgaccaag catagtagcc ttagtaactt gttccaagcc ttttaaccta caaaaagttc    5820
```

```
aagaaaaaca cacagcctaa gcaatgccca aacatgtgaa gaagcactaa tgtcatctttt    5880 atctgacaat ttctcctaaa ctgcacctcc ttaaactact taagcacttt cagcgatagc    5940
aattcagtcc acaaattttc caccttctgc cactgaggga gaggggaaga acagaaataa    6000
agctattaat agatttcacc ttcagtctct gattttgcc aaaaaattta taagctgcct     6060
tttttttttt tttttttttt gacaggctct cactcttgtt acccaggctg gagtgcagtg    6120
gtacgatcac agctcactgc agccttgatc tcctgggtac aagtgatcct cccacctcgg    6180
tctcccaaat tgttgggatt acaggtatga actacttagg ttctaggttc taggttgcta    6240
catggtgcat ttcatagcac ctttgaagca ctttacaaat ggattctaaa atgccaatgg    6300
ctactacctg taaagttctc ttgcctctgg ggctgctggt cactatgcta cacagtgact    6360
ctaaacagga ggaagtgaat ggctacaaca ttgattcacc tgcccagagc tgtgacatcc    6420
attactggtc tagagaaact gaggcttgtc tggggcatgc agaagcaggc agatttcttc    6480 ccccaattt ttttttttatt atggtaaaat aaacatagca caaatttac catcttaacc    6540 attttaagtg tacatttcag tgttattaaa taatgttgtg caaccatcac caccatccat    6600
ctccacaact cttttttgtgt tataaaaccc aaactctatg cgcattaaac aataactcct    6660
cattttcccc ttgcccccag cccccggcaa ccaccattct actttctgtc tctatgattt    6720
tgactcatct aagtaggcaa attttttaatt tatctttaaa atcacattct taatatccct    6780
gtcctctgct agaagagtta aggaatgtag aaagaaatgg attatgtaaa ttccttaagg    6840
ctacttagga tattggtagt ggaaccagaa acccaggctc tcccattaga cagaactacg    6900
tattactaag cctcaatgca atgcctatct gggttatact gttcccaatc ccaacctcct    6960
atctactctc tgggagtggg taagaaccaa gtccatagga acagacaggg ttacggaagc    7020
aaaaattaca ctgtaggatt cttttagatc tacagctcca acatgcaaat tgtcaaaaaa    7080
cacagtattc aatgcatctc taaaaacaaa ccagagcaga attttttttt tttttttgaga    7140 cagagtctcg ctctgtcacc caggctggag tgcagtggga tgatctcggc tcactgcaag    7200
ctccgcctcc caggttcagg ccattctcct gccttagcct cctgagtagc tgggactaca    7260
ggtgcctgcc accatgcctg gctaatttt tttttttttt ttgtattttt agtagagatg    7320
gggttacagc agaaatttta atgtgaaagg ctgagaaagg gctttattac tgtgaaagag    7380
aagtctgccc tctatatagg tcagccatgt atttggagaa gtaaaattac agtaaaatct    7440
tgaggtacca catcagtgtc atcctttgt tagcagttgg taagtcactt cttcctccca    7500 aaagtctttta tcatgaggaa actaagtgtg catggtgctg accttgataa ttaaaggaaa    7560
ggccattttg ggagtgatgg cagtagaagt ctcaagtggc agagattagg ctgtgccctc    7620
cacaacctcg ctacccttag atcatggctg ttggcccaat ctcacctgaa agcacatgaa    7680
agagtgtgac tgcacttggc tttcaaacac ttgccctttt agcctattct cacaaaaatc    7740
tctctatata aaattgatcc ttctatattc taaaaagatt taatttcaat aaacaaactt    7800
ttcttcccac agggcagctg gtcacagccc acaatccatt cctcacctct gctcacggtc    7860
tgctatgtca ctatttatga gggcagttgt gacctgctgt agcatttcca acacttcatc    7920
acatccagtc aggatttggg tggcaagagc caaaatactg acttttagct cctaggcaga    7980
aaatatcatc atattatttt taagctttgt gatgaacata cgttcacaat gacaacatga    8040
aatgatgtat ttaatgatgt atttccaaat gaaataatga ggtggacaga ataagcccaa    8100
agcagtaaat tctgctagaa ataatgaggt ggccagaata agcccaaagc agtaaatggc    8160
```

```
aagtagcaat ttgggaggcc aaggtctgga gagctgacag aaatacgcag tatttcagag    8220
ggatcacact gagtccctag gagaaaaggc tcccatccca gccagcacaa gaaatatttc    8280
ccatcccatc cagcacaaga gagctcctgg tggccagccc agaaactgtc caggtggaag    8340
actgccttgg gtggtatgag gatagctaaa gagaaaaaca gaacagtaaa aggcgcatgt    8400
agaggcggtg aataaaatga gacaaaaaca caacattcta aaacagtaca agtgaccttt    8460
tactcaatgt cctaaacaaa tcacagttaa aaacaggcag ttaaaaaaat tcaattaaag    8520
tagcaagcag ttacaggcta ttaaacatta aaataactat tagagagttc gtgggagtac    8580
aaatactaaa taatgtgtta agaaagacta gctaacatca tagaaatgtt tagtttacaa    8640
ttattttcag ttaaaaaaat acaaactctt tgggggacat gtttccccag aaacctagac    8700
aactgagcct attcagcctt tcctaagagt ctttacattt ctatgtttaa ttaagaattt    8760
actaaggcta ggccgggcac ggtggctcat gcctgtaatc ccagcacttt gggaggccaa    8820
ggcaggtgga tcacttgagg tcaggagttc aagaccagtc tggacaacac ggtgaaaccc    8880
cgtctctact aaaatttcaa aaattagctg ggcattacag atgggcgcac atctgtaatc    8940
ccagctactc gggaggctga ggcaggagaa tcgtttgaac tcagaagatg gaggttgcag    9000
tgagccgaga ttgcaccacg gctctccagc ctgggcgaca agagagact ccatctcaaa    9060 aaaaaaaaaa aaaaaaaaaa aaagaatct actaaggcta aaatttagcc ttcaaataga    9120
aaaaactttc tcattgttgg aattttctgg ggtctttatt attattatat tttttgaaac    9180
acagtctcac tctgtcaccc aggctggagt gcagtggcat gatcagggct ccctgcaacc    9240
tccacctcct gggttcaagc aattctcacg cctcagcctc accagcagct ggaattacag    9300
gggagtgcca tcacgcccgg ctaattttg tattttcag tagagatggg gtttcaccat    9360
gttggccagg ctggtctcta actcttggcc tcaagtgatc cacctgcctc agcctcccaa    9420
agtgctggga ttacaggtgt cagccaccac acccagctgt ttttagtatt attgagattt    9480
tttttaatct ttaagagagt aggaactctg aactaatgat gagccaaatc atgttttaag    9540
tcacactaat gacattcatg atcatctact gactccatac cacatggcag caaagtgcca    9600
ggtatttaca gggcttgttg ttaatacagc aactttacaa agaagatgtt attgtccctt    9660
tttactgatg agaaaactaa ggcaagagaa gttaaataaa tattatcaac aacttaaatt    9720
aaaagtgcat gtatgtctgc ctatttaaaa atggattata caatgaggta aactcataag    9780
tacaaactat cagatgtatt atttaaatag tatatatgca taaaggagta agaaaggggc    9840
aaactgcatt ggcttttatc tttaactgtg gcttccttgg ttgattttc agtgtgttta    9900 acattttaag aaagaataaa gttcttgtag atttctctga ttctcccaca aagatgaaat    9960
tctgaagaac aatgcaaaca acagccttga gcatctgtca aaattataac aaccatggct   10020
ataaaaaaat ctttggactg ctataaattg tcatgtggga acaagttagt gagtttacac   10080
agaagctaat ttaaaataa tcacagaaaa tgaaattgac tataggttta gaaattagat   10140
tattccatac aaagattgaa aaaattatca cctttaaaa gttattttaa tcaagagaat   10200
ataataaacc atctaaaatt ttgaaattat ttaatgctcc caagattttt atatatatat   10260
atatatacac acacacacac acacacacac acatacacat atatatgtct atgtagctat   10320
aactttcagg tacacatgag atcacttgta agtgccatat tttatagttc ttaaaagaag   10380
atggaagtaa acaaaggcac aaaaaggttg acaggagcac acggatgaca cattatgagt   10440
gtcacaagta ggtgactact gtgtaatgac ataaaaaatc tatggaatga gtggcctaat   10500
gttacctctc acaagaatat aagccacaag gtgaattctg acatcataaa acacagaaat   10560
```

```
ttagccaatt aagctgcttt tcacactggg tagaacgcat cgttaaaata aagcttggtg    10620
ttacctgta ccttcaatgt ctctccctgc aaggagctgt cactgtcatc attctcatca    10680
ggtttaatca aaatagtgtt actgagaagg tgattctgaa ctgccatcag atagcgcagg    10740
caggaggatg cagcctttaa tacaaataag ggcatttaaa tgatctaaat cctactgaaa    10800
gagcgatcat gtaatcctca tgttttaaa agattttgac aaagaaaaca aaagagaaa     10860
taaaaaaac agaccaagtt agtttttcag gtgccttatt tccacatggc tttccataca    10920
tactttgaca cacttactat aactttctgc cttttggtac acaatcctca ctaattagaa    10980
tacttacttg aattttgcc tcttaataat tattcttccc cctccctctc acacacatct    11040
ccattataga agaatactca aacccttaaa agaatctttt gattcctatt ggtctctata    11100
aaacactcat ggtttagaaa acaatgtaaa attaaaaatt aatagggaaa aaacactctc    11160
actagataaa acaaaaactc ccaaatctga tcaatttatt gcatcaagca atttaagcag    11220
ggggaatagt ctttggaaag tttttcaagt ggatttgtct agttctacat ttctagggta    11280
agtagtaatc cacggacttt cataaattat tattattatt atttgagacg gagtcttgct    11340
ctgtcaccca ggctggagtg cggtggcgcg atctcagctc actgcaaact ccacctcctg    11400
ggttcacgtg attctcctgc ctcagcctcc tgagtagctg ggattaccga tgtgtaccac    11460
cacaccctgc taatttttgt attttaata gagacggggt ttcaccatgt tggtcagact    11520
ggtcttgaac tcctgacctc aggtgatcca cccaccttgg cctcccaaag tgctgggatt    11580
acaggcgtga gccactgcgc ccggcctttc ataaattat gtaagtctgt atgtatacac    11640
acacctgtca atataataaa atgaaaacag ggatgcttga tataattttg ctttcattaa    11700
acacattttt acttacaggc acagttgaaa ggagcttttg aaaatcatct ttagagacag    11760
tttggcactt ggtgattaag atacaggatt ctcgtacaac aatcttcaga atgtagtgta    11820
aaagttcatc atttagtctt taaaatgcag gaaaaatgta acaataaaat attgatggtt    11880
tattcataaa aggataaatt ttatataatt agtataagat gacaaataaa agatacataa    11940
ttgattctta agcaaatcac cttagtaata atgctaacaa ctaggtatat tatttaaatc    12000
aaacttatag aaatcaaatg gcacccaact acaaagtcaa agtatttat aaataacata    12060
taaaaacaac accttcgtcc ccttcaccag ctctaacaca catactcagc ctttctcata    12120
aaccagcaat ttggatggta ctctgaacca agatctccta agtaagttcc atctgttatt    12180
tttgctaaag accctttccc caggcccaac ttactttact gataaaactg aaatgtgcaa    12240
ttatcagttc tgaggggaac tgtggaatct attatctttc aactggtcca tgctttaggt    12300
ttaacatgct aacgatcgta ttagtttataa caggagacta aagttgatca aacacattta    12360
aatgtaaact aacgactgag aacacaaagg ctagaagtga ataatataac tggtgtcacc    12420
tgtaatgatc atcctcatca ctgccaaatc ggttgttttg gagctgttca gccaggttgg    12480
ttaggatcac atcccgtagc tgggagagtc cactgtttct ctctcctaac acagaagaaa    12540
gctccatcaa ctaccctggt aatgactcct agaatactga tgctattttt aaaaagtttt    12600
taaacaaata gattgtcggc aagctagggg caccagacat acggacttat acaaataaga    12660
gtggcaaaaa cgacatcaca acgaatccga cttttaacc agcatcctga ttaaagtgta    12720
attaccctct tgatagatca tgaagtgtga ttttttattc cttaatgttg cttttaaatg    12780
ccaactgtct ttaacatagt acctttgtt gtgttgttta gtctaactta aaatgttagg    12840
ctctaatgtg tgaagataac tggcttagaa atcaccaata agtgattatt ttatttatta    12900
```

```
aacatctata gtcagataca ttatgctaag cagtggagac agaaagttta taaagcttgc   12960
agatatataa aacatggttt ttgctttcaa tctggttgaa gtgtaagcat atatgcagat   13020
acattctttc ttttttcttt gagacagggt ctcattctgt tgcccaggct agagtgcagt   13080
tgtgtcataa cagctcactg catcctcaac ctcttgggct gaagcaatcc tcctgcctca   13140
gactcctgag tagcttggat gacaaggcat gggccaccat gcccagctaa ttgttttat    13200
tttttgtaga gtcagggtct tgctatgctg gccaggctgg tctcgagctc ctgggtcaag   13260
tcatcctcct gccttggcct accaaagtgc tgggattaca ggtgtgagcc accgtgcctg   13320
gcctgcagat acatttctta aatatgctga ctaacataca tgaagaagtg taaatattat   13380
ctgaatatgc agttgtttcc ttggggacaa aaaaggacg gctgttcaaa gataattaaa    13440
ggataattct taccttctgt taagaccagt ttaagtaagt tattgatttc agtttcacct   13500
gggtacaaga tatttaaacc agagctgaaa tgacaaaaaa gtcaaaaaca tttaagcaaa   13560
tgttctagaa aatcaactct aaatatttaa attcatattt ttattaaaga tgtcaattgg   13620
atgtgagggc aatctggctg cgacatctgt caccccattg atcgctgggg ttgattcggc   13680
tgatctggct ggctaggcag gtgtgccctt cctccctcac cgctccatgt gcgtccctcc   13740
cgaagctgcg cgctcggtcg aagaggacga ccatcccga tagaggagga ccggtcttcg     13800
gtcaagggta tacgagtagc tgcgctcccc tgctagaacc tccaaacaag atgtcaattg   13860
attacataaa actgtgaaat aacttttatc actaaaaagg cattaaaaaa aaattgagac   13920
agggtctcaa tatgttgccc aggttagtct taaactcctg agctcaagcg attcacctgc   13980
cttggcctcc caaagtgctg ggattgcagg tgtgagctac tgcacctggc ctaaaaggc    14040
atttgaacct aaattcactg tcacgatcca gtccaatcac ttccctgata agtggcatcc   14100
ctctcctcct cttcctgtga attacccaaa tgataagtac ttggggctag atgcagaact   14160
ggttagagag aattggtaag ctatgaaaag tcaatgtagt caagcctaca tataactatt   14220
gtgcctcccc aaaaaaacac ttgagaaagt aaatttctaa ttctcagctt ttccgaagag   14280
aagggaagaa caatattgca aatggcatca gaatcttttt tcttttcatt aatttatttg   14340
tgtgtgtgct tatatgtgtg catgtgtgtg ttttagacag gatctcactg tcacccaggc   14400
tggagtgcat ggagtgcagt ggtgtgatct cagctcattg cagccttgac ctcccaggct   14460
caagtgatcc tcccacctca gtctcccaaa tagctgggac tacaggttct tgccagggca   14520
tcgggctaat tttgttttta cttttttttgt agagacaagg tcttactatg ttgcccagac   14580
tggtctcaaa cttggcctcg gcgatccacc tgccatggcc cctcaaagtg ctggggatta   14640
caggcatgag ctaacacact cagcctcttt tctttttaa ttgaggttta acatttaatc    14700
aagtgcacat atttacagtg tacaatctga taagtctgac atatgtatac accaatgaaa   14760
ccatcaccac aatcaagata gtgaatatac ccatcccctc caaaagtttc ctcagagcat   14820
cagatttcaa tcattgcctt aatgctccac agaaagagat tcgaagcata atgtgctgtg   14880
gaaggaaaac aacttcctgt catctatgct cacccctgtc atacagatct ttcagaccaa   14940
ccattcagct ctctcttgga cactaaatta tacttaatca ctttaaggct gtattcctgt   15000
ataaaagttt gctgaggcca ggcgtggtgg ctcacacctg taatcccagt actttgggag   15060
gccaaggtgg gtggatcacc tgaggtcagg agttcgagac cagcctggcc aacgtggtga   15120
aaccccatct ctactaaaaa tacaaaaatt agccaggcat ggtggcacat gcctgtaatc   15180
ccatctactt gagaggctga ggcagggaaa tcacttgaag ccaggaggcg gagattgcgg   15240
tgagctgaga tcacaccact gcactcgagc ctgggcaaca agagtgaaac tccgtctcaa   15300
```

```
acaagcaaaa agaaaaaaag ttcactgaac taaaaaaaca aaccaaaaaa aaaaaagact   15360
tacaataaat agaaaatggc ctataaattc tgctctcttg tctgaaaagg tttttttttt   15420
tttttttttt ttttgaggcg gagtttcgct ctgtcgccca ggctggagtg cagtggcgcg   15480
atctcgactc actgcaagct ccgcctcccg ggttcacgcc attctcctgc ctcagcctcc   15540
cgtgtagctg ggactacagg agcgcgccac catgcccggc taattttttgt attttttagta   15600 gagacggggt ttcaccgtgt tagccaggat ggtctcgatc tcctgacctc gtgatccgcc   15660
cgtctcggcc tcccaaagtg ctgggattac aggcgtgagc caccgcgccc ggccctgaaa   15720
aggttttaaa caggttgata aaggcttgca ttgttgagca cttactttgc atcaggcctt   15780
accttaggaa aacctcacaa acccataaaa caggtgctat ttttatgccc atcttacagc   15840
taaggaaatg cgaaccttaa accaaggtca cactagtgag tggcaaagtc tagaacccag   15900
gtctgcctgt tgccaaagcc tgcttcttaa ccaccctgcc acactctgca aaatgagatc   15960
agcttgcaaa caatcaaaat atccacttaa agggttggtt ttgtttgttt gtttgtttgt   16020
tttagatcca aacagtgaga taaggaaatg caggtacaca gttggctttg gtcctctgaa   16080 ggtgggggcca caaacccctc tccagtgaaa ttatccccaa tccatgaggt cccaattgtg   16140
ggatggggta agaggcattt atactaccag cttttcaggga agattacaat gccttgcaga   16200
agaatcattt tgcagagagc actacaaaaa tcattagctg tttacctgat ggcaaggcag   16260
acttccttct gaatttcagg gcaaatttga tcttttggag ccatcaacaa ctgccaaaga   16320
agcaatcccg accgtcgaat gatgtctcga ttcctttcag tttgtgggct gaagaaaaat   16380
ttaaatacca cctacagaaa cagaaggagt ctatctaaaa atgctaattc tactggggat   16440
aaaattatct ctacaaagaa agtacatggt agatatccta tgaacaaata accaggtgga   16500
ttttgtttaa ccacaatctc ttctactgtg taacggtata attatagtaa atattttgca   16560
tatattaatt gtaatacgct atgtatagca atactccatt aagcacagtg caatgaatat   16620
gataattcta actccaggat cagaaggtgg taagatgcag aacaggaaaa tcattaaatt   16680
tttcttctgg taaaaatgaa ctggctgaag ccaaggtttg cgtttccttt tctctatcat   16740
cttatttatt tcaaaacagt gtatttacct gaaagacaac gagaatgcag cgtataatac   16800
aggtatctcc attaaccatg gccttctcca taatgtcaca aatactgcta agatgatgtg   16860
cttcaattgg atgctgcttg cccaagacac ttgtgattgg aagattgggg ttggtggcaa   16920
gaagattgag ttggtgtatg cacatcgcac caacgtggtg caataattgg tttataacct   16980
cattcgtggt tatagcctct tctagaagat gaaaaggaaa ctgagtgagg aaagacatct   17040
ctatgggtgg tccccaaaga atagaccttt gacttacaaa aggtgtgtgc gcactagaaa   17100
aggatatttt ggctataatc tctttcactg ctgccagaga acgcttctcc ctgccacagg   17160
tgctggggta aaaacacttg gggagttcat ttgtttggaa cataagtagc taccacttcc   17220
tgagcccttt ttatatgctg aagaatgggc tgaatgcttt acatggttct caacttagac   17280
tattttagcc ctgttttgta gagcaataaa ccaagagtca gagaagttaa ggtacttgcc   17340
ctaggtcaca cagctaagaa gtggtagaac tgggatttgg attcaggcca cctcattcca   17400
cagcccctac tggtaaccat tctagtaaaa cctctccata tcctatgtct gctccatatt   17460
agaactcctg tctataaata gctcctcatg ttttgacatg ttaagctgaa aatgcccgtt   17520
agataaccaa gtggaagtga atccacagtc tggagttcag gcaagaggct tggtagtcag   17580
taatataaag tggactttct tttctacttt ttgcttttc aaaaaaaaag ctttatcaag   17640
```

```
atataattta cattccataa aactcgccca ctctaaatgc acaactcacc aagttttagt   17700
aaatttacac aaataccaaa atcaagaatg aaagctgaga aaaaacactg accctacaga   17760
tactaattac tgtggtgatt aacatttgtc tacatgaact ggctttggtc ctctgaagga   17820
ccaagtctac aagttctctg atatgcttct tctaggaggt ggagcttaat tccccttccc   17880
ttcagtgtgg tcgagactaa cagagtgtgg aaagggagaa gtggaatctt aatagtggag   17940
aaatctggca gacatcattt aaacaaagtg atcagttttt aatatcacta gtaataagtc   18000
atgtcaatat catgtaccct ggaatagaag taatgtgaag gggataccct ttctgtggta   18060
ttcttccccc aatccgtaac ttcagtctaa ccatgagaaa gcatcagatg aacccacagg   18120
gaaggaaatt ctattctgca aatgtgtgac cagtactccc caagtgtcct gttctgctct   18180
tcagacagaa caactctact aatctatggc ccaggtttgc tgctttcttc tcccagcagc   18240
tcagatctgc tgttgagcca ctctactgaa ttttctcttt caaatctgga atttccattt   18300 tttttgttg ttgttgtttt gttttgtttt ttaaaataat ctctttactg aaattctcaa   18360
tttgcttaat catagtcatc atacttgcct ttaatttttt taaacttgga ttccttcagt   18420 tcttaaatg tatttataat ggctgcttta agtcttcatc tgactttaaa gtcatcagtc   18480
caacatctgc atttctcctg cattgcatgg ttactgattt ctctgctcag tttatttttt   18540
caaatacttg tttctttctt gcatttattt tttttaattt tatcttattt tatttttttg   18600
agacagagtt tcaaaaaagt taagttgttg cccaggctgg ggtgcaatgg catgatctca   18660
gctcactgca acctcagcct cccagttcaa gtgattctcc tgccctagcc tcccaagtag   18720
ctgagactac aggcgcctgc caccacaccc agctaacttt tttgtatttt tagtagagat   18780
ggggtttccc cgtgttggcc aggctggtct cgaactcctg acctcaggtg atctgcctgc   18840
ctcagcctcc caaagtgctg ggattacagg tgtgggccac agcgcctagc ctcatttatt   18900
tttaattatt cttgttttc ttttcagcc tggcttccta gggttcaccc ctatctgtat   18960
tccttagtgg ttgtcaacca atgattgtgg tcaaacacct tgagccagta atactttcac   19020
cctggatgga tctgtgtatt tcgggagaag tgcagcaaag ttcacgcggt tttaaactct   19080
gctctggttt ttactttctg ttgggccctc tcacatcttt gcatgtgtat gcagactcat   19140
gtttagccag aattgtgtga gtagcttagg ctgtcttagg cctcttctgt gtagatgtgt   19200
ggtcccccac agctttctca ctatccagat ctcactagta aacttctagc tagtcagctg   19260
ggccactgct tgccctaact gggatcaaga tctaagacct gctgagccac tggtctctgt   19320
ttgtttgcca ccaagatgac tactgttact gacaatgcta ctggacatga ggttttttcca   19380 cgctctgctc cctatcaagt cagcccccte tggcagcaaa gctgctgctt ttcactatct   19440
tctccaccct gagagaaatt actgtgctga ccaagcttga ggtggtcagc atagtaattc   19500
tctcaatgca gactgaggtg gaggatagga gcagttctag ctaagaacac catggacttc   19560
cactgttctt acccaaagtt caaggttttt taaaatgaat aacaactctc aatttagtgt   19620
atgccttggc aatttccagg gcctggaaat ggttgttttt gataattgcc tgttttagtg   19680
ttgctttacg ggtaggggac ttgctgagtg attaattcct ccatattagc atagttgact   19740
ttaaagccaa aagattttaa tattaactta gtattaagaa tgttcatatt aatattgaaa   19800
aatacaaagg tccttcactg gtaattctat ctaagtttgt gtataattaa gtcattacca   19860
atgcaaaaca ttcaacagc aaataatccc atgccaaata caaataatca attttttgcaa   19920 caaagttcca acaatttcag gaaggacata acaattttcc tttaaaaaag tctatggacc   19980
acctcaaaag ctctatttat ttacatactt atttacttaa tcataactca tctttcatgg   20040
```

```
ttacagataa caaaggactt taggtttcaa aagttcaaag agggaaaact ggtgacacat    20100
tctggggttg ggctatgttt tcacctacta atgctgtggt attctctcat atttcagagg    20160
aaaatctttt cctgcaagac cctgagtgca cctcacctTt gggctcagtg ataatgtgac    20220
tgactccaag tctctggcag acataatgga aggcttgatt cccagggtta caccactgat    20280
cgatatagtc atttgagcat gtccatagca tgttgttcac tgtgtcataa acgctcctg    20340
caaaaagagc atactgtatt cagtcaccat gccaccagct acctgtatac atatttctca    20400
caagcactgc tacaaagtgg aagggcaagg atgctctcta atgttgacaa cccacaaccc    20460
tagtcccaca gatttatttg gtaaggcact aggttgggac tcggcaaagg ccagcattta    20520
attttttaatt ttgcttaact cctgtgtgag gagtaaatct cacaaaatag atagctctta    20580
gtaactgatt tatctgtgac ctacttccaa agaggattta agtggcttac attaaaaaca    20640
caggtataat aggaccaatt aacattaatg caaaataaaa agccctaata actgagccca    20700
aaacttagaa ataagcttcc taccacccac ggcaaagaga aagtccagta tattacttaa    20760
tgttcattTt ctaacaataa caggtatacc aattcctcac aggaaataaa ctttttgtgg    20820
cataaacctg agaatttctt ataggcatca tcacacaacc taatcaatag tatcttcaat    20880
tgcagtttat tcagaggaat tttacatatg gcaatgtctt atactcattc ccaaaattaa    20940
aatttaatat aaaaaaattc tttctggctg gacacaatgg ctcatgcctg taatcccagc    21000
actttgggag gccaaggcag gaagattgct tgagcctagg agtttgagac cagcctgggt    21060
gacatagtga gaccttggct ctacaaaaaa taaacaaaat tagctgggca tggtggtgtg    21120
ctcctgtagt cccagttact caggaggctg agatgggagg actgcttgag cccaggaggt    21180
agaggctgca gtgagccaag atcgtaacac ttcactccag cctaggtgac agaagagacc    21240
ctgtctcaaa caaacaaaa caaaacaaaa caaaaaacgt ctttcttttc aagaaaacta    21300
gaatgccaca gggaactggc aagacagttc aagagaaatt tgctaaaact tgaaattttc    21360
caaagatatg tgcaagttta tttcttaccc aatcctggta cgagagcacc acgccccagt    21420
gagcttccag cagcatctat gagatctgca cgacttgtaa actgaccatc cgaaatatta    21480
tacaccaagc tggaggctag gactttggaa acaaacatta agctgtttaa tgagcctgaa    21540
gattattttt aaagtttaaa ttttaggctt ttaacaagac ttttataaaa atcacaccct    21600
tttcttgttg ttgtgtattg gtggtaattg gtggtaaaga gatggagaat acatgcataa    21660
gaccacagaa agaaaactgt caccaccaga aattttccta aatttaatac cgaaccatag    21720
ttttcaaagt gtttttaaaa tggcaacttt tgcatgacgg ttctttccga tatacattat    21780
caaaagggta actgcaagag gggttatgat cactaatatc acaagatgca aatgtttaca    21840
agaaacactt ggcagttagt cagtgttcaa taaagcttgg tgtatactca aacacagctc    21900
agctgcaatc tttcctaata ctggctctac aacttggaca cccctggct ttttccctta    21960
acacaggata gtgcagtatt aaagagcatg gactttgggc ttcagagttt gaattccagc    22020
tctaaaactt tgggtggcc ctgggaaagt cattgaacat ttcagtttcc tcatttctag    22080
agtggaaata ataaaagtcc taccttatat agttatttta aagaataaat gagttaaaat    22140
atgtcaagga tccacaccag catatatata tatatatatg tattaattgc tatcattgat    22200
tttattttct tccccatttt caaacaaaac tttagcactg tgtctcttga gttttcttct    22260
ttttcatatt ttaatcaccc tagtagccca gatccgcatc gtgcctaact taagttataa    22320
cataaatgat actcttttTt ctattttcta ctgtttcatt aaacaaaatg ggacagtgga    22380
```

```
aaatagacct ccaaatctct tttttcatgg tacttaacca tacatatgct ttctccccac   22440
ttggccactt atatgaataa tatccgttct ttatggctta aactcaaaac ctcatgaagt   22500
ctctcctttc taccccactc cacaatgagc ctttctttct cagattgtgc agctcacaaa   22560
tctgctccac atggatcctt ccagcaggga tgcagcattg tctatcattt tctcattgtc   22620
tcacatatct acgtcatctc tcctaactag actaagagct gttaaaggca agcaccaatt   22680
cttccacttt ctgagcagcc cccacagtag ccgaagagga acaggacaca gaaggaattt   22740
aagcatttac tgatttgttg cactaaagca gaatcactgt gtaagctata tcctcatgaa   22800
agaatggtac catgaagacc cactttaatt aaatggggtc aatttcaact gagcaaaaaa   22860
gccatgccaa ggagactaaa cacaatttaa taagactaat ggtcataata tgtggtaata   22920
ggaggaaaaa agagggggaa aaaagaaaa gactgatggt caataacata aaaacccaat   22980
ttttattttt gttttatta tttatttaga gacagaatct cgctctgtcg ccaggctgga   23040
gtgcagtggc gcgatctagg ctcactgcaa cctccagctc ccaggttcaa gcaattctcc   23100
tgcctcagcc tcctgtgtag ctgggactac aggcacgcgc caccacgccc agctaatttt   23160
tgtattttag tagagatggg gtttcaccac gttggccacg atggtctcga tctcttgacc   23220
tcatgatctg cccgccacag cctcccaagt gctgggatta caggcgtgag ccactgcgcc   23280
tggccaaaaa acccaatctt taaatggata aagactttg gaggaataga tattcctcca   23340
aagaaggtat acaaatggcc aataagcaca tgaaaagatg ctaagcatca ttagtcatta   23400
aggaaatgca taaatcaca atgaggtaca acttcatatc cacaaagatg gctataatca   23460
gaaaaatgga aataacaaa tgttggtgag gatgtagaga aaatagaacc attatacttt   23520
ggagatgaga acgtaaaatg gtatggccac tttgggaaac agtttagcag tccctccaag   23580
ggtaaacata cagttaccat atgacccagc gattccactc ctacgtatgt gcccaagagt   23640
atgaaaaaca tccacacaaa acttacatac taatgttcat aacagcatta ttcaaaatag   23700
ccaaaaagta gaaacaactc aaatgtccat caacttatga atggataaac aaaatgggat   23760
attatccaca ctatgaaata taattcaacc ataaaaagta atgaagtact gattcatgct   23820
gtaatatgga tgaacctcga aaacattatg ttaagtttaa aaagcagtca cagactcact   23880
ccatcctgcc accctgtgaa gacgcctgct tctcctttgc cttccgccat gattgtaagt   23940
ttcctaaggc ctctccagca atgcgcaact gatggataaa acaacttgga accaataaaa   24000
aagagctggg tctggtgtca agagacttgg accacatcac ttcacctgtc tgagcctcag   24060
tgaccacgta gtgatcccat ggctaaagac tgagaaagat ctaggatcac tggtgtccaa   24120
taataaatgc acatttgcaa gcactaagga gaaaacctca ctccatgtac tttcttcctg   24180
gagaccaagc ccactacagc aaggagtatc ttcaagcgag ggtggaattg tgcatgaata   24240
gagaatactc tccatctctt ctcacatcac acagctctcc agttgataca atattcaact   24300
atatttacat cgagggaaaa atgattctat atttatatat aactctccat aatgtgtcaa   24360
gtgtcctcac actatcctat gtggtaggta taatcatctg cacattttt ttaatgggaa   24420 agttgaggct ttgaatgatt aatttcccca agataatagt tactaaaaga aacaagattt   24480
ttacatgtct gtctgcatct acttttatag ctcctgattt tattcgtagc tcagccacca   24540
taatatgcac agaatgagac aaaataataa gtggtatttt gctactatcg agtaaaacca   24600
aaaattaaaa atcaagcaaa taaacaaaca aacgaaaaag cagtcataaa aggccatatg   24660
ttgtataatt ccatttacat gaaaagtaga gtataggtaa ctccacagag acagaaagta   24720
gattggtaga tgccaggggt cagggagtag gagagcaact gttgatgagt atgaggtttc   24780
```

```
tttttggggt gacggataga ttagtggtaa tgactgcaca actctgtgaa catattaaaa   24840
accactgaat tgtatatttt aaaggggtga aatttacggt gtgtgagtta tatttcaata   24900
aagccaccgc ccccagcctg aggaacattt aattctatac tttatcccat ttaactatgt   24960
gtgcactctg aagccaaaat tacactgctt tcattactac agtgtgcctc cttataataa   25020
tatatggata ttttaaaata ctaacacatt tttacacatt tgcttttcta tgtcttatgc   25080
ttagtatttt gtatatgtgt cctaaaatgg aggtgtttta catatgtatt ttaatagctt   25140
tgaaattcta ttggcagggc gtggtggctc atgcctgtaa tcccagcact tgggaggcc    25200
aaggtgggtg gatcacctga ggccaggaat tccagaacag actggccaac atggcgaaac   25260
gccatctcta ctaaaaataa aaaaattagc cgggcatggt ggcatgtgcc tgtaatctca   25320
gctactaggg aggctgaggc aggagaatca cttcaacccg ggaggcagaa gttgcagtag   25380
gctgagatca tgccactgca ctccagcctg ggtgacagag caagactccg tctaaaaaaa   25440
aagaaattct atcatagtga gtagagctct tgctgtatca tcagtaaata atgtgacaaa   25500
atattatttt atttcctaaa actttgttga actgattatt tctattaatt ttataggaca   25560
atagttttca aaactatact aatatgccat ccacaaaaaa ttatattgtt aaatcttcct   25620
agcctatttg ataattggta ttttttgtta tcagagagct attgcaaaca actatttaac   25680
aaagtaagtt ttaaataatt aataggaaag ctttaaattt cagagtttga gataaatcga   25740
ggaaagtgcc acaagtaaaa ttcacttact ttttaaagat gacaaaccac ttgttccacc   25800
aaaaagagat cgggtggcag agctgcctga tcccctgga ggaggcacca gcatcaccaa    25860
gtaggtgcca caggtatata tgggtgtctt ccgcagcatt tttagaggca gcccacagct   25920
agtatttgct ggagaaagga atgaaaatgc taaatcaaaa tatttgacac aaaagttaat   25980
ttgattacca acacagatta ggatataatg agggagaccc aaactcaaac aaagatttgg   26040
aaaacagatt tccagattag gaaaacagaa taagaagtaa tagctaagga aaaaaataat   26100
tatcttctgg ctccacagcc tgaccctgag cctcctattt atatggtctg aacatttctt   26160
gacagtgctc ccaatcctca atatgccatc atgcctctac aaattattcc aaaaaaataa   26220
atcctcacat ggactaaatc tcaaaataag agaagaatcc tagtatttgt ttgtgtttcc   26280
cctagaaaac tgatataggt tgagtacatt tatctgaaat gcctgggacc agaagtgttt   26340
tggatttcag atttttttcag aatttgaaat atttggatta tacttaagag ttgagcattc   26400
ctaattgaaa aatccaaaat ccaaaatatt ccagtgaaca tttcctttgt tttcatttat   26460
ttttactcat tacatctgag attagtgaga acatttcctt tgagcatcat gtaggcactc   26520
aaaaagtttc agatttggga gcattttaga ttttagatt tgggatgaac aacctatatt    26580
ccaatcaaga tcttggtttt tttttcccat tttatataga acaaattctt gacaggcttg   26640
tgatattaaa ctcataataa acagctttca acatgaaatc ggccaaaatt tcaacctaat   26700
gaaagctttc acaatatcta tcacaaaaca attttatagc tgtgtaattt attataaccc   26760
cttatataca ttttttcttt tttaagggt caatgacata aactgtcatt aggaaaataa    26820
ttattgtttc taatcaagag gtgtaaaatg tactttaatc tcccttactg gcatatctag   26880
aaagtggagt gaatttacgg attttctata tacaagccta gcgaggattg attatgtcaa   26940
cagagaatca actggagtgc tttacttaga aagctgtcag gctataaaat ataacttatt   27000
atctatagcc tggatagatg aaaatcattt ttagatggtt tagattagaa gagtgagtaa   27060
agtgaaacct aatctatctg atatttgttt tgaatgcttg tgcttctaaa aagcttttt    27120
```

```
ttttttaagc tgcaagcccc caccaagtat attcttcatt aaggacataa attcaagaag    27180
ataaatttcc actggtaaga aacctaaaga cagcaataat tggaaaatta gcaactttgt    27240
gagtatacca ttttcaccaa gatgttttca atagacatat gcttattaag atggcaatag    27300
gtattagttt ttaatggaat aaaaactttt tttttttttt tttttgaga ctgagtctca     27360 ctgttgtctg cctgggctgc agtacaatgg agccatctcg gctcactgca acttccactt    27420
cctgtgttcc agcaattctc ctgcctcagc ccctcccgag tagctgagac tacaggagcc    27480
caccatcaca cccggctaat ttttgtattt tcagtagaga tggggtttca ccatgttggc    27540
caggctggtc ttgaactcct gacctcaggt gatccaccca cctcagcctc ccaaaatgct    27600
gggattatag gcataagcca ctgcccctgg ccaaaacctt acagacacct gaatgttcg     27660 cttacttttg aaaagtttct tagtttataa ctggtgaatt tttaatttaa tgtagcaaca    27720
tcacgttaaa gaatccacat aaaagtacga tgattgctta agcccaggag tttgagacca    27780
gcctggacaa cataacaaga cctcatgttt ttttaaaaa aaaaaagtac aatgagacca    27840
catgtttaga atacagatac ccgtttctac caaattctag tatatgtgct gccaaagcgt    27900
gcacatttct accaaattct aaatatgtcc ttgccttctg aggtctttct ttgatattat    27960
acatattttc aacaagcatt cttttagtat ttccattgtt tagggtaaga tttcattttc    28020
tcccaaggga caaacccaga tcaggccttc agcttgtcat gaaaatgttt atttaggtaa    28080
caacaaaaac aaaaacaaaa aaaactgtcc tctagaaagt atcttctaca gttggaatta    28140
tccacttacc caaatcataa aaactattaa caattttgcc acttaccttt gatacaaaag    28200
aagcctgtga aaataaaata ctgtccttaa attctaatat ggactaataa gtatttaatt    28260
tggtagtctc ataataaatt aactataaat attttctctt cctagcattt ccaactataa    28320
aaataaagca taagattaca ctgaattcat taaatgcata ttaattcaga tgcagttttc    28380
tacatatggc atctttttct agctttatct tttactgcag ttcatagttt gctataaatc    28440
caaatatttg gtatgtaatc tgtaaactct atggaataat ggttcttaat gtttttgggg    28500
gtcatagatg actctgaaaa tctaatgaaa gttatgacag atacatataa aatgatatct    28560
aaaactttga gggagtatgt ttaataacat actcccttaa aggtgtatcc tggttaagaa    28620
ctcctacttt aaaagtgcag aacagccagg cgcggtggct cacgcctgta atcccagcac    28680
tttgggaggc caaggtgggc ggatcacgag gtcaggagat cgagaccatc ctggctaaca    28740
cggtgaaacc ccgtctctac taaaaataca aaaaattagc caggcgtggt agcgggcgcc    28800
tgtagtccca gctactcggg aggctgaggc aggagaatgg cgtgaacctg ggaggcggag    28860
cttgcagtga gctgagatcg cgccactgca ctccagcctg gaagacagag caagactcca    28920
tctcaaaaaa caaaaacaaa aacaaaaaac aacaacaacg aaaaaaaaag tgcagaacaa    28980
tgtatatagt atactacctt ctattaagaa aaggcagaaa ttatgaacat ataaatttat    29040
ctttaattat atttgcataa acaaacactg gaaggataaa tgaaaactaa taatatagt     29100 tacctgtggt ggggtagggt ggggtcacaa tataaaattt accaacatgg taagaataag    29160
acttctctgc atatacccttt ttacattgtt ttgactttca aattctgtac gtgtattatc    29220
tattttaaaa cattaaatta aaaaactaaa tgataaattc taaaaaacaa aatatctact    29280
gtagaaggct tttctgttat ttgcttggtc aagactgtat ttagggaaga tgatgctaag    29340
tatcaggttt tctcattcac aaagcatacg caaaatatga aatcaactaa tttatatgaa    29400
tggtgatgat gataaggtgt ttacagttta acatggggct atttttgcatt cttcacaggtt   29460 catatgaatt tgtgtccata gcctacaaca tgtattggct tggaataaaa agctggacaa    29520
```

```
tgactggaag accaaataaa gtcaactatg caaaggaaag ggctttgtac agcacggacg   29580
aagtgctcaa taagacgtag ctgaacagag ctatacaagg aaacagatct gggaagcaca   29640
gagtaacata cctgcttgat cctctttcag tgtgttggag atggtggaac cagtcagggc   29700
agcaagcgtt gctgacgggg aggctctata ccgagaaagt ctacttagaa gcatctcatt   29760
aatgcttttg gcagattcgc cctcttttct cattagaatt gtacgttcct gaagtgggtt   29820
ggctacaaat acaccatttt caacctaaca tagaaaaaaa ggaggtccta aaatgatatc   29880
tgtttccatt tagttagcaa atttctactg aggatattat tgtgagtaaa taaaaaatat   29940
ttcaaaaact gctcctgagt agatgtatac cttaaaactt aaatgtgcta tagaaactac   30000
tacaaacaaa agagactatg ctaagtttga gatctttcac ttttcataat agctataatg   30060
tttaataggt ctatgaaaag ttgttgatta aaattcctta cactggattc cacaggcagc   30120
gcttactaat tacatgcctc tgacaggttg aagtcaaatg agaggaaaac aaatcaatca   30180
gtctttgatt tactgttaag gacaactatg aggataatgt cttctcgaaa tatcttcagt   30240
ggctaaaatc caaactcttt attaacagca gttaacatta gcaccagctg ctcaggccct   30300
ggcagagcaa gcctggacaa agccagactt tgctaaaaat acacatcaac ttcaactgga   30360
tctttgctgg tgcttgcag ttcttttcatt catcacttgg ttattcccca gaaaaatctt   30420
tggagtggtg actccaaaat tccttcacca attttgagct tgactttcag cagaccacct   30480
ggttttcttc tttcttcttt ttttttttt ttttctttt ccacctggct ttctgtattg   30540
ctaaaaagat ccagaccact tactataagc ttctcctact cacgtctctt ccaacttaag   30600
aatcttggga cccagcctca tttactattt cctttgtctt aattcagagg aagaaggatt   30660
tcacctcata ttattgaaga tgaaccctc cacttctgcc tcaagtcctg tgctcccctc   30720
tgcctcttca tcattagtgt ctccctctct attgagttcc ttctctttgt tttcaaatat   30780
tcacaggtct taaacaaaac cttggtggcc cattaaaata tcaccccttt tgtcaaatct   30840
ctcatggccc ctttctagat ccaagaactg ggtccccacc agcaaagaca ggcaggactg   30900
gcctgcagct gtgggtgtg gagataagag ggaatgggag tgcaaagtgg caaatcttca   30960
gaagcaaagg gaaagcaaaa gaggagtcca cagggaaagg ttggtaacac agaagggca   31020 agagaaagtg agtaaactca ggagcacagc caggaaagat tcccaaaggt gggtgtacgt   31080
agtgggggag tcttttatga catattcaca aatgataaag aaaaagattt gttacagagt   31140
ccaaaaatgc tgtttctatt tccccatccc ctgctttta accctttgca gttggtagtc   31200
tctgaattca gcacactcta atgagtcggc aatctcaatg gtccaccagt gacctaaaac   31260
caaaaccact gaccttttcc ttgacttcct tgcaggtcgc gccatcactg ccatccttct   31320
tgggattctg attccttagt gttggtggca gaacacaagc ctggtttgtt tcttttttgtt   31380 tctttttttt gagacagggt cttgctctgt cactcaggct acagtgtagt ggtgtgatca   31440
cagctcactg aaccctcaat ctccccaggc tcagatgatc ctcccacccc agcctctcga   31500
gtagctggga ccacaggaat gcgccaccac atctggctaa tttttgtatt aatatttttt   31560
gtagagacag ggttttgcca tgttgcccag gctggtcctg aactcctagg ctcaagcaat   31620
ctgcctgcct cagcctctca aagtgctgga attacaggcg tgagccacca tgcccagcct   31680 ggttgtttc tttttaacat gaacacttac ctctgtgtaa agtgctcact gtgctggcga   31740
gtgaagccag cacagtccct gcctccttc ctgtctctct ctttgctggt caacatcttc   31800
atttgcttaa atgggacctt tcccaagatt agacctaccc ctggtgtcca agacctccac   31860
```

```
ctggaatgct ctatccctag accttccaga gactggctct ttcctatcat tcaggtctta   31920
gttaaacgtt acccactcaa agaggtctgc cctggttgcc aatctaaaaa agaatcctcc   31980
ccagcacccc aacccagagc acatcatgct gtttcattat ctacacagca cgtactactc   32040
tctgaaatta ttttactcat gaagtcattt attctttgcc cttctacctt aacacgtccc   32100
aatgaatgcc aactccctga gaacagggat ccacctgcct tgtttgccat aacatcccca   32160
gcacttagga ggcattcaat gaatactcga ttgcttgctg aataaacaga tcagggccct   32220
cccccaaatc caactccgct tctctatggc aactcccaca tttctattta cagacccatc   32280
cttgctacta cgatctagtt ccacttttct aactgcccct caccctcccc accgacattt   32340
ctacttgaac agcctcctgt cacctaaaat tcaacacatc cacctcttac ttcattgtct   32400
taccccaact ctcctactag attaactttt agcaagcata gctctattta cattgcacaa   32460
ttctaaatat actccttcaa aagcatccaa gataaaaatc aatcacttta agcttggcat   32520
tcaaaagcat tacccaatct ggccctatga gaaaatcaat agataccttg aaaacaaaca   32580
aaacactata ttattgtatt tgagtacttt gaaaatactg caagaaaaa ctgataaaac    32640 acctgtgtga tacaagtagg gctgaagttt gctgcaaaat ggtaaatctg ctggaaatcc   32700
ctactttagc aaaggcgctc ttcagggtaa gaagctgctg atttaggaag acaggaagag   32760
ctgggaggag tgagaagcag cccaggcttc cttcctggca accactctgg tccaagtcca   32820
catcatctca agagagatta ttagaccagc ctcccaacct gtcttcccac ttccacaggc   32880
accccaatgg tttactctct gcatagccag tgatcattta aaaatgtaaa taaagccagg   32940
cacagtggtt cacacctgta atcccagcac tttgggaggc caagaaggga agatcacttg   33000
agcccaggag ttcgagacca gcctgggcaa catagtttga gaccaacctg tctcaaacac   33060
acacacacac atacacacac aaaattatcc aagggcagtg gcacacgcct gtagtccctg   33120
ctacaaggga gactgaggcg ggaggattga aagagcccag gaagggaagg ctgcagtgaa   33180
ccatgattgc accactgcac tccagcctgg gcaacagagg gagatcctgt cccacccgc    33240 cccaccaaaa aaaaggtaa aaccatgtct tccctcattt aaaaccctgc agtggttttc     33300
caacacactt atgataaaat ccaaattact gacagggcct cacaagggcc aatgtctgct   33360
gacctcctca gcatcatctg cctcaactca accctctctc actacatttt tagctacact   33420
cgccttctgt cacacctcca aaataccatg cttcctccta atgctgggcc ttggtacttg   33480
ctattccctc ttgtgctacc catccgttgc agtttgcctg gaactgcagg ttttagcacc   33540
gaaagttcca tgtcatgagc aatcaatccc tcagtctcaa gcaaactggg atagttggtc   33600
accctgtctg tcaggatgga tggcttctta tcattcaggt ctcagctcaa atgtctttcc   33660
ttagaaaggc cttatgtgcc ccgcaagcta aaggagctcc ccatctccac cccatgcact   33720
ccctctcaca ttatcctgtt taattttctc cccagcattt atcactagct gaaattattt   33780
tgttcttatt gtttgcttcc gtattgtccc acttcccata ctctaatata agctcccacga  33840 aaacaaaagc ttatttactg ggctacccag atacggcaat atagtatagg ctctcaatta   33900
atacagaatg aaggaagggt agcttagtca tctggatcat aactggaagg aaacaacaaa   33960
cccttaggga gaagagggga agactcttag tgtgtccatt actacattga caataccttt   34020
aggaagtaac ataaggagag aaaaatagca ataaaattgt cactaataaa atttaaaac    34080 tgcagtttat atagagcaca tggggggcaga agacctctca gaacaaaaca gaagtgagga   34140
tattttttca aaagaggctt gaaaaggtaa aaaagagtta taggctgggt gcagtggctc   34200
ccagctggat tacgcctgta atcccagtag gtagaggcag aggcaggaga acagcttgag   34260
```

```
cccaggagtt agagaccaca gtgagacccc actctctaaa aaaaagaaaa aaagagttat   34320
agaagattct caagcaggaa tgtgtccaga gtagaagtag ccaaatcagg cagaaagatt   34380
acatgcttca gctattttgt agtcttaaag accagaattg tgttctagag tttcagaagg   34440
cctgttgctc catgtgggta gactgtcaca ttggtggccc ctaatgaatg atgcatcctt   34500
gtattcatgc ccttgtatag tccccgtcca agtctggacc tggtcagatg acttttttt    34560 tttttctac attagaaagc aagttgctgg ccaggcacgg tggctcatgc ctgtaatccc    34620
agcactttgg gaggctgaag caggtggatc acttgaggcc aggagttcga gaccagcctg   34680
gccaacgtgg ttaaacccca tctctactaa aaatacaaaa ttagctaggt gtggtggtat   34740
gcacctgtaa ttccagttac tgaggcagga gaaccgcttg aacccaggag gcagaggttg   34800
cagtgagcgg agatcacacc tctgcactcc agcctaggtg acagagcaag actctgtctc   34860 aaaaaaaaa aaaaaaagat gcagcaaggg gcagtggctc atgcctgtaa tcccagcact   34920 tgggaggtt gaggctagcg attgcttgag cctaagagtt caagatcagc ctgggcaaca    34980
tggcaaaact cagtctataa aaaaatata aaattagcc aggcatggtg gcatgagcct     35040
gtagtcccag ctactcagga ggctgaggtg ggaggaatgc ttgagcccag agtggggagt   35100
ttgcagtgag tgagcagaga tagtagcacc actacactcc agcctgggcc atagagcaac   35160
acaatgtctc aaaaaagaa agcatgatgc aagcagagac ttgatatcca cttgtcctct    35220
tgaaaagctc cttcctgaaa accagcttcc atgatgtcga gcttcagcat acattactga   35280
ataatggatg ccaagtggag agaggcccta gaggatgaca ggccatcttc agtggcacag   35340
cccaagctaa gctcccagtt gaatgaagct gcagatgtga cttcagcttc accatgcaga   35400
gcagaagaac cacccagctg agccccatca acctatacat cattgttacc tgaagttact   35460
tagcttgggg attgttcact gagtaaaagt aaataactga ataccttaa aagtcagaga    35520 aattctatga tccaaatgtt agaggtcatt ttatattaat aatagtttgt tagttaagca   35580
ggataatctc gacattccat tttgttacat catattccta aatatatctc ttctcctctc   35640
ttctttttct tttcttttg agacagggtc ttggtgtatc acccaagctg gagtgcagtg    35700
gcacgatcat ggctcactgc agccttgacc ttcagggctc aagcgatcct cccacctcat   35760
gctacttact agctgagact acaggtgtga accaccacac ccagctaatt aaaaaaaatt   35820
tttttgtaga atggggtct cactatgttg cccaggctgg cctaaatata tttctatagt    35880 ctgccttta taacaactag ttatctaatt ccatgcttag ttaacaaggt atcattttga    35940
gaggtaagca tggctagtta gattctgctc tctgatctta gtcgtttcaa tccattagtt   36000
ttccctgagt cttaggtacc aagagatcta tttggtataa tcaagctgag ctgactgttt   36060
tatgaaaaat gacataatgg aggaatacag atggtgttcc aagaattttt ttaatgttta   36120 ggttttttt tctaatgata aaactaatat atggttactc ttggaaatct gggggaaga    36180 aagaaaacta taaataagaa aagctaccat tattctttgt ttgtttgttt gtttttttga   36240
gacagtctca ctctgtcagc caggctggag tgcagtggca tgatctcagc tcactgcaac   36300
ctctatctcc cgggctcaag caattctcct ccctcaacct cccgagtatc tgggattaca   36360
ggtgtgtacc accacgccca gctaattttt gtattttag tagagacagg gtttcaccat    36420
gttggccagg ctggtctcca actcctgacc tcaggtaatc ctcccgcttc ggcctcccaa   36480
agtgctggga ttacaggcat gagccaccgc actcggccta ttctttcttt ttaaagggat   36540
aatcagttaa tgttttaagt tctagcattt aaagaagtca ggccaggcac agtggctcat   36600
```

```
gtctttaatc ccagcacttt gagaggccga ggctggtaga ttgcttgagc tcaggagttt    36660
gagaccaacc tgggcaacat ggtgaaaccc catctataca aaacatacca aaattagccc    36720
agcaaggtgg tgtgtgcctg tggtcccagc tacttgggag gctaggtgag aggatcactt    36780
gagcccggga ggttgaggct acagtaagcc gtgatcatac cactgcactc cagcctgagt    36840
gataaagtga gagctagtct caaaaaaaat aatcaatcaa tcaatcaatc ataggctcta    36900
gaaaataatt ttttaaatta gctgggcatg gtggcgggcg cctgtggtcc cagctgtgag    36960
ggaggcagac gtgagaagat cgcttgagcc tgcaaggttc taggctgcag tgaactgtga    37020
tcacaccatt ccactccagc gtgggcaaaa gagcaacacc ctgtctcaaa aataataat     37080
aataaataaa atataatgaa gaaatcaggc cggatgtggt ggctcacgcc tgtaatcaca    37140
acactttggg aggccgagga aggcagatca cctgaggtcg gaagtttgag accagcctga    37200
ccaaaatgga gaaaccctgt ctctactaaa aatacaaaaa ttagctgggc atggtggtgt    37260
atgcctgtag tcccagctac tcgggaggct gaggcagggg aatcacttga acctgggagg    37320
aggaggttgc ggtgagctga gatcacacca ttgcactcca gcctgagcaa caagagcgaa    37380
actccgtctc aaaaaaaaac aaaacaaaaa aaaaaacaa atcacagata gttttggatg     37440
ctgcatgata ccactgggat caataaaagg atttgtcacc aattttttaaa agaatatatc    37500
ccgattctgc tcactttttt accacctcca tcattacttc accctcagtc caacacatta    37560
attatctttc acctggtctg tggcaacaac ttcctactaa tcccattcct gccccttct     37620
cacaaggtgc attcttttaa aaaatgtttc tttacaaaat ttttcttaat actaaaatat    37680
acacaaaaag aaacatgtaa aaaatgtttc tttacaaaat ttttcttaat actaaaatat    37740
acacaaaaag aactagtaat atccgcttac tatcactcta gatacaagtt atcaagattt    37800
tgacatattt gcttcatctc tcccagtcat tatgtcattt caccccaca tatttcagtg     37860
tatatcacta taaaatatag atattcttta ataactacaa tgtaatcaca cttattatta    37920
gcaataattc ttgacatcat ctaatattga gtccataatt caatttcccc aattttctca    37980
aaaatacttt ttacaggcca ggtgcagtgg ctcaagtcta taatcctagc actttgggag    38040
gctgaggtgg gagggtcact tgagcccagg agttcaaggc caacctgggc aacatagtga    38100
gaccccccca tctttaaaaa aaagaaaaa agagccaggc gcagtggctc acatttgtaa      38160
tcccagcact ttgggaggcc gaggcgggcg gatcatgagg tcaggagatt gagaccatcc    38220
tggctaacat ggtgaaaccc cgtctctact aaaaatacaa aaaatcagcc aggcgtggtg    38280
gtgggcccct ctagtcccag ctactcggga ggctgaggca ggagaatggc gtgaaccggg    38340
gaggcggagc ttgcagtgag ccaagattgc gccactgcac tccagcctgg gtgacagagt    38400
gagtctccat ctcagaaaaa gaaaaaaaat acttttttaca gttggcaatt ggtttgttg     38460
attcaggaac caaacaagat gcaacctaca cattatatac atttggtttg tctctttaag    38520
tctcttctgg ctttattctt taccccaaac ctacaatgaa cctttaaaac acgatcccat    38580
cactttcctg ctcaacaatt tccaggagtc tcccatctca cttagaataa atcccaata     38640
ccttgcaagg ccctataaga tatggccctg gctacgtctc caacttcatc tcccattact    38700
cactctcatc actccacttg agacacacag acttcttgtt gttcttcctc aacaagccaa    38760
cctcatgcct atctcagggg catctgcata tgccatttcc tgtctgtaat gctcttctgc    38820
cagatcttta catgtctcat tcctttattt tattcaggtg tcaatgtaaa taccacctcc    38880
tcagagaggc tccctgatc attacctaga atagtcccac accaaacaca cactaaatca     38940
tttctctatt gctttacttc atcttccttt ataatattta ccaatgcttg aaactgtgct    39000
```

```
tctgtctcct ccacaagaat gtaagctcca tgaggacaga gatctcactg tcttttctat   39060
actgtatcac cagctcctag gatactacct ggcatgtaga aggccctttg taatgtagga   39120
gatgaatgaa tatgtgaaga catagctatc taaacttgag gctactgcat gaagtgccca   39180
gcacttacat cagtaaggct ggatgagaag cttccatttg tatacagtgg attaggatca   39240
caagcatgcc acaaaataaa aataccggga aaaaatcttt tcggccaggt gcggtggctc   39300
atgcctgtaa tcccagcact ttgggagacc gaggtggaca gatcacaagg tcaggagttt   39360
gagaccatcc tgggcaacat agtgaaaccc cgtccctact aaaaatacaa aaatttagcc   39420
aggggtggtg gcgggcacct gtaatctcag ctactaggga ggctgaggca ggagaattgc   39480
ttgaacccag gaggcggagg ttgcagtgag ctgagatcac accattgcac tccagcctgg   39540
gcagcaatga gagactccat gtaaaaaata agtaaaaaaa tatttcatga gggatgttat   39600 tgagggatt caaatatcga atgagggcca gatgcagtgg ctcacgccta taatctcagc   39660
agtttgggag gccgaggcgg gtggatcact tgaggtcagg agttcgagac cagcctgacc   39720
aacatggtga aaccccgtct ctactaaaaa tacaaaaatt agctgggtgt ggtggtggtg   39780
cctgtaatcc cagctactca ggaggctgag gcaggagaat cgcttgaaca tgggaggcgg   39840
aggttgcggt gagccgagat cgcaccattg cactccagcc tgggcaacag agcaagactc   39900
tgtctcaaaa aaaaaaaaa aaaaaaatt agctgggcat ggtggtggtg gcttgcgcct   39960
gtaatctcag ccactcggga ggctgaggca ggaggattta ttgaacctgg gagacagagg   40020
ttgcagtgag ccgagatcgt gccactgtac tccagcctgg gcgacagaaa agattccat   40080 ctcaaaatca atcaatcaat caatcaatct tgctttaaag tagaaatttta cttcaataat   40140 agagcaaggt acagaagaat gtgtataata aatcaccatt tgtgtacaaa acagaaaagg   40200
aaaaacaaca caaacacatg cacttgtttg tatgtgctcc gtccgtggaa ggatgtagaa   40260
gaaaatgcta acctcacttg cctctgagga gggaaactgg gctaggaagc agggtaggtg   40320
agagacttct gtaccttctg agttgtataa ctatgtgaat atcatgttaa aaatattttt   40380
aattaaaaca acatagctat tactaagctt gaagagaaag ttatcaatac ttagtttttct   40440 ttctttttttt gtgggcgggg aggcaaggtc tcactctgtc acccaggctg gagtgcagtg   40500
gcacaatcat agctcactac agccttgacc ttctgggctc aagcaatccc cctgcctgag   40560 cccctaagt agctgggact acagtcatgc accaccacac ctggctaatt ttttttatt   40620 ttttggagag atgaggtctc actttattgc tcagactggt cttcttttt ctttcttac   40680 aggccatgct aatttttct gtatcattcc aatttgatg tctgtgctgc tgaagtgagc   40740
acttatcaat actcctaagt attggagtga aatcataatt accagcaaat ctaattcctt   40800
ccagtaatta ttattggcca catctatgtg acaagtatct acattatta gaaagcaaga   40860 ttaatcataa ctcagtagag aatttcaggg ctagaactct atgaatcatt tcatctaaag   40920
cattatttca taaagttttt tgcctggttt ggcccagcaa atcataggag gtctatggct   40980
aagccctatc atttgtgaat ttagaaacag gtacttttta aaatctattc ataacttaa   41040 atttttaaaaa atgaaattaa aatatttcca tgtccccaca gtccattcca tcatccccct   41100
ccgatttctc tcctgttttc acatcaaacc cctggagaga aagatctatt cttttccatc   41160
ttatcctccc taccttaccc tcaaccaact ccatctggct gccactccta ttattcctca   41220
aaacagctct tgttagcgct gcaacggcct ccatattata cattcaaaag gcctctttca   41280
gtctgacctt gacttctcca gcagaattca atgctattaa acaagttctc cttttttataa   41340
```

```
aaaaattcct tttttaaaag ttaattttc taaaaagccc attgttaaac tttaaaaaca   41400
tatgaaaaga tcaatggtgg aaagtaagtc ttgccccaac cagttgcctt ccccggggaa   41460
accaatactt ccagtctctt gtgatgttta attaattaat taattcattc atttagcaaa   41520
tatttaataa gcttctactg tgtgccgggt actattctag caccggaggg cgcagtggct   41580
catatctaca accacagcac tttgggaaga caaggcaggc cggactactt gagtccagga   41640
gttcgaggct agccgaggca acatagcgaa atcccgtctg aaaaaaaaaa agagagaaa    41700
acaaaaatcc cttccctgct ggagctgaca ttctaagcag gggagacggt caataaataa   41760
gcaaataaat gagcagtaag aagaaaacta aagcagggca aagaggatag ggaggaacag   41820
gattttattt tatacaaaat atttcatata gaatggtctt ttgttttata taaaatattt   41880
catatagaaa agtctttctg gtaaggtgat tttttttttt tttaagagac agggtcttac   41940
tctgtcaccc aggctggaat gcagtggtgc aatcctagct cactacagcc ttggactcct   42000
ggactgaagt gatccttcta cctcagcaac tggctaatat taattttttt tttttttttt   42060
tagtagagac agggcctcac tttgttgccc aggctcatct tgaactcctg gcttcaagtg   42120
atcctcctgc ttcagcctcc caaagtgctg ggattacagg catgagccac tgtacctggc   42180
cctttttttc ttttttgag acagggtctg tctcactccg ctgcccaggc tgcagtgcag   42240
tggtgtgatt gtacttctct gcagccttaa actcctgggc tcaagcaatc ctcccacctt   42300
agccctccaa atagctggga ctacggacat gcaccattaa attaaaaaa aaatatatat    42360
atatatacac acacacacac acacatagtg atgtggtctc actctgttgc ccaggctggt   42420
ctcaaatcct tggccttaag ctatcctccc accttggcct cccaaagtgc tgggattaca   42480
ggtgtgagcc actgtgcctg gcctgataag gtgatatttg agcagagaca tttaaaaagt   42540
gagagaagca gccatgtggt tatctacagt ccaatattcc agcacaaggg acagaggggg   42600
aacatacttg gtgtgtgtga gtaacatgga ggaagcatgg ctaagtgcca tgaacaagaa   42660
ggtatggtag gtgcagaggg tgtaggtgca gcaggtggta ggtgcacagg gtgtaggtgc   42720
agtggatgta ggttcagtgg atgtaggtgc agacagtggt aggtgcagac agtggtaggt   42780
gcagagcgtg tagatgcagt ggatgtaggt acagagggtg taggtgcagt ggatgtaggt   42840
gcagtggatg tgggtgcaga gggtgtaggt gcagtggatg tgggtgcaga gggtataggc   42900
gcagcaagtg gtaagtacag aaggtgtagg tggagtggat gtgggtgcag aggatgtagg   42960
tgcagagggt gtaggtgcag tggatgtaga tgcagatggt gtaggtgcag aggatgtagg   43020
cacacaaggt gtaggtgcag tagatatagg tgcagagggt gtaggtgcag tggatgtagg   43080
tgcattggac gtaggtgcaa agggtgtaag tacagtggat gtaggtgcag atggtgtagg   43140
tgcagaggaa gtaggtgcat tggatgtagg tgcaaagggt gtgagtacag tggatgtagg   43200
tgcagagggt gtaggtgcag caagtggtaa ctacagaggg tgtaggtgca gtggatctag   43260
gtgcagatgg tgtaggtgca gagggtatag atgcagtgga tgtaggtgca gatggtgtag   43320
gtgcagatgg tgtaggtgca gagggtgtag gtgcagtgga tgtaggtgca gaaggtggag   43380
gtgcagtgga tgtaggtgca gatgtgtag gtgcagaagg tggaggtgca gtggatgtag    43440
gtgcagatgg tgtaggtgca gagggtgtag gtgcagtgga tctaggtgca gattgtgtag   43500
gtgcagaggg tataggtgca gtggatgtag gtgcagatgg tgtaggtgca gaggatgcag   43560
gtgcagaagg tgtaggtgca gtggatatag gtgcagatgg tgtaggtgta gatggtgtag   43620
gtgtatggat gtaggtgcag agggtgtagg tgctgtggat gtaggtgcag agggtgtagg   43680
tacagtggat gtagatgcag aaggtgtagg tgcagagggt gtaggtgcag tgaatgtagg   43740
```

```
tgcagagggt gtagatgcag tggatgtagg tgcagaggat gtaagtgcag caagtggtaa    43800
gtgcagaagg tgtaggtgca gtgaatgtag gtgcagaggg tgtaggtgca gtggatgtag    43860
gtgcagaggg tgtaaatgca gcaagtggta agtgcagaag gtgtaagttc agtggatgta    43920
ggtgcagaag gtataggtgc aacaggttgt aggtgcagtg gatggcagta cagagggtgt    43980
aggtgcagtg gggacccaat cattcagcac ctctatagaa gtaatgggat gggatacatt    44040
ttgaagatag agcagacagt atttgctgac tagatatgga atttggcagg ggtaggggga    44100
gaaggcagag tccagagtga caccaaaggt ctctggccag cactggaaag acacagatgc    44160
cattatctga aatggtaaag attttggaag gagcaaatct gagctaacct caggagttta    44220
gctgggggca tatttagctt gaggtgacca tcagatttcc aactggagaa gtctaatatt    44280
ctgtgcacat acaagcaaac agccacatca atatgcacct agagttttgg taacaggttt    44340
tggctgagaa gaaaatttga gcatcatcaa catatacagg tgtttgaggc cacaaaacaa    44400
gaggagatca actaagaagt taagacagtt gacagaagca gacacagcag agagaagagg    44460
tcctacagat aagactcagc aggaacaatc agcaagtaga agtatcatgg ggtgtccaca    44520
gccaaagtga tcaaccatgt caaataatag tggaccactg aattcagcaa tgtgggagcc    44580
actggtgaac ttcggaagaa ctgtttagtg gcatgatgag gatacatcaa gagcaatggg    44640
ttcaagagaa aatggaagga gaggaggcaa agacaatgaa aataaatgcc gtcaagagtt    44700
tcactataat agggagccaa aaaaatagag tgccttgagg tgggcacgaa tcaggagagt    44760
tggttttgtt ttttcaagat gggatatact ctaacgtatc tgtatgctgt ggtggacaat    44820
gaactgagag aggaaaagtt gttaacacag aagaaagaca attgcagaaa aattctgtcc    44880
cctagcccct tttattacac agcaggtagt gaatacacac agtgttctga gcttagcttt    44940
ctgtactaaa catggaaatt aatctacttc attctaggta gatctgcctc gtactttttt    45000 aattttttaaa aaattatatt aatttttttt ttttttttt ggtagagata gggtctcact    45060
atgttgcatg ttgcccaggc tggtctgaaa attccagact caagcgaacc tcctgcctca    45120
agcctcccaa agtgcttgga ttggccaggc atggtgggtt actcctgtaa tcccagcact    45180
ttgggaggtc aagcccggtg gatcacctga ggtcaggaga tcaagaccag cctggccaac    45240
acggtgaaac tctgtctcta ctaaaaatac aaaaattagc cagtgtggtg gcgggcgcct    45300
gtaatcccag ctactcagga ggctgaggcg ggagaatcac ttgaacctgg gaggtatagg    45360
ttgcagtcag ccgagatcac accactgcac tccagcctgg gtgacagagt gagactccat    45420
ctcaaaaaaa aaaaaaaaac acaaagtgct ggggttacag gcatgagcta ccatgcccag    45480
ctgccgtata tatttcacag tgttccattc tgtgaaagta ccataggcag taagccagat    45540
atctatgttt agcttcccaa gttagcgttt aaggaaagtt gctaaattag tggctgagtg    45600
acacttaaaa agttttcaa tgatgaaaaa tttcaaacat atgcaaaaaa gagaatagta    45660
caatgagcct ccatgtaccc atgattcaga ttcaactatt gccacacctg tttaacctag    45720
cctcctattt tttctttttt gctcaactat tttaaggtga atcccagaca tcacgcaatt    45780
ccatttctga atattctgaa tacttcacta agcatcttta aaatacgga cattttctta    45840 tgtatttcac caccatactt aaaaattaga ctgagttcag atgtgtgggac ctcacatctg    45900 taatcccaac actttgggag actgaggcag gaggatccaa tgagcccaga gttcaagacc    45960
agcctggaca acatggagaa acctcccacc cccgtctcta caaaagatac caaaattagc    46020
caggcatggt ggcacgtgcc tgtagtccca gctacttggg aggctgaggt gggaggttca    46080
```

```
cttgagccca ggagtctgag gctgcagtga gccgagatct agccactgca ctccaggctg    46140
ggtgacagac agactctgtc tcaaaaaaca aacaaacaaa caaacaaaca aacaaacaaa    46200
gtaaactaag actaagcccc ttggtttcat ctaatattcc taatactttc atattcaaat    46260
tatctccaaa aagatttttt taattggttt gtttttattca gactctgaat attattcaga    46320
agttgttctt ttaatgtaga gcaggttcct tcctcctcaa cttttttattt catgccgcag    46380 gcagggactg ttttttaatt gttctatttc ctccaaggca ggtatcagct tttgattaca    46440
taactatacg tctaaatata tctttatgtt gtcttcacag ttgattgaca ctttggttga    46500
atatgtactt ctaggttgaa aaacaatttc tggcaggagg caggggacac tgaactatta    46560
aaaaggaaga cccaaggcca ggcacagtgg ctcacgccta caagtccagc actttgggag    46620 gccaagggg tggatcactt gaggtcagga gtttgagacg aggctggcca acatggtgaa     46680
accccgtctc tgctaaaaat acaaaaatta gctgggcatg atggcctgta gtcccagcta    46740
ctagggaagc tgaagcagga gaatcgcttc agcctgggag gtggaggttg cagtgagcga    46800
gatcatgcca ctccactcca gcctgagtga cagaggaaga ttccatctca aaaaaaaaaa    46860 aaaagaaag aaagaaaaag aaagaaacaa aaacaatttc cctcagaatt ctgaaagtac     46920
tgctccattt tcgcatccag gaatgctatt ggatagcctg gtgcttttcg aattgctcaa    46980
catttgtata ttatttttt acatttctgg aagctttaga atcctctttt atccttggta     47040
atctgaaatt tcatgatggt gtgggcattt tgcattaact atgtcagaca ccttttaatc    47100
cagataccaa cgtccttcag tctgaagtct ttcctgtatt gtttcttttt tctttccgag    47160
acaggttctc actctgtcac tcatgctgga atgcagtggt gcaatcacag ctcactgcag    47220
tcttgacctc cagggctcaa gcaatcctcc tgcctcagcc tcccgagtag ctaagactac    47280
aggagtgtgc catcatgcct gcataatcta aaaaaaattt ttgtagaggt ggcatccccac   47340 tatgttgctc aggctggtct tgaacttctt ggccctacta gcattatagg catgaactac    47400
tgcacccagc ctgtattact tctttttctt tttcttttt ttttgagatg gagcctcgct     47460
gtgtcgccca ggctagagtg cagtggcaca atctcggctc actgcaacct ccacctccca    47520
ggttcaagga attctcctgc ctcagcctcc cgagtagctg ggactacagg tgcctgccac    47580
catgcccggc taatttttt tttatttta gtagagacgg ggtttcacca tcttggccag     47640
gctggtctcg aactcctgac cttgtgatcc acccacctcg gcctcccaaa gtgctgggat    47700
tacaggcatg agccaccacg cccggtcgta cttttttttt ttgagatgga gtcttgccct    47760
gttgcccagg ctgagtgca atagcgcgat ctcagctccg ccttggtgga gcctaccagg     47820
ttcaaatgat tctcctgcct cagcctccct agtagctggg ctttacaggt gccaccacc     47880 atgcccagct aattttgta tttttagtag ggacaaggtt tcaccacgtt ggccaggctg     47940
gtctcgaact gctgacctca tgatctgccc acctcagcct cccaaagtgt tgggattaca    48000
ggtgtgagcc actgcaccca gacctccgcc tgtattattt cttgatcatg tcatcctctt    48060 tatttctgt tctcttttg gaactcctat tagcaagatt ttagatggat ggctccacca      48120
catcttttat cttttctctc atatttactg ttctttatct acttgtcctt tctgaaatat    48180
ttcttaactc tttcgataat catagtttta attttctctt tccctgataa ttccttttg     48240 aggcatcctg tcctgtttta taatgaat gcaatatctt cacatatctc acagagcagt      48300
tggtgcttat gtgaagtttt actctatttc ttcagctagc tgttttttt tttaaggaaa     48360 atttgtatta ttttcattat tttatgtac agaaaactca acagtataca tttaacccag     48420
tttagtggca agttctttag cctttgcctt ttcgagcttg gcaatgcaag ccacagactt    48480
```

```
gggacccaag atattgcctc cccagtgaca gcagatctca tcgtatctgt cattgtcatt    48540
ggtcctgata ccttccacca gcttagccaa agcgcctttg tcttccaagt tcacctgtgt    48600
gaaggcgaca gtggtgcagg tcttcctgtg gactagacgg cccagtcttg ccttcccctt    48660
gataatgcag taagggactc ccattttaca acacagggca ggcaagaaga caaccagctc    48720
gatggaatcc acatcgtgtg caatcaccac cagctgagct ttcttgttct ccaccaaggt    48780
ggtgatggtg ttaactcctg ctcgaagggc aggtggtctc ttagtgggga cgcccccttt    48840
gccagcagct ttcttctcag cctgggccaa cagcctctgc ttcttctctt gctttgtctc    48900
tggtctgtat ttgtgggcca gcttaagcag ttgagtaact gtttggcagt tcagggcctg    48960
ggtgaactgg ttaatagcag gaggcacttt cagctgctta tagaggatgg ctctctgctg    49020
ctgcaacctg acatagcggg ccatttcaca aagtaggtga gttctctttt gggctggatg    49080
tcctgtccaa taccaaaatt cttacgcctt ttctcaaaca gggaattcac cactttcttg    49140
gcctcctgct tcttcacaac agcaggggcc ggggccacct tcttcccctt ggccttcttt    49200
cctttcagcg tcttgggcag tgggaggcca gttagctgtt ttttaacttt ttctcatttt    49260
taatcttcat attagaagct ttcctcactt ttctaatgat ccttggtagt ctgctctttt    49320
tgtttaattt taaaactttt tattagggaa aattttcaac acacacaaaa gaaaaagaa     49380 tagaacaatg agcttcctat gtgctgaacc cctggcttca atcattagca ctattttttt    49440
aacccatttg cctcccctcc atacacatac ctctccaaag tttggaattt tgtttgtttg    49500 ggttttatt ttgtctgctc ttttttttt ttttttttt taacagttca gcactaatca     49560
ggaattctgt ggacagggtt gagtcttgct tgctggaaga catcacttgt gggtgattca    49620
ccagggaggc aagtcttttt cctagatgac cccaacatca gtatgagagg tcttttttcc    49680
agggtcattc agtttcttca gaaaataact aagtcttggg cctggacagc cagcatctga    49740
atgcaaatgt gtgaacagga aggggcctg caggcccta tgtaaactca cggtctacca     49800
ccttgtctca caatggctgt gtaccacatc tgatgtccca gttgctaaca tgctctaagg    49860
ctggtggggt gagtcatctc tcttcctctg ggtattcccc taaacgtata cttggctttc    49920
tccacacgga agtatgagaa aggatactac actctccatc ttatcttcta aaagtagggg    49980
gataagagat actgcctaga gttcataaag aagaaataaa ggtttaactg taaattacaa    50040
agataactaa aagaaaaact aaaacaaagg aaatcaatat gctaggcgga atcagaaaag    50100
aaagagggag gccaggtgtg gtggctcagg cctgttatcc tagcactttg ggaggctgag    50160
gcatgctgat cacttgagct caggagttcg aagccagccc aagcaacatg gtgaaaccct    50220
gtctctacaa aaaacacaa aaattagctg ggtgtggtca tgcacgccta agtcccagct     50280
acttgggagg ctgaggtggg aggatcacct gagcccagga ggttgaggcc acaatgagcc    50340
atgactgtgc cactgcattc cagcctgggt aacagagcaa gaccctctct ttctctctca    50400
aaataaaaaa aaaaagaaa aaaaaagga aggaaaaaaa gaaagagggg agaattgaga     50460
caaactctca tctatcacag caaaaagaa agaaaaatca actttgttta tatctggcgt     50520
tcataaatca agaaatagca atataagcgt tttacttagg gatatgaagg tcaccaccag    50580
aagaatgtga ttgcctgagg agcatgctgg gattggagga gtgggcaag ggtctcctgt      50640 ttttcattat gagcctgtat ccaaaaagaa aaaagtgtgt ggattttttt gatacaattt    50700
tttcttttaa ttaaaaaaaa gcatatcaga gaatcaggga attcttcaat gttcccatta    50760
ttcttaggct aaagacctaa tttttttttt tttttttttt tttgagaca gggtctgtct    50820
```

```
ctgtcactca ggctggagca cactggtaca atcagggctc actgtcaccc caatcaacct   50880
tctggtcgac cttccaggct gaagtgatcc tactgctcag cctccttagt tgctgggact   50940
acaggcacat gccacaacac ccagctaatt tttgtatttt tttgcagaga cggggtctcg   51000
ctatgttgcc caggctagtc tctgacagag caggagcacc gtcatctcag acaaacactg   51060
ccactttaag ttccagctcc cttttttaaaa ctcctgggct caagagatcc tcccatctca   51120
gccttccaag cactgggatt acaggcatga gccactgtgc tcagccaaga cctaaatgaa   51180
aattccttaa acagctggta agtctcttta aaaccaatt aaaaaaaaaa aaaagctttt   51240
ctgacaatta tgaacacatg ttcaatctgt agcagaccaa ttcaaagatt cactctggca   51300
gggacatttt gtaagataat ggttagagga cactgtgaga ttcaatagaa aaataacctg   51360
cacagttaaa ggttacgaga ctcctgatgg atagtctgct gctgggttgg atgactggct   51420
tcccagaaca tgttttaatc ctgttaaaat ttattagaaa attgcttcgg tgttttgtt    51480
tttgtttttt tacaggaatg ctaatttctt cccagaagga gactgtaaat tacctcatga   51540
aaaaaggttt tgtcacagac ctggcttggg gcaatttgtt cttttataag tctctacaaa   51600
tcctacctag accggctctg tccaatagaa cattcttcat gatggaaatg ttctatatct   51660
ttgctgttca acgaagaagc cactagccat atggctactg agcacttgaa ctgtggctaa   51720
tcaagctatg caactccagt tttaattta ttaaatttca agtgaaattt aaatagcaac   51780
gtatggctag cagccactgt gcaagacggt gtggatctaa agcgccgtgg ctcccagctg   51840
cttcttgccc caagccctcc tcctctctct gcattccagc cactctggcc cacttttct    51900
ccctaaaaca tgctgcctcc tgccacagac actttgcacg tgtggtatcc tctttctgga   51960
atgttcttcc ctcacctact ccccagcctc ttcatctggt acatgactac ttttccttca   52020
ctaattacga ttatctcgtg cgcttatttg ctcacttgtt tatggttaat ctttatgcct   52080
ctccaccatc atcaacccac ccaactctgg agcctgaata cacatcacat ttgggcaaga   52140
accctgccca ccctgcccat ctctgtactc ccaccaccta gacagaacac acttggctct   52200
cagtgagcat ttggctaata tctaaaaggt aagtgacatg tcacaatgtt gttatctctc   52260
tcagagactc ccaatttcta tctgtagacc cattcttgct actgtaatgt tgccccacat   52320
ttccaacaga ctgtgagcat ttctacttaa ataccttct gtctacacat taaataatgt    52380
tatctccagt catcagatta acattcagaa agcttggctc tacttattgt catacaactc   52440
caaacaaaga aaccttcaaa gacatctaag agaaaaatca attttaagga aacactgaac   52500
acactataca cgctgcaagg ttcttaggcc ctttgcacac caatataaaa agaaagcaaa   52560
cagaaatgtt tctgcaaaga tacaagcgag aaagttcaaa cttaccacaa gttcaaaaat   52620
gtccatgaag acagaatgtc ccttcggtgt tttctcattc aggctggcag gagaccagat   52680
ccaatagaag taagtgccat ctgaagacag gtgcacagtg ctcatggtgc tgccaatggg   52740
gaggtgattg gctggcattg gcaccacctg gcacacctgg gcatgaaagg gaggaaatct   52800
ccattagagc cacatataaa ttctgattaa tcctatcagc tcatcattaa tgccattatg   52860
cccaagatga gaattcacta ggctttctgg tcaaaataaa atggatattt atctctaata   52920
ataacataca caaattacat ggcaaaaata taaagttca tacaatgggc aatagaataa    52980
atatgaacag ccatgcaaca gatgaaaagg ttcttgggat caattcaaat tacttttaa    53040
taggaaaaag tatttactaa acactttgaa tctgttatgc atatgtgttg tatctaacac   53100
ttattaaaaa caaagtttta gagaagcaac acttttctgaa atttctttag taaatgaatt   53160
tatgataatt ttatttaaag gacaagaact gtgtcttatt cacctctata tctccagtac   53220
```

```
ctaacggaaa gcctaactca aagttattta atgaatatga aaagaaggaa aaaagagaca   53280
gcaaaagaaa gccaagagga aaagctgaga agagggagaa ggagaaacaa agtaaaaaat   53340
ataaaggccc atgacagatc ctaacttagc atatgagggc ttactgaaat tcaccaagtc   53400
catcaggagg aaaagacaaa caccaattct gtatattaaa catgaaggca tgtgtttcta   53460
atactaaaca tccttctgtt tcagcataat gaataagctt tgcatcattt cacattaaat   53520
gtgtagctac atactaattt ttactgccaa agacaggcac ttaaaatgac tgaacattag   53580
aaccacaaaa acctgctggc taggtttaaa aaaaaatcc agaaatagaa gagctgagaa    53640
actcaaaata aaataatta gagaaagtca gatgccttca gagaacagtg agaacaatgt    53700
tcaatttccc attactttgg gagggggcac tagttttccc aaggcgatct ctgacccctc    53760
aattgatttc acatgaactt ttttccagac ctgttttgtc tagctcaaaa gtaaaaactc    53820
atttagttga tgtaaccata ctttgaacct acagtgccag gaagactaga aagttgacag   53880
ctactaattg gcctgtgcta tccccaaagt gctccattgc aatgcacata tctagtttgt   53940
gacctacagc cctgctttct tggacagtgt caaagtttct gcaacaacac tgaggaacct   54000
ggcactactt caaatgtaaa tcatgttttg agatttaaca tctgtttaac taccagtctt   54060
ataacttcta tttcaaatga gtatgagaca ttctcatctg tctgcacttg tgacaagaaa   54120
ttaggttaat tgggcatcta tttgttaatt tgttcatttt attcatccaa caattattga   54180
gcacctacta tgtgctctgg agatgacagt ggtgaacaag actcagtccc tgttctctag   54240
gacaggcagt tgagtgacaa acaagaagaa atgtaacatt acacttaatt tctagatgtg   54300
actactctta gagcactcac tccacagacg ccaactctaa tcatttaatc caactttgtt   54360
tgaaaggcag aaagttgcag tgtaaagagt tcaaagtact gggcagagaa ccaaaggttc   54420
aagttctggt gccgctacta ttggctgtat ggccttaggc aagttactta acctctctga   54480
gctgtattct tacactcaac aataaacact tgctgaatgc ttactaggtg cctagcctca   54540
gtttccttat ctgtaagata aacctacata gtaatgcctc acaggtagga agaggaagtg   54600
tatgttaatt gcctaggcca aggcctagca cataggagat gctgaggaat ggtagttacc   54660
atcattgtta ttattatcag tcaaatgtct ggcagtgtgt tatgttctaa ggatacacag   54720
atgagtagga cagggtccat acctaaaggt gtgcatggtc agtgaagtca gacagaaaag   54780
caggtaactg cagtataata cagcaagtgc catggcagag tgcttacgag agcactaaag   54840
ccaagctctc aatccctagc acacaatgat tttactctac actcatttca aagctccctt    54900
tcccacagag aggctgttta gaacaaattg aataaggaaa tgatgccttc ccaaaataga   54960
tctggttcaa aaaagcaaa aaaaaaaca aaacaaaac aaaaaaaaaa aaccagctag     55020
tatttatacc atctttgact gtctagaatt ttttcttaat tataaaaaaa agtttgttgt   55080
aggctgcaga aacttagaga acacattcac tcagttcata tgggaaaagt ctaagacatt   55140
aaataaaaaa cagaatgccc aaactataac aattaaaagg atgccactct gggaggaaaa   55200
tatatcaact gtattattat tacttctgat gatataggaa ctttctttat tgcctctaaa   55260
atatgtttta aaaatgcctt ggttttctgt ttacctgaag ggtgttctgg tcaatgacct   55320
ggaaaaggga gtgaggttta ttatcgaaag agacaggccg gtggagaaga ctgccgctgc   55380
caaaagccac ccatcctggt tccaactcct cgttccggca gtacacaaaa cctctgtgga   55440
atgaaatgga gcacaggctg aatcacctgg ctatgtcaga aaccccacac aagctacaac   55500
agacacaaac aacattttcg acctaatttt aaaaatgag taagtatgta aaacatctga    55560
```

```
aggaaagtga atgtattaca ttaacttcag gactgccaaa ctatagcaaa tattgacttt    55620
ccacaataac ttagagggga gaaaaatttg ggggaaaaga tctaaatgta tacaaggctt    55680
tcaaactgta gtttcttttg gcagcagttt atagatctta tatcccaact gaaaatcact    55740
tgctaatcca atgtcaaacc caagttcaaa gagacttaag tagaaaaatg tccacttatt    55800
aacatggaga agtcactgat attgttacaa aaatactgat catggaggac tttctggctg    55860
gaaacaatga tcttggggct accaaactct tctgggccaa acaaggcta aaatgcatta    55920 acagaacaag atggggaaag gtggcaataa gagaagattg gaattatttg aattagttca    55980
gacttgttat ttagttacta gtctatgggg agctggaatc tacccacagt gtcttcttca    56040
gagatttatg taaggaggat aatgttctag cccaatcatt caggaagttc catgcaactg    56100
acctgagagt accatgtaat ccagatccca atttgcttac tcctcttcca actgagttag    56160
tagtatacag gtaaagacca tctgccgtga gacagcgtcc caagtcagca tctgaaatcg    56220 tttttcaca ggtaaattat atatatgttt tttctattga aattataaac atgcttttc    56280 taatgaaaaa gccattagga ggttgagtga aagattactt ctcacttcta aaataagagc    56340
ttcaatgtga ctttcaggga agatggcttg agcccccaaa tcaaacatcc aaaatgcatg    56400
tggaccagag accaagatat ggtcagacag ttaccagcag gggaatgtgg tttagcccgc    56460
caaatgtttt tctttctttt ttttgaaaa gcttgtactt agtcaagtca ttcctaattc    56520
taatttgaaa tgactaatca taattctaat ttgaaatgac taagaataca gtacaacact    56580
tttattagta attgcatagt aagagaggca tgagctctta tgagctcagt aagtgaccct    56640
gaacctcttt gaacgtcagt ttcttcatct gtaagatgag gataataata tgtacctcaa    56700
gggttacagt gatggccaga tgagataata gaggtaaata catctatact gctctctgat    56760
gcaaagctag tattccataa atggcaaatg aaattgtgtt aatatactaa tgatatacat    56820
taaactaaaa tctgcctctg tagattttcc attcagagat cctaatttta gtctctggag    56880
ggacaaagca caaaagtttc atatcttttc tattttaaaa cagcaatatg tttcccctta    56940
gctctgtctt cctcaatcta aaacagtatc tctctatatg atggtaattg gtttagtaac    57000
tcaaattcca aagaatttgc cttaaaatag agcttatgga taaaactttc attgtttatt    57060
ttcataatca ttctgctcac tatgtttaag tggagtcttt ccacctgaag catgccatat    57120
tagctggagg aaatgcaatg tcacaccgtc aaattagtac taaaaatgct gttagcttaa    57180
aaattcagtc tactaatctg agacaactgg gacctgtacc tattggttcc tcaatgaaaa    57240
aatttgttaa agtgggtaac catttttaaa acattaattt cacaccttaa acattttaat    57300
ttaaaactta tagattacat ttattcatca attttttagat taaggcccaa ggccttctgg    57360
gtatggctct gtcgaggggc agaagtgaaa aggacaaaca aaacaagatt ggccaggaat    57420
ggatacttgt tgaagctgag tgatgagtac acagggctta ttatagtatt ctctcaacat    57480
cagtcaaatg tggaatgttt caatattaaa agttacactg tggccaggca cagtggctca    57540
tgcctgtaat cccaacactt tgggaggccg aggcgggcag atcacctgag gtcaggagtt    57600
caagaccagc ctggccaaca tggtgaaacc ccatctctac taaaaataca aaaattagcc    57660
gggcatggtg gtgggcactt gtaatcccag ctactaggga ggctgaggca ggagaattgc    57720
ttgaacctgg gaggcagagg ttgcagtgag ccaagatcgc gccactgcac tgtagcctag    57780
gcgacaagag cgaagctctg tctcaaaaaa aaaaaagat tacataaatt agtctaaaaa    57840
ctatataaga aaacaggcc aggcgccgtg gctcgcacct acaatcctgg cactttggga    57900
ggctgaggtg gtgggaggat ggcttgagct taggagttaa agaccagctt gggcaacaaa    57960
```

```
gcgagatccc cgtctctaca taaataaata aataaataaa taaataaata aagtaattat   58020
ccaggcatgt tagtgcatgc ctgtggtccc agctactcag gtggctacgg tggaaggact   58080
gcttgagcct gggaggtcga ggctgcagtt gtgattgcac cactgcactc caacttgggc   58140
aacagagcga gaccccatct caaaaaaaaa aaaaaagaa aagaaaaaga aaaagagag     58200
agagaaaaaa agaaaaccat ttctccctag atgcaaaacc aaaggttcag gaaaatgaaa   58260
gcaaacagat cagcttaatg ccatcctcct cagtgagaaa ctaccccaag ggagatacca   58320
aatggagttt tttaaaagga gagaatcaag aaagaagttt tagttctata ttaagaagta   58380
agttggagcc gataatgtct gagaacttct tgggtactgc aggcattctc cctctcctgt   58440
tgactctagt tgaattagtg aaggaaataa atcacattta aaagccttgc cgcttcttct   58500
ccacacactc tcatgcctgt ttagaagaaa tggtagacca tggaaaggta caagccctgg   58560
gctgagagat gcgaggggc ctgccgctta gattctcctc cgtgctggtg gggttgccca   58620
ggaaggctgc cccatggaaa gtgggaaatg aaagggaggg aggaacagac tctctgtccc   58680
acacctgatg aacaccagtt tcttagagac tcacttcgtg gagttttcct aaaacattca   58740
acttcttaat ggcaactatt tcctgggttt ttttaaaatt cctatttcat cagttatgta   58800
agatttaatg ataaaatcac aataataagt accagttaca attaacaaac tggtttggga   58860
gcaagcctac ctcttggcaa gcctgcaatt ccgctggtgg gagcagagct gaccagccct   58920
gtgggttcag tgggccacgg cagggcagca gcctagacat tttactgagt gaatggagag   58980
gtctatccca tctgccaagt cagttaagag agcttctgcc attttttgttg agataatgta   59040
agaaactgac atgtaatact gtaaagctct gtaaaaacat tttaacctag cttatttgtt   59100
taagtagat gttaacaatt catgctccct tgaacctctt cattttttgc ttttaggaca    59160
ggagggctca ttaacacaca cacaataaat tactaaagga aatattatca agcagtaaga   59220
cctgatattc tattagcaga caaaaaaatt caacttaagg ctatcatacc caaactcaaa   59280
tatccagcag ccaatttaag taattcatgg ctccttggca agagtgtatg gatgatatct   59340
tttccttgtg ataataaaac ctatccattt tcttacctca ccagtatcag cttttatacg   59400
tttactgata aagcagacaa tgaacatact gaatagaaat ctggagctct taattaaaag   59460
gaacatacag agttatagcc atatcatttg ctacagtgat ctaaaacctc tttatttaca   59520
tcttactatt aatcacagga caaaactttt tacattacct ttattttcag aactggagcc   59580
agtgttgcta tccggcgcag gcaacatgtc ttcataaccc catgatacta tgtgtttgcc   59640
cccaagcaaa caggagggag atccaggccc cccttccaaa agcaacagcc tatatggggg   59700
agaaagaaaa tcacaaagac actgagacaa tccatttcag caagaagtat acctgctacc   59760
ccaaagagta gaaaccaaaa ttttaaaact aagatgtata atattttata caaatattat   59820
tcaaaaaaga catttatagt attttttattt tttatttatg tttcttttttt ttttgagaca  59880
gagtctcgct ctgtcaccca ggctggagtg cagtggtgcg atctcagctg actgaaacct   59940
ccacctcctg ggttcaagcg attctcctgc ctcagcctcc agagtagatg ggaccacagt   60000
cacctgccac aatgcccggc taattttttt tttttttttt ttttttgag acagagtctc    60060
gctctgtcac tcaggctgga gtgcagtggc gtgatctcgg ttcactgcaa gctccacctc   60120
ccaggttcat gccattctcc tgcctcggcc tcccaaacag ctgggactac aggggctcac   60180
catcacgccc ggctaatttt ttggtatttt tagtagagat ggggttttgc catgttggca   60240
ggctggtttt gaactcctga cctcaagtga tcctcccgcc ttggcctccc aaagtgctgt   60300
```

```
gatcacacgc atgagccatc acgccctgct acaatatttt taaattaaaa aattacgaag    60360
ctatgtttat aaaaattata tctgtgtgta aatatacta ttttatgtgt attttttgtgt    60420 gtgacagaga gacagagtgg gttatgaatt aggaagcata tgtaccaaaa tgttaggagt    60480
agttatcttt gggtaatgag attatgaatg attttcactt tcttcattat accttaatat    60540
attatcatct caaatttgc atcagaattc attataagct attgcatctt tattttttga    60600
aacagagtct cgccctgtca cctaggctgg agtgcagtgg tgtgatctcg acttactgta    60660
acctctgctt cctagcctca agcaatcctc ctgcttcagc ctccctagta gctgggacca    60720
caggcacgca ccaccacact catgagttat tatgccccac cagctattgc attttttaaag    60780 acatagaact aaaaaataat gaaaaataac atgctctaaa aactttccaa aaaggaaaga    60840
taaaaaataa aattcttaag aaggtaaata tgagtctata cttattttaa aatgaatcac    60900
taattgataa gagtttagca atctacttaa taaaggaagc atttggcaca aatctgccta    60960
gtttggaagg agggtaagga tacaaagtga caacttacct atatagcaca tcagctacag    61020
gcagggaccc tagatccgtc tgtttctgta atagatggac tgtgtggacg aaagttttca    61080
atgatcccct aaaataaaa ggaaggaaca gtaaatcatc aaaatttaaa atcaaataat    61140
ttaggtcatt aatgctaatt taattaacca catggaaaag ttccaaaatg tgtctctctg    61200
cttctgctgg tcagatgatg tgttgtaaaa aaaatacttg attattaact atcaccattg    61260
gctcatacac aaagatacaa tgaaaacaac accatgccaa ttatgaagaa gttctccttg    61320
catttggaaa agtaaacaat tttcccctgg cataaaagtt caaaacataa ggctcgagca    61380
caaagaactt gtggctatta tgcttggtta ctatatcacc aagtcaccct ctggaggatc    61440
ataaagtcta acagtatttc caggcttgat tttaaaatct ttgctaagtt cattcatttg    61500
gaaaaacagc taactaaact ccatcacatt aaatatgacc aaaaagaata tattcaaata    61560
aataatgctc tgtgctgaga gatgctcctt ctgtatccct ctgactgcac atagttgtaa    61620
tacttgcaac agggctcacc gctacctgaa ttccttgtgg tttccaagac tcaaggctct    61680
gggaagtctg tcatatggtc agcaagatct aaaagaaggt gcttttaaga tgcacaagac    61740
ttacctggcc gcatcccaag tacaaatcac cacaagaaca cttcctgaac taaatgatcg    61800
cctgtatctg acgggctgac ttcgacttgc tgccttagtc tcttagccaa ggctttaatt    61860
gctgggtatc atatgcctaa acgccaatag aaatggaata cctaacgcag aaccaagtag    61920
gcctagagtc ttcctgttaa ttgccccttt cactatctct agtttcagag aataaaaaca    61980
aaagaatagc attaatagaa ggcaaggagg cagcagatag agtataaaaa caagttggaa    62040
tcgggacaca tgggttctga aacctggctc tgccactcat cagctgcaca atctcagtcc    62100
tgtcacctaa ctcctatgga ttttgcttc ttcatctgcc caacagggac actttcctgg    62160
ggaacagtga ggtttaaaat aaagaagcaa aacctttaac atttagaaag tttagaacta    62220
ttaaccaact ctaaggaatt attacctgcc agattcaatc agatttgttt ttttaaaga    62280 gacagggtct ggctgggtgc agtggctcac acctgtaatc ccagcacttt gggaggctga    62340
ggcaggagga ttgcttgaac acaggagttc aaggttgcag tgagctatga tcacaccact    62400
gcactccagc ctaggcaacg gaatgagacc atgtcttaaa aaaaaaaaa aaaaaaaaa    62460 gagagacagg gtctcattat gttgcctaga ctggtctcga actcctggcc tcaagagatg    62520
ctcctgcttt agcctcccaa agtgctgaaa ttatagatgt gagccaccat atccagcctt    62580
caatcagatt ttaagagtaa aatgtaaagt ccttccatgg ctcacaaacc cctatgtgat    62640
ctgggccctg ccaacttcat ctcctgcccc tctccttcta ctatcacgtt ccagaaaccc    62700
```

```
tgcccactgt gctgtccect cagatacccc aagcacaaga ataatgtcag ttttgtcact   62760
cgccactcca tttacgtgga actctctgcc actggctgct tctcatcatc cagggcccag   62820
ttcaagtgtc atctcttcag taaggccttc cctggcatct ccagctaatg ctgctctcca   62880
cctccacagt cattctctat caaaatatct ctctgtcttt tcctatagtg aatattcctc   62940
tctacaatga tctgttacct atatttgttg ctcactgtct gcctccctca ctcctatgta   63000
agctctgcaa ttttaggcac ggtctacctg ctctccactg tatccctacc accaagagaa   63060
tgccttccgt gcagtaagtg agcaataagg ttttgcagaa tgacttaccc tgagtccatt   63120
caaccgtaag ctctgtgagg taagaaacct agaatcacta tatccctaag accgggcaag   63180
attcctgtac atcagaaatg ttcaataaat gttagttggt tgaatgaata atcttcataa   63240
taattttggg aagggttac tttgtctttg agagcatcaa cccaaaaatt caataatatg   63300
ccactaataa ctttagtaag atgatctaac actgaaaagc acatgacttc tgaagtccag   63360
aacatgatat tggcaataaa atgtaggaac catgttaaaa aaaaaaaaac caagaagaa   63420 taaataaata aatacatcca tttcaacatt tctgctgaat gaaatttaga atgtccagca   63480
caggaagtaa gttcaataac tattttggt ataggctgaa tttgggtaca caataaaaat   63540
gtgagtttta tgaaccaaca attaataact taaactgttt gaaactaaag agttgataat   63600
tattcctaac atcctaaatc tgtctaaaga tagtactgtc taaaagcaca ttttctcaaa   63660
tggaatttgc acagtgataa cagatcttgg acttgaaatt gtctctgcat atgcagaaaa   63720
taaatcaatc caatataaag cctttacaag gaaacttgtt tcagtaccac acaatgactc   63780
tagaattaag cacatgtcag gattcacaaa ccacagtttt aggggatcta aaactaggct   63840
atgacagctt gctcagagca aagaaactta caataaacac tggtgccatt ttgccttaaa   63900 aaaaccettg agattcaatc atttgaaggt caactttgaa actatacaga gaaaaacagg   63960
gcaagaagac ttataactaa gaacttcata attatccaag aagaattctc ccacagatgt   64020
ttggctaaaa gaaagaagat cccaaccaag gaaaaaattc tacggaagac agacagaata   64080
ctgacactaa tctgtcaggc tgtggtccta actgttctct aggcaattag tctactggaa   64140
aacaaaggta gtgaaacttc tttctcacaa acagatgcca gtgatcatac gggtcaatgg   64200
gtagaagaat gtataaaatt cctagaaaag caactccagg ccgggcaggg tggctcatgc   64260
ctgtaatccc agcactctgg gaggccaagg ccggcagatt gcttcagctc aggagtttga   64320
gaccagcctg gcaacaagg ggaaaccccg tctctaccaa agatacaaaa aattagccag   64380
ccatggtggc aggtgcctgt agtcccagct actcgggagg ctgaggtggg aggatcacag   64440
tgagctgaga tcatgtcact gcacttcagc ctggtctttg agagcaagac cccatctcaa   64500
aaaaaaaaaa aaaaaaaaa aaaagagag gaataggcca ggcacagtgg ctcatgcctg   64560
tattccagta ctcttggagg ctgaggtggg cggatcactt gaggtcagga atttgagacc   64620
agtctggcca acatggtgaa accccatctc tactaaaaat acaaaaaat tagttgggca   64680 cctgtaatcc cagctacttg ggaggctgag gcaggagaat cacttgaatc cgggaggtgg   64740
aagttgtggt gagccaagat catgccactg cactccagcc tgggtgacag agtgagactc   64800
tgtctcaaaa aaagagaaa agaaaagaga aagagagaa aagcaaaag aaagcaact   64860 ccaagcatat ttcctattga tagtgggttg atgacttgca catgaagaac agcatacaat   64920 ttttttttt tttaaagaca aagtcttggt ctgttgccca ggttagggtg cagtggcgcc   64980
aacttggctc actgcaacca ctgcttcctg ggtttaaatg attgtcctgc ctaagcctcc   65040
```

```
aggtagctgg gattacaggc acccaccaca acgcccggct aattttttgta tttttagtag   65100
agacagggtt tcaccatgtt ggccagggca gtctagaact cctgacctca agtgatctgc   65160
ccacctcagc ctcccaaagt gctaggatta caagcgtgag ccaccacgtc cagccatgtg   65220
tactactatt aaatctagat atatactgag aaatcttcca attaaattga tcaaaacaag   65280
tattaggtcc aaaaatataa tttgtgacca attttgtgac tgagtccagg tgaataatag   65340
cccactagct tgctgatgta cttcttatag acaggtatga aaaattaata gctctataaa   65400
gttttgacca tcctcctagg agaagtagac ataacatcct ctgctaacta cttgatgtaa   65460
aacactaacc atctaaggga caattagata tgtcaaggga tgattctcca tttttctgctg  65520
gttaagatgt tatcatggta taccagaaac agaaaacatg aactttggtt ccaactcagg   65580
cacctggtgc caagtttggt gaaagcatct catgcactgt caaggctgtg aaattcaata   65640
ctgaaagcaa agaaggactt ctgaatgtta agacttctat caaatatact tggcctcttc   65700
ttcattcacc caacccaggt ggcagtagtc acaaggtcac caaatgatac attcgatttt   65760
ccttacctgg cacaagccaa agccaccagg gcagcagcag catttctttt ttgcttatgt   65820
gggatgtgtc ggcctgtgtc agaagtctcc tctagccaag agcacagcaa agtttcaatt   65880
ccattgagac agtcagcagg ctccttggtc aagctcaaag gctggcagtc acgaaggcag   65940
ttcaatagca cctcagcagt tatgttacag agagaggggg ctgttctact ctgggactga   66000
ataaggggga agaccagcag gagccccatc ctcgatgtga agggcgcttg ctcaggttgc   66060
tgcaacaagc cctggcgttt gagcagggcc aaagtttcct catcacctga actttccctt   66120
tcatgctgtt cttctaaggc cagctggcgc tgggcattcc acagtcctcg caaggcattc   66180
aggcggtatt ccagcagccg ggcataggca ttgctctgat tcccacaaac agagcgcaaa   66240
cgttctgcta attccgacgg gttcttggtc tcaaaggtta aaatctaagg aaaaagacga   66300
tggagaagtg ggtaaatatt actttcacca aagtcatcta aggaagaaaa tatgtttaat   66360
gatatcccaa aatagtcaac gccaaaaatt attttaatta caatcaaatg gaaaacgtat   66420
actgtaaagc cagctctttg ctgatggaat tgttcccctt ttggcttttc tgttaatgct   66480
tccatgaaaa ttgggattag acctaattga aagagcccaa atcataaaag aatatagtta   66540
agtgtgaaag tcagaaatta actccataat ttatttaga aaattgaagt ataaagccag   66600
gcgtggtggc tcacgcctgt aatcccaaca ctttgggagg ctgaggtggg tggatagctt   66660
gagcccagca gttggaaacc agcctgggca acatggtgaa accctctctc taccaaaaat   66720
acaaaaaata gccaggcttg gtggtgtgca cctgtcgttg cggctacttg ggagactgag   66780
gtgggaggat tgctaaagcc cgggaagtag aggctgcagt aagccatgat ggtgccctgc   66840
actacagcct gagtgacaga gcgagaccct gtctcaaaaa ataatactac aaaaaaaaag   66900
gaaaaaaatt gaagcataaa cctttagtaa atgatcttga gttataaatg ttgtttctag   66960
gacaggcgcg gtggctcacg cctgtaatcc cagcactttg gaaggcagag gcgggcagat   67020
catgaagtca ggagttcgag gccagcctgg ccaacatggt gaaacaccat ctctactaaa   67080
aatacaaaaa aaattagcca ggcgtggtgg cccacgcctg tagtcccagc tactcaggac   67140
cctgaggcag aagaattgct cgaacccggg aggtagaggt tgcagtgagc cgagatcgca   67200
ccactgaact ccagcctggg tgacagagtg agactctgtc ttaaaaaaaa aaagttaaag   67260
tttctaactc ctattaccag atagagtact agtaaaaatg gaaccaagtt ttatctctgt   67320
tcttcaaaac ctaatatata tatgtttaat aaatgatgga ttattcacgg ttctttggtt   67380
gtgaagcata ccccattctt ttttttttgag atggagtctt gctctcttgc ccaggctgga   67440
```

```
gtgcaatggc cgatctcagc tcactgcaac ctccacctcc caggttcaag caattctgcc   67500
tcagcctccc taatagctgg gattacaagg gtgtgccacc atgcccggct aattttttgta  67560 tttttagtag agacgaggtt tcgccacatt ggccaggctg gtcttgaact cctgacctca   67620
ggtgatctgc ccacctcggc ctcccaaagt gctgggatta caggcctgag ccactatgcc   67680
tggcagcata ccccattctt aatagtgtta acccattatt ttaatttgtg acatggtaga   67740
gatttatcca attcatatta gattgttttc ttgccaaaac attcaattat caggaggcct   67800
ccattttcag cagctgggga taataaaacc attatatctt ctatcagcta agaaaggaac   67860
cagctctcaa gatcaaacta aatctcaaga atcaaactaa atttacaatg caaagagttt   67920
atgcacataa atttgactag atcaaaacca acagactact gtaatcaaca aaggagggca   67980
ctctaggagc aagcacactg aaacagatta tcagacaata gaggtgcctg gttcacagta   68040
gaccagaaag tcagggtggg aagaggcctg ggacaaaagt aaagaaaatt ctgccaggtc   68100
tttggcactg acattaagaa aggtcatagt gcagtttatt tcccttacaa actggaaaaa   68160 tactcttttta tctcaaattt tgcctttaga aacttgttat taatatttta gcccaataaa  68220
ataacaagaa tttccaaaac aatgcaaacg ctgtaattgc cttgcttagc tacatatgca   68280
aatcactgaa ttgaactaaa aaaaaagttc acaatttaaa aacaacaaca caaaaccaaa   68340
acaaaagaag caagaagcta aagaaaaaca aagataagct gaattagaag ctactcaatt   68400
agcaaaggag aaagaactta taattagaca acaagtatta ctggcaaaga aagaaaaaga   68460
catccaaaaa aaaaaaacatt acaaagaaat ggtaagctag gtgggtgaca tacgcctata   68520
cttccagctg cttgggaggc tgaggcagga ctgcttgaac ccaggagttc gaggctgtag   68580
tggctatgat cgtgcctgtg aatagccact gcactccagc ctaagcaaca tagtaagacc   68640
ttgtctgcta aaaaaaaaaa aaagaagaa agaaaaagaa agaaaggcaa aaacttcgaa    68700
actcatctaa gatctggaat cacttttcca acaatgaggc agggtgggtt aaaatgatgg   68760
aagaaggcca ggtgtggtgg ctcatgcctg taatcctata actttgggag gccaaggtgg   68820
aaggactgcc tgaggccagg agttcaaggc tgcagtgagt tatgatggca ccagtgcact   68880
ccagcctggg tgacaggggg agaccctgtc tcaaaaaaga aaaaaaaaag aaatgatgca   68940
agtagaaaaa ctttgtaatc agcttgaact agaaagctta cagtagttga atgaaacaca   69000
tcatctacaa agaagtagg aatggctgct ctggaaaaac agaagaaata aatgaacaaa    69060
ttacgaagga gaaacaggaa ggtggggctc gtatgtaata agcatctaag aatgcagaga   69120
aataaactgg cagaggtgga aatggcagca acaactggta agaagatgat ctgcagctac   69180
aagttaaagc tatgaatctc ttccctgctg gtatgaattc aagatgggaa gttggtaagt   69240
tattgctaat tacatcaaca tacattcttc tactgatgtc aagacaacca ccaaaggtgt   69300
tactggcaaa gcaagagcc tccaaaaatt ggaccctcat caaaaagatg acaaacaaaa    69360
aaggcttttg ataaacttta aaagaacat tgcctcaagc agacaatgaa acaccttcag    69420
aatgatttta cagtccatgc acccacttca ccccttggag aacgaacaga agcttttga    69480 acaagctttg aaaacacacc cagtcaacac acctgaaaga tgagagaaaa cagcacaaac   69540
tgccagtacc tggcaggaca aagaaaggct gcatgaaaag atgcaaggaa cttgccaaga   69600
tggtaaaagc aaagaaagct gctcaagagc aagtgttggc tgggcgcggt ggctcatgcc   69660
tgttatccca gcacttaggg aggaggaggt gggaggatca cttgaggcca ggagttcaag   69720
accagcctag tagtgagacc ttgtctctaa aaataaataa ataaaataaa ataaataaaa   69780
```

-continued

```
agagcaaggg tcgaatgcag atagagttaa gaaatgactt aatctttatt gggtgtgtac   69840 tttatataata aaactgaaaa tactgtgaaa acaaaacaac aaattccaat tcaaaaaatt   69900
aactataagt atctcagtta actaatatga aaaatattca tagttttaaa aaaattcagt   69960
gccagcttat cagatctgat gtaatatcag gatgccataa aatttcaacc cacaacttag   70020
caaagaaaga aactattgat aaacacaact actttaagga atctaatggc attttgttga   70080
gagaagccaa tttccaaggg ttatgttctg tatgatttca tttctgtgac attctgggaa   70140
aaaaaaaaaa ctatggtaat ggagaataga tcaatggtta ccggggttta ggggtaaggg   70200
gaggtagggt ctgactacac agggatagta tgagggagtt ttttgggg ggttgaagga   70260 attgttccca gttgtggtgg tggttacatg aattaataac atgttaaaat tcatagaact   70320
acacacctcc caaaaaggc cagtttgact gtataacttt aaagattaaa taaaggaaa   70380 aaaattccaa ccagactata gttgtattca actagatatc actgggtaaa gatatattga   70440
aaataatatc attaaaaata aaaattagag gtatttttta ctgaggtgct tctttctttc   70500
tttctttctt ccttccttcc ttccttcctt ccttccttcc ttccttcctt ccttccttcc   70560
ttccttcctt ccttccttcc ttccttcctt tcttctttc tttctttctt tctttctttc   70620
tttctttctt tcttctttc tttctctct ctctttctt ctttttttta tttttttttt   70680
gacggggtct cactcaccca ggctggagta cagtggtgca atcttagctc actgagcct   70740 caagcttccc aggctcaggt ggtcaatcat cccacctcag cctcctgagt agctgggact   70800
agaggcatgt gccactatgc agctaattt ttgtatttt tgtagagatg ggggtctccc   70860
tacattgccc aggctagtct tgaactccag agctcaagcg atctgcttgc ctcagcctcc   70920
caaagtgcta agagtatagg catgatccac tgcgctcagc tacttactta gttttttaata   70980 caaccacatc aaacaaataa tgattgatta aatgtccttc accatcaagt aatataaaac   71040
tgtatttccc tacccttta tttagattca ccaaacacac attcccttt tatttttcag   71100 atggcagcag ataaaataac tcaagttcct taaaaaatga tcacatttca agggcaacca   71160
cctgccttga agctgttatc aaactcaaga aagtcatact gcctattttc atttgttttt   71220
tagtgctatt accccaaaa atcagtaacc agcctccact attacaatca ataaagatta   71280
ctgaaatatt tttcaatgat atgaaaaact gcaaaatttt aactttgatc atcttcccag   71340
tcataaacat ctaaacaaat aataaagttt ttggcacttt aaaaaagctt ttcagtattg   71400
ttatttcttc cacccaaaac aactcttta tataaaatac ctaccatgt actcaacata   71460 catttttatt tatggtacac caatcatcta cttatgttat atgaagcaac tactaaaaaa   71520
attcaatata gtctttatt gaactcaaat gatgaacaac tcagtaacat aaaacagggc   71580
tatttatttt tattattaaa catgagtact tctgaaatat gacatttcat ggtacataaa   71640
atgatgtgta tgacaaaatc tgttgctaac tccaaatatt aacttaatat agcttagaaa   71700
aatgacataa tatactctgc attttttctga ccattctatt tttacaagta ctccagttat   71760
atttagcatt caatttaaaa gacaagtgca ctgaaagaat ttgagttata atataattaa   71820
ccaaatatta tataacatac acacttaaat gactgttgtg tttattgatt tagcagtatc   71880
taaagcacac tatgctttca gaaatccatt aggctactca gcgttatcca tttcaggggc   71940
cccttatgaa aactcagaac tgtttgctat gccactgttt tttcagaatt ctaaagtttg   72000
aaggtcatgg cctaaaatca ttttataaaa agacatcata cctttggggtt tttgtaagtc   72060 agctatggca tatctattct ggtacttatg aatattaaat gatttgtctc agatcctcac   72120
ataaaaccac tgctcttgac caaaatgtca ttagaaatta atatttttct ctttaaaaaa   72180
```

```
gtggaaagct atttaaggaa aagggaatat ccctgtcatc cttaatcaga agtgttacta    72240
actgtacttt ggtgataatg ctaacgttac cctaattaag ggagtgactg ccaaagtaac    72300
tcacagcctt catgtatttt ttttaatcac acataacata tgtgttttgt tgccgttttt    72360 tttttttct tttgagacag gttgactcca gcagccttgc tctgtcaccc aggctgctgg     72420
agtgcagtgg aacgatcatg gctcactgca gcctgagcct ctcaagtagc tggaaccaca    72480
ggcctgcacc accacactcg gctaattttt tgtatagaca gggtctcgct atgttgccca    72540
ggctagtctc aaattcctgg gctcaagcaa tcctcctgcc tcggcctccc aaagtgatgg    72600
gattgcaggc atgagccacc gcacctggcc aacataagtg ttttaaact aaggaaacag     72660 tcattctgga aagtctaatt gaatgtgggt aaaatattct ttgctggcca aatctggctt    72720
tgaacaagac tacaatatct gatagaagaa cagagtggtc aggccagctg tgatggctca    72780
cgcctgtaat cccaacactt tgggaggttc aggtgatctt gaggccagga gtttgagacc    72840
agcctgagca acatggcaag acagtctcta caaaataaaa aataattagc tgggtgtggt    72900
ggcatgcacc tatagtccca gctacctaaa aggctgaggc aggaggattg cttaagccca    72960
ggagttcaag gctgcagtga ctatgattg caccactgca ttccaacctg agtgacagag      73020
tgagaccctg tctcaaaaac aaaaacaaaa acaaaaaaaa cagatgatca atcagatcat    73080
tttagccaat ttactaattt atttccattt ttttctggga aaatactgga caacagatac    73140
cagccagcca tgatgtgaaa tgtgaaatgc caacctgcat ttcaagtaag tgtaggagtg    73200
aggataggca tatagacgct tttgaagttg tagagaatat tatatataca tataaggaca    73260
ttaactagac taatcattag cataaactac tataatcctg taaggataaa catcgatttc    73320
catctacttt gctgttcaga atagcagaga gataattatt gaaagggtc aagtaagaag     73380 ctaaaatcat cttctctctt gtctatacaa atatatatac aaatatatat ttgagcatat    73440
ttctgaaaga aatagaaatt atatttctag gaatttgtcc taaagcaata ttctagaagt    73500
aagaaataca cagagatatt cattgcagta ttgtttatta tagtgggaaa ggtagaagca    73560
atctcaatgt ataaaaggga agtgttgggc caggcgcggt ggctcacgcc tgtaatccca    73620
gcactttggg aggccaaggt gggcagatca tgaggtcaag agttcgagac cagcctggtg    73680
aaaccccgtc tctactaaga atacaaaaat tagccgggtg tggtggcgca tgcctgtaat    73740
cccagctact cagaaggctg aggcaggaga actgcttgaa cccgggaggt ggaggttgca    73800
gtaagccaag atcgtgctac tgcattccag cctgggcgac agagcaaaac tccatctcgg    73860
ggaggagaaa aaaaggaagt gtttaattaa attataacat ctcaaaatga aatattaatg    73920
attttttatt tatattaaat aaaacattaa attaaattaa atcattaaat aaaaaattat    73980
taaaaccaca atagaaagca gtataaaaat tgcatatgcc ctctaattag gagtctgtaa    74040
aacacacttg ttcaattttg aaattagtgt ttgtgaaaat agaaacatgg atgttatttt    74100
ttctctgttt caaaaacaac agactaatga caagttacat tgttcataca gaagaaatgc    74160
ttagaacatc tgagtttcca aagacaaaaa aagaaaagc agtcataact agcactgata    74220 attttcaca cgcaaacgct atctttcaat aactggtagt caaacaaatg gtgacacaag     74280
taccacagga aatgctttcc ttacatcagt tcactagtcc catctgttgt actttggcag    74340
cagttaattt caaataatgt agagctgatt atgttcctgg ttaggacgga agacaggatg    74400
gtaaatggga aagaccctgc agatattggg aactatcaat gaacaataaa accttttcaat   74460 ttccaaaagg aaatgatgtt taaaactcag ggtcacttgg gctctaagca gatgaattat    74520
```

```
attactatac tccccggtat gggacattaa ccaattcaat tcattatatg aacctgtcag    74580
cataaaagga atttatactt ggattatttc aaaggagatc gactggctag acttgcaacc    74640
tcaatgtaaa actatttatt tatttattta tttatttatt tatttattta tttattttga    74700
gacagggtct tgccctgtca tccaggctgg agtgcagtgg tgcaatctca gcttactgca    74760
acctccacca cctgggctca agtgatcctc ccacctcagc ctcctgggta gctgggacta    74820
caggcattca ccactatgcc tagctaattt aaacatttttt tagaggtggg gtttcaccat    74880
gttgtctagg ctgatctcaa actcctgggg ttcaagtgat cctcctgcct cagcctccca    74940
aagtgctggg attacaggca tgagccagta tgccctgcca atacaaaact tttaagtaaa    75000
ggcagaatac tgaaaccctc tcaaatgtta gaatagatgc ttaaacccttt ctacagattt    75060 tttttctacc atttttcaca taatgaagac agcaatcata gccaaattga attgcatgtt    75120
gcaatcaaca aagacttgaa aagctctcat gcgagccaag taagtacatc atgatgggag    75180
ggtggaattc tctcttacta aagcccaaat ccagggtgga tcacttatca attaaattag    75240
accctgaagc tgcacgacct tatccaactt ggaaatatgt gtttattcaa actcactttt    75300
caacatctct tatttgtaaa aagggtctta aacctaactg agaacgagga tattaaattt    75360
ccacacttta attcatgagt tttagcctct aactggatgc caaaactgga atggactctg    75420
acttcttgct agatttttta gttttggcta agccctgcaa aactttctcc agcatatggt    75480
gactttccca gatcttcata taactgctgg tgacagcagg attgtcagaa ttgtgaggac    75540
tccaatacat aagaaattac tgttcaaatt cttttaccat gaaagttcca tcttgttgtg    75600 gccctgccc agttttcatc ttttgtgctg tcccttgac cagggttcta ttttttccatc    75660 tccctgctct tgttgcctga atgcctaccc gactcagtgt aaatcctacc tttcaaaatt    75720
cagccctgct ccatcaagac ctactttgag aaactctgat ttcctctctt tctcttcccc    75780
tttccaaaac agtttctctg agttttcaca gtactgtata catacttctt atcagaaagt    75840
cagctacaaa ctataaggaa aagtgtttta gctgttttaa taagaatgta ttgatttgtt    75900
ttgggttttt tgttttttttt ttttttttta acagagtctc gctctgttgc ccaggctgga    75960
gtgcagtggt gcaatctcag cttattgcaa cctccgtctc ctgggttcaa atgattctcg    76020
tgcctcagcc tcccgagtag ctgggattac agatgtccac cacaacattg gttaatttc    76080 tgtattttg gtagagacag ggtttcgcca tgatggccag gctggtctcg aattcctggc    76140
ctgaagagat ccgcccacct cggcgtccca aagtgctgga attacaggca tgagccacca    76200
cacttggcct attgatttgt ttttaataaa tggtatctca gaggcatcaa atccatatct    76260
aaaattttct ccatgttaca aaatcatttt ttcatcaaca tcaaatcttg acaaaataaa    76320
tacagatcat ataccttatgc ttagtaatta acagaataga atttggaggt tgggtacagt    76380
ggctcacgtc tgtaatctca atacttggga aggcctaaga ggtaggatcg attgcttgag    76440
cccaggagtt tgagacaaat ctgggcaaca tagtgagacc ccatctctac tttttttaat    76500
aaaaatattt tttaaaaatc aaaaatttgg aggactagcc gggcgcagtg gctcacgcct    76560
ataataccag cactttggga ggccaaggtg ggcagatcac ctgaggtcag gagatcgaga    76620
ccagcctgac aaacacagtg aaaccccatc tctattaaaa atacaaaaat tagccgggcg    76680
tggtgatggg cgcctgtaat cccagctact gggacgctg aggcaggaga tcccttgaa    76740 cctgggaggc ggaggttgca gtgagctgag atcgcaccac tgcactccag cctgggcaac    76800
agagtgatac tttgtctcaa aaaaaaaaaa aaggaagac ataggactaa actcttcaaa    76860
atggtttgaa tactattgta catttttatta ttaggagtat ttagagaaag aagatatttc    76920
```

```
cacaaaattt ctgcagacta actttatctg ttgcttgaat tacatactta aagactaata    76980
tagtgcaaca tattcaccaa atgcttggca taaatatatt atggtaagaa aatcactatt    77040
gacaattttt aatacaaaac tataacaaat ttaaaaagga aactgaacag ctctgatacg    77100
tgtaacagtt accacactcc actatgatgt tatttattta cagtttgtct tcccttcaa    77160 ctgtgagccc caaaggggg agaccatgtc atactcatgt ttgtgtcccc agagctgagc    77220
acagtgtctg gcacataaat gtttgataaa ttaatgaatg agaagataaa taaattccaa    77280
gaataatcct cttagggctt acacctggtt tccactgtac atctgagtaa tcctctccca    77340
cttggactaa ttttactttt gccttctgga atgatggaaa ataatcctct ctcttccaca    77400
taagaacctt ttaattagat gaagaaaata catgtggtga gggggagggg acatcagaat    77460
atgatttagg gcagctgttc tcaatcctga atattagaat tgttttgaca gcttttaaac    77520
aagagtagtg agttggtccc gccccggtct ggttacctca gaatatgtga ggatggggcc    77580
taggcatcgg ttttttgtt ctggtgtgtt ttggtttgtt ttgttttttt tgagatggag    77640
tctcgctgta tcacccaggc tggagtgcac tggcatgatc tcgactcatg caactgccgc    77700
ctcccggatt caagtgattc tcatgcctca atctccctag tagctgggac tacaggcacg    77760
tgccaccacg cccagctatt ttttgcattt ttagtaaaga cagggtttca ccatgttggc    77820
caggatggtc ttgaactcct gacctcaggt gatcctcctg cctcggcctc ccaaagtgct    77880
gggattacag gcatgagcca ccacaccttg tccagcatca gttttaaag cccacaggtg    77940 aatccaatgt gcagccaaga tttcaaacca ctgagttggg ggaactaggt tctatgccag    78000
cctctgcaaa taactctccc tccccttagg cattttactt caggtctctc agtctgtatt    78060
tccgcatcta taaaacgagg gtagcacctc ccttcatttt acacagttgt taaaatctaa    78120
ggagatcatg tacagtcaat gctctgaaaa agttgaaatt gctaaataat tgttatgaca    78180
ttaaagatac tctttccatg tatagaccag atcaccaaca agaaagggaa ttttcctga    78240 tggtcataca acaaagacct gactagataa aagctgggag agtcagggt ggcataagcg    78300 aggtttgagt taaacacaag cttcacttga gccaacactg ttttcaaaag ctaatgcaat    78360
cttagaatgc atcagtagaa ttccagtgtc agggacaagg gaggtaataa tcccatttat    78420
attctgcaat ggtcaaacta taactggaat atcctgttca gttccaagta cctcatttta    78480
agaagccatt aagagactag agtgtgtcca gaagaagatg atttgactaa tctggaaatc    78540
atgtcacatg aaaaatggtt aaggaactgg ggatgcgtgg cctacagaag agacgggtgg    78600
gaagggggag ctgtcttcct aagactgaag ggctgtcatg tggaagagga agacctattc    78660
tctattatac cacaagcaga aataggaagt tactggtatg cacaaagcat aataaagaac    78720
tttgataata tgtcactcaa acagtgtgca tcaaaatccc tggatgtgct cactttatat    78780
aaagattcct ggggcagggc gcggtggctc acacctataa tcccagcact ttcaggggct    78840
gaggcaggtg gatcacctaa ggtcgggagt ttgagaccag cctggccaac caacatggtg    78900 aaacccatc tctactaaaa atacaaaaat tagccggtcc tggtggtatg agcctgtaat    78960
cccagctact ggggagggtg aggcaggata attgatcgct tgaacccagg aggtggaggt    79020
tgcagtgagc caagattgtg ccactgcact ccagcctggg tgacagatta agactctgtc    79080
tcaaaaaaaa aaaaaaaaa aaagattcct ggaatccatt tctaaagatt tttccagagg    79140
tctaggatat tgccctggaa tctgcattta agcaagctcc ttgggtgact ttacggactc    79200
cttttataaa aaataatata atctttatta aagatttgtt gtaacataat tcacgtacca    79260
```

```
taaaattcat ccacctaaaa tataattcaa tggcctttag tataatacat tcacatttca    79320
gaacattttc atcacacacc cccaccctac tgcaaaaaaa aaaaacaaaa atcctgaacc    79380
cattagcagt cactctccat tttccccaaa tctcccagcc cttggcaacc actattctat    79440
tttctatatt tatagatttg cctattcttt acatttcata taaatggaat catattatgt    79500
gaggtctttt gtaattggtc tctttctctc agtatactgt tttcaagggt catccatatt    79560
ttaacatgtg tcaatttttc attccttttta ttgctgaata aaattccttt gtatagctag    79620
accacatttt atttatctat tcatcagttg atggacattt taattgtttt cattttcggc    79680
tattacgaat aatgctgcta tgaacattca tgcacaggtt atacagacat gtttccatcc    79740
cccttgtgta aatatctaaa aatggaacag ccgagtcaca tgttaactct atgtttacca    79800
tctagaggaa atgctagact gttttcctag atggctgcac cattttacat tcccactagc    79860
aacacatgag gattttaatt tctccacatc tttggtgcca cttgttatta tgtatttctg    79920
attatagtca tcctagtggg tgtgaagtgg tatgttcatg tagttttaac ttgcatttct    79980
ctaatgggta atgacgttga gcatcacatc ttttaatggg cttattggcc atttgtatat    80040
cttctttaga aaaaaaatta tccatttgga gaaacaatga tattgccaga ttagtatgga    80100
caatagaggc cagacatggt ggctcatgcc tgtaattcca gcactttggg aggccaagga    80160
gggaggactg cttgagccca cgagttcaag accggggcaa cagagcaaaa tccctgtatc    80220
tattaaacaa acaaacaaaa aaagcacaat aatgcaaggg atagaaaaac atcaaatgtt    80280
taagtccaca agttcatact cttacaaaaa ggaaaattat cactagagga tgttggcaaa    80340
ccaattcatt attttgaaaa ttgcttaata taaggagaaa tgcaaacatt tatcctgatt    80400
tctcatatgt attctacacc taggtaagca aatggctgat gagagaaaac ttcactttaa    80460
gtaagtgggg ccaggtgcgg tggctcatgt ctgtaatccc agcagtttgg gaccccaagg    80520
tgggtggatc acctgaggtc aagagttcaa taccagcctg gccaatatgg tgaaacccca    80580
tctctactaa aaaacacaaa aattagctgg gtgtggtggt gcgtgctgta gtcccagcca    80640
cttgggaggc tgaggcagga gaatcgcttg aatcctggag gtggaggttg cagtgggccg    80700
agatcatgcc actgcactcc agcctgggcg acagagccag actccctctt aaataaataa    80760
ataaataaat aaataaataa ataaataaat aaagtgggag aaaatcttca caatctatac    80820
atctgacaaa ggactaatat ccataatcta cagtgaactc aaacaaatta gcaagaaaaa    80880
aaaaacaatc ccatcaaaaa gtggcctaag gacatgaata gacaattctc aaaagaagat    80940
atacaaatgg ccaacaaaca tatgaaaaaa tgctcaacat cactaatgat cagggaaatg    81000
caaatcaaaa ccacaatgtc ataccaccett actcctgcaa gaatggccat aatcggccag    81060
gcacggtggc tcacgcctgt aatcccagca ctttgggagg ccgaggcggg cagatcacga    81120
ggtcaggagt tcgagaccag cctggtcaac acagtaaccc ctgtctctac taaaaataca    81180
aaaaaaaaaa aaaaaaaaaa aatagccggc atggtgtggt gagtgcctgt aattccagct    81240
actcgagagg ctgaggcagg agaattgctt gaacctggga gggagaggtt gcagtgagga    81300
gagatcctgc cattgcagtc cagcctgggt gacaagagtg aaactctatc tcaaaaaaaa    81360 aaaaaaagc cataatcaaa aaaattaaaa aataatacac gttggcatgg atgtggtgaa    81420
caaggaacac ttctgcattg ctggtgggaa tgtaaactag tacaaccact atggaaaaca    81480
gtgtggagat tccttaaaga actaaaagta gaattaccat tgatccacc aatcccacta    81540 ctgcatatct acccgaaaga aaagaagtca ttatacaaaa aagatacttg cacatgcatg    81600
tttacagcag cacaatttgc aattgcaaaa atgtgccacc cacccaaatg cccatcaacc    81660
```

```
aacaagtgga taaagaaact gtgatacaca cacacacaca cacacacaga cacacacaca   81720
caatggaata ctactcagcc ataaaaagga atgaattaat ggcatttgca gcaacctgga   81780
tgggactgga gactattact ctaagtgaag taactcagga atggaaaacc aaacatcgta   81840
tgttctcact tgtaagtggg agctaagtta tgaggatgca aaggcctaag aatgacacaa   81900
tggggtttgg ggactcaggg ggaaaagggt ggaagtggg tgaaggataa aagactataa    81960
attgcggctc atgcctgtaa tcccagcact ttgggaggcc gaggtgggca gatcacgagg   82020
tcaggagttc gagaccagcc tggccaacat ggtgaaaccc tgtctctaaa aatataaaaa   82080
ttagctgggc acagtggtgc gcgcctgtag tcccagctac tcgagaggct gaggcaggag   82140
aatcgcttga acccaggaag cggaggttgc agtgagccaa gatcacaccg ctgctctcca   82200
gtctgggtga cagagtgaga ctctgtctca aaaacaaaag actataaatt gggtgcagcg   82260
tatactgctc agatgatggg tgcaccaaaa cctcacaaat caccactaat gaacttactc   82320
atggaaccaa gcacaacctg ttccccaata acctatggaa ataaaaata aaataaata     82380 aataagtgtt ctagttaata agtgaaagac aaacaatcat tgttttgcaa tctctaccga   82440
tttaatagat ttaggcagtg agctttagca gctgcaaaca tcacaaaaag agacaagcag   82500
acattatgtg tgcactgatg aagttatata ccatcaccca tgaagaagtc ttgggaaaaa   82560
aaaaaatcaa acctgagtgg taccaaatca cggtctagag atccaaatat gaatttacag   82620
aaaatagtga acaagaaaaa aatatattaa actatatcat gaggatgaaa taagcaaaat   82680
ctagactgca gaaaacaaga caaataacca atttcttcg acaataaac tgcaaggcag      82740 aaagtttgtg tgtggcggga aagaattata gtttaaaaaa catggccggg cgcggtggct   82800
catgcctgta atctcagcac tttgggaggc cgaggcaggt ggatcatgag gtcgggagat   82860
caagaccatt ctggctaaca cggtgaaacc ctgtctctac taaaaataca aaaaattagc   82920
tgggcatggt ggcaggcacc tgtagtccca gctactcagg aggctgaggc aggagaatgg   82980
cgtgaacctg ggaggcggag cttgcagtga gccgagatcg ctccactgca ctccaacctg   83040
ggcaacagag caagactccg tctcaaaaaa aaaaaattc gcacaattat aaaaattgga    83100
aatttgaata ctgccaatat atttaattat attaaataat tattgttaat tttaaaagat   83160
atgattgatt gtggttatgt tttaaaagga gtactcatct tttgatatat acttaaatat   83220
ttatagataa gataacatgt aatggattta cttcaaagta atatgggaat aacatgggaa   83280
agagaaaaga aggtagaagt acaaatgaaa taagattagc cacgagctga taattgtcga   83340
acttgctgat gggtacataa gggtttatta tgtgattcac ctactcttac gtatttttac   83400
aattttccaa atttgttata ataagttttt taacaaaagc ttgtcaaaaa tgaaatagggg  83460 tatattgaat gattatgatc actggctgtg atcaagaaga aactgatagc ctttcatgat   83520
agttcttgta atgtaaatga cacacaagaa ttttttcttc caatgctagg aagctattaa   83580
aatcagcagc gttttaaaac aggcctagct aaatcacctc aattcaccac ttagttttgc   83640
agatagaaac tttgagactc aaaactgttt ataacaact aatattaatt cagtttcctc    83700
agaagtaaat atatttgttt aaaagactta cctctaaggc acacaaatta atcaaatgag   83760
aaaatgcatt taaactttt aagtgtcaaa tgcaattcac ctctaaggtc cacttactgt    83820
tagtatgagc aatattttta tcatcaaatg atatacttga tgagacaagg gggtaataca   83880
ttttctggga ttaacaacta atatctgttc cctcaaaata tatgcacaaa tatactatct   83940
aattgagcag aaaggttagc gttatcagaa agagagaaac agaaaaaaac tcttaccaat   84000
```

```
ctatgtttag ccaaaaaaga ttttgtatga tggcatagag taaaactaca agtaaacaaa    84060
acagaaacaa aagagtatga caattcacgt aatgagtacc aacaaatcac tggattattt    84120
tctagagaga agaaagaata tgtgcagaaa atattaactg gttgatggat gaggcaagtg    84180
aaataatagt tataatgcat tatctacaac acatgcataa acttaaccaa atccctcaac    84240
ttcattacta tagtattcaa cactacagta ttaacggttt tactttctta ttaatgtact    84300
ccattatttc ttgttttttgc attccaaact aaatttttta aaatttgcac tagttttaca    84360
gaattgctta gtaaaaatct cctgctggaa aaatgttgaa agaatgtgga gcaattcttt    84420
gacactcctg gtagaaatag aaattggttc aaaaaccttg gaaatcaatg tggcattatc    84480
cgattatgct gaaaatgcat tatattagtt tcctgtgcct actgtaacaa atcaccagga    84540
attttgtggc ttaaaacaac agatatttac tctctcacag ttctggaggc tagaagtctg    84600
aaatcggtat cactgggctg aaatcgaagt gtcggcaggg ctgcactccc tccaggggct    84660
ctagtaaaga atcggtttct tgcttcttcc agcttctgtt ggccaacagc attccctggc    84720
ttgtggccac ataactttaa tctcttcttt gtgtaatctc tctctgcctc tgtcttatgt    84780
agacacttat gattccattt aaatactgat gattccacat ctacaaagac cctttctcca    84840
tatgtgttag gccattcttg cattggtata aagaaatacc tgaggccggg cacagtggct    84900
cacgcctgta gttctacttt gcgaggctca agtgggcaga tcactggagg ccaggaatttt    84960 gagaccagcc tggccaacat ggtgaaaccc catctctact aaaaatacaa aaattagcta    85020
gacatggtgt gcgtgcctg tagtcacagt tactcaggag gctgaggcag agaatcgctt    85080
gaacccagga ggcgcaggtt ggagtgagcc aagatcacac cactacactc cagcctgggt    85140
gacagagtga gactctatct caaaaaaaga aagaaagaaa gaaagaaaaa agacatacct    85200
gagactcggt aatttataca gaaagaagt ttaactggct cacagttctg caggctgtac    85260
agaaagcatg gtgccagcat ctgcttggct tctggggagg ccttacggag cttttacttg    85320
tggaggaagg tgaagcagga gcaggcatct ctcacatggc agagtgggag caagagagag    85380
ttaggaggag gtgccacata cttttaaaga aacagatctt ctgagaactc actcaccagt    85440
gaggacagca ccaagaatac gcccctatga cccaaacacc tcccatcagg cccaacccc    85500 aacactgggg attataattc aacgtgagat ttggtaggga catatattca aactacatca    85560
ccatatagga taacatttac aggttgcagg gactagccta caatccatca atccactcct    85620
aggtaattcc ctatagaaat tcttgcacat gaacaccaca tgacacgaac aagaatattc    85680
gtagcaacac tgtttataat atcaaaaagt ggaaacaacc caaatatcca ccaacaggag    85740
aatgggtaca ctgtgtcata gttatataat ccaaaattat gcagcagtga aaataaatga    85800
agtatagtga cacatatcaa cacacaagaa tcatgtaaca catgcagggt ccaagaaaat    85860
gcaagtcaca aaaaaataca catgacatac tacatttata taataaagtc ttaaaacaca    85920
caaaactaaa ataagcccta tattgtttag ggctatatgc ataatatgat aaaataataa    85980
aagcaaaaga aaaacaaaat tcagaagggc agtttcctat gtggaagaga gggagtgttg    86040
gtcttgtaca gctgaccagg agctttaaag gtactagtaa gggtctatat cttaactgga    86100
tggtaggatc acaggaaaat aagggggtgtg tgtgtgtgtg tatgtttgtg tgtgtattta    86160
aaatggctac tcaaaagata gagatacaca aacatgcaca tacacatcca ctcagaccctt    86220 ttaaatacag acagtccctg acttacgatg tgcttacatc tagataaacc taccataagt    86280
ggaaaatgta aactgaaaac acactttcag ccaggcacag tggctcatgc ctgtaatccc    86340
agcactctgg gaggctgagg caggtggatt acctaaggtc aggagttcga gaccagcctg    86400
```

```
gccaacatgg tgaaacccg cctctacaaa atatacaaaa attagccagt catggtggta    86460
cacacctgta atcccagcta cttgggaagc tgaggcagga gaatcgtttg aacccgggag    86520
gcaatggttg cagtgagcca agattgcacc actgcactcc agcctgggtg acagagtgag    86580
actcaaaaaa aaaaaaagaa aagaaaactc actttcaact tacagtattt tcaatttatg    86640
atgggttttt caggatgtaa ttcatcataa gtcaaagaac atctgtatat gatataatta    86700
ataataaaaa attgtaattc ctattggttg ttattccagt actggaaagc agactaagat    86760
caccatcccc actgctgata agcacgaaat ggtttctcta gagatgtggc tctatcactg    86820
tataatgaaa gtattcccaa tgcaaggtgt gatgagccca agtgcttcac atttttagaa    86880
acagtgtgag ctgatgcaca agctacactt gggatgatgc tgcaatcagc tctgcctctg    86940
gaaggagcta ttgcttgtct gggagactaa agcctagacc aggagctctc ccattgaggt    87000
aggagggaga aactgtcttc caggtggcat ctggcaaggt ctagagatat ttttggttgt    87060
cgcaagtata gacgagctac tggcatctag tgggtagaga ccagggatgc tgcttacatc    87120
ctacaatgca caggacagcc ccacagcaaa gaatgatctg gctcaaaatg tcaatagtac    87180
tgaggatgag aacgcctggt ctatagtgac cccttgatag agtgtgtgca gtaaggctaa    87240
ctattgccat atgacattaa gtacaacaat accatctctc ataaaagata tagaaagccc    87300
ctgtttgcaa aatttatcaa tcctcagaat tgtgcatagg aacgattcta ttcatgtgcc    87360
gaatttgaca aattttatat ataattatta ggtaccagaa ggatgctgat agactgcatg    87420
ctcaagggtg gggatttaca ttaattcatc tttataccttt ctgcattcaa acctcaatgt    87480
gtcttgaata gtttctcctg aaatgaggca caaaacacaa tacctggcac aaggtaagca    87540
ctcaataaca tttactaata ttattttttaa aaatctttttt cgaattaact ctaaactctt    87600
gtcagtatag cttatagctt tgtctgtttt gctcaccaat gtatcacaag tgccagagaa    87660
cttggcacat aatagatgct agacaaatat ttactgaatg agcagcagat taaaaatgct    87720
acctgtcagt gcacatacat taaaaatgcc acctgctagg gaacatacat gctcccccaa    87780
acaagacaaa caagctacag aaggagcaac agacacaata aggcaccact tccaaatgca    87840
ctcccaggtc agcacttctg tttgagactt ctgacccttc acctttttta agatcagagg    87900
cattaacctg tgcctctaaa cctgtggttt gtaactgttt ggctgaatgt gaatatgcac    87960
ccagtgacta ctcaataaaa attcccaata actatggctg accactaagt ccctctaaga    88020
aacataagaa aggttaccta tttttatgcca ctgaatcttg cccttcctgt caattcctgc    88080
tcacagctgt gcctgactaa ttaaaactcc ctggaaacct cgtctatcgc tttacgggtt    88140
atttcttctg ctacatcaaa agactccact ttagaattca aatccatctg tctccctcag    88200
tctgcaaaga acaaatgttc agaaaaacta accgactagc taaaattaaa tgtaccttc    88260 ccagctaaga cttaatatgt gttgggggca gggagcaagc aatctaagga taaaccacta    88320
aaaagaagat aaaacaaagc ttaaccatat gagatagtac ttagatagtc attcaactcc    88380
catcttagca gaccagggac aaatccagaa attcttggtt gaaatggatt tatatccaaa    88440
ggcaaaattt tctggtgaag ctaatatatg acaaacattg ctcacccaaa ataatatgac    88500
tctagacccc aaaggtttgc tcatccattt tcctctcatt tggacctcag agagcctaaa    88560
ttggctcata acctatagct tcacttttttg atatatgaaa tgatttattg ttgaaggcta    88620
actattgcca tctgacatta agtacaataa aatctctcac aaaaggattt attgttgaac    88680
tattggtcct atcccatgat cagaaaaaca ctaaaggccg ggcatggtgg ctcacacctg    88740
```

```
taatcctaac accttgggag gccaaggcaa gaggattgct tgagcctggg agttcaaaac   88800
cagcccgatc aacacaggaa gaccctgttt tcaacaaaaa aattaaaaat tagccagttg   88860
tgatagtgca tgcctgtagt cctacaggct caggaggctg aggtgggagg atcgcttgag   88920
cctaagagtt tgaggctgca gtgagcaatg accgtaccac tgcactccag cctgggtgac   88980
agagtaagac cctgtctatt taaaaacaaa caaacaaaca aaaaacaata agaaatgtaa   89040
tctagttttt atgacctttc tttggaacct ataacttcaa acttctaaga attgtttcaa   89100
ttattgaagt aaaatatata aaattgcctg atcttaatgc tgcttttact atcgcatctg   89160
agttacagtt ttgcctagaa gtaattacag gatgaataca cgaaaatatt ctagaacact   89220
gaaaaaaact ctagtgcaaa atggattttta agcaagaagt tgcctctgtg agatctgatt   89280
aaatttttgc tgccaaaacc acgtatgcca aattatgcca tgtcatacct atcttctgtg   89340
atgtcacaag acatctaaag ttcaacttct ctttccaata tgctttttca ccaaagaaat   89400
cctttcccta gtaagcaatg taacagttaa aatgaagcat aaatcacaac caaaaaattt   89460
tacttcttag aaagttcctt caaaaacact gtaatttatt acactgatgc acatgtaatt   89520
tacaacactc tgtaacactc agaggttact agtaaaatga aacaagtttc cttcttttat   89580
gttcaaaatc atataactgt acaattttag aatttcacaa aaactcctaa agctacagca   89640
aaatcacctc caaagacatg tcaaatcttt ttttattaca ctggaaatct gctgtaccaa   89700
atataacaga aaataaatgt acaaccactt aggcttaaac atattttgt tacataaata    89760 tgttgtaaaa ggtttaacct gcatccttga tgtcccacag cacataggta gcattctttc   89820
aaaactatcc ttcaaattat ttgacattct atttctttga cactatttc taaataaatt    89880 aattaaacag caggttccaa atgcaattca acaagcttta tgtatgacat ggcttctgat   89940
gtacaaagca gtaatatgca ctgcaaggat taaaaaacat ttgaaggtac aaaaatattg   90000
aacactgttt gtattagaga aaaaactgag gctgtgcatg gtggctcagg tctgtaatcc   90060
cagcacttgg ggagaccagg gagggaggat cacttgaggt gaggaatttg agactagcct   90120
gggcaacacg gcaagacctc acctctacaa aaaaaaatta aaattagctg gcatgatgg    90180 tacaagcctg tagtcttagc tacatgaaag gctgaagtgg gaggatttct tgaggccagg   90240
agttcaaggc tccagtgagc tatgatcacg ccactatact gcagcctggg caacagacag   90300
agagacccca tctcttggga aaaaaaaag tgaaatcaac ctaaaatatt taccaacagg    90360
agaagggcta aatcacctgt gaggaagtta aaaaataaag aggctgagtg atatacatgt   90420
gaataaagct gaggccagat attgagtgaa aaaacaagt tgcaaaaata tgcatataac    90480
aacattgatg tttttaaaaa gacaaatactg tatgaatagc tccgatgggt agcatcttca   90540
ggttttgtga ctgaacaagc taagagttga gatgaacttg cctggaggac gccaactatg   90600
gcagggagga aaatggaatg ggttttgaat agggcttaat gtgaatccta aatctctctc   90660
cacaaggctt cctaaggcaa gtctgtagat catttaacaa cttttagtaa taaattttga   90720
tttccactca tttaaaactg taagggacaa cttttagaat tttaactcca agtatttcca   90780
acccttaatg gctttaagga gaaaatcaa caacaactac agaaatatcc tagaatgtcc     90840
tgttttagca aaacactaaa actgaaaacc aaaaactgca gggggttat aactggtcct     90900 ctggtttctg taacaattca gatgagtgtt atgcataaag aacatgacct ggtaaaccgc   90960
cacactataa gaaactaaac aagccatcca acacttctgt tcaaaataca aactccaaaa   91020
ctagcttaac tcagagctca caaaaaggtc aacagggcag aggcacataa gtatgaatac   91080
agaagaggat agactggggg gaagatggca gtaggtctct ggactgtctt gagttttcc    91140
```

```
tatcacatat aaaatgtttg gattaagaaa aaaatcaggg ccagatgtgg tagctcacac    91200
ctgtaatccc agcactttgg gagcctgagg caggtggatc acatgaggtc aggagttcaa    91260
gaccagcctg accaacatgg tgaaaccccg tctctattaa aaatataaaa taagccaggc    91320
gtggtggcgc atgcctgtaa tcccagctat ttgggaggct gaggcaggag gactgcttga    91380
acctgggaga tacaggttgc agtgagctga gatcacgcca ttgcactcca gcctgggcaa    91440
tgagaatgaa actccgtctc aaaaaagaa aagagaagag aagagaagag agaagagaag     91500
ataaaagata agatcaggct gggtacagag gtgcatgcct gtcccagcac tttgggaggc    91560
caaggcaaga ggatcacatg agcccaggag ttcaagacca gcctgactag tatagtaaga    91620
ctccatcttt taaaaattgc caaaatagt agggtgtgat ggcatgtacc tgtggtccca     91680
gctactcagg aggctgaggc aagaggatta cttgagccta ggaggttgag gctgcagtaa    91740
gccatgatgg ccctgctgca cactccaacc tgggtgacag agcaagaccc tatcccctac    91800 caaaaaaga aaaaaaaaa gtgtgatgga agaacaaggt cagaagaaga aaaagaaga       91860 aaaaaccag gacaatgaaa cgatatgaaa acaataaaca agactctaac tcctgtctac     91920
aaaaacaaac aaaaccaacc aaccaaacaa gcaaaccta atagtataag aaacacaaaa     91980
gtaaatacca gataagcaa ttagaggaaa attagtttac aagagaaaat taactatata    92040
ttaattatat tatggcattt gttacagagc ctggaagtaa attcatgaaa taatgaggtt    92100
cgagtaattt atcttttctt cctttgtctt tttcaaattt tgtcaggtga gtatgtatgg    92160
cttttgtaag atgctatttt agaaagaaca ggaagtagct ggccaggccg gtggctcacg    92220
aggtcaggag atcaagacca tcctggctaa cacagtgaaa ccccgtctct actaaaaata    92280
caaaaaatta gccgggcatg gtggcgggca cctgtagtcc cagctactcg ggaggctgag    92340
gcaggagaat ggcgtgaacc cgggaggcag agcttgcagt gagcagagat cgtgccactg    92400
cactccagcc tgggcgatag agcgagactc cgtctcaaaa acaaaataaa gaagaaaga    92460 agagaaagca aacatggatc tttcctgaat gttctggagc tatggctcaa gaactcacag    92520
gaagtctggt agttaggaga aacatttacc aaatgtttat gatgtgctgg aataagaagc    92580
ttccattcgc tatagtcctt aacctggaaa accacagcat gaggtagcta aggagtgcga    92640
ctgccccatt tcacaggtga gaaaactgcg ggtttagaag gttaacccat tggccaaggt    92700
tacctcactt gtaattggtg tactagaatt aaaaggcagt ctctaaactc agagcccact    92760
ttgtgaacca cattacctgt gtttctcaca cacacctgat aagaatcacc ttgagcactg    92820
gtgaaaaaat catattcccc ctatgccttc tgccagagat cctgggaatc tgcatgttta    92880
acaggcatcc cagaaattct tttctctctc tccttttgtt tccttttctt tccctccct    92940 cagatcactt tggtacatac cagcaattct taccaggtgc agcttgagaa actctgccca    93000
ccctcgactg ccactcaaac tttttattta ggatgaagcc tattactaca tataaactgg    93060
ctctcattgc aagatgagct atttaaatgc cagatactgc actccaagac aagcacaaac    93120
aaaacctaga ccatctatag ttgaagctac tcttggcttt ccagagagag agagaaattg    93180
tcactttata acataaatca ggaaagattt ttgtgttgag gctgccatag ttcttgaatt    93240
tctccagccc cgacagttgc tctgagagtc atattttccc cagccagaac tcagtggtgg    93300
ggaaaggagc agggcaatat gttgagtgac cactctattt gattgctctc cttttttaaa    93360
atacgagaaa aggagacaga atttcacatt cctaaatcag agctttccta gctcttaatt    93420
atcaattatt atcaattatt tggattagta tttcatatat ccatatatac tggaaatgtt    93480
```

-continued

```
ggtgcccaag gcaaattgga gaattcatgt ccctcctaaa ggtattcaaa gtattttga    93540 aaacctctgc acatcaaaca aaatctgtgg gttgaatctg gccttctaac tacagtttgc   93600
aattcctctg gcctcgactt ttcatgtttc tttttcata aatatataca tttatcatat    93660
aaaatatata tttatatatt tcaggaagga ggagcaaatg ttgaataaaa aatatctgat   93720
gataaatgag ttggtgtctg tcaagcaggc tctttgaaaa aggagactca gccaggcatg   93780
gtggctcatg tctgtaatcc caggactttc ggaggccgag gtgggtggat cacttgaggc   93840
cgggagttca agaccagcct ggccaacacg gcaaaaccc atctctacaa aaatacaaaa    93900
attagccggg tgtgatggag cacgcttgta atcccagcta cttgggaagc tgaggcataa   93960
gaatcgcttg caacccggga ggcagtggtt gcagtgagcc aagattgcac cactgcactc   94020
cagcctggga gtcagagaga gaccctgtct caaaaacaca aaaagaaag aaaagaaaac    94080 agagactccc ggattgggaa gaacctagca attgaaatac aaagccaggg aaacttaagg   94140
aatttacttg cacttcagtt acctaatatt aaccatcaat atgcaaatat catacgtcag   94200
aaccctagtg gagctatgat tcacaacctt tcttctattc caacatagct gagaaagaca   94260
tcacactctg tggtttccta aagccaagat gctcagggca gaaggagatg ggggcccat    94320 ggcaggtggt aagaactgct gatttagaac ataaggacag tatgttagcc caagctgtgt   94380
ttgctctcat gccaattgct tgccagatga actgtacaca cattccattt atatggatga   94440
cgtgtaacag gacaatatac agaattccat gcttgagctt tttcaggctg tcacctcatg   94500
ggctctgcct ctatctttgc cccagtcttg agcagaaata gttcgcttct gagtctggat   94560
aggccataga gatctaccat aaaatagcag aacaccatga acttttataa tctgaacatt   94620
ttaaagacca agcattctaa ttgcaggtgg aaaaacttaa aaaattttta aatttaatca   94680
aatcgctgca gcacagagaa aagttatggt tgatattaag aaataaacta gattaacaca   94740
agagtagttc tacaagggaa tgcattagga ggagcatata ctttatctgg gtaaccctag   94800
catctttcta ttttttataag cgacctctaa agcaagaggt gagaaaccta tcaatttat   94860 agttgagaga aataagcctc accaaacaga ctctactatg cccttgaaat aggttttaga   94920
atgctcctga atgttgtatc aaacagaact atagatggaa aacttaaaac ttatattcac   94980
taaaatatta tgtggagcat aatcctattt ttataaaaaa tgtgggccgg gagatcatgc   95040
ctgtaatccc agcactttag aggtcgaggc agatgaatcg cttgaggcca gaatttgag    95100 accagcctag caacatagct agaccctgtc tctataaaaa aaaattaaaa gatgagctgg   95160
acacagtggt gtgtgcgtat agtcccacct ccttgggatt gcttgagcac aggtattcga   95220
agttgcagtg agctatgatc acaccaccgc agtctagcta gcttgagcaa caaagtgaaa   95280 cccctatct tttggggaaa aaaaagtgta tattagcaag aaatgaaaaa atatataaat    95340 aaataaagt gcatgcatag gttttatata taaacctatg tatgtatata tactaagcat    95400
ttatatatct agagagagga agaggaggag caggttcaaa atcttaacag aggaattatg   95460
gttgattttc atcttctttt tttgttatct ttattttcca agttgtttac aataaacaca   95520
aattgccttt gaatgaggag gagggatatg atatcctggt aaaatactta aaatataaca   95580
ttaggtgaat aaacaggcta caaaacaaaa ataaaatatt tttactactt ttagaaatat   95640
tatgcataaa gaggccaggt gcggtggctc acgcctgtaa tcccagtttg ggaggccaag   95700
gcgggtggat catgaggtca ggagttcgag accagcctag ccaatatggt gaaaccccat   95760
ctgtactaaa aatacaaaaa cttagccggg tgtggtaaca catgcctata gtcccagcta   95820
ctggggaggc tgaggcagaa gaatcgcttg aacccaggag gcagaggttg agtgagccga   95880
```

-continued

```
gatcgcacca ctgcactcca gcctgggcga cagagcaaga ctcttgctcc aaaaaaaaaa    95940
aaaaaaaaaa aagaaagaa aagaaaaga aacattatgc ataaagaaac ctagaagaaa       96000
atacggccaa atcaacattt aaaaattttg ttgcatgtta tttccttatc aagttacttt    96060
ccagtgaaga gtctaattgg caaagataag gcatgctcct ggggaagaag tcagatgaaa    96120
acatctagtt ttgcttccct cttgttatat gaatctcaat ctcatgctga aacagatgg     96180
caaaaaaaaa aattggcaca gaatgcaact acggcagtac aaatatggtg gtcagcagga    96240
aatacattat tcttaatttc aacctttcc tggaaacagt gcctggagtg ttatggagta    96300
aaaatgggtg aacaggtgta ggaggatttt attttggca agggctgaaa gcaaaggaga    96360
aaaattagtt tgatttaagg agcctactta attctagaaa agaaataaaa cagactggga    96420
acacattgaa taattttata tttctgtaaa tgttcatatt ttttggaaag gctatcaata    96480
atatgatatt tttcttttc ttttctttt tttgagaca gggcctcatt ctgttgccca     96540
ggttggagtg cagtggcaca acacagctc actgcagccc caaactcctg gactcaagtg    96600
atttcctgc ctcagcctcc catgtagctg gtcccacagg cgcgcaccac catgcctggc    96660
taattaattt attttattgt tgagacaggt tcttgccatg ttgcctaggc tgaactcctg    96720
ggctcaagtc atctcgtgcc ttggcctccc aaagtgctgg aattacaggc atgagccacc    96780
acacccagcc atacgatact ttttatttgg ataccaaatg tcttcttaga actctaaact    96840
caaaataaac gtgccattct catgatatgc taaaaggagg taataatcat ttctggggaa    96900
acagtatgtg ttatcagaaa taatattatt ttgtataact ctcttgctt tggcttcatt    96960
gattttagag cagcatcgtc atgttctcat aagcttttaa gtattctacc caagaatctg    97020
cttctgagag gtttaaagta cccatgttgt ttttctttat taaggatatg tactaacgct    97080
acacatgaag ccaatgaagt caaacaggcc ctccccaatc tgtcagtata ttttatcta     97140
acaagtttta gtgttcttgg atgaattcat ttttctaatc ttcaaagaat caaatatctt    97200
tatagtgtcc ctcaagtgag taagacttta tttcatcata agaaaaaata atacaatttt    97260
aaaagcttaa ggttgccagc aagacacacc ctcaatgttc attctccaca tacagcttgc    97320
tctgatttat ggtgccagta cttttggcca cacaattcac tacactttgt tctcctggtt    97380
actggtgtca gtgacagggc taggtcaact cttttggctaa tgtggctagc tcagtagatt    97440
agaaccaaat gcaagtatgg ctcaatttaa attaagggcc cattagtctc cctaaaaaag    97500
agcttaattc catgtcagaa atctactgga gtgtgaatgg cagcatacat catcactttc    97560
attcaaaatg tgtggtcagc ttggtcactg gccacctcgt ttcatattct acagaggaag    97620
acatgtttgg tttgggtaag ggtttatttc ccatgtcttg cagatctgaa gatctgtacc    97680
tagctttctg tgtaggtata tcaaatagcc agtccctgca ctcccctcct gacttgcttt    97740
atcaatgttt tcaaagaatt caaatctctt gcttccaaat agaagcttac tgtaagatga    97800
gcagtccctg tgcacaaagg agacaaggag accagcctca tgatcgcgtc agaagtggtg    97860
gtttggcact atcatctcta accaaatgtg cagggcaggg caggtttgca tctgccagga    97920
cacagataag ggagtatggc tgggcttcct tctcctatct caaaatatgg ctcataacag    97980
catggagatc ttctctaggt aaccaattta aataatcttt taatagtaga aaaccaggcc    98040
agtggtttag gaaacaagtc tgtttaagca agtattccaa caaagacaaa tctataaatt    98100
tccaggtctg tctataaact attcatagtg gctaaataaa tatcatgctt taataaatac    98160
aaatttctag gcaaggggta aaagtgaaag gtgttaattt agtgtgttta gttgtcttct    98220
```

```
tgcattaaag ctacagataa atcatggaag atcataaatg actatttta ctttttttat    98280
gctacactga ctgacataaa gattttacta ccaaggatgg cataagtacc tacgtagtaa    98340
catagcctaa tagataaaat tactgtcggc atgtttaaaa ggcaaaaatt ctaacccaaa    98400
gtatctcagt catctcagtc actaatcttt ctgttattca gtttcttaat ctttaaaaca    98460
aagacagaat gaatatggcc taccatttcc cttcactttc ctattttggt gttttcattc    98520
aatttaacag atattcagca aaactaccac actatgggta gtgagaaggc tgaggagctc    98580
tcatataaat gcatatgcag ttatagggaa actaataact tttcctatta agaagctttt    98640
gcttttaat tttttaaatt ttttgagac agggtatgct cttgcacata agaacgtttc     98700
aattagatga agaaaatacc tatggtggcg aggaggggac atcagaagaa tatgagttag    98760
ggtagctgtt ctcaaccctg ctgaatatt agaattgctt tgagagcttt taacgagac     98820
taatgagttg gtctcatccc agtctggtta ccttagaata tctgtggatg gagcatcttt    98880
ttttttttt ttttgagaca gagtcttgct cttgttgccc aggctggagt gctgcagcac    98940
aatctcggct cattgcaacc tccgcctcct gggctcaagc gattctcctg cctcagcctc    99000
ccgggtagct gggattacag gtgcctgcca ctacgcccag ctaattttta tattttagt    99060
agagacaggg ttttaccatg ttggccaggc tggtctcgaa ctcctgacct caggtgatct    99120
gcccacctca gcctcccaaa gacatcattt ttttcccttc ttttttgaga caaggtcttg    99180
ctgtgttgcc caggctgaag tacggtggtg ccatcacagc tcactgcagc ctcaacctcc    99240
tgggctcaag caatcctccc acctcagcct cccaagtagc taagaccaca tgtatatgcc    99300
aaaatgccca gctagttttt tgattttttg tagagacaga gtctcgctat gttgccaggg    99360
ctggtctcga actccagggc tcaagttatg ctcttgcctc agcctcccaa agtgctggga    99420
ttgcaggcat gagacaccac aaccagccca acataagtgt tttaaaataa gacaaccatc    99480
attctggctt gtgatgagac cttgtctgta atgaagaaaa cttcagaatt cctataagtc    99540
agttgccaaa aggctagaag catcattgat ttcctgttag caaacatcca taacaaagac    99600
taagtccttg ctttaccccca gaccaaaaca gaacatcaac tctatggaaa ccagcagaag    99660
aatttcataa gaaccaagga gctgactgac agccacctga ctggcagcca ccattaccag    99720
gttaaaacta tgtctgatga tgtttcttga cagctctgcg ttccaagaat gagcacatgg    99780
cttcattaca atcaaggggc aacttaaaga acaggtgagg gattctttct aagtatcttt    99840
ctaggctaat ggatatttta tcaaacctgt cttatttccc taaattctaa acatgctact    99900
gagagaaaag gctctaaaat tattaaccca tgtacagact attttgtttt tgtcatttct    99960
cttatagaag aacatatatt actaaaaaaa gtcagcttcg tattgtcttt tatattttgt   100020
aaaatgtggc tctttcctga gtttcaacaa tgactggttg aatagagatg agtcatttta   100080
agaaactaca ggcggggtgt ggtggctcat gcctgtaatc ccagactttg ggagaacaag   100140
gagggtggat cacaaggtca ggagttcgat accagtctgg ccaatatggt aaaaccccat   100200
ctctactaaa aatacaaaat tagctgggtg tggtgggaaa ctacaaccag atcctttcat   100260
gcatcaaaga aaacccaaa ataagttcta aacttcagct ttaaaagtt aggctagaag     100320
aatcatttcc tgtcctcata gaatccactt gcttgctgaa atattatag aaatagaact    100380
ttattaatgt gaagggtaat tttaatctca tcagttaaca tttgccaaaa tggaatatgt   100440
gctcgacagg attaataata gtggttttta gccagcacag tggtgcatgc ctgttgccca   100500
gctactcagg aggcagatgt aggacagtca cttgagccca ggagttcaaa gccagtctgg   100560
gtaacacagc aagaacctac ctctaagaat aataataata atagattttt attttttatt   100620
```

```
ttgattttttt ttgagatagg gtctcgctct gttgtctagg ctggagtgca gtggcgtgaa 100680
cacagctcac cgcagccacg acctaccagg ctcaagcaat cctcccacct cagcctcttg 100740
agtaggcacg tactaccgtg accagctaat tttttaattt tttgtaaaag caggatctcg 100800
ccatgttgcc aagactggtc ttgacctcct aggctcaagc atcctcctgc ctagggctcc 100860
caaagtgctg ggattacagg tgtgacctat cacccaatag tgtcttttt taatccattg 100920 gtttgaaatt cttcaccctg cctcctaaaa gagacagaaa gagggaaaaa cctgggtatg 100980
ttattcataa tgcttctatt aaaccaagg agcagccagt agtttgagac tagtctgagc 101040
aaacatggtg aaacctcgtc tctacagaag atataaaatt agctgggtgt ggttgtacac 101100
acctgtagtc ccagctgctt gagaggctga gggaggagga ttgcatgagc ccaggaggca 101160
gacattgcag tgggccaaga ttgcgccatt gcacaccagc ttgggcaaca gagcagactg 101220
tctcaacaaa acaaacaac aacacacaca cacacgca cgcacaaaca cacatacaca 101280
cagcaacact tcaaatctca aattattttg ggtcaccacc aaaaaattat attctcaacc 101340
atggtctatg ctggttattc caatcctagt tcaatttcaa atcatcataa atattaagaa 101400
tttgagcctt tgtacaaata aaaactagac tcaaacaaa gatgagcgct gccctacagg 101460
tcaaatattt attctatgct atatttaaat aagcataagg ttaagggttt gccaaatggg 101520
attttaattt tttttttttt gagatggagt cttgctgggt cacccaggct ggagtgcagt 101580
ggcgctatct cggctcactg caacctccgc ctcccgggtt caagccattc tcctgcctca 101640
gcctccagag tagctggaat tcaggtgcgt gccaccaggc ccagctaatt tttgtgtttt 101700
ttagtagaga cagggtttcg ccatgttggc caggctggtc tcagaactcc tgacttcagg 101760
cccgccttgg cctctcagag tgctgggata acaggtgtga gccaccgcgc cgggcgccaa 101820
atgggattca aaaaaaaa aaaaaaaa ttgtgggcca ggcacggtgg ccgacacctg 101880
taatcccagc tactcgggag gctgaggcag gagaatggct tgaacccgga aggcggaggt 101940
tgcagtaggc tgataccgcg ccactgcact ccagcctggg cgaccgagca agagactccg 102000
tctcaaaaat aaaataaag gccaggcacg gtggctcaca ccagtaatcc cagcactttg 102060
ggaggccgaa gtggacagat cacctgaggt cgggagttcg agaccagcct gaccaacatg 102120
gagaaacccc atgtctacta aaaatacaaa aattagctgg gcgtggtggc acatgcatgc 102180
ctgtgatccc agctgcttgg gaggctgagg caggagaatc gcttgagccc gggaggcgga 102240
ggttgcagtg agcggaggtc gcaccactgc actccagcct gggagacagc gagactctgt 102300
ctcaaaaaaa caataaaaat aaaaataaaa ataaaataaa atgtgccatt ctatttcatt 102360
atataaagat ttattcaatc acattgtgtg gatgatatca cagatgcgaa cagtattagg 102420
aagcaaaaag caatcccttc acctttctta atactcaaat aattttttt taatttgcca 102480 aaatgaaatc tagtaagtca aagggatctt atttctaagg actcttggat tataaacaga 102540
atttctagcg gggtgataac tggggagagt cacttggctc agtcactgac cttcctttat 102600
ccttaaattg agagtggcaa tttcatgacc ctgaatagta taaaaatat gtccctcaaa 102660 cgtataagca ccatatgaag ctaatagcct ttgaaggtct atatttactg tgtcatagat 102720
aagctcaact acaattcgat ttgattaaaa aatcagtaca gtgatactct aatccaaaaa 102780
atatcaaatg attgctaaaa ataaagggga tattgtaaat ggcataaatt gcatcaaaat 102840
gggaatgaac actaaataat tacagctata tatgttctaa aaactaatga caaaagaaag 102900
ctgaaaaatc cccagtaact tctcattaga tcttttccgt ctcactctct ttctggtgtg 102960
```

```
tgttttttgt tgtttgttt ttttgttttt tgttttaga aagacagggt tgggctgtca    103020
cccagggtgg agtgcagtgg catgatcttg gctcactgca acctccattt cccaggctca  103080
aaccatccat ccacctcagc ctcccaagta gctgggacta caggcgtgca ccaccatgcc  103140
cagctaattt ttgtattttg gtagagacag gttttgcca tgttgcctag gctggtctca   103200
aactcctggg ctcaagtgat ccnnnnnnnn nnnnnnnnnn nnnnnnnnnn nnnnnnnnnn  103260
nnnnnnnnnn nnnnnnnnnn nnnnnnnnnn nnnnnnnnnn nnnnnnnnnn nnnnnnnnnn  103320
nncaagtagt tcatcgatct tcttttttt tttcatttga gatggagttt tgccttgtca   103380
tctagatggg agtgcagtgg cccaatctca cctcactgca acctccgcct tccgggttca  103440
agcgattctc ctgcctctgc ctcctgagta gctgggatta caggcacccg ccaccatgcc  103500
tggctaattg tttgtatgtt tttagcagag acagggtttc accatgttgg ccaggctggt  103560
ctcaaactcc tgacctcagg caatccaccc acctcggcct cccaaagtgc tgggattgca  103620
ggtgagagcc actgcaccca gcccattata ttcttatggg accaccatta tgtatgccgt  103680
ccatcatcaa ctgaaccatc attatgtggc aaatgactat atataatatt ttttattttg  103740
acaaatattg tcaaaccacc ctcaaaataa ggtactggtt tggacgggca tagagtgtga  103800
aatcccctgt tttccctcac ttgtgccaat actacataca ttaccaaact ctttcatctt  103860
tgtctatctg attaatggaa aatggtacca tgttagtttg catttctttg tgagactgag  103920
cactttttca tgttttcaga ccacttgtgt ttcctttct atgagttgtc agtttgtcgt   103980
tgctcatttc ctattagatt tttttctta ctgatttgta ggagctcttg atataaccag   104040
aaaattaccc tttactgtat gtgttgcaaa tatttgtctc tggtttttt cccccctttt    104100
tagtctgtgg tatttttttt cctacagagg ttcatgttgg cattgttaaa tttatcagat  104160
ttttccatta tgatttctgg gtttcttgcc atgcttagaa actgtcttaa ttcacagcaa  104220
tgttgtgtgg tggaaattaa ttaatacatg caaaatgttt agcacagaac gcccttggag  104280
tttcacattt ggaactagaa atttagatgt tatccagaag aaaacgttta gaaaaaagtc  104340
acagatctta acaggaccct gtacggcatg gcccctggtt gactctggtt ctctgatcac  104400
gtctccgatt tcctccagtt ggtacacgca gcttttacat gtgcttttcc ctctggtggt  104460
cccacagtca gatcccccat cctaccttct caaaaaaaac cctgcttctc aggggtgaca  104520
ctcaacatgg caatatagca tctaatcaca catttctaca gtcaccaggt tgaaggctag  104580
actggcagtt ccatgagggt gaaggacaca tctatttctt ttattgtttt ttagagatag  104640
ggtctcgctc tgtcccccag gctggagtgc agtggtgtga tcatggctca ctgcagctcc  104700
aactcctggg ctcaagcaat cctcccacct cagcatcccg agtaggaaca tgtctatttc  104760
ttcaccaccg tatctgcagc ccctagcaaa tggttaatac agagcagttc cttactaaac  104820
atttgtggcc agagggaagg aagagcaacc ttggggtaag ccccatcact gctctctcct  104880
acatccacac agtttcacat ctgtgacccg ggtggtgtca acaggaggct gtcaaggatg  104940
actccaactc cacgtactca agaggaagag gcagaaggca gctgacaaag ccctcttcaa  105000
actggcccca ccagcaattt atgtggcaaa aagatggtca ttgttttaa tatacagtct   105060
cttctcaccc aatcggtggt actgacaagg atattttcc ctatctgtat gctactgtag   105120
tcattttaat aagaatttgc aaagtgaatg tctaggacac ctatgcatat gagccaaaaa  105180
cttgctccaa agcctccccg tgcatttgga aacaccaaat gttgatatct gaaactaact  105240
tgcagtctgg gtaacaaagt aagaccgcat ctccaccaaa aaaaaaaga aaaaaaattt   105300
taattagctg ggtgatggca catgcctata gtcatagcta ctctaaaggc tgaagcgagg  105360
```

```
tcaaaggttt gagaccagcc tgggcaacat agtgagacct catctctaga aaaaaaaaaa 105420
aaagttttgt aattacccag gcatggtggc ccacacctgt ggtcccatct actctagagg 105480
ctgagacggg aggattgctt gaacccaggc atctgaggct gcagtgagcc atggttgtgc 105540
cattacactc cagcctgggt gacagaccaa gactctgtct caagataaaa acaaaacaac 105600
aacaacaaca acaaacctat atgaatcaca aaattaaaaa gatgatttat ccatacttac 105660
attgttacaa acactatttt tccacaatta tgaactggct ctgataataa gaaaaaagca 105720
atatatggcc aggcgctgtg gctcacacct gtaatctcag cactttggga ggctgaggca 105780
ggcggatcac ctgaggctgg gagttcaaga ccagccccat ctctactaaa aatgcaaaaa 105840
atagccgagt gtggtggcac acacctgtaa tcccagctac ttgagaggct gaggcacaag 105900
aatcacttga actcaggagg cagaggttgc agtgagccga gatggtgcca ctgcactcca 105960
gcctgggcaa cagagcaaga ctctgtctca aaaagaaaa aagaaaaatg tgatatgttg 106020
gctattatac attacagctg gttaaaatta cagcatgaag aactacannn nnnnnnnnn 106080 nnnnnnnnnn nnnnnnnnnn nnnnnnnnnn nnnnnnnnnn nnnnnnnnnn nnnnnnnnnn 106140
nnnnnnnnnn nnnnnnnnnn nnnnnnngca agtagttcat catcaaataa tattagctaa 106200
tactgactgg gtgcagtggc ttacgcctgt aatcccagac ctttgggagg ccaagatggg 106260
aagatcactt gaacccagga gttcaagacc agcccaggca acatgatgag atcctgtcta 106320
tacaaaaaaa aaaaaaaaaa aagaaagaa attagctggg cgcctgtggt cccagctact 106380
cgggaggctg aggttggaga atcgcttgag cccaggagga gagtttgca gtgagccatg 106440 atcatgccac tgcactccag cctgggcaac agagcaagac cctgtctcaa aaaaaaaaa 106500 aagatgaaga gtagtagcaa ctatgagttt cagcctgtta aactcaagac gtgccagaaa 106560
taatgaattt ttcagttttt atttattttt tatttttggga caggatgtca ctctgtcacc 106620
caggctggag tgcagtggca tcatcaccac tgctcactgc atcctggact gcctggctc 106680 aagtgatcct tcagctttag cctcctgagt agctgggact acaggtgctt gccaccatgc 106740
ccagctcgtt tttgttgttg ctgtttgttt gtctttctgg gtttttatttt gttttgcag 106800 agacagggtc tcaccatgtt acccaggctg gtcttgaact cctgggctca gcaatcctc 106860 ccatgtcggc ttcccaaagt gctggaatta taggcatgaa ccactgtgcc tgccccagtt 106920
tttagaagtc gacttgcttc tgactttaa aaccctgtag attaaacttt aggtattctt 106980 aattttttt tgtcttttgg agacagtctc actctgttac ccaggctgga gtgtagtggc 107040
accatctcag ctcacagcaa cctccccctt ccgggttcaa atgattcttg tgccttagcc 107100
tcccgagtag ctgggatcac aggcaccagc caccaagcct ggctaatttt ttttttttt 107160 ttttttgagac agagtctcgc tctgttaccc aggctggagt gcagtggtgc aatctcagct 107220
caccacaacc tctgcctcct gggttcaagc aattctcctg cctcagcctc ccaagtagct 107280
gggactacag gcatgcacca ccatgcctgg ctaattttg tattttagt agagacaggg 107340 tttactatg ttggccaggc tggtcttgaa ctcctgacct cgtgataagc ctggctaatt 107400
tttgtatttt tagtagagat ggggtttctc catgttggcc aggctggtct cgaactcttg 107460
gcctcaagtg acctgcctgc cttggccttc caagtactg ggattacagg cgtgcgccac 107520
cgcacccggc ctacattcgg tattcttagg gcttgaggta gatcatatta ttcaaaagat 107580
ggcaacaata tctcccaccc aatttggtat tcttttttta tttttatttt ttatatattt 107640
ttattattat tattactatt attattatta ttataatcac ttcggctgcg gagtctcgct 107700
```

```
ctgtcgccca ggctggagtg cagtggtggg atctcggctc actgcaagct ccgcctcccg   107760
ggttcacgcc attctcctgc ctcagcctcc caagtagctg gactacagg cgcccgccac    107820 tacgcccggc taattttttg tatctttagt agagacgggg tttcaccgtt ttagccggga   107880
tggtctcgat ctcctgacct cgtgatccgc ccgcctcgtc ctcccaaagt gctgggatta   107940
caggcgtgag caccgcgccc ggccggatct agggatcttt agatgttcct gagatcctta   108000
aaaagggacc tgtgaagtta aaacaatttg tcatactact gttaagacat tgtccttta    108060 actcgagtgt agaatggagt tctcctgagg tgtaatacat aatgtgatac tgcaatagat   108120
tgaataaagc agatataaga atctgtctcc tacgaagcca gacatgaaat acatttgcag   108180
aaatgtaaaa ccattgtcct cataattttt tgttttggaa aaattatttt tttagagaca   108240
gggtcttgct ctgttgccca ggctggagtg cagtggtgca atcacagctc actgaagact   108300
cgaactccca ggctcaagcc atcctcccat ctcagcctct caagtagctg gaaccacagg   108360
tacacgcagg ctgggcttat ttattttttg agacagagtt ttgctcttgt tgcccaggct   108420
ggagtgcaca cattacaggt gtgagccact gtgcctggct caagtttttt ttttaataa    108480 aaatgttact tatataaaca tgacatgtca ttttaaaata ttctagcaac ttttttttt    108540 tgagacagtc ttgctctgtc gcccaggctg gagtgcagtg gtgtgatgtc acttactgca   108600
acctctgcct cccgtccaaa ttctcctgcc tcagcctccc gagtagctgg gattatagat   108660
acctgccacc atgtccagct aattttttt tgtattttta gtggagatgg ggtttcacca   108720
tgttcgccag gctggtttca aaatcctgac ctcagctgat cagcccactt cggcctccca   108780
aagggctggg attacaggtt gagccatggc acccagcctt ttttcacctt ttttggacac   108840
agggtctgtc atccaggatg gtgtgcagtg gtgaaatcac aggtcaccac agcctggacc   108900
tcctaggctc aagtgagcct cctggcccca cctcccaaaa tgtgggggtt tcaggtggaa   108960
gccagcacac acagcccatt tttcatttc cattggcaaa atccaagtt tgataaccta    109020 cctataagaa gatgggtact ctgtacattt ccagaacaaa taaagtggtc taacacttgg   109080
gagtgtttgg aagaatctgc caaaattaaa atgcacaaat ctggcagggt gtggtggctt   109140
atgcctataa tcccaatacc ttgaggtcta ggcaggagga tagctagagc ccaggagttg   109200
aaccagccca ggcaatagga actggggcca tatgtgataa acgtgcccat gaacagccac   109260
tgcactggcc tgggaaacaa gagcacggcc tcataattat tggggaggag ttgagaattg   109320
agcacagcgg ggagaaatgg gagtttgttg tctgagtagt cagcagttat tctcttctct   109380
catccatgta cagtttagca ctgacttctt cagggacgag tgagaaaatg ccaccacttc   109440
acaatggtag agggtgggtg aaaaagttat tagccaggca ccaagaacca atctgaagcc   109500
aagaacagca atgcaaagcc aacaaactag ctctcttgta gacaccactc ccttccaatc   109560
ccattctcta ctaaggaaaa cccccaggtg agctggcatg tcaaactac accttcaggt    109620 aggtaagaat ttttttttaaa aaccaaaaat taaaaaaaga gacacaaaat gtagtcagct   109680
atttaattag gttcttaaga catttagaac accaatttgt gaggataaat tccattcgtc   109740
agagcaaaca cagatcgcag gtagccctgg agctgaggaa tagctttgat ttttggtaaa   109800
atttgtgagt ccacagcttt ctgatcaatc ttgcgctgct ccgtaatctc atatttctaa   109860
ataaagagaa aatcaaacat tttaaaacag gcacatacca aattacttgt aggtcaacta   109920
aggagtcctg tctcacaagt actaatcccc aagaatattt agaaaacatt aaagacaatt   109980
ttgacaatcc tttccttgga atgctgtgaa acacaaccca ttttttaatg taataaaagt   110040
agctcttaag cttttgtata ctttaggaca catcaaggat aagtaagggc acattcccaa   110100
```

```
tacgatggta gcagttaatt cccacacaat tccaccaaac tttaggattc taagttgagc    110160
tcccagactg ccaaaagaac tactcaattt agaagaatct ggaatactaa gtatctccca    110220
gcattcctca ttatttaacc tttcatttt cttcttttg tgcaacctgt ttcttttcac     110280
tcccaggtag aagggccagt gctaacacag gagatgacaa gtagaaactt acctcttttt   110340
ctgtgtcgaa gatctcacct tcctggtgtc tgggcttccg cagcttcttc ttcttgaagt   110400
aagcatcagt aagatgtttt gggattttta cattgctgat atcgattttg gttgaagtgg   110460
caatgacaaa tttctggtgt gttcttcgta gaggaactcg attgaggacc agaggtccta   110520
agggggaaaa attaatttag caaggaaaag ggggaagaat catcatcctg caatttaggt   110580
gaccattact tgttatgttg ctacacaaag aagaccactt gtctaaccca cttgcacaca   110640
aggcaatgaa atgggcctca gacacttgtg gcaataagtg tctaccatgt aggcagtagc   110700
aaacaaacgt gtatactgca agcatttaaa atggaagtt tcacagaaca tcacaatcca    110760
aggattttct taccagtcac aagtaataag ccactagcca gctgcttcag gaaaaccacc   110820
ctctgtaagt taaaagaaa ataattagtt ttctgcaatt aaaaactgac ttctgaattc    110880
ataaaatcac aggcatctaa atttgggtaa aggaaatttc tacatgtata tgtatacagc   110940
tcggcagttc tggaagcaac cacagcaagc tactaaggta gtactccaga cataaacacg   111000
tttttgagta aatgaacatg tgtaacataa tcaacagcag gaaatggcta ataaatcacc   111060
atggattaca cttcttattt gcaacaacta agttgtatct tgcagatcat ttccccttgc   111120
cccaaacata ggtaaataaa ggaaaagtac acctagcgtg caaacgcatt gccaccaggc   111180
accccaggca gctgcagtga agcgccccaa gcacaggtac tctcaccttg cccctgtggc   111240
gtccagtgag gatgatcaga atggtcccgg gggtaatgct ggctcgcagt tttctcacgt   111300
gctgactgaa gggttttttg ccgtggctca acagctttcg aggcacatct tcagtaggat   111360
aatatctagg ctgtggagag tccatagatc caacttattt aaataagcca ttcagattac   111420
tagaagcaag ctatgtcagc caaacttttg ctacagcctt tttattttaa agtataatac   111480
tgtatttata tgattccatt ttcatttctg ctaagtagac ttggaaaagg tcaattatgc   111540
ttctgcatcc tgtgtgcaaa aaaggagaca ccatttaatg aatgagatgt gtgctcaagc   111600
aaagaaagca tcaagcaagt caccctttgca atcttgagca aaaactaaac ctcagagatt   111660
acacgtgtga catgccacat tttgcagatt agggatacat ggcttgtttt ccaattcaag   111720
taaagtgtgt ccatatccta gccacttcat ctgatcctca cagcaacaag tcttactccc   111780
acttcatcca caaggaaaa caaattgcat aaagccagac actaggactg gcagatcatt    111840
tattgcagaa gttagacacc atgcaagggc cattaaagac atgactacaa ataactcaca   111900
ataacctatt tccaactata ccatatcatt agtgcagtct cactttcacc acaaacatga   111960
tcacctaatg ggaaaacgag ttcacaaaac aactgtcatc ttccctctca tgcagtaatc   112020
ttcaactgtg aaactgtatg gtgttaactt atttgggaat gttcccataa tgaaaattac   112080
agagcaaatc ctgagattac attgggtctt gtgtgtggta aagggggcca agaaacactg   112140
ctctagtggg aaatgttcta tagaacaggc tatgtattat ttcatttaat ctccataaaa   112200
actctttgag gtaaaccctc attcccatct tatcttttt tgagatgaag cctccctctg    112260
tcgcccaggc tggagtgcag tagtgcaatc tctgcctccc gggttcaagc gattcttctg   112320
cctcagcctc cagagcagct gggactacag gcacgcaacc agctaatttg tatatttta    112380
ctagagatgt ggtttcacca tgttggccag gctggtcttg aactcctgac ctcaggtgat   112440
```

```
ctgctcgcct cagcctccca aagtgctggg attacaggca ttagccacca cactcagcct    112500
cattcccata ttatatgcaa aggaacaaag cacagacgag taatttaaat tacttaagat    112560
taacagtaaa tgttgaagcc aagttacaaa cccagagccc tttatttttct atcagaaatt   112620 ctccggtatg cagaaactta cagtatctaa gtattcaaaa acatcttcac agtattcaag    112680
cataaacaga aaatccaatt tacagtcccc acatcttacc attttgcgaa gtttaaccac    112740
ccgggtaccg ccgttcttgt caccaccaac tggttttgta acagttgcga gaaccttctc    112800
cttctttttc ttttcaacct acaaggacac aaatgcatca acagtaagag aatgccaatt    112860
aaggttaaga cataatggtc cgtggtcctc ttcccttacc ttggatttag cggctgagta    112920
cttcctcttg tacatggcct ttctggaata catggcagat cgggaatacc tgccaattcc    112980
tctgacaagg acagggttgc ggctgcaatg gggcttcccc ttcttgggct ttttagcttt    113040
gaggttaccc ttttcacct tgccaccagc atcaaccttc ttggcttcgg gtttcttctc      113100
tttagtatct ggcttctcaa cttttcacc cgccatctaa aaatatttt ttgtagataa       113160 aaaaaggcat ttcaccagtc atctctctaa caagacaata atgaacctgt acatgaatgg    113220
gctgggctcc ccagactaca atccctcccc cggtaagata caggccttcc tctcaaactc    113280
tacccattct actccaacct tcactatgac tcatttgggg tttgtctccc caatacacta    113340 taaactttt tttgagaat ttgaaactac ctcacaccta ttaggttttt tgccaaatac       113400
tgagcggtca gaagtccgta caaccattat tttttattac tgttttgcga attagaaaac    113460
ttagatgcag aatgtgtcca caggttagaa gcaccaagac cagaacttga aatcccttac    113520
tttcagtacc tttcgtctta acccttaaga ccagtgtctc ttttcaagaa actcgattta    113580
ggaattgcgg acacaaacgg aatcagccca aattgagcca gagaaaaaga tcgcaaagac    113640
caagaggcga cttccggtcg gggacgctgg gagacgcgaa acctttttggc ttcagtgcgg   113700 aaccccaacg tggctgcgac aggctcagtg tcatcctctg gaaccaggaa ccaggaacac    113760
agtgcacgcg ccgtctcccc gcttcctcta acacccacca gtctgctacg ggtccccgaa    113820
agggcctcgt tcccccagcc caagagagtg gcgaagaacc ggagggagcc actacggcat    113880
tctacctcac cctctttgtg ccctgccgca aacccaaaca acaaaaatga agcgtctgga    113940
aggcctctca gttagccttg gacatgtccg acccctgtag gtgtcgactg gatgccctcc    114000
aggttcggat ggcgaaggat tgggagtcct gaactcaagt cttgcagaca ggcccgcgat    114060
tcttaccttg caagatggga aagagaatta aggtcccggc ttccggtcta taagcaatca    114120
tgggaagtgc gagtctcact tccttccgga tctggggcat catggggaat gtagtatttc    114180
cccgttaaga aaaagtagt aaatcctagg ccgggtgcgg tggctcacgc ctgtaatccc      114240
agccctttgg gaggccgagg caggaggatc ctctgaggtt ggcagttcga gaccagcctg    114300
gccaacatgg tgaaatcccg tctctactaa aaatacaaaa ggtagccggg cgtgggtggt     114360
gcgtgtctgt aatgacagcc agtcgaggcg cggaggcagg agaatcactt gaatctggag    114420
gtggagattg cagtgagcca agatcgcgac actgcgctct aggcaacaga gcaagattct    114480 caaaaagaa aaaaaaaaa aaagggccg gacacggtgg ctcacgcctg taatcccagc        114540
actccaaaga tcgtgccact gcgtgccacc gcactccagc ctgggaaata gagccagact    114600
cagtctcaaa acaataacaa caacaaaaaa aagaaaaaa gaaaaaaat tagccgagtg       114660 tggttgttag tgcctgtagt cccagctatt cgggaggcta aggcgggagg atcacttgag    114720
tcttggaggt ctgggctgca gtgcagtgaa ctctaatctt gtcacttgag attaggtcag    114780
tggtcccctc ttcccttacc ttggatttag cggctgacta cttcctcttg tacatggcct    114840
```

```
ttctcattcc cgtcctccgg cctggcctac agaatgagac tctgtcttaa aaaaagtaaa    114900
aaaaaattaa agtgaggata acaatagtaa cttacttcat aaggatgttg ggaacattaa    114960
ataatatata caacagtact gagaagcata tttgattatt tgatggatgg taaatgctac    115020
ataagtgtta gctctttttt tttttttttt tttttttttt tttttttttt tgagatggag    115080
tctcgctctg tcacccaggc tggagtgtgg tggcacgatc ttggctcacg gcaacctctg    115140
cctcctgggt tcaagtgatt ctcctgcctc agcctcccaa gtagcaggga ttacaggcgc    115200
acaccaccat gcccagctaa ttttttgtat tttagtaga gacagagttt caccatgatg     115260
gccaagctgg ttttgaactc ctgacctcaa gtaatccacc cgcctcagcc tcccaaagtg    115320
ctaggattac aggcgtgagc caccgcacct ggcgaactgt tagctcttgt tattgtcacc    115380
atcaccacta caatcatctg atcatcaaca tcctagttgt tgtcaagtat tctgctaaag    115440
tttatgcatg ggagataata ggcaatattg catacaatgt gccttgcttt atttcattta    115500
attctcccaa caacctgtga atgatactat tatgaggaaa ctgagtctca aggacattaa    115560
gtaacttgct cacagcatag atctgattcc aaagattgca ctcttaacca ttaggctgca    115620
agattaaaga gatgattaat gaagatgcat gagagttttg ctcatgttag aattaaaaat    115680
aagaatattt attatctttt acaaaataca caacacagta tatgtgatag ttctttactg    115740
cttcaaagcc cttaagccaa catgtacaca tttgtaatac cttctagctt gcgttttcca    115800
ttttcctcca ttcgtttctt tctggttgct agagcttttc accttgatttt tttcagatcg   115860 aaaccacctg cttcatggct gtgtctctgg gaatcattta gcctttttct ggttctgatt    115920
cactgaggat acaaatacaa tgatcagatg aacactgccc ttttttttga gaatgggaat    115980
gtcagcagct ttatttgttt agcttcctca gcaaagcacc tcttagaaac ttcaactgca    116040
gaaaatgtac cacaatgaat gaatgagatg cacagttgct tacgtgggcc cctcaaaatt    116100
gctggcaatc tcagataatt tcacctagtg aacgccccaa aatatgtgtt gaatgacctg    116160
tcattaaaat aaaaacgtag atgaaccccc tcttgtgttt tgttgcggta ttgcaaaatt    116220
tacaattcat tagttgggca aaataccatg ttagttataa agtaaatgtt tttattaagt    116280
ttagttttgc catatataaa attctctgaa atttgtgcag cactttaatc acaaagcaga    116340 cattttttgca gacacttaat ctttttttttt ttttctgag atggagtctt gctctgtcgc   116400
ccaggctgga gtgcagtgcc gtgatcttgg ctcactgcaa cctctgcctc ctgggttcaa    116460
gccattctcc tgcctcagcc tcttgagtag ctgggattac aggtgcccgc taccacacct    116520
ggctaatttt tttttttgaa acagagtctt gctcttttgc ccaggctgga gcgcggtggc    116580
atgatctcgg ctcactgcaa ccttcgcctc ccgggttcac gccattctcc tgcctcagcc    116640
tcccgagtag ctgggactac aggcgcccgc caccatgcct gactaatttt ttgtattttt    116700
agtagaggtg ggggtttcact gtgttagcca ggatggtctc gatctcctga cctcgtgatc    116760
tgcccgcctc gacctcccaa agtgctggga ttacaggcct gagccacctt gcccggccaa    116820
ttttttgtgt tttattgga gacaggattt caccatgttg gccaggctgg ttttgaactc     116880
ctgacctcag gtgatctgct cacctcggcc tcccaaagtg ctgggattac aggcgtgagc    116940
cacctcgccc agcctaattt tttttttttt ttggagacag agtctcgctc tgtcgcccag    117000
gctggaatgc aaggtgagat catggctcac tgcagccttg acctcctggg ttcaagcaat    117060
cctcccacct cagcccctg agtagctggg agtacagtgc acaccaccat acctggctaa     117120 ttttttaca ttttttgtag agacagggtc tcacaatgtt gcctcagctg tatttttgt     117180
```

```
ttgtttgtta ggcagtaaat cttttaaagc ctggccaaca tggtgaaacc ccatctctgc   117240
taaaaataca aaaattagcc aggcatggtg gtgcatgcct gtaattccag ctacttggga   117300
ggctgaggca cgagaatcac ttgaacccgg gaggcagagg ttgcagtgag ccgagattgt   117360
gccactgcac tccagcctgg gccacacagt gagactctgt ctcaaataaa taaataaata   117420
aataaataaa taaataaata gaaaaatatc tttatatgtg ttatgtatgt gtgtgagcct   117480
gtgtatggga tgagtttgtg tgtttgtata tgtataaagt gtggaaagac atacaccaaa   117540
ccattaacac tgctggggat tgggatatgg agtacgtatg catcaaggaa cagagaaaat   117600
tactgtttgt tatttagttt gttgcaagga acttgtattg cttttgtaat tgagaaagaa   117660
attcaaataa agtaatggct attatctgaa ttaatctcta aatgaatata tcttttttaaa  117720
attaagatgg agttggccgg gtgcggtggc tcacgcctgt aatcccagca ctttgggaag   117780
ccaaggcagg tggatcacga agtcaggaga tcgagaccat cctggctaac acggcgaaac   117840
cccgtctcta ctaaaaaata caaaaaaatt agccgggcat ggtggcgggt gcctgtagtc   117900
ccagctactc gggaggctga ggcaggagaa tggtgtgaac ccggaaggca gagtttgcag   117960
tgagccgaga ttgtgccact gcactccagc ctgggcgaca gagtgaagac tccatcttaa   118020
aaagtaaata aataataata ataaaataat tcagattgag gtttttttgt tttgttttgt   118080
tttgttttgt ttttgctatg ttgcccaggc tgccagtctg gtctcaaact cctgtctcaa   118140
gagatcctcc tgttagctac catgcccggc catataaatg aatatgccag gcactactcc   118200
aggcatataa agatgggaag accggccgga catggtagct catgcctgta atcctagcac   118260
tttgggaggc ggaggcagga tgattgtttg agcccagggg ttttagacca atctgggtaa   118320
catggcaaaa ccctgtctgt attaaaaaaa aaaaaaaagg aagacaatga ctttgtctta   118380
aaaggagatc ataatctaaa gaaagacaca gaacaacaat gacagaaccc acaatgatgt   118440
tgaaatgtgt taggtgctga tagaagcatg aagaggcagc cccaggagca taggaaagga   118500
gtctctcttt tattctcaaa aagtgaaaga atgttttctg gaggagctgc ttaagttgga   118560
gtttaacctt gcatgactgt tttccaggtg gagaagggtt tgaagagtat tccaggcagt   118620
aggaactaaa ttttggaaga cagggatgca agaaacagct agaagccttt agaaactgct   118680
agattatgtg agggtgttgg cacaggccat atctagaacg gactgatgtg ctaagggaag   118740
gagttcaact taatgctaga gggttgaac ctccttcata caacagggga ggggagtgac   118800
gtgattagat ttgtattttt aaagattat tcattctagc tgcagagtgt gcagaatata   118860
ggaaacacta ggaaggtagt agttcctgca ctcaaagagc taatagttta ctttggaaaa   118920
gagacaaatg atagccagct tttatcaagt gctgactttg ccagacactg ttctgagtat   118980
ttcacaaacc tatcctatgg taggattttg attcctactt tgcagagaag gaaacagaca   119040
cagaggagtc aaatgacttg cttatagaca cccaggcagc tagatcaaga acttaattgg   119100
cagccaggcg ccgtggctca cgcctgtaat tccagcactt tgggaggccg agtcgggtgg   119160
atcacgaggt caggagatca agaccatcct ggctaatgcg gtgaaaccct gtctctacta   119220
aaaaaataca aaaattagc cgggcgtggt ggcaggtacc tgtagtccca gctacttggg   119280
aggctgaggc aagagaatgg cgtgaaccca ggaggcggtg cttgcagtga gtcgagatca   119340
cgccactgca ctccagcctg ggagacagag tgagactgtc taaaaaaaaa aacaaaacaa   119400
aaaaacccca caaaacttaa ttggatgctt cctatatgat acggctctta gatttatagt   119460
gtagcatgtt aggttctaag gataggtgtc ttggtgacca tctgacctgc actagagaat   119520
cgggtgaggc ttgtattcca gaggaagtgg ctcctagcct gagatcagag gcatagagtt   119580
```

```
gatgtggagg acagtcagga agaaccctct ggggaaagaa agcagattgt taaaaggctc 119640
tacgctggga aagaatatgg catattgagg ggagctgaaa gtcattcagc atggctgggt 119700
catagagaat gaagcgagta gtggggagac ggggtggtga agtgattggg gaccagagtt 119760
aaaaaaactc tggtgcattg ctcacgcctg taaatccaag gccttgggag gtcaaagtgg 119820
gaggactgct tgaggccagg agttcaaggc cagcctgggc aacatagcaa gaccttgggt 119880
ctaaaaaaat tttttttaaac ttttttttgg gccgggcatg gtggctcacg cctgtaatcc 119940
cagcactttg ggaggctgag gtgggtggat cacttgaggt caggagttgg agaccagcct 120000
ggccaacatg gcgaaaccct gtctctacta aagatacaaa aaaaattagc tgggcatggt 120060
tgtgcgtgcc tgtaatccca gctacttggg aggctcaggc aggagaattg cttgaatctg 120120
ggaggtggag tttgcagtga gccgggattg cgccactgca ctccagcctg ggtaacagaa 120180
tgagactcca actcaaacaa aacaaaaaac tttttttttt ttgtagggac aggggtctta 120240
ctctgttgcc caggctgttc ttgaactctt tgggctcaag aaatcctccc acctaggagt 120300
cccaaaacac tgggattaca gaggtgagcc accacatcca gggggataaa cctttttttt 120360 tttttttgg acttcattct aaaatcaagg agaagccatt ggtgaattca atgtaggag 120420 tgactagttt tgcagttttt tttttttttt ttttgagat ggagtctcgc tccgacgccc 120480
aggtgggagt gcagtggcgc aatcttggct cactgcaagc accttcct gggttcaagc 120540 aattctcttg cctcagcctc ctgagtagct gggactacag gtgcctgcca ctgcacccag 120600
ctaaattttg tatttttttt tttttttttt tttttgaga cagagtctcg ctctgttgcc 120660
caggctggag tgcagtggtg tgatcttggc tcactgcaag ctccacctcc tgggttcacg 120720
ccattctcct gcctcagcct cccgagcagc tgggactaca ggtgcccacc accacgccca 120780
gctaatcttt tgtattttta gtagagatgg ggtttcactg tgttagccag gatggtctcg 120840
atctcctgac ctcgtgatcc gcccgcctca gcctcccaaa gtgctgggat tacaggcgtg 120900
agccaccgcg cccagcccta aattttgtat ttttagtaga gattgtgttt gaccatgttg 120960
gccaggctgg tctcaaactc ctgacctcag gtgatccacc caccttggcc tcccaaagtg 121020
ctgggattac aggtgtaagc caccgcactt ggccacagtt aattgtattt ttagtagaga 121080
cgagggttca ccatgttggc cagactggcc tcaaactcct gacctcaggt gatccacctg 121140
ccttggcctc ccaaagtgct gggattacag gcatgagcta ccgcgcccg agtgacccgc 121200 ctagttttgt agtttagatt actctggcta ctatgtggag attggattag gaagtttagg 121260
cctgcaggcc tgagatcagt taaaatgtag cttgtcatct agctggccag gatttaggga 121320
gagggacaac tgcttgttaa atggctctta tgtgaattaa attggcatat attaaaggtg 121380
atctttgtaa ggagcacatg atgctgaagc agttagcaca cagtatgaga ctcacttgta 121440
tatgaatgaa atgggcaagc attaaaaaaa tgaggatttt ggagctatac agatatgggt 121500
taaacttatg gctctgccat tcactagatc tgtagccttt atttatttat ttttgagaaa 121560
gagtctcacc ctgtcaccca ggctggagcg cagtggtgca gtctgggctc actgcaacct 121620
ctgcctgtcc ggttcaagca attctcccac ctcagcctcc ggagtagctg ggactacagg 121680
tgtgcgccac caagcccgac taatctttgt attttttagtt gagacggggt ctcaccatgt 121740
tggccaggct ggtcttgaac tcctgacctc aagtgatctg ctctccttgg cctcccaaag 121800
tgctgggatt acaggcgtga gccaccacgc tcagctagat ctgtagcctt caatgagtca 121860
tatgcgcatc aatcaagtaa aagctctact cttctcaatc tggtctgagc taccattatt 121920
```

```
cccagaccag aatactatag tattccgtat tttgactggc ttctctgttt ctggccttgc   121980
tctcttgctc gagcttcaca gagtgtccaa agtaatactt ccgtaccacc cggcccggct   122040
tttttttttt tttttttttt tttttttaag agacatggtc gcaccatgtt gcccaggctg   122100
gtcttgaact cctaggctca agcaatcctc ctgcctcagc ctcccaaagt tctgggatga   122160
aggcgtgagc caccatacct ggcctgagtg cagtggcgcg atctcggctt tcagcagcct   122220
cgaccttcca ggctcaagca atcctctcac ctcagcctcc cgagtagctg ggactacagg   122280
cgcgcgccac cacgcccggc taattttttgt attttttgta gagatgggat ttcactattt   122340
tgcccgggct ggttcccaac tcctggactc aagcgattcg cccgcctcag cctcccaaag   122400
ggaagtgctg ggatttcagg cgtgtgccac cgctcccacc ccaaagtagt atttattgta   122460
attattatta ttattttgag acggagtctc gctctattgc caggctggag tgcagtggcg   122520
cgatctcggc tcaatgcaac ctctgcctcc cgggttcaag cgattctcct gcttcagact   122580
cccaagcagc tgggactaca ggcgcccccc accacgccag gctaattctt gaattttttag   122640 tggagacggg gtttcaccat gttggccagg atggtctcga tctcttgacc tcgtgatccg   122700
cccacctcgg cctcccaaag tgctgggatt acaggcgtga gccaccgcgc ccagcctatt   122760
attatttttt taggcagtgt cttgccctgt cgctcagggt gtagtgcagt ggcgtgatca   122820
cgactcactg cagccccgac ttctcgggct taagttatct tcccgccgca gcctccacgc   122880
ccggttagtt ttttgcattt tttgtagaga tgaggtcttg cttttttgcc caggctggcc   122940
tcgaactcct tggcttaagc gaacctcttg ccgcagcctc ccaaagtgtt gggattacgg   123000
gcgtgaacca ccgcgcccag cctactatct ttatcttaca gaaagaaaag aatggaggaa   123060
accgaggctc ggagacagta ggtaatttcc ccaaggttcc acagctaatg agtggagcgg   123120
cgatttgtgg aacgaaatga atgaaatcga tgtggcagcg ggcccggacg ggtcggtggc   123180
gtagacgcgg agcgcgcagc tcacacctgg cggccgcggt ttccaggagg aagcaaggat   123240
gctttggaca ctgtgcgtgg cgcctccgcg gagcccccgc gctgccattc ccggccgtcg   123300
ctcggtcctc cgctgacggg aagcaggaag tggcggcggg cgtcgcgagc ggtgacatca   123360 cggggggcgac ggcggcgaag ggcggggggcg gaggaggagc gagccgggcc ggggggcagc   123420
tgcacagtct ccgggatccc caggcctgga gggggggtctg tgcgcggccg gctggctctg   123480
ccccgcgtcc ggtcccgagc gggcctccct cgggccagcc cgatgtgacc gagcccagcg   123540
gagcctgagc aaggagcggg tccgtcgcgg agccggaggg cgggaggaac atgacatcgc   123600
ggaggtgagg agccccgagg ggcccggcgc gggcctcggc ccggccaccg ccgcgttcgg   123660
ttagccccgt ccggaagggg gcgccccggc cgggcttcgg gctcccgccc cgggtcgggg   123720
ttgggggccg gttccctcct cgtcccctcg ccctccaggg gccggggcc ggccccaccg   123780 cgcccccacc cctcgggtcc ccattcattt cctgcctccc cgagttccgg ctgcggcagc   123840
cccggggatg cccgtcaggc ccggggcagg tagagccgcc gagggaacca cgggtgccag   123900
cggccaggct cagcgccgca ttcctgaccc attgcctcat gagaattgcc tcatggtgat   123960
tccgaaataa ccctgctcac ttggggaggc tccttgggac acgagagggg agttgcgcgg   124020
ggccgggccc ccagtggtct agtcgttctg gctcactgtg ccactttcgt gcatttgggg   124080
acttcacgca ggaccctga cccttttata tgcctctttg tgtcttcttt tcctcctacc   124140
cctcacgtgc cagaaatgga aaaactgact gtatctgcag ccactagaag tatttccttc   124200
ctctgcgatc ttcgctttgg gagatggaaa ggaagggagc cgcatctcgt tatttaatcc   124260
ttcactgcaa ccttaacagt caggtcactt tactggtacc cgttttatgg atgaggaaac   124320
```

```
cgaggcccag aagcaacatg ctagtaaatg acaagatttg aaacttagga ggattagtga   124380
gttaatgaga tcctttgaaa ggtcagggta atactactac taatagctaa catttgctta   124440
gttctgacca cagccctatc agatggctac tattatcccc attgtaaaga tgagtaaacc   124500
gagtttcaga ggttaagtaa attgcctaac ctcacagcta gtaggtggtg gagacagaat   124560
ccctactttt aatcactatg ttgcttctat tattttgtaa ctattgctaa ccatttgtaa   124620
gccttaattt tgttgtcaaa cagtagtgtg acctgttgtt ttcagatagt gatcctgcta   124680
ttttgtatag tcactctata taccactcac acttaagacc cattgtctat tcttttccat   124740
gattgttcaa ttatggtcac tgtctcagac atttaaaaaa cgattcaagc tattgaggct   124800
atttgaatga gattttcttt tcttttttc tttttttt tggagacgga ggctcactct   124860
gttgcccagg ctggagtgca gtggcgcaat ctcggctcac cacaatctcc gcctcctagg   124920
ttcaagcgat tctcctgcct cagcctccca agtaactagg actacaggcg caccactatg   124980
cccggctaat ttttgtattt ttagtagaga cagggtttca ctatgttggc caggctggtc   125040
tcaaactcct gacctcgtga tccgcccgcc ttggcctccc aaagtgctgg aattacaggc   125100
gtgagccacc gtacccagcc tgaatgagat ttttcaaaat attaggaatg tctcctccaa   125160
acacacctgg catgttattc atacatggat ctggaattta aaaagggag aaaaagaaaa   125220
ctgagaactc gtaggaagtg agtgacttgg acaggtcggt tggcaagtgc ttacagatct   125280
gggtaatata taactgcatt tcaacagaac agtgtatagc ctcaaatgtt ctaattcttt   125340
agggagcttt taaataaaca gttgtctatt ctttaatctg tcaaatagtc attgagcctt   125400
ttgttcctgg tgtctgctct tccagacaag taaggatctg ctgctttagg agacatcaga   125460
cggggctggg ggttgggaaa aggtctgggt agtaatagac cctacattgt ccagtttgtt   125520
catttagaag catagaagtg tgggcatagt caaagtagca agtggtaaag atgacagttt   125580
gaaatggagt aattccttct cccctccagc cctggtatta tgcaccaccc aaaaagccgg   125640
gttatgaaca taatacacat aattttgaat gattcattat tttttggatt ataagcctgt   125700
tttatttgtt aaccagcctt aatgaggtat aaatgacatg caattaattg catatattta   125760
aatgtacaat ttgatcagtt ttgacataca tatacacttg ggaaaccacc accatagtca   125820
agataatgaa cacatctatc acccctggta attttgcctt atgttcttta taatccttcc   125880
tttgttctta ggcagccact attctgcttt ctgtcactat gtattagttt gcatttccta   125940
gaattttatt tttaaaaatt ttaaaattgt ttgaatagag atggggtctc actgtgttgc   126000
ccagggcagt ctcaaactcc tgggttcaag tgatcctctc accttggcct cctgaagtgt   126060
tgggattata ggcatgagac accctgccca gccctagaat tttattatta ttgttattat   126120
tgtgtttttt tgagataggg tctcactttg ttgcccaggc tggagtgcag tggtgcaatc   126180
actgcagcct tgttttccta ggctcaatcc atccccctc ctcagctttc cggttactgg   126240
ggctacaggt gtgcaccacc acacccggct aattttttgta tttttttata gagacagggt   126300
tttgccatgt tggccaggct ggtctcaaac tcccgggctc aagcgatctt cctgcctcgg   126360
cctcccaaag tgctgggatt acaggcatga gctattgcgt cccgccttca aattacttta   126420
acctagtatt aattcattca acaggaagtt aatgagccag gcaggataaa gcagtaagat   126480
aggaaaatat tgctattttc atggctgaga gagagcagac aaacacatga ctaaataggg   126540
caatttcagg tagtaataaa ttctaggagg gaaaaaatcc cacagaaatg tgaggatggg   126600
agaatgcagt tagttttgat aggtggttta gagaaggtga tcgtgtgagc tgacacctga   126660
```

-continued atgacaatta gtagtctgaa ttttgttttg cttaattatc aaaataactc ctcttgggtt 126720
cggcttttat atgcatccag taattaaaat gtaagtatat tcaatgtact gatatctctc 126780
agcatcatag gtaggaaaac taaggcattc agcaattaag tgactcctcc cttgatcatg 126840
tagcagtgat agtactggat ttagattttg aggttgcttc tctgcccttt tctgcctttg 126900
tgaaaccaac aaagctgcct gtattttcca actcttcctt cagcatgtgg tacctccttt 126960
acatctgttt ttgttgctct gaaatccata cgcgacgatg agctgagagg ggcagaaaat 127020
tgagcttgtt ctgagactgg aggcttttgg tttatctctt gcaggtcaag tacattttgt 127080
cctgggctct ccctggtggc cacgtttgtt tatctcctgc gggagtaaat aaacttgcct 127140
tgctgaaaaa taacagttct gtgtctttgc agtggaaact gggatgtctt tattaacgtt 127200
aggtcctgat gtaaggccaa gtttttggtt agagttgctc aagtgcagag gccactgcta 127260
agatgactta cccctcgtgt ccatggtcaa tgtggagact gttatgagtg gcacatgatg 127320
ctggaaaagc agagccaact catgtttgta attgtcctag caggccgtgg tgtactttgt 127380
taggcagcca cagaacaata gagaaactca gcttattccc cttccctctg ggaaacacag 127440
acagtacttg ccatccaacg ccaatgtttt taaggaagaa agaggcaaaa agtgatgttg 127500
gcaaggtctc tgggagttgt ggaccccaac caaggattgg agaccctgaa atggattcag 127560
atgccctaaa atgcagccca gttcattact atgaattttg gaggactttg tgccttgagc 127620
aaatgtgtat atgtgacgct ctttgacaac actgaaatag gaaaaatact atccatgttc 127680
gcgaggagca ctgaatttag agagggagac agacttttat gccagcatca aatgaatttg 127740
ataaagctag taccaaaatg aaatttgaaa tttttttttt ttgaaataga gtcttactca 127800
gtcacccagg ctggagtgca gtgatacaat attggctcac tgcaacctcc acctcttggg 127860
ttcaaacaat tcttgtgcct cagtctcctg agtagctggg attacaggtg cgtgccacca 127920
tgtctggcta atttttatat ttttagtagg gatggggttt caccatgttg gccaggccgg 127980
tcttgaactc ctggcctcaa gtgatctgcc caccttggcc ttccaaagtg ctgggattat 128040
aggcatgagc taccacacaa gcctgaaatt tgaaatgtat tggtatagaa tatactgttt 128100
agaatgtatg tgtatatatg tatatttgta tactcatata aacacaaata cacattgtat 128160
gtgtttctgt aatatgtata tctgtctaca catacatgta tatacacaca tacaatgtct 128220
tttttttttt tttttttttt tgagacaggg tcttaccctg ttgcccaggc tggagactgc 128280
agtggcataa tcttggctca ctgcagcctc gacctcctgg gctcaagtga tcctcccatc 128340
tcagcctcct gagtagctgg gactgactac aggcacgtgg catcaaactt gtccaatttt 128400
tctatttttt tgtagagtta gggtcttgct ctgttgccca ggctggtctc aaattcctgg 128460
gctcaagctg tctgcctgcc tcggccttcc aaagtactag gattacagat gtgaaccact 128520
gtacctggcc tttacaatgt ctattttaaa gataatggtt caagttttta tcatcccact 128580
ggcctactct aatgaaacat ctatccattc attgaagaat tatttatggt gggataactc 128640
tgtgccaggt accgtgctag gcattgagta ttccaggttt taggaaacag cacatgcaaa 128700
agtgctgaag tgggagaaga tctcggagtg attgaaggct aggagagagc aagtgtggga 128760
gctgtgaggc tgggaaggtg ggaggtaggt gggagcagac cacataggga ttcttaatgt 128820
ctttagtgtc atgtggacca tggagaggag tgtagattgt atttttagag caatgcaaaa 128880
tcatagaagg atgtgatcgg gggagtggca tgagctgatc tatttaaaaa tatttctctg 128940
gctgctgtga aggaaggatt gtaggaggca ggagtagatt cagggagatg agacaagtga 129000
tgagagaggc tttgaacttg ggtaaaagta gtttgtggaa agtctttttt ggaggtagtt 129060


```
tttgtttatt gccttgtcat caaagcagag atgctgacca atgaaactcc atgagaaaat  129120
agtgatttat aaagacatat ctatgcactg ccattaaaaa gctgcttgga aaaaaaggat  129180
aaaaagctgc tttaacaact ttttttttg  agatggggtc ttactctgtc acccaggctc  129240
acgacctcag ctcactgcaa cctctgcctc ccaggctcaa gcattctccc acctcagcct  129300
cccgagtggc tgggactgca ggcacacgcc accatgtcag gctaattgtg tgtgtgtgtg  129360
tgtgtgtgta tgtgtgtgtg tgtgtgtgtg tgtgtgtgct gggactgcag gcacacacca  129420
ccatgtcagg ctaattgtgt gtgtgtgtgt gtgtgtgtgt gtgtgtgtgt gtgtgtgtgt  129480
gtgtgtgtat gtagagatgg ggttttgcca tgttgcccag gctggtctca aaatgttgcc  129540
caggctggtc tcaaactcct gagctcaggt gatccacccg cctcggcctc caaagtgctg  129600
gagattacag acgtgagcca ctgtgcccac ctaacaactt taaaaaaatt ttgacattta  129660
gtaggatatt tattgcatta ttgttgagat ggcaaaatat tggagacaac tgaaatgttc  129720
atcagtgggg ggggctagtt aaatgaaata cagtgtagca tgcattagaa cacttttcaa  129780
gaatttaact tttttttgtag cctttttactt ataatgcttg tccctattga tgcctttttt  129840
ttcagcatga cttactcttt tactatagga tattaaaatt taattagatt agaaatgagg  129900
aatattcttg taatctgtag aaagtaacaa actataaact tattccccaa gaacaaatat  129960 aataatttttt ctggagtagc aggtaagaaa gatataaatt tatatgtata caagaaactg  130020
aaattagact ttatacattt aaaggttaca agtgcagttt tattacatga atgtattatc  130080
cagcattgaa gtctgggctt ttagtgtaac cagcacctga ataacataca ttgtacccat  130140 taagtaatttt ctcatccctc aaaccctcc  caccctgaaa ttagactttg  gatccctagt  130200
ttaaattcca ccctctcttt ttttttgagac aaggtctcac tctgtcaccc  aggctggagg  130260
gcaatgttgc aatgatagct tactgtagcc tcaacctcct gggctcaagg gatacaccct  130320
cctcagcctc ctgagtagct ggaactgcag gcgtgcacca ccacattcag ctaattttt   130380 gattttttta tagagatgag gtcggaactc ctgggctcaa gcgattctcc ccaagtgctg  130440
gggttacaca catgggccac tgcccccagc ctaaacctcc tttctcagta tagcagcctt  130500
gagatgaagt tcctgaaatt actggccagc ttgactgttt ccccacatca ctggaggagg  130560
gggatgcata gataaaacaa aatattcagc atcattgtat tttctttttg tttcatcagc  130620 atctttttt  aaaactcact tgacataagt ccctagcctc aaagagtaaa gcctttgcag  130680
aatctgcatt cagatttcgg gtgtgatttc ctgacagata gttcaggttt gtaaactctt  130740
ttttttttct ttgagacaga gtttcactct tgtagcgcag gctggagtgc agtggcacca  130800
tcttgcctca ctgcaacttc tgcccccttg attcacgcga ttctcctgcc tcagcctcct  130860
gagtagctgg gattacaggc atgcgccacc acacctgggt aatttttgta ttttttagtag  130920 agatggggtt tcaccatgtt ggccaggctg gttttgaact cctgacttca ggtgatctac  130980
ctgcctcagc ctcccaaagt gatgggatta caggtgtgag ccaccgcagc cggccaaaac  131040
tttgtttttt ttcctctttt tgttgctgag aaatgtaaac tcttacagac acaaattatg  131100
tctcccattt tttaaaaccc actcaacaca ggggtcatgt gtaataggcc ctggagctta  131160
ttttagacat tgatttgagg ctcttttccc caagtgctgg tttgtgtgtg tgtgtatgtg  131220
tgtgtaagtc tttctatgag atgagtggta cctacctggg ctgtgtgatc tttttttattt  131280 tatttatttt attttgtag  atacgaggtc tcactatgtt gctcaggctg gtcttgaact  131340
ctggggctca acctatcctc cctccttggc ctcctagagt gctgagatta caggtgtgag  131400
```

```
ccactgcacc tggccagcga tccttaataa atatagataa tggccgggcg tggtggctca 131460
cacctataat accagtactt tgaggggccg aggctggcag gtcacctgag ctgaggagtt 131520
tgagaccagc ctgggtaacg tgggtgaaac cctgtctcta cagaaaatag aaaaattagc 131580
caggtgtggt ggtgcatgcc tgtagtcaca gctacttggg aggttgagac aggagaattg 131640
cttgaacctg gaaggtggag gttgcagtga gccgagatcg tgtctttgaa ctccagcctg 131700
ggtgacagag tgagaccttg tctcaaaaaa aaatatagat ataggctggg cgtggtggct 131760
cacacctgta atcccagcac tttgggaggc cgaggcgggt ggatcaggag gtcaggagat 131820
cgagaccatc ctagctaaca tggtgaaacc ctgtctctac taaaaataca aacaattagc 131880
caggcctggt ggtgggtgcc tgtagtccca gctactcggg aggctgaggc aggagaatgg 131940
cgtgaacccg ggaggtggag gttgcagtga gccgagactg tgccactgcc ctccagcctg 132000
ggcgacagag cgagactctg tctcaaaaaa aaaaaatcta tatctctata tatctatatc 132060
tatatagata tagatataga taatgccaga tgatggctgg ttagaaggga ttgtcagggg 132120
ctggcaggtt ttgcaggtgt tagaatgagc aagatgagga gaaggatgct tacttccctc 132180
tccttgtaac tctctacccc ctcccctcag tgttttttta ttttttatttt tatttatttta 132240 tttttttttga gacaaggtct tgctctgtca cccacactgg attgcagtga tgcaatcata 132300
gctcattgaa gcccaaactc ctgggctcaa gtgatcctct tgcctcagcc tcccaagtaa 132360
ctgggaccac aggtgcgtac aactatgccc agttaagttt ttcattttttt atacagacgg 132420 ggtcttgcta tgctgtccag gctggacttg cacttctggc ttcaagtgat tctcttgcct 132480
cagtttccca aagtgctggc attatgggca taagccactg tgcctagccc atcagtgtct 132540
ttttatcctt tactcctatc aaaattcatt cactcagcag ccattgatca agtgcctact 132600
atatacatgt tgaggactgg aaatttattt gtctcttctc atcttatctg gaccctctgt 132660
gttaattgta attaactgta atcattctgt attaattgta ataaacttgt tgataaaactc 132720 aaatgaggcc ataccgtttt gccacttccc ctccttccag gttatatgga tgtacttaca 132780
ttgcaggttt catttgttgg ttcagttttt aaactaagcc ctattgtgtc aaattatgct 132840
aggtgtgaga tggggagttc aagctgtgtg ttgtcttttt tttttttttt tttttgcct 132900 cacttactaa tatacaagcg cttataacct ttgaggctgg ccctatacat taagattttt 132960
attaattcca ctgttctttta tcttctctta ctaagttctc agggtcgaat gaactctaac 133020
tgctccttgc tagtgataag caagttgcaa attacagaat tgtcagtgat tgaatacacg 133080
tattaaacct gtaactggga agcattttttg gtaattatga atacttttgg aaaaaaaaaa 133140
gctatggaag gaaagtttaa aatctacgaa agctcaagta gatggtcatg gaatagctat 133200
ttcaatttct aactatatat tacttattta tttatttatt tttgagacgg agtttagctc 133260
ttgttgccca ggctggagtg cagtggcacc atctcggctc actgcaacct ctgcctcctg 133320
agttcaagtg attcttgtgc ctcagcctct caagtagctg ggattacagg tgtgtgccac 133380
cacactcggc tattttttgc atttttagta gagatggggc tggtcttgaa ctcccagcct 133440
caggtgatct gcctgcctca gcctcccaaa gtgctgagat tacaggtgtg agccacagcg 133500
cctggccata tattgctttt tccttattat cagagccagt tcataattgt ggaaaaatag 133560
tgtttgtaac aatgtaagta tggtgatgaa ctacttgcnn nnnnnnnnnn nnnnnnnnnn 133620
nnnnnnnnnn nnnnnnnnnn nnnnnnnnnn nnnnnnnnnn nnnnnnnnnn nnnnnnnnnn 133680
nnnnnnnnnn nnnnnnnncc tgaaaaatta cacgttgtt ctaggttttc tgacttattt 133740
ccacaacttt ttagtctttc cccctggaat catgccccctt tgcataaaca ggactctgat 133800
```

```
gtacctgaag tattttcaca cttcgggtgg actttctgtt tctggggtg gttttagagc  133860
aattttaggc ctgccactag ctaccctgtt ctctacacca tgctgttttt ctcagaatgc  133920
tcttcttttg cacaaaggct tggagtagga ggttgagcag tcactcactg acgtttggta  133980
tattttcttt tttttgctta caggtactct ggaagtttgg gcattctctt taagttgagg  134040
gtgtggtttt catgtcattt tatttgttta ttgttttctt gtgtgtgttt cttagagaca  134100
gggtcccact cttgccctgg ctgaagtgca gtggtgatct gggctcactg caagctccgc  134160
ctactgggtt cacgccattc tcctgcctca gcctcccgag tagctgggat tacaggcaca  134220
tgccaccacg cctggctaat ttttttgcat ttttagtaga ggggggtttt cactgtgtta  134280
gccaggatgg tctcgatctc ctgaccttgt gattctcctg cctcagcctc cttagtagct  134340
gggactatag gcacacacca ccatgcatgg ctaatttttta tattttttg tagagactgg  134400
gtttcgccat gttgcccaag ctggtcttga actcctgggc tcaagtgatc cacctgcctt  134460
ggcctcccaa aatgctagga ttacaggtgt aagccactgc gcctggccct aattttttgca  134520
ttttttgtag agatggggtt tcactatatt gcccaggctg tcttgaact cctgggctca  134580
agtgatcttc ccatcacagc cccctaaagt gctgggatta taggcgtgaa ccactgtgcc  134640
tggctgagga ttaagtttca acctcaggggg agcggcattc aaactatagc attgtccttt  134700
agtgactggc ttagttcact tagaatgttt gtctattcat ccatctatag acactgtttt  134760
ctttcacctt ttggctttgc aaataatgct gctgtgaata tgagttatag aaaaatacca  134820
atttgaatcc gtgttttcaa ttactttgag tatatacctg gaagtggaat ttctggatca  134880
tatggtactt ccaagttttt tttttttctt ttttgagaca aggtctcact ctgtcaccca  134940
ggctggagtg tagtggcacg atcttggctc actgcaacct ccgcctcccg ggttcaagcg  135000
attctcctgc ctcagcctct caagtagctg ggattacagg cacgcgccac cacgcccaac  135060
taattttgta tttttagtag agatgggttt ctccatgttg gtcaggctgc tcccgaactc  135120
ccgacctcag gtgatctgcc tgcctcagcc tcccaaaatt ctgggattac aggtgtgagc  135180
caccgcacct ggcctccatg tttcaatttt taaacaaaca attagttaaa aaaataggaa  135240
actaagagaa tgaactattt cctgttttat tcagtgggtt ataatctgtt actatcattg  135300
tttattttga ggtacaaatt gtccctactt tggccagcag aggatcctgc agttgtctc  135360
ctgtgtcctt ttcatagctc cttgttggaa ctcttactgg cccacaatag gatgttccaa  135420
gttcatcttc ttacttttac tgccccaacg ctgggatcag ccatttcttc aaggaggcca  135480
gttcctttca ttggagaatg gaaaacccaa tatgtagaaa ccaagataga ggtgttaggt  135540
gtgattgcta ctggagtgtc attgcttcca aaccctttca gaagagacct aggaaatgtg  135600
tgtgtgtgtg tatatatata tgtgtgtgtg tgtgtgtatt cataaaagca catacacata  135660
cacataccc gaagcatgta tttctgtatt attattattt ttttgagatg gagtcttgct  135720
ctgtcgccca ggctggagta cagtggcacg atcatggctc actgcaacct ctgcctcctg  135780
gattcaagca attctcctgt ctcagcctcc tgagtagctg ggattacagg tgtccaccac  135840
cacgcccacc taattttgt atttttagta gagatggggt ttcaccacat tggccaggat  135900
ggtcttgaac tcctgacgtc aagtgatctg cccgcctcgg cctcccaaag tgctgggatt  135960
ataggcgtga gccactgttc ccatccagaa gcatacatat ctatttctat atctacattt  136020
ctgtctttac atgtatatat taaaaattac agtttgcact aatacctcca attcaatct  136080
aacatcatgg gatttattct ggctttctcc cttctcatat ttgtgtctcc ccaacagtga  136140
```

```
gaaacctggc ttgctatcct caacatggta acttatttat taagaaactt attcttttt   136200
tttttttttt tctgagattg agtttcgctc ttgttgccca agctggagtg cagtggtgtg  136260
atcttggctc accgcaacct ctgcctcctg ggttcaagcg attctcctgc ctcagcttct  136320
caagtagctg ggattacagg catgcaccac catgcccagc taatttcgta ttttagtag   136380
agatgggttt ctccatgttg gtcaggctgc tctggaactc ccgacccag ctgatctgcc   136440
tgcctcggcc tcccaaagtc ctgggattac aggcgtgagc caccgtgccc tgcctctagt  136500
ttatttattt ttattccatg tgctcagtct tgcgagcacg tggtctgttt tcttgggcct  136560
ggcccctca gtgcactgtc ttaataccct agccccagt ccctctgatc atatcccag     136620
acacccctac tgaatcccag gtctctacca agggaaaggc agggaggagg cattgaccaa  136680
ggagaagagg gggaagggac agggaaggtc ttgatttgta ttttctaaaa ttttctactc  136740
tgctcataat gcgtcttagc tgtgttgttg tggaaagtag tgctgacagt gtcttgtttt  136800
tttattactt actttgtctt tcttttaag atggtttcac ccaaatatca ctggtgtgga   136860
ggcagaaaac ctactgttga caagaggagt tgatggcagt ttttggcaa ggcctagtaa   136920
aagtaaccct ggagacttca cactttccgt taggtaagtt ggaatgaaaa gagaggatcc  136980
tgagagtgtt ttctaggtag gaagtggtaa aaccatgctt ggatagcttg ctgcctgcat  137040
ttcgagtttg aaggccttat ctgagccctg ggctgccttc agggtttggg gagtggcctc  137100
ctggacattt agcagaagag gagtaaggag ggccttctt ctccctctga gacctcatgg   137160
aaggtgagtt ggagcaggtc atagaagttc ttaagccctc cagtgcttga gacttgttcc  137220
acacatcttg aacctggttt ctgcatttt cttttccttc ctgttgattt atttaaaaat   137280
tttatttctt ttcaattttt tttttttttt aaatagaggt gggatcttcc aatgttggcc  137340
aggttggcct tgaacttctg gcctcaagca atcctgcctc ggcctcccaa agtgttagga  137400
ttacaggcgt gagccactat gcctggcctt cttttttga cacagctgt tgctctgttg    137460
cccaggctgg agtgcagtgg tacgatcaca gcttacagca gccttgaact cctgggctta  137520
agtgatcctc ccgcctcagc ctcccgggta gctgggactc caggcttgtg ccaccatgct  137580
cagcatttt aaaaaatatt ttttgtagag atgaggtctc actgtattac caaggctgat   137640
ctttaactct tagcctcaag tgatcctcct gcctcagcct cccaaagtgt tgggattaca  137700
ggcatgagcc accacactca gactttgttg acttcttaat aagaaaaata cttgttaaga  137760
gtttcttcag atcactttcc tttatcaaca agtaaaacat gactgaggaa gttgtggtcc  137820
cctttgcttc cctgcccagg cccgtttccc tccctctttc cccagaggaa accaccaaga  137880
ggttggcata tattcttcct gaacgtgttt ttatagttgt actgcacttg tactgtgtat  137940
gaacaatata aagttggttt gtgtgtttaa aaaattcaca tacatggatt tataatgtat  138000
gtatcatttt gcaacttaaa aattttttt tgagctccat gctgattgat aacgatctat   138060
tttttttttt tgagatggag tttcagtctt attgcccagg ctgaagtgca atggcgtgat  138120
ctcagctcac tgcaacctca gcctcctggg ttcaagctat tctcctgtct cagcctccgg  138180
agtggctggg attacaggtg catgccacca tgcccagcta ttttgtat ttttagtaga    138240
gatgggttt caccatgtcg accaggctgg tctcaaactc ctgacctcag gtgatctgcc   138300
tgccttggcc tcccaaagtg ctggaattac aggcatgagc taccatgcct ggcctttttt  138360
tttttttttt tttgagacaa agtcttgctc tttttcccag gctggagtgc agtggccaca  138420
atcttggctc actgcaacct ctgcctcctg agttcaagca gttctcctgc ctcagcctcc  138480
tgagtagctg ggattacaga catgtaccac catgccaagt taattttgt atttttgta    138540
```

```
gagactaggt tttaccatgt tggccaggct ggtcctgaac tcctgactta aagtgatcca 138600
tctgccttgg cttcccaaag tgctggggtt acaggcatga gctatcgcgc ctggcctgag 138660
aaatctcatt cttactccta ctcccttgca cactatctcc attctgtagg tagccatttc 138720
tattaatttc ttgtttaccc ttctgtgttt cttccattct ttttcttttt ttctttttt 138780
tttttgagac aatcttgctc tgttgcccag actggagtgc agtggtgtga tcttggctca 138840
ccgcaacctc cacctcctgg gttcaagtga ttttcatgac tcagccacct aagtagttgg 138900
gattacagcg cctggtgtac actaccacac ccagctaatt tgtgtatttt tagtagagat 138960
ggggtttcac catgttgtcc aggctaatct ccaactcttg gcctcaaggg atctgcctgt 139020
ctcagcctcc caaagtgctg ggattatagg catgagccac catgcctggc cctatgtttc 139080
tttttataaa aataagcaaa ttaatatttt tattactatt ttcctttat ttttacacat 139140
caagtagaac attaaatata tttctctgta atttttttca gttacctaaa tcttttagtg 139200
atctctctca tctttttaat cagctggatc gcattctatc atgtgaatat tttataactt 139260
ctatatactg tcaccagcag gtagcgattt agttgtgtct aatattttaa aatgatatat 139320
aatgcctcaa tgaatatagt aaccttttgc atatattgtt ttgtgctttg ggataacact 139380
acctcgtatt ggaaactgtg tcattacatg tgtctttaaa attacatgtg tcttttattt 139440
tttattttta ttttttttga gtgggagttt cactcttgtt gcccaggctg gagtgcagtg 139500
gtgagatctc ggccgactgc aacttccgcc tcccgggttc aagcgattct cctgcctcag 139560
cctcccgagt agctgggatt atagacatgt gccaccacgc caggctaatt ttgtattttt 139620
agtagagacg gggtttctcc acattggtca ggctggtctc gaactcccaa cctcagctga 139680
tccgcctgcc tcggcctccc aaagtgctgg gattacaggc gtgagccacc gcgtccggcc 139740
tcttaactat tgtttgaaat aatgtagaga cagctccaga gccatgaaga agtgtatgaa 139800
gaagcagtgt tagcttaaat gacatacatg tcacaattgc ctatgtgaaa ctatcataat 139860
tatgcatgag aagtatctat cctgcataac ctccaccaat aataataatg ttaataatag 139920
tgaaaactaa tgtttattaa gtccttactg tctccagcct ctgtgctaaa tactggttac 139980
taagtttccc tgaaaatact attctcatct gtttgttctt aataacagga tagcataatt 140040
gtaagttgta aatgaaataa tacagtgtat gtaataaaag gtacggttag taacgtcggc 140100
aagtgatccg tatnnnnnnn nnnnnnnnnn nnnnnnnnnn nnnnnnnnnn nnnnnnnnnn 140160
nnnnnnnnnn nnnnnnnnnn nnnnnnnnnn nnnnnnnnnn nnnnnnnnnn nnnccggtag 140220
ttgttttgtt tagccaacac tgcaaggcgg tgcagtagtt catcaacgga gtcttgctct 140280
gttgcccagg ctggagtgcg gtgatgcgat ctcggctcac tgcaagctcc gcctcctagg 140340
gttcacgcca ttctcctgcc tcagcctccc tagtagctgg gactacaggc gcccgccacc 140400
acgcccggct aattttttgt attttagta gagacggcgt ttcaccatgt tagccaggat 140460
ggtctcgatc tgacctttg atccgcccgt ctcggcctcc caaagtgctg ggattacagg 140520
cgtgagccac tgagcctggc ctatatttt gttttttatt atactttaag ttctgagata 140580
catgtgcaga acttgcaggt tcttacata ggtacacatg tgccatagtg gtttgctgca 140640
cacatcaacc catcttctag gtttaagcc ccacatgcat tagttatttg tcctaatgct 140700
atccctcccc ttgccctcaa ctccctgaca ggccccagtg tttgatgttc cctccctcc 140760
tgtgtccatg tgttctttt ttttttttt ttgttgagac cgagtctccc tctgtcgccc 140820
aggctggagt gcagtggcgc aatctcggct cactgcaacc tccgcctcct gggttcacga 140880
```

```
cattctcctg cctcagcctc ccgagtagct gggactatag gcgcccgcta ccacgcccgg    140940 ctaattttt gtatttgtgg tagagatggg tttcaccgtg ttagccagga tggtctcaat     141000
ctcctgacct cgtgatctgc ccgcctcagc cttccaaagt gctgggatta caggcgtgag    141060
ccactgcgcc tggccctgtc catgtgttct cattgttcag ctcccactta tgagtgagaa    141120
catgtggtgt ttggttttct gttcctgtgt tagtttgctg agaatgatgg tttccagctt    141180
catccatgtc cctacaaagg acatgaactc attctttttt atggctgcat agtattccat    141240
ggtgtatatg tgccacattt tctttatcca gtctatcatt gaagggcatc tgggttggtg    141300
ccaagtcctt gctattgtga atagtgctgc aataaacata cgtgtgcatg tgtctttata    141360
gtagaatgat atataatcct ctgggtatat acccagtaat gggattgctg ggtcaaatgg    141420
tatttctggt tctagaatct tgaggaatcg ccacactgtc ttccacaatg gttcaactaa    141480
tttacactcc caccaacagt gtaaaagcat tcctatttct ccacatcctc ttcagcatct    141540 gttgttcct gattttttaa tgatcatcat tctaactggc atgggatgat tacctcattg     141600
tagttttgat tcgcatttct ctaatgacca gtgatgatga gcttttttc ataagtttgt      141660 tggctgcata aatgtcttct tttgagaact gtctgttcat atccttcact cacttttga     141720 tgggattgtt tattttttc ttgtaaattt gtttaagttc cttgtagatt ctggacatta      141780
aagctttgtc agccgggcac ggtggctcac gcctgtaatc ccagcagttt gggaggctga    141840
tgtgggcgga tcacgaggtc aggagatcga gaccatcctg gctaacacgg tgaaacccca    141900
tctctactaa aagtacaaaa aattagccgg gcgtggtggc gggggcctgt agtcccagct    141960
actcgggagg ctgaggcagg agaatagcgt gaacccggcg ggtggagctt gcaatgagca    142020
gagatcgcgc cactgcactc tagcctgggt gacagagcga gactccgtct caaaaaaaaa    142080
aagctttgtc agatgtacag attgcaaaaa ttttctccca ttctgtaggt tgcctattca    142140
ctctgatgat agtttctttt gctgtgcaga agctctttag tttaattaga tcccatttgt    142200
caattttggc ttgagaatgg cgtgaacccg ggaggcggag gttgcagtga gctgagatcg    142260
caccactgca ctccagcctg gcaacagag cgagattctg tctcaaaaaa aaaaaaaaa       142320 aaatttccct ccaaacactt ctttagctgt gtcccagaga ttctggtaca ttgtgttttt    142380
gttctcattg gtttcaaaga acttatttat ttctgcctta attttgttat ttacccagta    142440
atcatacagg agcaggttgt tcagtttcca tgtagttgtg tggttttgag tgagtttctt    142500
aatcctgagt tctaatttga ttgcactgtg ttctgagaga ctgttatgat ttccattctt    142560
tttcatttgc tgaggagtgt tttacttcta attatgtggt caattttaga ataagtgcta    142620
tgtggtgctg agaagaatgt atattctgtt gatttgggt ggaaagttct gtagatgtct      142680
attaggtcca cttggttcag agctgagttc aagtcctgaa tatccttgtt aattttcttt    142740
ctcattgatc tgtctaatat tgacaatggg gtgttaaagt ctcccactat tattgtgtga    142800
gagtctaagt atctttgtag atctctaaga atttgcatta tgaatctgtg tgctcctgta    142860
ctgggtgcat atatatttag gagagttagc tcttcttgat gcattgatcc ctttaccatt    142920
atgtaatgcc cttctttttc tttttgatc ttggttggtt taaagtcatt tctattggag      142980
actaggattg cagcctctgc ttttttttg ctttccattt gcttagtaaa tattccccca     143040
tccctttatt ttgagcctat gtgtgtcttt gcatgtgaga tgggtctcct gaatacagca    143100
cactgatggg tcttgactct ttatccaatt tgccagtcta tgtcttttt ttctttccc       143160 gagatggagt cttgctctgt tcccagact ggagtgcagt ggcacaatct tggctcacta      143220
caacctccgc ctcccaggtt caagcaattc tcctgcctcg gcctcctgag tagctgggat    143280
```

```
tacaggtgtg agccaccaca cccggctatt tttttttgtat ttttagtaga gatggagttt    143340
caccatgtca gccagggttg tctcaaactc ctgaccttgt gaaccacccg cttcggcctc    143400
ccaaagtgct gagattacag gtgtaagcca ccatgcccag cccagtctgt gtcttttctt    143460
ttttttttga gatggagtct cactctgtca ctcaggctgt agtgcagtgg cacaatcttg    143520
gctcactgca agctccgcct cccatgttca cgccattctg ctgccttagc ctcctgagta    143580
gctgggacta caggcgcctg ccaccatgcc tggctaattt tttgtgtttc tagtagagac    143640
ggggtttcac cgtgttagcc aggatggtct cgatctcccg acctcgtgat ctgcctgcct    143700
cggcctccca aagtgctgag attacaggca tgagccatgg cgcctagccc agtcagtgtc    143760
ttttaattgg agcatttagc ccatttacat ttaaggttaa tattgttatg tgtgaatttg    143820
atcctattgt catgatgcta gctggttatt ttgcacatta gttgatacag tttcttcata    143880
gtgtcattgt tctttatatt ttggtatgtt tttgctgtgg ctggtaccag ttgttccttt    143940
ccatatttag tgcttccttc aggagctctt ttaaggcagg cctggtgggg acaaaatcct    144000
tcagcatttg cttgtctgta aaggatttta tttctcctcc acgatgaagc ttagtttagc    144060
tggatatgaa attctgggtt gaaaattctt ttcattaaga atgttgaata ttggccccca    144120
ctctcttctg gctcataggg tttctgcaga gagatccgct attagtctga tgggcttccc    144180
tttgtaggga acctgacctt tctctctggc tgcacttaac atttttttcct tcagttcaac    144240
cttggtgaat ctgatgatta cgtgtctttg ggttgttctt atcaaggagt atcttagtag    144300
tgttctctgt atttcctgaa tttgaatgtt ggcctgtctt gttaggttgg ggaagttctc    144360
ctggataata tcctgaagtg tgttttctaa cttggttcca ttctccccat cactttcagg    144420
tacaccaatc aattgcaggt ttggtctttt cacatagtcg tatatttctt ggaggctttg    144480
ttcattcctt tttattattt tttctctaat cttgtcttcc cgctttattt tattaagttg    144540
atctttctt tctttctttc tttttttgag acagagtttc attcttgttg cgcaggctgg    144600
agtgcaatgg tgcaatctcg gctcaccgca acaccacct cccaggttca gcgattctc    144660
ctgcctcagc ctcccgagta gctaggatta caggcatgtg ccaccatgcc tgctaattt    144720
tgtatttta gtagagatag tatttcccca tgttggccag gctggtctcg aactcctgac    144780
ctcaggtgat ccgcccgcct cggcctccca aagtgctggg attacaggcg tgagccactg    144840
cacccagcct ctatgtttaa tttttaaagg aactgccata ctgctttcaa cattaaagta    144900
aatacttttt tttttttttt tttttttcc tgagacagag tctcactctg tcacccaggc    144960
tggactgcag tagggtgatc tcagctcact gcaacctctg cctcccaggt tcaagcgata    145020
cttgtgtctc agcctcctga gtagctagct gggattacag gtgcacacca accatgccca    145080
gctaattttt tttctttct ttcttcttt tgagacagag tttgctcttt cgcccaggca    145140
ggagtgaagt gactcaatct tggcttactg taacttctgc ctcccaggtt caagtgattc    145200
ttctgcctca gcctcccaag tagctgggat cataggcgcc ctgccaccat gtctggctaa    145260
gttttgtatt tttagtagag atgggggttt c accatgttgg ccaggctggt ctcaaactcc    145320
tgatgttcgg tgatccacct gcctcagcct tccaaagtgc taggattaca ggcgtgagcc    145380
accgtgctca tccgcccagc taatgttttt gtatttttag tagagatggg gtttcaccat    145440
gctggccagg ctggtctgta actcctgacc tcaagtgatc cacctgtctt ggcctcccaa    145500
agtgctggga ttacaggcat gagccactac acccagccta agtatatac ttttaactca    145560
ctttatacta ccacagttgg aggcatttat gaatgggaaa gaagtacctg aggctgggta    145620
```

```
attttgttta tttgatattt tttttgagat aacgtctcac tctgtcaccc aagctggagt 145680
gcagtgggtc catcacagct ccctgcagcc tcagctttct gggctcaagc gatcctcctg 145740
cttttcagcc tcctgagtag ctgggactat aggcatgcac cacaaagtcc agctaatttc 145800
tatttttttt ttcttttttgt agagataggt ttcaccatgt tgcctgggct ggtcttgaac 145860
tccttggctc aagtgatctg cccacctcag cttcccaaaa gtgctgggc tataggtgtg 145920
agccaccaca cctggccaag gctaagtaat ttataaagag agagtgttta ttttggctca 145980
cagttctgca ggctgtacag gaagcgtgga attaacatca gcttctggtg aaagcttcag 146040
gaaggttaca atcatggtgg aaggtgaagg ggagcagtgt atcaaatggc aagagagaga 146100
gtaagaggtg gggagaggtc ctagaatttt taacaaccag atctagtata aactgagtga 146160
gaacttaatt atcatcaagg gtgctaaagc attcacgagg catcttcccc atgatccaat 146220
cacctcccac caggccccac ctccaacact ggaaatcata ttttttcatat ctcttttttgt 146280
tgttgttttt gttttgtttg agacggagtc ttgctctgtc acccaggctg aattgcagtg 146340
gcgcgatctt ggctcactgc aacctccacc ttctgggttc aagcaattct cctgtctcag 146400
cctctcgagt agctggaact acagacacat gccaccacgt caggctaatt tttgtatttt 146460
tagtagagac agggtttcac catattgctc aggctgttct tgaattcctg acctcaggtg 146520
atccacccgc ctcagcctcc caaagtgctg agattacagg catgagccac cacacccaga 146580
ggttttttga tcgttttttt gagatagagt gtctctctgt tgcccaagct ggagtgcagt 146640
ggcgcaatct cagctcactg caacctctgt ctcccaggtt caagtgattc tcgtgcctca 146700
gcctcccaag tagctgggat tacaggcgcc tgccaccaag accagctaat ttttgtattt 146760
ttagtacaga cagggtttca ccatgttagc aaggctggtc ttgaattctt gaccttaagt 146820
gatctgtccg cctcagcctc ccaaagtgct gggattacag gtgtgagcca ctgtgcccga 146880
ccccgggaat catatttcaa catgagacat aaaaggaata aacatccaaa ccatatacat 146940
ttgattgcag ttaagataag tactactatg aaaagaaata gtgtgcaaaa atgactgaga 147000
aacaggagga cctattgtgt ttgggggaat cagatgtcct ctacgaggaa gctgataact 147060
ggagaatagg taggagtttg ccaagtgaag caggtggcga agggcattct ggcaggggga 147120
acagcaagtg caaaggccta gaggtaggaa aatggtacaa ttgttaaaga aactgcaagc 147180
agtcagggtg gcttgctgag atgaagatgg gcattgtatg cctaagatct cagaagcaca 147240
gacaacaaaa acagacaaac aggacttaaa ccaaaaagct tctgtacagc aaaagaaata 147300
atcaagataa tgaaccaaca acacacacaa tgaaagaaaa tatctgtggg ccaggcacag 147360
tagctcacac ttgtaatccc agcatttttgg gaggccaagg tgggcagatc acctgaggtc 147420
aggagcttga gaccagcctg gccaacatgg taaaacccca tctctactaa aaatgtaaaa 147480
attagctggg tgtggtggca tgtacctgta atcccagcta cttgggaggc tgaggcacga 147540
gagttgcttg aaccccggag atggatgttt cagtgagcca agattgcacc actgcactcc 147600
agcctgggag acagagtgag actgtctcaa aaaaaaatca atacataaaa aacccacaaa 147660
acttaattgg gatgcttcct atatgatacg gctcttagat ttatagtgta gcatgttagg 147720
ttctaaggat aggtgtcttg gtgaccatct gacctgcact agagaatnnn nnnnnnnnn 147780
nnnnnnnnnn nnnnnnnnnn nnnnnnnnnn nnnnnnnnnn nnnnnnnnnn nnnnnnnnnn 147840
nnnnnnnnnn nnnnnnnnnn nnnnnnngca agtagttcat caatatatat aaaaagagag 147900
agagagagag gagagagagt aaacatggta caggttgagt atcccaaatc taaaatgctg 147960
caaaatccat ggccaggcgc ggtggttcac tcctgtaatc ccagcacttt gggaggcgga 148020
```

```
ggcaggtgga ccacctgagg tcaggagttc gagaccagcc tggccaacac ggtgaaaccc 148080
tgtctctact aaaaatacaa aaattagccg gccgtggtgg caagcgccta tagtcccaac 148140
tactcagggg gctgaggcag gagaatcact tgaacccaga aggtgaagtt tgcaataagc 148200
caagatcgct cactgcactc cagcctgggt gatggagcaa tactccatct caaaaaataa 148260
attaattaaa taaatttaaa aagtgcccac ataacactca aaggaaatgc tcatcatagc 148320
atttcagata tttcagattt gagatttggg gattagagat gcttaagtat ataataaaaa 148380
tattccaaaa ttcgaaaaaa tctgaaatcc aaaacacttc tggtcccaag cattttggat 148440
aagggatact caacctgtat aaggttgact tgtaaatctg gatgaaaagt taacacgaat 148500
tatttgtact attttgcaac tcttatttaa atttgaaatt atttcaaaat aaaatgtttt 148560
ttaaaaccca taaatgatga aatccatcat gaatggcatc tgcttcagag gagtcctctc 148620
tagttaccag caaaaagata ttcttgggca ggcgcggtgg ctcacgcctg taatcccagc 148680
actttgggag gccgaggcgg gcggatcaca aggtcaggag atcgagacca tcctggctaa 148740
cacagtgaaa ccccctctct actaaaaatg caaaaaaatt agccaggcgt ggtggcatgt 148800
gcctgtaatc ccagctactc gggaggctga ggcaggagaa tggcgtgaac ccagtaggcg 148860
gagcttgcag tgagcccaga tcaccactgc actccagcct gggcgacaga gtgagactcc 148920
gtctcaaaaa aaaaaaaaag atattcttca tggatttcaa aagtcattga gattcatggt 148980
aacagtaact tctaaagtca aattatcctg gacctttcta agctaataga atgctctgaa 149040
atgctcccag gaatatgtca atattaaatg tagagttcta gtactgacaa tcaagtgaac 149100
ttttaagaga cttctccaca aatattgacc caattcaagt atcttacaac agtgaaggag 149160
accaggcaca gtggctcaca cctgtaatcc cagcactttg ggaggccaag gtgggaggat 149220
cacctgaggt caggagttca agaccagcct gggcaaaatg gcaaaaccct gtctctacaa 149280
aaaaatacga acattagcca ggtgtggtgg catatgcctg tagtcccagc tactcaggag 149340
gctaaggtgg gaggattgct tgagtctggg aggcagagaa tgcagtgagc agagatcgca 149400
ccactgcact ccagcctagg caatcgagca agacctcttc tcagatttaa aaaaaaaagg 149460
ctgggcaagg tggctcatgc ttgtaatccc agcactttgg gaggccgagg caggtggatc 149520
acctgaggtc gggagcttaa gaccagcctg accaacatgg agaaaccctg tccctactaa 149580
aaatacaaaa tcagccgggc atggtggcgc atgcctgtaa tcccagttac tcaggaggct 149640
gaggcagaag aatcgcttga acccgggaag cggagggtgc ggtgagccaa gatcgccacc 149700
actgcactct agcctgggca acaacgcaaa actccatctc aaaaaaaaaa aaaaagaaa 149760
agaaaagaaa aatcgtaaag ctcagatcaa aataatgaaa tattcatttg ctttttactc 149820
tctctgagag cttgtcagaa gattgagtct gggcccggtg actcatgcct ataatcccag 149880
cactttggga agagctgagg caggaggatt acctgaggtc aggagtttga ggccagcctg 149940
ggcaacatgg caaaacctca tctgtactaa aaatacaaaa attagccagg catggtggca 150000
cacatctgta atctcagata ctcgggaggc tgaggcagga gaatcacttg aacccggag 150060
gcggaggttg caataagctg agatcatgcc actgcgctcc agcctaggca acaaagcgag 150120
actctgtctt aaaaaaaaaa aaaaaaaaaa aaaaaaagg ccaggcacag tggctcacgc 150180
ctgtaatccc ggcactttgg gaggccgagg caggcggatc acgaggtcag gagattgaga 150240
ccatcctggg aaacccgtc tctactaaaa atacaaaaaa attagctggg tgttgtggca 150300
ggcccctgta atcccagcta ctcgggaggc tgaggcagga aaatggcatg aacccaggag 150360
```

```
gtggagcttg cagtgagccg agatcatgcc actgcactcc agcctgggcg acagagcaag   150420
attccgtctc aaaaaaaaag gaaaattgag acagaataga atttcacccg ggaaaacgtc   150480
aacctcaatt tatgtgatac ctattattct agcatccaat acttttgcat tcagaatggt   150540
taaactattc cgttaagaaa aaaaatcctt ccttgcagct tctttcatct gtggttccag   150600
atgaaagatg cccagaattc taaggaatca aaaagtaatg acaactggct tctagctatt   150660
tatagttttt caaaaggta taatgaaact cttacattag gcctcaattt gtctacctac    150720
ataagctaat taaaatgtca actctctttt gcttttggct gcaaaacaat tatgttaatt   150780
gggtgtggca actggaaact gagtggcata tgtgccttct accaagagga aaaaaatgga   150840
aaaactaatt attatataac acaggtgtgg agaccaaatc tttcagaata ttgggtttat   150900
ggtttgggtt ttttttttg ttttgtttt ttttttaaa aaaggacaat ccagccatgc      150960
atggtggctc acacctgtaa tcccagcact ttggaaggcc aaggcaggta gatcacctga   151020
ggtcaggagt tcgagaccag cctggccaac atagtgaaac cccgtctcta ctaaaaatac   151080
aaaaaattag ccaagtatgg tggtgcgcgc ctatagtccc agctactccg gaggctgagg   151140
caggagaatc acctgaaccc aggagacgaa ggttacagag agccgagatc acagcactgc   151200
actccagcct gaacaaaaga gcgagactcc gtctcaaata ataataa taatacaaaa       151260 attagctggg catggtggct ggcaactgta atcccagcta cttgggaggc tgaggcatga   151320
gaatcacttg aaccccagag gcagaggtta cagtgagctg aaatcacacc actccactcc   151380
agcctcggca aagagggag actctgtctc aaaaatataa taaaataaga ataaattttt    151440
taaaagtttt aaaaaaaagg gcaatcccct ccccaaatga caggctgaga atcactaaca   151500
catggtggca aagccttagg ggtagccaca tagactctgg tgccagattg tcttggtctg   151560
aagcccagct ctctgtgacc ctgggctaca tatttaacct ctctgttaag tcctataaaa   151620
tggaaggtgt aacagtaccc atgtcatagt gttgttgaga ggataaaatg agttaatatt   151680
tataaagtat ctagaagagt gcctggactt tcaggtagcc aaggacaacg atgattgcct   151740
aaatccatct ctccccatac atccttcaaa acaacatag aattaaaaac aaaacaagcc    151800
aggcacaatg gttcatgcct gtaaatccca gtgttttggc aggctagggt gggaggattg   151860
cttaaggcca ggtgttcaag accagcctgg gcaacatagc aagatcccat ctctacaaaa   151920
aaattaaaaa ttagccaggg accaggcaca gtggctcaag cctgtaatcc cagcactttg   151980
ggaggccaag gtgggtggat cacttgaggt caagagtttg agaccagcct agccaacatg   152040
gtgaaaccct gtttctacta aaaaatacaa aaattagccg ggtatggtgg catgcacctg   152100
cagtctcagc tactcgggag gctgaggtga gagaatcgct tgaacccggg aggcagaggt   152160
tgcagtgagc cgagattgca ccactacact ccaatctggg ggacagagca agacttcgtc   152220
tcaaaaaaaa aaaaattagg tatggtggtg tgctcctgta gtcccagcta ctcaggaggc   152280
tgaggtggga ggttcatcta agcccagcag cttgaggatg cagtaagcta tgatcaagac   152340
gccactgcac tccagccagg gcaagagtgg gaccctgtct ctaagaaaca cacacaagaa   152400
aacaataaac aaataaaatg acatgaaaac cacaccctca acttaaagag aatgcccaaa   152460
cttccagatt acctgtaagc aaaaaaaaga aaatatacca aacgtcagtg agtgactgct   152520
caacctccta ctccaagcct ttgtgcaaaa gaagagcatt ctgagaaaaa cagcatggtg   152580
tagagaacag ggtagctagt ggcaggccta aaattgctct aaaaccaccc ccagaaacag   152640
aaagtccacc cgaagtgtga aaatacttca ggtacatcag agtcctgttt atggaaaggg   152700
gcatgattcc agggggaaag actaaaaagt tgtggaaata agtcagaaaa cctagaacaa   152760
```

```
acgtgtaatt tttcagggaa atgcagtcta caaaaattaa cccattagag taagaaaact  152820
taggcagacc aacttgtatt aaaaaaaata gagggagcct ctctgaacct attctggttc  152880
agaggctacc tgattaaaaa taagaaaaaa tagggaaaac aattaaggaa ctaccgcaca  152940
gaaaatcacc aggcccagat ggattcccaa tggacttcta ccaaaccttc aaagaccaaa  153000
tagtctcaat tcttaaaatc attcctgagt actaaaaaga aaggaaaact tccaacttcc  153060
ttttacaaac taaatataac actgatacct ataccaataa agatggcaca agaaaaacaa  153120
cagagaccaa tggtactcat gaatattgat gcagaacttc taaacaaaat ataaagaat   153180
ccaataccac atttagaaaa taatgcaccg taacaaagta gttagaacca tacatcatat  153240
cacatatcag aataaatttt aggccgggca cggtggctca tgcctgtaat cccagcactt  153300
tgggaggcca aggcgggtgg atcacttaag gtcaggagtt cgagaccagc ctggccaaca  153360
gcaaaccccc atctgtacta aaaaaaaaat acaaaaatta gccaggcgcg gtggcaggtg  153420
cctgtaatcc cagctacttg ggaggccgag gcagcagaat cgcttgaacc cgggaggcgg  153480
gaggcagagg ctgcagtgag ccaagatcat tccactgcac tccagcctga gtgacacagt  153540
gagaccctgt ctcaaaaaaa taaaataaaa taaataataa acgtaaaaga tgaaacaatg  153600
caatactaga ggaaaacatg ggtgaatgtc ttgttaacct tagaataagg aaaggctttc  153660
tatgactcaa atccaggggg caataaaaaa aagattgata aatctgggat aattttaaca  153720
tcacctttca tcaacaattc aattgctttt taagaaaaat tcattaaatg gtaaaattta  153780
ttaccatttt taccatttat taccatttat taccataaat ttaattattc attaaatggt  153840
aaaaaacctc aaggactgaa gtcagttcta acttgcaatt tgagggtctt taaatcaatc  153900
attctttgga aaccaagaaa cttaaattca actccattca gaggcggaca acttacaacc  153960
cacagtccct cccactgagt tcagtgctat tctcagccaa aaaaaaaaaa aagccttcat  154020
ttctattata aaagcaatga aatgccaagg ctcagaaaaa cagacatact attaaatctg  154080
gatgcatatt ttgctcttct agcacttact catgttttc aacccaaaag actaacaccc   154140
atgtaagggg agaagtatca ggaaaatgct tctgaaaaac atattttaaa aatctgattt  154200
gaagcatctc ttggttattg aagcaaccta cagagccaaa ccactgtctc aaatcccaga  154260
atgccacatc tcctgggcaa gctaattaat ctctctgctt cggttttac atctgtaaaa   154320
tgtggataat aatagtgttt acctcatagg aaatgagaat taatgaatta atgcacataa  154380
aagaactata aagcatataa agcatttaaa actattaaag cttgtttgct tgttgttacc  154440
ttaatgaata cataaaacaa ttattgacta taatatctct accatagatt atgtttcatt  154500
aatatgcaat tactctagta ttaactaact tattatttaa taatctttat cttgaatgct  154560
acttagcccg atattggtac cacctgaatc tcttttgccc atgtttgttt tatttattct  154620
ttgacattct gtgccaattt gtctttttaa agcagaacac aactgaattt tttttttcttt 154680
tttcaaaata tttttataaa atagagatgg ggtcccacta tgttgttcag gctggtctca  154740
aactcctgga ctcaagtgat cctcccacct cagcctccca aagtgctggg attacaggtg  154800
tgagccacca tgcccggcct ggattttttc ttttaattcc atctggctca gccattattg  154860
aaggacttaa tccattatca ctgacagctc atgtttggta tcatatctgc tgattgtttc  154920
ctactttcaa ttttttttct gtcttttgcc acttagtgac ttcagtgact gtctacttca  154980
ggcagacacc tatttcttac tcaaatagaa ttctaatcat ttttaaatta tactggtagt  155040
catattgtag tatttaaaaa aaaaaaaaaa aaaaccttaa tcctacagtc ccaggttatt  155100
```

```
gaagggaaaa taactttttgc ctctcttaga tggaaagtga agaatttctg gctgttgttt   155160
tactagtctc cattaaatga aatacagcag gctcagcggt tgcttcattt taaacaccag   155220
ttagacagcc tagacccca caatctacct gcttatctgt tccctgactg tcaccactgt   155280
catctcttct ttttttaaaa tagattctaa aagaatttct cacacttgtc cttgacctca   155340
cccctgtgat ggcagcctca aacatagtat tattaactgc ttttatgcag atctttgtac   155400
agggcagggc aaggtggctc acacctgtaa tcgcagcact ttgggaggct gaggtgggag   155460
gattgcttga gaccaggagt tcaagatcag cctgggcaac gtagggaaac cccatctcta   155520
caaaaaatta aaaaattggt ggggcattga tggcacacac ctgtagtccc agttacttgg   155580
gaagctaaga cggaaagatt gcctgagcct gggacgtcgg ggttgcagtg agctgcgatt   155640
gtgccactga gctccagcct gggcaacagc actttcggag gccaaggcgg gcagagcact   155700
tgaggccagg agttccagac cagcctgggt gatgaactat tgnnnnnnnn nnnnnnnnnn   155760
nnnnnnnnnn nnnnnnnnnn nnnnnnnnnn nnnnnnnnnn nnnnnnnnnn nnnnnnnnnn   155820
nnnnnnnnnn nnnnnnnnnn nnttaatcgc agatggaacc agaaaggttt ccccaatggg   155880
aaaacggggg cacattagac ccaaagcaaa ttcaattggg agttagccca aaccaattag   155940
gcacccccaa gaggctttaa acctttaaag cttttcggta tcgtatatcc tgtgtgggaa   156000
attggggacc tgaataacaa ttttaaccca gggaaaccag gttatggccc atggatacgg   156060
cggtacagtt agtttaacaa tttcacccag caacataaaa ttaaattaat tccaaccggc   156120
aattttccct tttgtttccc ctttgccttt ttcaacatgt cctaacaatg ggcaatttta   156180
aagattaagc aaaagcttca ctctgcatcc ttttttttg ttttgttttg gagatggagt   156240
ctcgctatgt tgcccaggct ggagtgcagt gacgcgatct cagctcactg caagctccgc   156300
ctcccgggtt cacaccattc tcctgcctca gcctcccgag tagctgggac tacaagcgcc   156360
cgccaccacg cccggctaat ttttgtatt tttttttta gtagagacgg ggtttcactg   156420
tgttagccag gatggtctca atctcctgac cttgtgattc gcccgtcttg gtctcccaaa   156480
ttgctgggat tacaggcatg agccactgcg accggcgtaa aattctaaga cgtctattgc   156540
actcttctgc agtaaggttg ccagtcataa ttagtcaact tgagtcccgt tcctcataat   156600
ccgaaagtgt taactgaagg attctatata ttataaaact ctgtggaaaa tggccattat   156660
tcacccagat gtccactgga aggagaggct tgaaacactg tatttcatag gtgtggtggt   156720
attcaaaag atagctttta aaaaattaat aaaccggcca gacgctgtgg ctcacgcctg   156780
taatcccaga actttgggag gccgaggcgg gaggatcaca aggtcaggag attgagacca   156840
tcctggctaa catggtgaaa ccccgtctct actaaaaata caaaaattag ctgggtgtgg   156900
cggcatgcgc ctgtagtccc agctgctggg gaggctgagg caggagaatg gtgtgaaccc   156960
aggaggcgga gcttgcagtg agctgagatt gtgccactgc actccagcct gggcgacaga   157020
gcaagactcc gtctcaaaaa aaaaaaccaa aattaatag accacgaatc ttcctcaaat   157080
atgaaaaaga aacagttact aaaagaaaat agagattctt ccttctgtag ccagttatga   157140
aatttaaaat aattgcaaat aaaaatacta tacatgcatg gaggcaataa aatattatga   157200
tgaggagcag atgtgcagtg aacagaacta ggttaacgtg caagctcttc atgtgctctt   157260
gaacaagtcg aatacctact ctgcacttcc ttcatctgta caatgagtgc aatatttcca   157320
attgttaggc tcttttgaga atttaataaa ataatgcctg acatgtagga tacatttaat   157380
caatattatt aagtaattaa atatgtgctg ggcatggtgg ctcatgcctg taatcccagc   157440
actttgggag gccaaggcag gcggatcacc tgaggtcagg agttcgagac ttgcctggcc   157500
```

```
aacatggcaa aaccttgtct ctactaaaaa tacaaaaatt agcccggcat ggtggtgtat 157560
gcctgtaatc ccagctactt gggaggctga ggcaggaaaa ttgcctcaac ccgggaggtg 157620
gaggttgcag tgagctgaga tggagccact gcactctagc ctgggcaaca gagagagacc 157680
ctgtctcaaa ataaaaaata aaaagatttt ttatatatat atatatatat gtggatacac 157740
ccacacaaac acaaatctaa tagccacaaa aacattctta gctatctatt tctcctgata 157800
ccatggagcc tgtataacat ggaaagaatg aaacaagtta ttcactacta ccagtcataa 157860
atgtttatca cccatacaca tactagttgc tgagaaatca gaccataaat ttaaaaagca 157920
attaaaaaaa aaaatctagc aggccagaga ggttctttcc tttgaaaacc attcttctgt 157980
ggaaatagct gacaaattca cgcaatacat ttataaacat tttaggaaaa ccaacatcac 158040
agatatttta actaatccta ctctttctaa tcctaaaaat aaactacata aatgacatat 158100
atgtataaat tttggttctg tgaacttgga ttagtcttta agaaacaaag agcataggca 158160
cggcatagtg gctcacgcct gtaatctcag cactttggga agccaaggca ggcagatcac 158220
ttgaggtcag gagttcgaga ccagcctggc caacatggtg aaaccctgtc tctactaaaa 158280
atacaaaaat tagccaggca tggtggcgcg tgcctgtaat cccagcaact cgggaggcag 158340
aggcaggaga atcgtttgaa tccgggaggc agaggctgca gtgggctgag atcgcgccac 158400
tgcactccag cctgggcgac agagcaagac tcggtctcgg ggaaaaaaa agaaaagaaa 158460 gaaacaaaga gcatccactt tccaccttc acacacaaca cagccaatta aatcaaaga 158520 ttccactatc atagcataat accccttgag ttttcaggca gataagacac tcagacacac 158580
cttgcttgtt atagaacagg cccaaatgag acacaataaa acgatgattc catgttagga 158640
attccctacc aaccatatcc tcctcttttt ggtgactaga ttgtaaaata agtcaattaa 158700
gagttcataa cggaagtgct gaagcaaccg caaatccaga cacaaaaata cagtggaacg 158760
tattcgcatc tcaagcacgt ccaaatgtct cggccaatgt gatccgatca ctgccgtttc 158820
cagaaacaca cagtaatggc ttttaattca tttctataaa tgttcgttgt gcgtaaagcc 158880
aaactgcacg caaaaccgca aaacacaaaa gatccctcgc atgccgttta tagccagaag 158940
ataggccatc ctctctgcgc cctaccccag aaagctctcc ttacggcagt aaaaatttga 159000
tgacacccca tgctacctac acatcaaaat gtcatcccac aaagtggaag gggagcagtg 159060
tcagcatccg ttggcctcca tgaaacgaca ctgccagtat tcccacctct aggcaaacac 159120
gaacccaagt gaagtcgatg gaaagttccc accaaccagg catatttggt tcccttctgc 159180
ccccaaggcc aagcagctca actgatgaga tctgctgttg cacctgccac ggctctgaac 159240
ccgggatgct tggcgacccc cggggcacac aaaaaggccc tgcggcctaa cgcgccagtg 159300
acccttcccc gagagtgcat ggagggccgc tggagcatcc ctctcgctgt ccacagcgcc 159360
cgcttccctg acaaaggccc cgtgtcaatc catccgagac acaacacaga gaagttgctg 159420
gattgcccat cgcggacccg cagctgccac tacctctcc cggaaaaaaa ccaaaccaaa 159480
ccaaacaaaa aaaacagaac tagggaagaa aaggatggga gggtacacag cgtgaaaatc 159540
aaaatgttcc caaagctaag caacctgggt gtgccctgga agtgggtcct gggggcccgt 159600
gggggagggg agggagggcc cggtggtgg cggtggctcc tctggggcat gaaggccgag 159660
ccaggcgcta gcctaataaa atgccgggtg tcggaacgct caaaagaaaa ccacaaatga 159720
aatcccctgc gggcgccagg ccccgaggag ggagggaggg agagcggggc gggcggtccg 159780
cagacctgcg gccgcggccc cacctgcccg ccccgcgccc acacacacct gccccggcag 159840
```

```
ccgccgggag gcgaggccgc ggctgaggcg aggaggggc ccgacccggg ggtgccgggc   159900
gagtgggtca gtccgatggc gggggccggg ggccgcctcg ctcacctcca ggtcggtgtc   159960
cgcggcctct ggggccccga ggatctcgct gggcagctcg gccaggtcgg tgacccggat   160020
cagcccgtcg tgcaggaaga tggtctcttc cttcaccgag agccactgcg ccgagtcagc   160080
ggccgccgcc gccgccgccg ccgcggccgc cgacgagccc atggcccgg ctgaaggctt   160140
ggcgctgagg agcagacgcc cggccggggg aaacggagca ggagccgccg cgatcaccag   160200
tccatggcag cggccgccgc gcccgccagc ggcgcccac ttgctgcctc gcccgtgcaa    160260
ctccgcccta ggcggtccga gtcgccatac ccccgacccc ggcccgggag accccggccc   160320
tgccgccgcc gccgccgccg ccgccgccgc cgccctcagg agcaggatcc gcctctgccg   160380
ctcggcaacc aactgtcagt gagacgccat gttggggcg gggctcccgg catgcctcgc    160440
ggagcggaca atacaggccc cgcccgccgc tccgcccacc gctccgcgga cgaggccacc   160500
cgggtggcct ggacgtccgc ctagcccttc gctgccgcct gccctcggcc tgacctccgc   160560
cggccccttc tccccctggc cattcagggt agccctggct ttgcagcgcg ccagggaaga   160620
ggacgccgct tccccgtcc tgtccctact caggtgtgca ccccttgctc gggcccgcgc    160680
ccccaccctg ggcagagcat agagatcact ccttgttttc acgtttaaat gagatgcaag   160740
caaaaggctg gcgcagaata ggcgctgcac acttgttcat aagcacttgg tagaatcaca   160800
tagtagatga ttaatattga ctgaaaagtc tagtacccag taagcactca aaacctggtg   160860
aaaataaagc gtctgtccac aatgcttggt gctcaatgcc cgacacttaa tatgtgctcc   160920
atgagtggca attctaatta ttgctatgtt cgttccatca gtgttccaca ctaattgaca   160980
tacaccttaa aaatatgctc actaggccgg gtgcggtggc tcacacctgt aatcccagca   161040
cggaggtcaa ggcagaagga ctgcttgagc ccagaagttt gaggccagcc tgggcaacat   161100
agggagaccc catctctaca aaaataaaa attagcgggg cagggtggca agcgtctgta    161160
gtcctgctac tcgggaggct gaggcaagag gatctcttga actcaggagg tggaggctgc   161220
agtgagctat tatcttgcca ctgcactcca gccgggcga cagagggaga ccccatccct    161280
ccctccccac caaaaatata tatgcccca ccagtgccat tttataaaaa caagaaagga    161340
aaactatatg tataaagaac aatgcatgaa caaatacaca ccagatgttt aaggtgagtt   161400
gccatgggag tgtgggctg gtctggaact actgagatga gattgttctc tattacttgt    161460
atattttat cacttaaaaa ataataaaac aggccgggca cagtggctta cacctgtaat    161520
cccagcactt tgggaggcca aggtgggcag atcacctgag gtcaggagtt cgagaccagc   161580
ctggtcaaca tgatgaaacc ctgtctctgc taaaaaaat acacaaatta gccaggaatg    161640
gttgcacatg cctgtagtcc cagatactca ggaggctgag gcaggagaat agctggaacc   161700
caggaggcgg aggttgcagt gagccgagat catgccactg cactccagcc tgggcaacag   161760
agcaagactc catctcaata ataataataa taataataat aacaataaca ataacaggag   161820
aacattaagg tgcataccct ttgatccagc aattcaactt tgaggaagtt gtctgaagga   161880
aataatcaga ctcgtagtca aggatggata tacaggttg tgtagctcaa tattgtttac    161940
aaaaggaaaa acttatcaat ctagatgtcc aacaatatgg ggctggttaa ctaaaatatg   162000
atatatccat aagatggaat attatggccg ggcacagtgg ctcacgtggg taatcccaac   162060
actttgggag gccaaggctg gcagatctct tgagcccaga agctcgagac cccttgggc    162120
aacatgacaa aaccccgtca ctacaaaaaa tacaaaaatt agccaggcgt ggtggtgcac   162180
acccatagtc ccagctactc aggaggctga agcaggaaga tcgtttgagc ccagaaggca   162240
```

```
gaagttgcag tgattcagct aagattatgc cactgcactc cagcctgggc aacagagtaa 162300
gaccctgtct caaaaaagaa gaaaagaaga ggaagaggag gaagaagaga acaataaatc 162360
cagcagttca gagttgatca gaaccatgga aacaataaaa caggcaagtg taatggaatg 162420
gccatttcat caaatcctcc caaatgtctg agaggggag tattattatt cctactttca 162480
gctgggaagt caagactcag ttagatactt tgctcaatgt cacaaagcca gtaaacatca 162540
aagctcagat gtaaacccag gtctgtccga ttttacaact tcagcttcct tattttgact 162600
gtaagaaaac tccttcattc ctttttttt tttttttgag acggagtctt gctctgtcac 162660
ccaggctgga gtgcaatggc atgatctcgg ctcactgcaa cctcttggct cactgcaacc 162720
tccatctcct gggttcaagt gattctcctg cctcagcctc ccgagtagct gggattacag 162780
gcatgtacca ccacgctcgg ccaatttgt attttagta gaggcggggt ttcaccatgt 162840
tggtcaggct ggtctcaaag tcctgacctc aggtgatcca cccacctcgg cctcccaaag 162900
tgctgggatt acaggcatga gccactgcgc ctggcccatt ttattttatt tatttatttc 162960
gagatggagt ttcactctgt cacccaggct ggagtgcaat ggctagatct tggctcactg 163020
caacctccgc ctcccgggtt caagtgattc tcctggttca gcctcccgag tagttgggat 163080
tacaggcacc caccaccaca cccggctaac ttttgtacgt ttagtagaga tggggtttca 163140
ccatgttggc caggctggta ttttttcatt tttaaaaaaa ttttttaga gatgggtctct 163200 gcctgtgttg cctaggctga tctccaactc ctagcctcac gtgatattca caccttggcc 163260
tccccaaagc actgggatta caggcatgag ccactgatgc cggcccatca caattttaa 163320 atgcttagat tcaggactct aaccatctta aatagttcag ataaaattc ttctatactt 163380 agtcttattt cttctactct taatgatgtt ttaagatcag gagtcaaggt gcccaggaac 163440
tcttgtcctt cagcctaagt gatgaaaaca gcacagatct agggcttaaa gtctttagac 163500
tgcataatga atagttattt aatattttag caacagtaat taattagtca taggactgca 163560
tggctgccac tgcaccatga tgaggcagct gatgaattaa tatttataga accccctccg 163620
gaaaggagac catttagtag ggatttctag aacagatcag caagacaaag aaaatgcctg 163680
gtcaaaagaa ctttaggttg gaagctacga ggaagagaat ctgtatctag tctagacaac 163740
acacacatac acacacaaga cattcattta taggaaggaa agatttatgg cttatgactt 163800
cttttctttg gaatcgtcat ttctactctt ctattcaaga atgggggatc aggatgggaa 163860
aaggagcaag agaaagtgtt ggctgggcaa ccctaagtta gaagcagaga agaaatatga 163920
ggaaaatagg aagaatagct atgactaggt tggacctcag ttactcctgg gaggcatctc 163980
cccaagaggg agcagcaggc ttgttgatgg agatcatctc cctcctgccc cagctgctga 164040
cgtgatactc gctagccctg gctcaagctg gggcccctct gggattttgc aatatctctc 164100
ccttctgctg gttttctata ccagctgact gtctaaaatg acttcgtaat ccttcctggg 164160
tccaaaaata tgtgagtgtg gtgtgaagat aagtggtcct tgataaactt tattagagct 164220
taaaggtggt tttagatgag gcagccatgt taatttttaa ggccttcaa aacaccaagg 164280 aaaaaataca cacacacaca cacacacaca cacacagaac ctatggggga gattgattat 164340
ttccgtctta ctaattacag tctcaaagag gaaacacaca cacctactca aaatcttttt 164400
tccaagtgtt ctggtaggcc ctgttcatat ttttattca aagaagatta ttttggctca 164460
tgggtggatc tatgtggtaa cagggaaaag aaatcagatg aaagagatat ttgaaaacga 164520 ggaggggaa attctccttg gagcaccact gaattgctaa aactaaagga cgggtctcca 164580
```

```
cattgatgaa aagccagaag atgaagcagc attaaatgcc tttctcattt gaaaagatca   164640
tcagcagcag ggagctctga aagatgctat gtcctccatc gccaccttgt gtgcatcaca   164700
ggccttgctg cactgggatt tgtagttcag acttggaaat ttgctaacat tcgtctcctg   164760
caaaaaaatt agattaagaa aaagttgtgg ccgggcgcgg tggctcacgc ctgtaatccc   164820
agcactttgg aaggccgagg cgggtggatc acgaggtcag gagatagaga ccatcctggc   164880
taacacggtg aaacccgtc tctactaaaa atactagccg tgcgcggtgg caggcgcctg    164940
tagtcccagc tactcgggag gctgaggcgg gagaatggcg tgaacccagg aggcggagct   165000
tgcggtgagc cgagatcgcg ccactgcact ccagtctggg caacagagcg agactccgtc   165060
tcacaaaaac acaaaaaaac aaaaacaaaa agttatggct catgcctgta atcccagcac   165120
tttgggaagc cgaggtgggc ggatcacctg aagtcaggag ttcgagacca gcctggccaa   165180
cagggcaaaa ccccatctct actaaaatta caaaattagc caggtgtggt ggtgcgcgcc   165240
tgtaatccca gttacccagt taccaggagg ctgaggcatg agaatcactt gaacccggga   165300
gatgaatgtt gcagcgagcc gagattacgc cactgcactc cagcctgggc aacctaacga   165360
gtccatctca aaaataaaa ataaaaataa aataaaaaa gttgttagca caaaggaaaa     165420
gtggacaaaa gatattattg aagagttttc actcaaggaa aagcaaacac tgtacgtttt   165480
tgttccttca gtattcatta aatgcctact ctgtgccagg cagagttagg tttgaggatc   165540
gagttcccaa ggagactggc agcttccctt tctcatgaaa gacagggagg ctgcttgaag   165600
gaatcattcc aacggggatg agaagtccgg gcacctagtc tggggtgag gttcccgaa     165660 gatgttgagt ttaaagctgg taactgctac gtatgagtta atgaatgtga ggatggtggg   165720
ggaaacttca atactattat tcaccaaaaa aagcacatgc aatgcagtgt ggtgtttgaa   165780
tcatggactg cttggatttg gtcccagatc ttttgcatgt taccatgaag aagtaattcc   165840
acctacctgt ttcccagttt tctgggatga tggtggtggt atctaccttc ataagtaagc   165900
aaggttggtt ccttctgagg attttttgtt tgtttctttg tttgtttgtt tgagacaggg   165960
tctcagtctg tttcccaggc tggagtgcag tggtgcgatc tcaactcact gcaacttctg   166020
cctcccaggc tcaagtgatc ctcccgcctc agccttctga gtagctggga ccatgggcat   166080
gcaccaccat gcctggctaa ttttttgtatt tttttgtaga cagggttt cgccatgttg     166140 ctcaggctag tctcgaactc ctgagctcaa gcaactgccc acctctgcct cccaaagtga   166200
taggattaga ggtgtgagcc accacacctg gcccttctga gagttttgaa agaagaatct   166260
attccagacc tctctccatg gcttgtagat gaccatagtc ttcctatgtc tctgtatatt   166320
gtcttccctt ggtgtgtgtc tgtgtccaaa tttgttcgtc tctctctttt tttttttt     166380 tttttgagac aaggtctcac tttgttgctg gagtgcagtg gcacgatcac ggctcactgc   166440
agtctcagcc tgctaggctc aagtgaacct ccctcttcag cctccctagt agccgggact   166500
acaggcatgt gccaccacac ctggctaatt tttttttttt aaagatgggg tcttgctgtg   166560
ttgcccaggc ttgcctacaa ctgctggact caagaagtcc tcccgccttg acctcccaaa   166620
gtgctgggat tacaagcatg agtcaccaca cctggcccaa attttctctt tttacaagaa   166680
cattagtcat attggattgg gccccatct taaggacttc attttaactt gattctctct     166740
ctctctgaag accctgtctc caaataacat tacatcctga ggtactgagg ttaggacttt   166800
catcatgtaa attttcaaag ggacacagtt cagcccataa cagaaatgga gctatgattc   166860
cctgagatag gaagtattag ggaagaaaca tgtggggaag gagggcagag aaccaagaat   166920
tggaaagaaa aacagttaaa gtcatgagac tattcattta taatgattta cattttatgg   166980
```

-continued

```
gatctaatta cactaaagag cttctgcaca gcaaaagaaa ctaccatcag agtgaacagg  167040
caacctacag aatgggagaa aattttttgca atctactcat ctgacaaagg gctaatatcc  167100
agagtctaca aagaactcaa acaaatttac aagaaaaaaa caaccccatc aacaagtggg  167160
cgaaggatat gaacagacag ttctcaaaag aagacattta tgcagccaac agacacatga  167220
aaaaaggctc atcatcactg gccatcagag aaacgcaaat taaaaccaca atgagatacc  167280
atctcacacc agttagaatg gcgatcatta aaagtcagg aaacaacagg tgctggagag  167340
gatgtggaga aataggaaca cttttacact gttggtggga ctgtaaacta gtttgaccat  167400
tgtggaagac agtgtagtga ttcctcaggg atctagaact agaaatacca tttgacccag  167460
ccatcccatt actgggtata tacccaaagg attataagtc atgctgctat aaagacacat  167520
gcacacgtat gtttgttgtg gcactattca aatagcaaa gacttggaac caacccaaat  167580
gcccatcaat gatagactgg attaagaaaa tgtggcacat atacaccatg gaatactatg  167640
cagccataaa aaatgatgag ttcatgtcct ttgtagggat atggatgaag ctggaaacca  167700
tcattctcag caaactatca caaggacaaa aaaccaaaca ccacatgttc tcactcatag  167760
gtgggaattg aacaatgaga acacttggac acaggaaggg gaacatcaca caccggggcc  167820
tgttgtgggg tgggggagg ggggaggggg gagggtatagc attaggagac atacccaatg  167880
taaatggtga gttaatgggt gcagcacacc aacatggcaa atgtatacat atgtaacaaa  167940
cctgcacgtt gtgcacatgt accctagaac ttaaagtata attaaaaaaa aaaaaaaat  168000 atatatatat ataagatt acattttaaa ataaatagg ctggctgtgg tggctcaagc  168060
ctgtaatccc agcactttgg gaggctgagg tgggcggatc acttaggcca ggagtttgag  168120
accagcctgg ccaacatgat gaaacccccgc ctatactaaa aaaaaatca aaaattagcc  168180 gggcatggtg gcggaccccct gtaatcccag ctgcttagga ggctgaggca ctagaatcac  168240
tccaacccag gaggtggagg ttgcagtgag cggagatcgt gccactgcac tccagcctgg  168300
tcgacagaat gaggctcggt ctcagaaaaa taaataaatc aaacaaaaac aaaacaaaaa  168360
ataatttgca ttgtatactc tcacttgtca cctgcttcag gtcatctcag gccagtgccc  168420
atctttatat gcatataaaa acatagatat ataagacat atatatatat atatatatat  168480
atataaagac ggatatgaag aactactcnn nnnnnnnnnn nnnnnnnnnn nnnnnnnnnn  168540
nnnnnnnnnn nnnnnnnnnn nnnnnnnnnn nnnnnnnnnn nnnnnnnnnn nnnnnnnnnn  168600
nnnnnnnngt ctgagcaaac atggtgaaac ctcgtctcta cagaagatat aaaattagct  168660
gggtgtggtg tacacaacct gtagtcccag ctgcttgaga ggctgaggga ggaggattgc  168720
atgagcccag gaggcagaca ttgcagtggg ccaagattgc gccattgcac tccagcctgg  168780
gagacagcga gactctgtct caaaaaaaca ataaaaataa aaataaaaat aaaataaaat  168840
gtgccattct atttcattat ataaagattt attcaatcac attgtgtgga tgatatcaca  168900
gatgcgaaca gtattaggaa gcaaaaagca atcccttcac ctttcttaat actcaaataa  168960
ttttttttta atttgccaaa atgaaatcta gtaagtcaaa gggatcttat ttctaaggac  169020
tcttggatta taaacagaat ttctagcggg gtgataactg gggagagtca cttggctcag  169080
tcactgacct tcctttatcc ttaaattgag agtggcaatt tcatgaccct gaatagtata  169140
aaaaatatgt ccctcaaacg tataagcacc atatgaagct aatagccttt gaaggtctat  169200
atttactgtg tcatagataa gctcaactac aattcgattt gattaaaaaa tcagtacagt  169260
gatactctaa tccaaaaaat atcaaatgat tgctaaaaat aaagggggata ttgtaaatgg  169320
```

```
cataaattgc atcaaaatgg gaatgaacac taaataatta cagctatata tgttctaaaa    169380
actaatgaca aaagaaagct gaaaaatccc cagtaacttc tcattagatc tttccgtct     169440
cactctcttt ctggtgtgtg ttttttgttt gtttgttttt ttgttttttg tttttagaaa    169500
gacagggttg ggctgtcacc cagggtggag tgcagtggca tgatcttggc tcactgcaac    169560
ctccatttcc caggctcaaa ccatccatcc acctcagcct cccaagtagc tgggactaca    169620
ggcgtgcacc accatgccca gctaatttt gtattttggt agagacaggg ttttgccatg     169680
ttgcctaggc tggtctcaaa ctcctgggct caagtgatcc tcccacctcg gcctcccaaa    169740
gtgctgggag gcatgagcca ccaggtcagg cccctttcct tttcttaacc aagaaggtaa    169800
catacaaaaa ctgccatgat atattcaaac acttatggat agggctagct accaaaaagt    169860
ttaaggttct tctgaacttt taggcttcct gattaaaaag aattataaaa agttccttca    169920
acctttctga gctaggggtt taggcactat aagtctctaa atgtttactc tctgtttttg    169980
tacttatctt gtcattacat taacagacag ttcgtggtat gtggaccata ctttgagagg    170040
cattgttctg tacggaacat actttatttt ccagagtaat ttaaaaagcc tccaagttca    170100
cagtaatgac caaaatagac caaaggaact cagtgttttc tgaaaaaag caggactaaa     170160
tgatttcaag atccttttca gccccacaag ttctatgatc ctaaagctaa agatgtgatt    170220
tgactggtaa gtaaaacgct cattgcctaa tgataggcat ttctgtcaca ccaacagagt    170280
agctaaaaga ggaaaagtca taataaaaaa aaagtgggggg ttgggggggaa taagctcaga  170340
gaagagaaag aatttaactg tgaagtagac acggacagtg aggagatgta gctcagtaag    170400
acagataaaa cgccaatagg ctgaacaaca tggtgaaacc ccatctgccc agctactggg    170460
tgggggggcta aggtgggaag atagcttgag tctgggaggt tgaggttgca gtgagctgtg   170520
atgataagga gggtgggagg aaggatagag aaaacaaaca aacaaactac taaagcagtt    170580
acttccactc agggtaggag atgcagttct cacaaattag cctctgaaaa ttggccattt    170640
taataattaa gcctaagtca tgaaagaaag gttaaattat ctttaagaac cttgtttacc    170700
aaagcaaaga agtatgtaat acataaaaga cttatatcac aaagattaca tagcattcaa    170760
aaaagactcc tagattcatt atttcagaat ctttattata cagtattagt tttatgttac    170820
ttacaaaatg ctaatgtatg gtatgaatgg cattaatcca attctaggct tctagtagga    170880
gctcaataaa ctgctactac catgtatttt attctttaac tgcagaagcc tccatgttct    170940
catatctaaa agataattct ggccaggccc agtggctcat gcctgtcatc ccagcacttt    171000
gggaagccga ggcaggcgga tcacttgagg tgaggagttt gagaccagcc tggccaacat    171060
ggtgaaaccc tgtctctact aaaaatacaa aaattagctg gacatggtgg caggcacctg    171120
taatcccagc tattccagag gttgaggcac aagaaattgc ttgaacctgg gaggcgtagg    171180
ttgcaatgag ccaacatcac gccactgcac ttcagcctgg tgatagagca agattctgtc    171240
tcaaaaaaaa taaaaaataa ttcctattgt atctatccca caagtttatt tttagaggaa    171300
taaaataatg tggtcagtta aaatatgatt catccataaa ataaaatatt ataacctact    171360
aaaaagtatt aagagctggg tacagtggca cacacctgaa atcccagcta ttcaggagcc    171420
cgaagcaggg ggatcacttc agcccaggag ttcaagacca gcttgaacaa catagcaaaa    171480
cctcatttca aaagaaaaa aaatcaaaaa agcattatg taaattttat gttatgaata     171540
tgaaaaatat ccttacacat attgtttagt ataaggtaca aatagcatat atagtatgat    171600
ctcaatgaca gaatattatt cagggggtagt aataaatgtg cctatctgtc tatgaccata   171660
gacagattat gatcaaagaa aggaggatta aactaacatt tcgaatcata attgacgaca    171720
```

```
ccaaaaagat tcattcaaaa catgtatcaa gaaaatttag aggagatact gtttctcagt   171780
tgtaaataat gccagaaaaa ctcataaggc tacaagagac agagatccaa agctacattt   171840
gctaaaaaga aatttgtgtc actgtcaaca tagtaagaaa gacgcttact ctcaacaaac   171900
acacattcta gatcctgtag tataagaacg gccggccggg cgcggtggct catgcctata   171960
atcccagcac tttgggaggc cgaggcaggt agatcacgag gtcaggagat caagaccatc   172020
ctggctaaca cagtgaaacc tcgtctctac taaaaataca aaaaattag ccaggtgtgg    172080
tggcggatgc ctgtagtccc agctactagg gaggctgagg caggagaatg gcgtgaatgc   172140
gggaggcaga ggctgcaatg agtcgagatg gccactgca ctcctgcact ccagcctggg    172200
caacagagca agactccgtc tcaaaaaaaa aaaagaact gccactcagg tgtggacctg     172260
ggccctcagc atcatcagca ttacctggga cctagttaga aatggagaat cttctctacc   172320
atgtgaatca tgctttttt tttttaaagg aataatataa acgaacaaaa agaaatgcc    172380
aaaaaaaat tgcaaactct caggaccacc ccctcccca gcaaccacta catcagactc      172440
tatgtctaca tattacttta ttatgtattt tattttgag acggagtctc actctgtcgc    172500
ccacactgga gtgcagggga gtgatctcag ctcattgcaa cctctgcctc ccggattcaa   172560
atgattcttg tgcttcagct tctgagtagc tgggattaca ggtgcctgcc accatgtcca   172620
gctactttt atattttag tagagatggg gtttcaccat tttggccagg ctggtcttca    172680
acttctggcc tccagtaatc cactcacctt ggcctcccaa agtgctggga ttacaggcgt   172740
gagccaccgc gcctggccta catttttt ttttaataga caagatctct gtcgtcaggc    172800
tgagtgcagc agcatgatga tagctcactg caaacttgaa cttctgggct caactgatcc   172860
tcctgcctca gcttcccaaa gtgctgagac tacaggcata agctaccacg cccagcctta   172920
ctctacattt taacaaaacc tccaggtggt acgcacatta agtttaaga agagctgcta    172980
caaagcccaa agagaattaa gagggaggaa tacgcacagg tgcaacaatg gactttccc    173040
aattgatgca acagagatat cttctggttt ggatgacaat cacatggaca agaagttaca   173100
atgatctttc caccactgtc tagaaagtat ttttcttggt aactagaaga aagctagagt    173160
atttctagaa agtatctagg tataggttta aacacataaa agtagcaaaa gagtcagggg   173220
cagtagcatg cacctatagt cccagctact gggaggctg gggcaggagg atcgcttgag    173280
gccaggagtc tggggctgca gtgtgcaatg attgtacctg tgaatagcca ctgcactcta   173340
gcctgggcaa cagagtgaga ccctgtctct aagtaaataa atgaataaaa tgtataaagt   173400
agcaaaatac tattcttacc attcacaaat ttttccatca tcaaagaagt tatatatcaa   173460
aagggttcc attggaagca tccatcatcc caagaataaa gttttccttg aggggcagtt     173520
ctcaagaact aagtaccttg atcttatatc tctaacaaag tgaaaaaata aaacagaaat   173580
atagagaaag gaaagtatta aaatatatac cagaaaatgt atcattaaga tgcacttttg   173640
caaaaatgtt ttaaattcaa tctagggaaa taaattatac ctgatcccat atatctctag   173700
caaaaataac caacaacatt atttctgtta aaggtaagat tggccggggg cggtggctca   173760
cgcctgtaat tccagcactt tgggaggctg aggcaggtgg atcacctgag gtcaggagtt    173820
cgagaccagc ctggtcgaca tggtgaaacc ccatctctac taaaaataca aaaattagct   173880
gggcatggtg gcatgcacct gtaatcccag ttacttggga ggctgaggca ggagaatcgc   173940
ttgaacccag gaggcacagg ttgcagtgag ctgagatcgc gccattgcac tccagcctgg   174000
tgaacaagag agaaactccg tctcaaaaaa aaaaaaaaa ggtaagatca aaacagtatt   174060
```

```
attagtcaac tacattaata aagacaagga tctaattttt tccagctttt aaaaacctga 174120
aagataatgt ctgttcatcc gcgacaatac acgattttag aatggaacac accaacaaaa 174180
acttgaggga cccaatactt gaattataac aggtatttta accacaaagc tcttctccca 174240
tccatatttt cttcattatt atatgtcata tgtcagttgc tattctgggt gtgttacccc 174300
atttatctca tttagtcttc ttatttaccc ttttttttca gacagagtct cactctgtcg 174360
cccaggcttg agtgcagtgg tgcaatcaca gcctcaacct ctaggctcaa gcgatcctcc 174420
cacctcagcc tcccaagtag ctgggactac aggtgcatga caccacacct ggctaatttt 174480
ctaatttat ttttgtagag atagggtctc actacattgc ccaggcttgc tttgcattcc 174540
tggggtcaag caatcctccc acctcagcct cccaaatgct aagattacag gtgtgagtca 174600
acatacccgg cccttattta cccttgaagg ggggcatttt ataaccaaga aattgaaatt 174660
ctgataggtg gtagaactga actaacagct ggcgagatgt gtcaatgcca aagcctacag 174720
tcttaaccac taggctcact ctgtgttcat aaggatcccc tgaaggaccc tgcattttaa 174780
agtcccaggt tatttgtcac tgactccata taccatcctc ctttaaatcc cacagggcac 174840
aatattctgt atggccctga atgttaacgt gtattccaaa aacaacaaaa aactctacaa 174900
tatagtactt tacatacatt taaaaaccag tcatgtgcaa gatatatact tattttttgt 174960
gtaagtacct gcttaactcc agaagcagga agaaggacat tgaagcacca aatagaacta 175020
cttggagaaa gatgaaataa accggtagga tcagaatttg ggagcactct tctagttaac 175080
actataggtt cccaattaca atgtatgtag gaattgtcaa acagacttgc aaccagaggg 175140
cctttgaatt cattacaagt cctctgtctc tattgctgtg atacttaagt atctatctgt 175200
actcaatggg actgtgctta tgtacacaac tgtatatatc tgtttgaaaa gatttccgtt 175260
tcagttgttt caaagctgtc cccattgatc tgctaacaga gctgaagctg ccctgggtga 175320
tatccttgct ttttgttttc ttttgttttt ctaacatgtt aagtttctaa gtacttcata 175380
ctttaatatt ctcaaaaata ccaccttcat cacctggtgg actattgcct tatggaagtc 175440
aatattctcc agagtgaaca gtaagggctc tgtggaagcc aacctgcagg cctcctctat 175500
gggaacacaa ggaagctatg gagactgcag tggagtgatg ggagggaggg gagcacatca 175560
ggagaccagg tcagagagga atctgcctac gcatcactca tacgtgcact cactacctct 175620
ggggagcatc taagtaacta ctaatactgg ctgctgctgg gaagttggtg gtggtggagg 175680
caggtgggga gcgttatgtt agcaaggaga catttccctg tattctctct tgaactaatt 175740
ctaaaatttt ttttttttt tgagatgggg tctcattctg tcaaccaggc tggagtgcac 175800
tggcaaaatc agctcactgc agcctcaaac ttccaggctc aatcagtcct cctgcctgag 175860
cctctagagt agcagggact acaggcacac atcaccatgc ccggctaatt tttgtatatt 175920
tagtagagac ggggttccac catgtttgcc aggctggtct cgaattcccg acctcatgtg 175980
gtccaactgt ctgggcctcc ccaagtactg ggattacagg catgagccac tgcgcccagc 176040
ctcccttatg cttttctaca tcttctaaat tttcaaaaat tcctctaaca ttttaatttt 176100
tttaatttt aagcattttg taatgtttta ataaaattat aatcaatagt tttattacgc 176160
taatcagtaa ttagattata ttaaatctta aaacttctgt aacagttcca ttctttttta 176220
attttttaaa atttatatat aacatgtaat atgtattcat gtgtatataa aatttatata 176280
tgtgtgtata cacacaagca tacacacact ctctctctct ctcttatata taaagatgag 176340
gtcttgttgt gttgcccagg ctggtctcct gagctcaagc aatcctccca tctcggcctc 176400
ccagagtgct gggattacag gcatgagcca ccttgtccgg cccagttttc aaggtactgc 176460
```

```
tactcaataa aagtggctta atggacatag aataggttta ctaaaaacct aaaaatgtgc   176520
aaaataaata gaatagtgct caagttcact acttgatcat agaacaacta agttaagcaa   176580
aaaattcatt caaagtcatt aatattttta gaacgatgat caaagcaaca tattttcaat   176640
taactccatc taactagcta ttttcagaaa tctctctgga attcattatt ctctacataa   176700
aatgcactat gctctataca aaaatcaaag gtcaggccag gtacagtggc tcaggcctgt   176760
aatcccagca ctttgggagg ccgaggcagg tggatcacga ggtcaggagt tcaagaccag   176820
cctgggcaac atggtgaaac cccatctcta ctaaaaataa aaaaattaac caggcagtgg   176880
tggcgtgcgc ctgcaatcct agctactcag gaggctgagg caggagaatt gcttgaacct   176940
gggaggtaga ggttgcagtg agcagaggtt gcagtaagcc gagatcgtac ccctgcactc   177000
cagcctggat gacagagcaa gactcaatct ccaaaaaaaa aaaaaaaaa aaaaaaatca    177060
aaggtcgtga ccccacatta cttatctagg ttccaatatt aaaaatatta ataatattac   177120
aactgttgag aagtgtttcc ttcttatcta aaatgcaaaa tgggctgggc acggtggctc   177180
acgcctgtaa tcccagcagt ttgggaggct aagacaggtg aatcacctga ggtcaggagt   177240
tcgagaccag cctggccaac atatagtaaa accccatctc tacaaaaaat acaaaaatta   177300
gctggacata gtgccacaca tctgtagtcc cagatacttg ggaagctgag gcaggagaat   177360
cacttgaacc tgggaggcgg agcttgcagt gagccgagat tacgccactg cactccagcc   177420
tgggtgacag agcaagactc tctctctcaa aaaaaaaaaa aaataaataa ataaaaggca   177480
aaatgtatgc caggagcagc agctcaggct tgtaatgcca gcaccctgga aggccaaggc   177540
agatagatag cttcagccca ggagtttgag accagcctga acaacatgat gaaacccat    177600
ctctacaaaa acacaaaaat tagccagccg tggtggcatg ggcctgtagc cccagctact   177660
ctagaggctg aggcacttga atcaattgag cccgggaggt ccagactgca gtgagccgtg   177720
actgcgcgcc actgccctcc agccatggac aacaaagcga gacctgtct caataaaaaa    177780
ataaaaattt taaaaataaa aagtgtaact gcaattaaaa ttcctagagt ctcatgtgaa   177840
ctactttagt tcatcaaaaa taactaccta ttccttatttt attctccatt agtgaatttt   177900
tcctgacctg tgtcctcaac ttatgatctt atttgatcac agagccctag aaggcttgtg   177960
gggcataaga tcttgtcaca actactcaat tctgctttgt agcatgaagg cagacaatat   178020
gtaaacaaat aggctgatta tgttccaata aaactttatt tatgaaaaca gctagttggc   178080
tggatatgac cctgaaagcc agtttactga cctctatcta aaaagcgtta tctaacagaa   178140
atacataaaa cacatatgta atttaatatt ttccagaagc catgttaaaa aaggtaaaaa   178200
taaacagata aaattaattc tagtattttt aatttaaata tattttactt aacccattat   178260
atatacaaat catcatttca acatttaatc aatatggatt attactagcc gggtgtggtg   178320
gcatatgcct atagtcctag ctgctgggga ggctgagccc aggagttcaa ggttacagtg   178380
agctacgata gtgccactgc actctggcct aggtgacaga gtgagaccct gtctctaaaa   178440
atgtaaatta aaattaaaaa taaaatatta ccactgagtt cttttaaaat ttttttttgca   178500
tgaagccttc acaaatctga tgtgtattat actttcagca catttcactt ctgaccagcc   178560
acattcaact gctcaatagc cacatgtggg tggtggctac caactggaca gtgcagttct   178620
ggaggctatt taagtaaaac tcctgaacct tgacaatact aatgtaaaac aacaatctga   178680
acaacaaaag aaactgcagg catataattg tactctataa gtggacagaa gcaaaaatga   178740
atttagattt taaaaacaat gtttctcttg ggatagcaac tgttactgct gcttctttgt   178800
```

```
gtttttttttt tgttttttttt tttttttttg agacagggtc tccctgtgtt gcccaggctg  178860
gagtgcagtg gagcgatctc ggctgattca ctgcaacctc tgccttctgg gctcaagtga  178920
tcctcccacc tcagcctccc gagtacctgg gacttgggtg tataccacca cgcccagcta  178980
attttttgta tttttagtag agaccgggtt tcaccatgtt gcccgggctg gtctcaaacc  179040
cctgggctca ggcgatccac ccgcctcagc ctcccaaagt gctgggatta taggcaacag  179100
ttaccgtttg aggttacctg tttaaaatga ttagcagtat aagataccaa tactaacaaa  179160
attttattaa attttattcg catactttca gctgaccaac attctccctc agacaagagg  179220
ggaaaaaccc aaaatacctg gtgaacaaaa aaaaattgtt ccattttggc agagcacagt  179280
ggctcacatc taatcccagc actttgggag gccaaggtgg gtagacaact tgagctcagg  179340
agttcaagac aagcctgggc aacgtagtga accccccatg tctacaaaaa aattttttt  179400 aaataaaaaa ttagtaaggc atggtggtgt gagcctatag tcccagctac ttgggaagct  179460
gagatggcgg gattgcttga gctcaggaaa ttgaggtggc agtgagctat gattatgctg  179520
ctgtactcag cctggacaac aaagtgagac cgtgtctctt aaaaaagaca ttgttctttt  179580
ttgaaaaaat tgcctgttgc tgggcgcaac attcttaatt atttcaacat taaaaaaaag  179640
aagaagaaaa aaaagagcgc ctgtaattcc agcactttgg gaaccccaagg tgggcagatc  179700 acctgaggtc aggagttaga gaccagcctg gccaacatgg tgaaacccca tctctactaa  179760
aaatacaaaa attagccaga catggtgatg ggcacctgta ataccagcta cttggaggct  179820
aaggcaggag aatcgcttga acccaggagg cggaggttgc agtgagctga gatcgcgcca  179880
ttgcacttca gcctgggcaa caagagtgaa actctgtctc aaaaaaaaaa aaaaagaaa  179940 gaaaagaaa aagaaaaaat tgcttgttac tattttttt ttgtatcgta catgtgggta  180000
cactgccaat actacttggg tttgttgact gccttcagag ggagaaaatg ctaaattttg  180060
gctgggtgta gtggctcacg catgtaatcc cagcactttg ggaagccgag gcaagcagat  180120
tacttgaggt caggagtacg agaccgtct ggccaacatg gtgaaacccc atctccacca  180180
aaaatacaaa aattagccag gtgtggtggc gcacacctgt aatcccagtt cttgggagg  180240 ctgaggcaga atcacttgaa ccggggaggt agaggttgca gtgagccgag attgtgccac  180300
tgcactccag cctgggtgac agagtaagac ttggtctcaa aaaaaaaag aaagaaagaa  180360 agaaagaaag aaagaaagaa agaaagaaaa caaaacaaaa ggctgaattt cagctaaagg  180420
tatgtgaaaa taaagataca tattttcttt cccatccaag gtcacagatg ccatgaattc  180480
tattcatgga tcccatgcat ctctgaatcc tatttaggtt cagaacccct gagggaaagg  180540
aaagtttatt tataaactca actgaaaaaa tgcttccggc agggcccagt ggctcacgcc  180600
tgtaattcca gcactttggg aggtggaggt gggtggatca tctgaggtca ggagttcaag  180660
accagcctgg ccaacatggt gaaaccccat ctctaataaa aatacaaaaa tttagctggg  180720
tgtggtggca tgcacctgta atcccagtta cttgggaggc tgaggcagga aatcgcttg  180780 aacccgggag gcagaggttg cagtgagcca agatcttgcc attgcactcc agcctgggca  180840
acagagggag actccatctc aaaaaaaaaa aaaaaaaaa aaaaaaaacg ctaacacgtc  180900
atagagatag aaggtccaga ttttctactc tgccccataa atagctacat ctattgtatt  180960
agactttaca cagtagaaat cataacacaa actacagagc acaaagcaaa tatagtaaac  181020
attgaaaaga tccattacaa atacaaactg aatgttaata ttttgttagt ataaaaccac  181080
tacttgaatg ccgaatctgt agttattagc attactaaac ctacaatttg cataaaatac  181140
tttgcaaatt atgcatctta ttgttaatct aaaattgcta cacactgtgc tctgacctag  181200
```

-continued

```
taattcagcc aactgcaggt tttagtaaaa gcgctaggga tccaaatgtg tccactccaa    181260
agtgtcccat catggaacat taattattca ccaaatgtgc ttaatagcac tttctaaact    181320
acaagctcca tgcaaatatt caacattatt gggagaggat tcatacagca ctattaaaat    181380
ccctcgaaat tataaagtag taacagtaat aagtcacaga aacactttaa aaatcactac    181440
aaatttataa tttaccaaac tatcaaacag ataacacttt aaatactgaa aattatttcg    181500
cttcctataa attgatatta tcttaaaata gtagattatc tttaaaatag cagatttaaa    181560
gaaacagcag aagacaatta tagtatatcc acaaattact atgcagacat taaaaattat    181620
atctttaaat cttattcaaa atgttcccag taagtaatca caggatccaa aactgcaaat    181680
agcatataat cccaattta tctatataaa aatatgagct gaagaagcaa ataataaaaa      181740
attaatttcg ttctggtgga atggtgtaat cccagggtat ttattgtctc tcttatactt    181800
ttagatgttt tctctatttt caacaacatc cctgtattat ttacttataa tcaaaaaggt    181860
tttacatagc ataaaaatac aatccactta atataggtat ttttcacata ggtaaaaaaa    181920
atgtggaatc actcatgtta ttagcatgta agagagaaaa ttttcagggg ctctaagtcc    181980
aaataatctc cctcacaact gctgtgcatt ctgagcacac ttcgggagcc aatgcttctc    182040
ttcccggtat gtgcagctcc ctcgctctcc tggtctctgg cactatccac aaaccatcac    182100
ggagtaagga gtcattgttt ccctcctgcc tatatataga catggtctct gtattaaccg    182160
gattactgac caaaatgagc ctatgccggg acaagaaggc tatcaagcca caagagaggt    182220
gctctgaagt gaactcataa gagctggatg gcactgacag aaaactctgg cttctttggc    182280
tgaccagggt tcagcgtgca tttctaggta cccaattaca tccattggat gcatcttttg    182340
gagcgaaagt tattgcctta ttaagcaaac ctaggatttc tttttttttt tttttttttg    182400
agacagagtc tcgctctgtc atccagactg aagtgcagtg gtgtgatctt ggctcactac    182460
aacctccgcc tctgaggtgc aaacaattct cctgcctcag cctcccaagt agctgggatt    182520
acaggcaccc accaccacgc ccagctaatt tttaaaacat tttttgtaga gatggggttt    182580
tcccatgttg gccaggctgg actcgaactc ctgacctcaa gtgatccacc tgcctcagcc    182640
ttccaaaatg ctgggattac agtgtgagcc acctcaccca gccaaattaa gcaaacctat    182700
gagttctaaa atggcctctg agagggtgtg cggaaaagag gtcctatcaa acactaatac    182760
cgggactata attggtaatc acacaggagg gcaatttggt agtatctatt aaaattaatt    182820
tgtcaccaat gacccagcaa ttccacttac cctagcgaaa taatctcagg tgtgcatgag    182880
caggcatgca agaatctgta ctgaaggact gttttaaga gtgaaaaact gaaacaacc      182940 aaaatacccca tcgtgctcaa ctgaataatg gcgtccacca aaatgtccac ctactaatcc    183000
ttggaacctg taaatgtgac cttagatggc aaaagggact ttgcagatgt gattaagtta    183060
aagatcttga gatggaggga ttatcctgta ttatctgggg gggccctaaa tgtactcaca    183120
agggtgctta taaagggat gtgggaagag tgggtcagag gagaaggcga tgtgatgaca     183180
gatgagagac tgcagtaaca tactctgaag atggaggaaa cagcaacaag ccaagaaata    183240
caagtggcca caagaagctg tggaaaaggc atgggaacag attctccct agagcctgca     183300 gaaggaacca gacctaccaa tgcttgactt ttagcccagt gagactcatt tcaaactttt    183360
gacttccaaa aatgtgagaa taaatccatg ttgccttaag ccacgaaatt tgtgataatc    183420
tgttaacatg gcaacaggaa actaagatac tcatcaatag ggaatgtcta aataaaactg    183480
tggcatttct agagtcttgt gcagcactta aaaataatgt ggtagatata tatatggaga    183540
```

```
cacagaatga tcaaaacata tccttgagtt taaaaagaaa gcaagttaca gaaagatatg 183600
tctagtatga catctttatg taaaaaagaa aaaaatagaa tgtgttatat acacaccaaa 183660
attttaaaat ggtcttgaag aatatacacg aaaaaatttt cactaattta gccagggcaa 183720
gaaggacaca gagatccaaa ttagagatgg tgcttaaaag ggacttcagt tttacctgtt 183780
atttccgttt tgtcaagaat gtattcatgt actactcata gttttttttt taattaatag 183840
atacataagc tgtgcttaaa atacaggatc aaaataaaag ttacacaatt tctgcaattt 183900
ctctcctatg catttgtccc atagttgatc acctgctgtt atttacattt gtctacaact 183960
attgactaaa catcttgtaa agcagactac actccttgtg ttcaccccac aaccactgtt 184020
gtaaaacaag agggaaaggt ggggagggga aagcatgggg cactttcggc aattgacagt 184080
actttcataa ttaacaccac agttaccttc agacctagga agaagagat gtatgaccac 184140 ccacccagca gctcgagcca acaggtagta ttttatgaca gtaaagatgg aagccaagaa 184200
gacagataat aatcaaagct gatttattta gcaagacctt aggtatacaa ttggagaaaa 184260
actgaaacag agactatcta ttatctcatc tgcctagcca cactgcaaac aaattgagaa 184320
ggaagaaaat tccagccagg cgcggtggtt cacacctgta atcccagcac tctggaaggc 184380
cgaggtgggt ggagcacctg aggtcaggag ttcaagagca gcctgaccaa cgtagtgaaa 184440
ccccatctct tctaaaaata caaagctagc tgggcatggt ggcacatgcc tgtaatctca 184500
gctacttggg aggccgaggc agaagaatag cttgaaccca agaggcggag gttttagtga 184560
gccgagatca cgccattgca ctccagcctg ggcaacaaaa gagaaactcc atctcaaaaa 184620
gaaaaaaaaa ggaaagaaaa ttccagccag gtacagtggc ttgtacctgt aatcccagca 184680
ctttgggagg ccaaggcaag cgagtcatct gaggtcagga gttcgagacc agcctgacca 184740
acatggagaa accccgtctc tactaaaact acaaaatgag ctgggcgtgg aggcgggcgc 184800
ctgtaatccc agctacttgg aaggctgagg caggagaatc gcttaaaccc gggaggcgga 184860
ggttgcggta agccgagatt gtgccgttgc actccagact gggcaacaag agtgaaactc 184920
tgtctcaaaa aaaacacaa aaaaacaag gaaaagaaa attccgcagg gatcaccaac 184980
caaacaaaca aacaaaaac gattccacta ctatagaaaa aattatgttg atgggatagt 185040
tttgctttca aatacaatag gcagctggct gaatatgcat aaaataaccct ccaagcaaca 185100 tagcacctta taaagagagt caatacactt taaacataat cacatctttt tttttttttt 185160
tttaatattt tggtgtcagg gaatcactct gtcatgcagg ctggagtaca gtggcacaat 185220
catagcttac tgcctcttcc agctcctgga ctcaagtgat cctcccacct cagcctccca 185280
agtagccaac cacgccccgc taattttttt tattttttta agatggagtc tcgctttgtc 185340
gcccagtctg gagtgcagtg gcgcaatctc ggctcactgc aagctccgcc tcctgggttc 185400
acgccgttct cctgcctcag cctcccgagt agctgggact acaggtgccc gccaccatgc 185460
ccggctaatt ttttgtattt ttttagtaga cgggggttt caccgtgtta gcgaagatgg 185520
tctcgatctc ctgacctcgt gatccgccca cctgacctcg tgtgatccgc ccacctctgc 185580
ctcccaaagt gctgggatta caggcatgag ccactgcacc tggcccatgt ctagctaatt 185640
ttaaaatgtt ttgtagagat gggatcttgc tatgttgccc aggctggtct tgaactcctg 185700
gcctcaagca attctcctgc tttggcctct caagtgctgg aattacaggc atgagccacc 185760
acactcagcc cacatccatc ttattattat tattgttatt tttgtttggt ttttttgaga 185820
cagggtctgg ctctgtcacc caggctggag tacagtgaca gtcttcgcct actacaacct 185880
ttgcctccta ggctcaagta attttcagc ctcagcctcc tgagtagctg ggactacaag 185940
```

```
tgcatgccac cacgcccagc taattttatt gtatttgttt gtagggagag agttttgcca 186000
tgttgtccag gctggtcttg aactccagtc cactccttgc cctcccatag tgctgagatt 186060
acaggcatga gacaccatat ctggccacct ccatcttttt aattctgaca ttagccctat 186120
cattatccca ctcttttaga tgatgatagt ataacataat agttcaagaa tatggactca 186180
gggctggaat cagacagacc tatttcagtc ttagctttgc cactaactat cttacctttg 186240
tcaagttact taacttttgt ctgtgccagt ttcctcattt ataaaataaa gataatcctt 186300
ggccaggcac ggtggctgac gcctgaaatt ccaacacttg ggaggccaag gagggtggat 186360
cacttgaggt caggagttag cctggccaac atggtgaaac cccgtctcta ctaaaaatac 186420
aaaaaatagc caggtgtggt ggcacgggag ttactcggga ggctgaggca gaagaatcac 186480
ttgaacccag gaggcggagg ttgcagtgag ccgagatcac gccactgcac tccagcctgg 186540
gcgacaaagt aagactccat ttcaaaacaa acaaaacaaa acaaaaataa taaaagtaaa 186600
gataatccag taccaacctc atgtttttg tgaggatcaa ataaaataat ggatgtgaag 186660
tacttagcac agaacatacc actcaatatg ctggcgctgt tgtcgtggga gtggtagaga 186720
tagtgacaat gatgactaag aagatgcacc agaagataac taggggctga gcgcagtggc 186780
tcacacatat aatcccagca ctttgggagg ctgaggtggg cagatcacca gaggtcagga 186840
gttccagacc agcctggcca acattgtgaa accctgtgtc tgctaaaaat ataaaattag 186900
ccaggcatgg tgatgcatgc ctgtaatccc aactactcgg gaggctgagg caggagaacc 186960
acttgaaccc gggaggcgaa ggttgcagtg agctgcgatc gtgctattgc gctccagcct 187020
aggtgacaga acgagactct gtctcaaaaa aaaaaaaaa aaaagtaac tagtgatttc 187080 tgaaggtatg gaatttggcc aggtgcagtg gctcacacct gtattccag cactttggga 187140 gactgagaca ggaggattgc ttgaggccag gagttcacaa ccagcctgag caacacagca 187200
tgactccatc tctataaaac attaaaaaat tagtagcaca ccggtagtcc cagctactca 187260
ggaggctaag gtgggaagac cacttaaagc acaggagtgt gaggctgcag tgaactatga 187320
tcacaccact gctctccagc cagtgacaga gtgagaacct gtctctagaa aaatatgttt 187380 aaaaaaggt atggaatttg cccaaggtca tacagcaagc aaggagcaga gctagaattt 187440
caatcccagt ttgactcttt aaacctgact ttaacttcaa ggcaatactg tctcccacag 187500
ccctcaaata cttcattctc attttacagc tcgagccaga caagcctgaa agcctgttgg 187560
gccttttgcc caagctcaca gaatactgca ccaagattca gtgactccta ttacagtgct 187620
cattaattgc atggtaatca acactactgg tgaacaaggg tagtttattc gcttattcat 187680
taactcatcc aaatctagaa ttctataaaa gtacataaac actttccaaa ggattttgcc 187740
caaaggatat ataggctagc agtgtcctcc taggagaata gaccaacata aatctaaata 187800
tcatctcaaa gatttcactt gagtgtatga taagtattta aagccttgat gatttcagct 187860
gatcaacttc aaacccaaat gccccttttc ttatctggca aaacaaaata ataaacaaaa 187920 acccttgca tctattaggt tccatttgtt aattaacata taattggcgt acagtaaact 187980
gcacatattt aaagtgtgtg atttaatgag ttttgacata catatacaaa tgtgaaacca 188040
tcaccacaat caaaataggg aaagagccat cgccccaaaa gtttcttcat gctcctttat 188100
actccgtccc tctcatcctt tcctgcctgc ctgcctctat cccaggtaa ccactacaga 188160 ttagtctgca tttctagaat ttcatagaaa tggagtctta cagtatatac tcctgttgt 188220 ctggtttctt ccactctgca taaatccatg ttgtgagtac caacggttca ttcgttttg 188280
```

```
ttgctgagta atactccatt gtatggatgt accacatttg tttatccatt cacctgctga   188340
cggacatttg gattgtttcc agctttgggc aatcacaaat aaagctgact tgaacattca   188400
cgttcaagtc tttgtgtggt gtgggcggg gtggagaggg agtacttaaa agcaaacaca    188460
atgaaatatg agaagcacta accaaaatgc ttaaatttaa aatgaacttc aactgtggag   188520
taagaaatat cttagccacc ttgggtaagt caatcagctt ctctgtcaat actcttatat   188580
acgatgcctg cttgttccca accgcagttt gtaaagaaaa atggaatagg aagcagaatg   188640
cttttggaat tctcacaagt aagctattcc ttcttttccc cctcttaaat tccctttatc    188700
ttaaaagaa taatgttcta tgaaatgcaa tgcaaaatgc aataacattt gagatgttat     188760
ttttgagtta ttgcttttttt atttctctta aatgtatatt tatttcaaca ttttaaaaaa   188820
atttcctaag ccgtcgtgg tggctcacgt ctgtaatccc aaaactttga gaggtagagg     188880
cggctggatc acttgaggtc agcagttcaa gtccaccctg gccaatatgg cgaaaccgca    188940
tctctactaa aaatacaaaa aaaaaaaaaa aattagctgg ggtgagggtc gcttgtaatc    189000
ccagctactt ggcaggctga ggcaggagaa tcccttgaac ctgagaggca gaggttgcag    189060
tgaaccgaga tacagccatt gcaccctagg ttgggcaaca gagcaggact cctgtctaaa    189120
aaaaaataat aataaaaatt cctatatgcc ttttgctttc caccagcaac ataaaattaa    189180
aataaataca aacggctatt ttttctttt ttttctcttt gccttttcc acatgttcta      189240
acaaatggct attttaaaga ataagcaaaa gcctcactct gcattctttt tttttgtttt   189300
gttttggaga tggagtctca ctctgtggcc caggctggag cgcagtggcc tgatctcggc    189360
tcactgcaag ctccgcctcc tgggttcacg ccattctcct gcctcagcct cccgagtagc    189420
tgggactaca ggcgcccgcc accacgcccg gctaattttt tgtatttta gtagagacgg     189480
ggtttcaccg tgttagccag gatggtctcg atctcctgac ctcgtgatct gcccgccgtg    189540
gcctcccaaa gtgctgggat tacaggcatg agccaccacg cccggccaca ctctgcattc    189600
ttaattcact catagtaaga tccaaagccc tcacctacaa ggatctactt gatttgtatc    189660
ccctgctccc catctctcct ctccccttta gcttactggg ctcagacctc caaatatgct    189720
gaggacgctt ccctctcaag gacttggctc ttgctgtcgt ctctgtatgg gatgttcttt    189780
cccatatggt atactccctc cctcccttca ggtctctgct caaaagccat cctgggcttt    189840
ccttttgtgt ccaccctata taaaacagga caggctgggt gcagtggctg acgcctgtaa    189900
tcccaactct ttgggaggcg gaggtgggca gatcacctga ggtccggagt tcaagaccag    189960
cctgaccaac atggtgaaac tcatctctac taaaaataca aaaattagcc aggcgtggtg    190020
gtgcgtgcct gtaatctcag ctcctcaggg ggctgaggct ggagaatcgc ctcaacccgg    190080
gaggtggagg ctgcagtgag cagagatggc actactgcat tccagcctgg gaaacagagc    190140
aagaatctct gtctcgaaca taaataatta aaaataagat aaaataaaac aggacagttg    190200
gctgagtgca gtgactcatg ctgagcactc tgggagtctc aggtgggaag atcacttgag    190260
gccaagagga attcaagacc agcctggaca atatagcaag gccccaactc taataaaaaa    190320
aaaaaataaa acaaaaaaac ggagccctct ttccaatgct ctccatctct ttactgagct    190380
atacttttct ctttagcact tatcatttgc ctctatgtca tgttacatat ttgtcattgt    190440
ctatatcatc ccactaaatt ataagctttt tgaggacaag gatttatttt tatccactgc    190500
tatatcccca acatccagga cggttggccc agctcactct aaattccacc aatacttgtt    190560
gaatgaatta gttgattaaa cattatttat tgctttaaaa aaaaatcgt ttagaaattt     190620
actgggaaga ggccgggtgc ggtggctcac gcctgtaatc tcggcacttt gggaggctaa    190680
```

```
ggaaagcaga ttatttgagg ttaggagttc gagaccagcc tggccaacat ggtgaaaccc   190740
agtgtctact aaaaatacaa aattagctgg gcatggtggc acatgcctgt aatcccagct   190800
cctcaggggg ctgaggctgg agaatcgcct caacccggga ggtggaggct gcagtgagca   190860
gagatggcac tactgcattc cagcctgggc gacagagcaa gactccgtct caaaaaaaaa   190920
aaccaaaaat taatagacca cgaatcttcc tcaaatatga aaagaaaca gttactaaaa    190980
gaaaatagag attcttcctt ctgtagccag ttatgaaatt aaaataatt gcaaataaaa    191040
atactataca tgcatggagg caataaaata ttatgatgag gagcagatgt gcagtgaaca   191100
gtactatgat gaacgtatnn nnnnnnnnnn nnnnnnnnnn nnnnnnnnnn nnnnnnnnnn   191160
nnnnnnnnnn nnnnnnnnnn nnnnnnnnnn nnnnnnnnnn nnnnnnnnnn nnnnnnnngg   191220
atcctcctgc ctcagcctcc caaagtgttg ggattacagg catgagccac cacactcaga   191280
ctttgttgac ttcttaataa gaaaaatact tgttaagagt ttcttcagat cactttcctt   191340
tatcaacaag taaacatga ctgaggaagt tgtggtcccc tttgcttccc tgcccaggcc    191400
cgtttccctc cctcttttcc cagaggaaac caccaagagg ttggcatata ttcttcctga   191460
acgtgttttt atagttgtac tgcacttgta ctgtgtatga acaatataaa gttggtttgt   191520
gtgtttaaaa aattcacata catggattta taatgtatgt atcattttgc aacttaaaaa   191580
ttttttttg agctccatgc tgattgataa cgatctattt ttttttttg agatggagtt    191640
tcagtcttat tgcccaggct gaagtgcaat ggcgtgatct cagctcactg caacctcagc   191700
ctcctgggtt caagctattc tcctgtctca gcctccggag tggctgggat tacaggtgca   191760
tgccaccatg cccagctaat ttttgtattt ttagtagaga tggggttca ccatgtcgac    191820
caggctggtc tcaaactcct gacctcaggt gatctgcctg ccttggcctc ccaaagtgct   191880
ggaattacag gcatgagcta ccatgcctgg cctttttttt tttttttttt tgagacaaag   191940
tcttgctctt tttcccaggc tggagtgcag tggccacaat cttggctcac tgcaacctct   192000
gcctcctgag ttcaagcagt tctcctgcct cagcctcctg agtagctggg attacagaca   192060
tgtaccacca tgccaagtta attttgtat ttttttgtaga gactaggttt taccatgttg    192120
gccaggctgg tcctgaactc ctgacttaaa gtgatccatc tgccttggct tcccaaagtg   192180
ctggggttac aggcatgagc tatcgcgcct ggcctgagaa atctcattct tactcctact   192240
cccttgcaca ctatctccat tctgtaggta gccatttcta ttaatttctt gtttacccctt   192300
ctgtgttct ttcattcttt ttctttttt ctttttttt tttgagacaa tcttgctctg      192360
ttgcccagac tggagtgcag tggtgtgatc ttggctcacc gcaacctcca cctcctgggt   192420
tcaagtgatt ttcatgactc agccacctaa gtagttggga ttacagcgcc tggtgtacac   192480
taccacaccc agctaatttg tgtatttta gtagagatgg ggtttcacca tgttgtccag    192540
gctaatctcc aactcttggc ctcaagggat ctgcctgtct cagcctccca aagtgctggg   192600
attataggca tgagccacca tgcctggccc tatgtttctt tttataaaaa taagcaaatt   192660
aatatttta ttactatttt cctttttattt ttacacatca agtagaacat taaatatatt    192720
tctctgtaat ttttttcagt tacctaaatc ttttagtgat ctctctcatc ttttaatca    192780
gctggatcgc attctatcat gtgaatattt tataacttct atatactgtc accagcaggt   192840
agcgatttag ttgtgtctaa tattttaaaa tgatatataa tgcctcaatg aatatagtaa   192900
ccttttgcat atattgtttt gtgctttggg ataacactac ctcgtattgg aaactgtgtc   192960
attacatgtg tctttaaaat tacatgtgtc ttttatttt tattttatt ttttttgagt     193020
```

```
gggagtttca ctcttgttgc ccaggctgga gtgcagtggt gagatctcgg ccgactgcaa    193080
cttccgcctc ccgggttcaa gcgattctcc tgcctcagcc tccccagtag gtgagattac    193140
aggtgcctgc caccacgccc agctaatttt tgtattttta gtagggacgg ggtttcacca    193200
tgttggccag gctggtatcg gtctgctgac ctcaggtgat cctcccacct cagcctccca    193260
aagtgctggg attacagacg tgagccacca tgcctggcca tcactttttt ttttttctta    193320
attgctgcat agtggccggg cacagtggct cacgcctgta atcccagcac tttgggaggc    193380
caaggcaggc ggcggatcat gaggtcagga gaccaatacc atcctggcta acatggtgaa    193440
accccgtctc tactaaaaat acaaaaaaat ttagctgggc gtcgtggcgg gcgcctgtag    193500
tcccagctac ttgggaggtt gaggcaggag aatggtgtga acccgggacg tggagcttgc    193560
agtgagccaa gattgcacca ctgcactcca gcctgggtga tggagtgaga ctctgtctca    193620
aaaacaaaca aacaaacaaa aaaattgctg catagtattc cattgtatga gtagtaacac    193680
aacaattttt ataatgcata gtattccatt gtatgaatag taatgtagca ctatttgttt    193740
atacattttt atgattaaaa aacaaaatgt ttttctatta tgaataaagt ggcaatgaat    193800 attttttgtac aagtgttttg gtagctatac agttattgtc acttaatata tgcaattcga    193860
taggccagtc attcaaaata gaagatatac aaggtaggcc gggcgtggtg gctcacgcct    193920
gtaatctcag cactttggga ggccgaggtg ggtggatcac ctgtggttag gagtttcaga    193980
ccagcctgac caacatggag aaacctcatc tctactaaaa atacaaaagt agctgagcgt    194040
ggtggcgcat tcctgtaatc ccagcttctt gggaggctga ggtaggagaa tcacttgaac    194100
ctggatttat aatgtatgta aatccaccgc gaaggttgcg gtgaaccgag atcacgtcat    194160
tgcactccag cctgggcaat aagagcgaaa ctccatctca aaaaaaaaaa aaaaagatat    194220
gcaaggtaaa gatactaata aagacctttg tgttgagttg gttgacatgt ggttatttca    194280
cccatcgtat ttcttatagg gaataggtaa attcgttcct tgggtttctt tcaacactta    194340
ggtaaaatcc gacgtggaag atgagatctg attttactgg tgtaactctt tatttgtccc    194400
cttgcctccc tttccaatgg actatttag aagaaatgga gctgtcaccc acatcaagat    194460
tcagaacact ggtgattact atgacctgta tggaggggag aaatttgcca ctttggctga    194520
gttggtccag tattacatgg aacatcacgg gcaattaaaa gagaagaatg gagatgtcat    194580
tgagcttaaa tatcctctga actgtgcaga tcctacctct gaaaggtcag taacatttta    194640
gtgaccacaa agtctgctgc tcccttgtgc cctgagtgtc agaaatgcat gacggtctgt    194700
gtatgactct ctgactccaa aggcttgtga ctgttttttg agctgtaatc tttaaagaat    194760
tactaaagtg agactaatag catcaaatta ttttcagagt acctttttcc tgcaaaagtt    194820
ttaatcagtg ttacttacac tcatcctata ggggttgcat accattcctg catatacttg    194880
gtacgtgtat tagttttaag acttattgaa cttcagcaga taatctttga gagttattag    194940
aggaaaacaa atgataatgg agacaccaaa atagcagcag ttttctatgg tggctctcga    195000
ccagttattc agcaatgtca ccaacagatg tcagtttaag ctcagaagtg gaaaagcaga    195060
gagctcagag ggtcagcttt ttcatcagtt ctttttaatgt tatcaccaca attatgtgag    195120
aatgaccttg cttagagaaa attatgttat tttcgagatc tttcccctg tgttggaact    195180 aggctgatga aagcatgggc ttgacttatt tattgattgt attcgttttg tacattccca    195240
atctcctctc tgacttggtg caaattcagg atctcttagt tagtttgtat attttgtgtc    195300
ttcaggtatg attttttcag cttataccttt tatgtcagtg ctattatgtg ctgataattt    195360
gtttctctag ctaccaccgt agcttcaggc aaaaggctgt cagccaactc tgtacagttt    195420
```

-continued

```
atttctaaat tttactgttt tcagttgagt atggatgaag aataactcaa agtttattct 195480
tttgatgatg agcccttaac accacctgcc atgatagtac ttgctttctg accaagatcc 195540
tgagggaaaa agccacttta ttattagaac tatgttaaga tgcttcccaa aaaacatgga 195600
gcagtattgt ctcaaagtct gtccttggat ggctttggat gcctacatca ggactgtctg 195660
atgtgctggt taaaatgcag attcctgggc ctcattcaga cttacatgta ttgatattgc 195720
tggttgtgga gcctgggaat tcatatttt agcaaaatcc ctcatttta ctccaagtct 195780
tatgtgcatt atacagtttg agatgatcac ccaggatata gtccaaagac actggaggct 195840
gttgaagtat aggttgtata tatggaaaag gttggaatgt ttgaattaat ttataatgaa 195900
gatccttttt aattgagtgt tcacatgcca aggcaaggac aaacattcaa aatgattttc 195960
tgtctctgtt acaactttt ctttcttttt tttaatttat ttatttgaga tggagtctca 196020
ctctgtcacc caggctggag tcaagtgacg cgatctcggc tcactacaac ctccgcctcc 196080
cagattcaag taattctctt gcctcagcct cccgagtagc tgggactaca ggcatgtgcc 196140
accatgccca gttaattttt gtattttag tagagacagg gttttgtcat gtttgccagg 196200
ctggtctcaa actcctgaac tcaggtgatc cgcccacctt gacctctcaa agtgctggga 196260
ttataggcgt gagccaccgt gcctgtctct attacaactt tttattacaa cttctttatt 196320
ttgactttat ttttacaaat tatttattta ttttttttga gatggagttt cgctcgtcac 196380
ccaggctgga gtgcaatggt gcgatctcag ctcactgcaa cctccgcctc ccaggttcaa 196440
gtgattctcc tgcctcagcc tcctgagtag ctgggattac aggcacttgc caccacaccc 196500
ggccaattt gtattttag cagagacagg gtttcaccat gttggtcagg ctggtctcga 196560
attcttgacc tcaggtgatc cacctgcctc ggcctcccaa agtgttggga ttacaggcat 196620
gagccaccac gtccggccga cttttatttt ttttcttga cagggtct tgctctgtca 196680
cccaagctgg agtgcggtgg catgatcata gcgcactgca gcctcgacct cctggactca 196740
agtgatcctc ctgcctcggc cttgtgtata gctgggatta caggcagttg ccaccatgcc 196800
aggctaattt ttaattgttt tgtgaagatg gggatttcac tgtgttgccc agactggtct 196860
tgaactcctg gcctcaagtg atcttcctgc cttggccttc caaagtgttg ggattacagg 196920
cataagccac tatgcatggc ctgtaacttc tttaaatggc tataattaaa cagttggtcc 196980
ttttaagatt gggcaatgga cgaatggcaa attgcatttt taaagagga gggatttaaa 197040
aaaaaacagg aaagattggg gcatttgtct ctaaaggact gtggactcat ttaagaagtt 197100
tagtggtcat tcttaccatc tttgtggttt ttcctgcctg catgggatgc agattttctg 197160
tctcaggtgg gattgatcaa tcccttggag gaatgtgtct acttttaat tgtgtttagg 197220
agagctgact gtatacagta gttttgtgaa agaacaacat gaacccatag tagagctaaa 197280
ttcttttta ttttttaaaa actttaggtg gtttcatgga catctctctg ggaaagaagc 197340
agagaaatta ttaactgaaa aaggaaaaca tggtagtttt cttgtacgag agagccagag 197400
ccaccctgga gatttttgttc tttctgtgcg cactggtgat gacaaagggg agagcaatga 197460
cggcaagtct aaagtgaccc atgttatgat tcgctgtcag gtaaatctcc agttgaaaaa 197520
tgggtctggc aagatgttac ctttgggtga ttttctgct gacagaagac agacaccatt 197580
acattcaaag tcagattgtc ttttatttat ttatttattt atttatttat ttgagacagg 197640
gtcttgctct atcacctaca gatgggggttt caccacgttg ggtctggtga cccaaatctt 197700
tgggtgattt ttctgctgga agaggacaaa caccattaca ttcaaagtca gattttctgt 197760
```

```
tttttttttt tttttgtttt tgttttttta atattcattt gtttattcat ttgagactgg  197820
gtcttgctct gtcacgcagg ctggagtgca acctccctgg gctcagttga tcttccctca  197880
gcctcttgag tagctgggac tacaggtgtg tgccaccatg cccagctagt gtttgtattt  197940
tttgtggaga tggtgttttg ccgcattgcc cagtgtggtc ttgaactagt gctcaagagg  198000
cctgcctcct tcaacctctc aaagtgttag gattacagat gtgaactact gtgcctgatc  198060
caaagtcaga ttttctttgc ttacttagtc aagttcgtct atgcttttat tatacttaat  198120
atattagtat agttactgta ttagtatatt agcatattta atatattatt atacttatca  198180
tacttgagta tattgagtat atttacactt ttagtatatt tgtatacaca caccacattt  198240
ttattattta tcttttttt gagacagagt ctccctctgt ctcccaggct gaagcacagt  198300
tggctcactg caacctctgc ctcttgggct caagtgattc tcgtgcctca ccctcctgag  198360
tagcagggat tacaggtgtc caccaccaag cctggctaat ttttgtattt ttagtggata  198420
tggggtttta ccatgttggc caggctggtc tcgaactcct gacctcaaat gatctgcccg  198480
ccttggcctc ccaaagtgct ggaattactg gcgtgagcca ctgcacccag cctattatct  198540
gtcttttgat ggacatttaa gttgtctcta tatactagct attgtgaata atgctgcagt  198600
gaacatgaga gtgcttgaaa acactaatgt aacataaagg taacaaataa taaatgtcat  198660
gtgtttatct tgaaaggaac tgaaatacga cgttggtgga ggagaacggt ttgattcttt  198720
gacagatctt gtggaacatt ataagaagaa tcctatggtg gaaacattgg gtacagtact  198780
acaactcaag caggtgagca gattggaaag ctcaagcttt ctccttaaaa acttaaaaca  198840
aatcctaata gagaattttg caaacataca gaggtagaca gaatagtatc atcagcctcc  198900
atgtacccat tgcagcttca actatcaaat cttttttttt tttttttttt ttgagacagt  198960
cttactctgt cacccagtct ggagtacagt gttgcaatct tggctcacta caacctctgc  199020
ttcctgggtt caagcgattc tcctgcctca gcctcctgag tagctgggac tacaggtgcc  199080
caccaccatg cccggctagt ttttgtgttt ttaatagaga tggggtttca ccatgttggc  199140
ctggctggtc ttgaattccc gacctcaggt tttctgcccg ccttggcctc ccgaagtttt  199200
gggattacag gcgtgagcta ccacgcccgg ccctaaatct tttcttatta tgattccact  199260
cactgactgc cgctatagta cttggaaaca tattccagat ttatattatt cccatattta  199320
tctgtaaaag gcattacaga ggttcttttt tttttttttt tttttgaga tggagttttg  199380
ctctgtcgcc caggctggag tgcagtggcg tgttcttggc tcactgcaac ctctgcgtcc  199440
cgggttcaag agcttctcct gcctcagcct cctgagtagc tgggattata ggtggtgcca  199500
ctacacccag ctaattttg tatttttagt agagatgggg tttcaccatg ttagccaggc  199560
tggtcttgaa ctcctgacct caagtgatct gcctgcctca gcctctcaaa gtgctgggat  199620
tataggcatg agccactgca tctggcctaa ggctgtacag agttttaaag caagttttca  199680
ttatagatcc acttctggtt acctttaggt aacctcactt attcactttg gcattgttgc  199740
tatttcaaat ttcaccttta tgatagtgga aaatgatata atctctctaa ataatgtggt  199800
ctattcataa agaaaaatag gcttgaattt atatcagcag agtaaagtgt atgtgaagac  199860
tgaagaaaga tacattttct ggctgaacag aaaacacggt gaaacgattt gaaaacttt  199920
attgtgaatt acagggtcct atgaaccctc tgtccgtgcc tttatgaata tcaacataga  199980
catgtttttt tttttttttt tgcattaaca ccgttttctg taatattttc tttatttttac  200040
atcaactgct gtactcgatc agccccttaa cacgactcgt ataaatgctg ctgaaataga  200100
aagcagagtt cgagaactaa gcaaattagc tgagaccaca gataaagtca aacaaggctt  200160
```

```
ttgggaagaa tttgaggtaa gttattaaaa aactgttttt acgtgagttg ttatatccta    200220
tttttagtgg aggagaagtt gctcttgtgt ttggaattgg acctgagaga cttgaaactg    200280
acgtcctttt ttaattcggc cattgattga cacggagcaa gttgctgaga gggcttcttc    200340
gaaacagaag agcattgtgt tctgagggaa gggagttggc agtgagtagt caatggatgt    200400
gctagccgct ccatttggct cttttggttt ggactggtgg caaaatctca gagaaacaaa    200460
aggatctaat ttcttcgaaa gatttccagc atgcactggg gtctttagaa acaatctata    200520
gccttagtgc agcaaatgag tatgagtaaa agagaaacac cttgtggtgg ctttttttt     200580
tttttttttg agacagggtc tcgctctgtc gccgaagctg gagtgtagtg gcgtgatctc    200640
ggtttactgc agccccgtcc tccctgggct caagtgatct cccatctca gcctactgag     200700
tagctgggac tacaggcaca tgcccctatg cctggctaat ttttgtattt ttggtagaga    200760
tgaggttttg cagtgttgcc caggctggtc ttgaactctt gggctcaagt gatcctccta    200820
cttaagcttc ccgagtagct gggactacag gcacacgata ccatgcccat ctaattttg     200880
tattttttg tagagatggg gttttgcagt gttgcccagg ctggtcttga actcttgggc     200940
tcaagtgatc ctccagcttt gacgtgccaa atgtggtggc tttaatttca gagttcaaat    201000
tgataactct ggtaagttaa gtgaactgat ttctttttt tttaaattat ttttgttgat     201060
tatactttaa gttctgggat atatgtgcag aacgtgcagg tttgtacata ggtatacatg    201120
tgccatcatg gtttgctgca cacattaacc catcatttag gttttaagtc ctgcatgcat    201180
taggtgtttg tcctaatgct ctccctcccc tttaatgcat cagtgaaaaa gtgatgatag    201240
gctgggcgtg gtggctcact cctgtaatct cagcactttg agagggtgag gcaggtggac    201300
cacttgaatc caggagtttg ccccccatccc cagacagtgt gtgtgatgtt cccctccctg    201360
tgtccatgtg ttctcattgt ttggttttct gttcctgtgt tagtttgctg agaatgatgg    201420
tttccagctt catccatgac cctgcaaagg acatgaactc attctttttt tatggctgca    201480
tagtattcca tggtgtgtat gtgccacatt ttctttatcc ggtctatcat tgatgggcat    201540
ttgggttggt tccaagtctt tgctattgta aatagtgctg caataaacat atgtgtgcat    201600
atgtctttat agtagaatgt tttataatcc tttgggtata tacccagtaa tgggattgct    201660
gggtcaaatg gtatttctgg ttctagatcc ttgaggagtc accacactgt cttccacaat    201720
ggttcaacta atttacactc ccaccaacag tgtaaaagca ttcctatttc tccacatctt    201780
ctccagcatc tgttgtttcc tgactttaag tgaactgatc tctttcctga aactaacttg    201840
ggttggagaa tgtccctgat gggaatgtgc tgtgttccca ttgcactctt ctatatcact    201900
tacccattga caatgtgatc tctttcattt tctcctcatc catttgacag aaaacttcaa    201960
aaacaaggat tctggcatat ttacctttgc agttgtcccc agcatgtagc acggtgccta    202020
gtacacagaa gaaactccat aaatgttttgt tgaatgagat ttacatttaa ctcatgttta    202080
catcatttta ttttcctgtt ctgttttatg ggaatgatta ttctatgctt tttgaggact    202140
acaatttata aatatttgtg gattgaatga ataagtgaat actgggcaaa taaagtcctt    202200
ttagccagag tatgtctgaa caacttgctg agatagatat gatttcccat tttccagctg    202260
aggggcctaa gggaggttaa gtaaattatt caatcttcat accacagttt ttgttttgtt    202320
ttgttttgtt tttttttcctc ctgagacaga gtctcacttt gctgccatac tggagtacag    202380
tggtgcaatc atagctcact gcagcgtcca acttctgggc tcacgccatc ctcccacctc    202440
agcctcctga gtagctggta ctacaggtgt gcaccaccat agccggctaa ttttttcattt   202500
```

```
tttgtagata tggggtctca ctgtgttact caggttggtc ttgaacttct gagctcaaac   202560
aattctcctg tcttggcctc tcaaagtgtt gggattacag gtgtgagcca ctgtgcccgg   202620
cccataccac agatattgat tgaattccag cagtggggag gagtgtggaa tagaacattc   202680
tcagtccttg ctcaacatta ctgaacagag acttgaattt gagtttattc tctcatccca   202740
ggcttcgcgt taggctctga agacactagt gaacaagaca gacagggtta ctgcctttaa   202800
agggagcttt tagttgagag aaggaaaaca gtgatgaaaa gcatcagtga aaaagtgatg   202860
ataggctggg gcgtagtggc tactcctgta atctcagcac ttttagaggg tgaggcaggc   202920
agctcacttg attccaggag tttgagacca ggctgggcaa catggtaaaa ccccgtctct   202980
acaaaaaata caaaaagtag ctgggtgtgg gggtgcgcac ccacagtccc agctactctg   203040
ggggttgagg tgggaggatt gctcgagcct gggagattga ggctgcagtg agctgagatc   203100
acgtcactgc tctccagcct gagcaacaga gccagaacct gtcccaaaaa aaaaaaaaat   203160
tgatgataaa catagtgaga cagaattttg aaatctcagc ctcactgttg ccttccttgt   203220
cccctgcctg cctaaataat aaaaggcagc atttcagcag tcattcattt cattactttc   203280
acttcatttc accttcataa agcctcatga ggtaagatgg gaagatacag aagttttaga   203340
aaccgctcat caaaattgaa tggaaagccg attgttccaa aacttttag tgtggaaaat   203400 ttctattata tgcaaaagta gagagaatgg gatagttata gcagtatacc tgacacccag   203460
cattaacaac tgttgataat atggccaatc ttttcgact ctgccccact cacttcccca    203520
gccctgactt gtcttgaagc aaatactttt tttttttttt tgagatagag ttttgttttg   203580
ttttgttttt tgttttgag atggagtctc actctgtccc ccaagctgga gtgctgtggc     203640
ttgatcttgg ctcactacaa cctccgcctc ctgggttcaa gtgattcttg tgcctcagcc   203700
tcctgagtaa ctgggattac aggtgtgtac caccatgccc agctaatttt tgtatttta    203760 gtagggacag gttttcact atgttggcca cgctggtctc aaactcctga cctcaggtga     203820
tccgcctgac ttggcctccg aaagtgctgg gattgtaggt gtgagccact gctcccggcc   203880
ttgaagcaaa tcttaacaca tcatttcgtc tgtaactatt ttatttcaaa aaattataac   203940
ctgaatagca ttatcatatc taaaactatt aacagtattt ccttaatatt aacacatatc   204000
agtcacattt tcctgattgc tacacacaca cacacacaca cacacacaca cacacttgca   204060
atttgtgttt ttttcttttt agatggatct cactctgttg cccaggctgg agtgcaatgg   204120
tgcattctca gctcactgca acctccacct cctgggctca actgattctc ttgcctcagc   204180
ctcctgagta gctgggacta caggtgccca ccacctcacc tggctagttt ttgtattttt   204240
agtagaggtg gggtttcacc atgttggcca ggttggtctc aaacttccga cctcaggtga   204300
tccacccacc ttggcctccc aaagtgctgg gattacaggc atgagccact gtgcccagca   204360
gcaatttgtt tgaattggga gtgctttctt ccaccttgat tatgaaaaaa tttcaaatgt   204420
gtataaaaca gattcatata aaggatcctg atatgccatt atcagcttta tcaattatcc   204480
ctgtcatcat attttttatt tataaatatt tcaatatttg tggaatcctt aaaaatgcat   204540
cacataaccc aacattgttc atattatacc aattgtctta taatttaaaa atattttgtt   204600
caatcatttt tcagataagc ttcacacact gtggttggct aagtctcata atatttctgt   204660
tgtaaaaatc ttaagtctgg gcgtggtggc acacggctgt cattccagca ctttgggagg   204720
ctgaggtggg cggatcacga ggtcaagaga tcgagaccat cctggccaac atggtgaaac   204780
ccggtctcta ctaaaaatac aaaaattagc tgggcgtggt agtgcgtgcc tgtagtccca   204840
gctactcggg aggctgaggc aggagaatcg cttgaaccca gaaggtggca gttgcagtga   204900
```

```
gccgagatcg cgccactgca ctccagccta gagacagagt gcggcttcat ctcaaaacga 204960
aacaaaacaa aacaatctta agtctcttag aatactttga tgccccttcc atctctcttt 205020
ttctgtcttc cttccccctc tccctgtctt ttctgctgtt gaagaaagca gatcatttgt 205080
cctgagagtt acttatagtc tgaattttgc tgagtgcctc tctgtggtgg acttaagcat 205140
gtatccatcc cttatatttc ttgtaagttg atatatctag agacttcatt ggatacaagt 205200
tttctttggc aagatagcat gtatggtggt gtatcaggag gtgtttatgt cctgttgttt 205260
cttctctgat tttcttagca gctcctgatc attattactt agatccatta attcataagg 205320
gactatatgg tagtgatatt gtaattttat cattcttctt catttgttag gttggcatat 205380
ttctataaaa agcttttcat cgccgagggt tgatttttc cttcttacta agcagttttc 205440
ttttcttttt cttttttttt tttttgaggt aggtctcact gtgttgctca ggctggtgtg 205500
cagtggcgca acacacagt tgcgaactct tgggctgagg tgatcctcct gcctcagttt 205560
cctgtgtagt tgggaccaca ggtgcatgcc accatgcctg gctaattttt tgattctttt 205620
gtagagatga ggtctcactt tatttcccag gctggtcttg aatgtctggg ctcaagcaat 205680
ctttctacct cagcctcctg agtagctggg actacaggca cataccacca tgcccagcta 205740
attttttaat ttttattttt agtagagatg tggtcgtatt atgttgctca ggatggtctc 205800
gaactgcaga gctcaagtga tcctcctgcc tcagcctccc agtgtgctgg gattataggt 205860
gtactacagg caagagccaa tgagcctggt cagattttt tttcctgatt tgaaatctgt 205920
tatgggttca attgatactt ccaaatcaaa ctcagggttt caggattttt actaacctca 205980
ttgatcttac ccatgtatct cctttctcta atgccaaaaa tcctacttct tgaagccata 206040
ataagattat tcatttgttt tatcccacat tacacacaac aatcttagaa taatgacttc 206100
ccaataatat gattactgaa aacagtttaa ttttttttgc gcttttcaaa aaaatccttc 206160
agagatgtgt agtcaagtta ctgtattctg ctgggcacag tggctcacgc ctataatccc 206220
agtactttgg gaggacaaga agggaggatc gctggacctc aggagtttga accagccgg 206280 ggcaatatag tgagaccctg tctctacaaa agaaaattaa aaattaacca gacatggtgg 206340
catgtcccta tagtcccagc tattgagagg ctgtggcgag agtaggctta agcccaggag 206400
tttgaagctg cagtgagata cgattgtgac actgtactct agggtgacag agcagggacc 206460 ctgttttta aaaaaaaaaa tgaaaaaact tcctgtgcct tagactcatt tgtaatcgtc 206520
cttctctctg tgtggctata tgctaactgg gtatatggtt agtttatttg tttcatttaa 206580
aaaatctctt tctgttaagt tttatttata attacacaaa tactggcttt gatagtcaaa 206640
ttgaaaaaac aaagtgtatt caagaagtc taccttctat ccttgtcctt tcctatgttt 206700
tagccatagt ataaaaagtt atggtttatc attatatttc aaaatataa gaagatattc 206760 ccatatccca ctttttctta aacagtagca taacttaca tactttttc taaccttgct 206820 tttttaaata tcctggacat cctggatatc cataatagtg tctagagata gtcttcattc 206880 ttttttact gtatagtaat ccactgtgta cttgtaccat agtttattca acctattgat 206940
gggcatttgg gtagtttcca aatgtatcac agagaggatt acagtgaata gccttgtgta 207000
tgcatcctgc tttacttttg ctgactactg gtaaatattaa catttttat gttctgtatt 207060 taaaaaatgg tggttattat tcatctataa cttttattat acatgacttt ggttagcatg 207120
ctttaacctt ttagcataac atttgcaagc tacttgtttt aattaaaatt ttggttaaat 207180
gtaaaaaata gtgagctatt ttgtaatcta gattcaatag aatcttatac ttcctttaca 207240
```

```
aatgatagct gagttgatca tttgtgtaaa tgactgtgaa cttaaaaatt acagcatttt 207300
ttaaaataaa ttttttttaac attttaaaat tatttaaaat aatagacaca caaagtaaaa 207360
agagaagaaa aaaaaaagag acagggtctt gctatgttgc ccaggctggt ctcaaactcc 207420
caggctcaaa tgatcctcct gccttggcct cctaaagtgt aagccaccac acttggcaaa 207480
aattagtttc tttaaaacaa aaacattaca ggttatctgg taccatggta gcttctttaa 207540
cactaggttc acttagaaca aagcttagga acaaagtcag actttcacaa agagcttgtg 207600
tggcaatggg gtattttttg caaattccat tggtggggtc aagatgtgag tttagaagga 207660
actcttagcc tgactcttct ggccatggaa aaagatggtt gcttctaaat gctgacctgg 207720
tgattttaca ctgtcacatc tcaaattgtg gtcatctttt atacattatt aacaacaaaa 207780
gggaaaaatt gagttgactt taagaggaag tggaaaataa cgagatcaca tctgtactct 207840
acaggctctc cacagaggtc agactgaggt ggtaaaattg ttgtgcacta aattagggca 207900
ttaacgtttc atggaaactg aagctatatc taaatagctg atggcctgct ttctagatct 207960
cctatatacc tgcttctcaa attcagtctg ttttaaaaaa ttgcccttg aggttggaac 208020 cagcgaaata aggctgaaaa cagaataagc cattattgaa aaaattagga acttggaagc 208080
agatactcat aatctaaatc ctctgaagct aaagtttgat ccacaatagc aaagcattat 208140
cattttagtg attgtacctt agttgtttcc tggcaggtga taaatttggg atcactttct 208200
tcttacagtg tgctctgata gtcttaaaa caaccagag ctctaaattg taatgccatt 208260
ggtaatttaa ctctgatttg tctctatgcc tgtctcctgg tgttctgtaa aattctacac 208320
gtcatttcag gtatcactat ccagaagacg ttacttttgc ctttgatgca cttaaaatg 208380 tgaagtctct tgtgaagctc tttggttatt ttctcctttg ctgctgaaat aaattcaggt 208440
tgatgatttt cttgtaggat atgttgtgtg atctagacat tgcaaaccca agtctttgat 208500
ttttttttcc ctacagattg cctgtttctt ttttattta atttttatta gttattatta 208560
tttttgagat ggagtctcac tctgtcaccc aggctggagt gcagaggtgt gatagctcac 208620
tgcaacctcc acctcccggg ttcttgtgcc tcagccaccc aggtagctgg gattacaggc 208680
acgtaccacc actctcagct aattttttg tattttttagt agggatggga tttctccatg 208740
ttggccaggc tgatctcaaa ctcctgacct taagtgatct tcctgccttg gtctctgaaa 208800
gtgttgggat tacaggtgtg agccactgtg cctggccagt tattaatttt tttaaagaga 208860
tggggtctca ctatcttgcc caggctggag tgcagtggct cttttacaggc actgttgtag 208920 tgcactgcag ccttgaactc ctgggctcaa gtgatcctcc tgagaggctg gaattacagg 208980
cacacaccac tgtgtccaac agattgccca tttgtgatct gtgtaaatat ctctcacttc 209040
ctgcagtatc tctgctcaag aatgtaaaga gatggataat atttttagat tgttgaaac 209100 aaagtaaagt tctgctcaaa tgagaatgac actaactaaa tgaaaaggcc ggttataatt 209160 ctgtaattt gtgcctgcaa tgtgtgtgtt attgtacact tgaatcggcc ctgtgcattg 209220
tggcgaggtg catattgcat ggttgtattg aaaaggtgct tgggccgggc gtggtggctc 209280
acacctgtaa tcccagcaat ttgggaggct gaggcagctg gattacctga ggttaggagt 209340
tcaagaccag cctggccaac atggtgaaac cctgtttcta gtaaaaaata caaaaaatta 209400
gctgggtgtg gtggtgggtg cctgtaatac cagctactag ggaggctaag gcagggagaa 209460
ttgcttaaac ctgggaggca gaggttgcag tgagctgaga ttgtgccact gcactccagc 209520
ctgagtgtat cacaaaaaaa aaaaaaaaag gttttgccc tctctctgtg cctgctgctc 209580
cctgttgagt cctataggcc tgagctgcca gggggtactg tgggctgaga ctggacattg 209640
```

```
caaccgactg caaggcaccg tgggacccag gttgtggatg gactgtctct cgggctttct 209700
tctttccatt catcttcctc ctctaactcc cctctgtatc cagtatcctt gctctccata 209760
cacctgcttc attcttttc cttcagtaga tttttctgct tcttgactta caaaccctac 209820
ttctagcccc tttcagatat tgaaactagc aactttcagg ctttgtacca aagtctcaga 209880
gattctcatt gactcggatg ccatccatct ctagtccaaa gaacaatgtc aaggacatga 209940
acatgtggaa caaaagtgtc tgctgtggac acctttgggg agaaatagtt ttcagtgatg 210000
agggttgtag tgagttgggc agatatccca aaaatatctg ccaaaaacta tagacacttc 210060
tggttgcagt gacttattcc ttccttcatt cagcaaatac tgattgaaca ccgactgtat 210120
gtctggatct attctaggtt ttgggggtgg agcagtgaac aaatcagtct ttatctttat 210180
agagtgtaca gtcaagtggg agagacaggc agtaaacaaa gaaacagttc aatattcaat 210240
ctgtgagatg gtgataagtg ctacagagaa acaaactag tgtaagataa aagggtgtt 210300
ttgataggcc tttactattt aggtctcttt gataaggtgg catttgaaca aagctctgaa 210360
ggaaataatg gagccaacca tgcatataac ctcagggaga acattctagg tagagggaac 210420
agcaagtgca aaggccctga agtgggggtt tgtttacctt gttgcacaat ctgcacacag 210480
gccagtacaa ttggaatgga tgggaaatgt aaaagagaga agttgaaaag gccaggtgca 210540
gtggctcatg cctacaatcc cagcattttg ggaggctgaa gtgggaggaa tttgagatca 210600
gcctgggcaa cagaaccaga cctcgggcta attttgtat ttttagtaga cagggttt 210660
caccatattg gccaggctga tctcaaactc ctgacctcag gtgatcctcc tgcctcagcc 210720
tcccaaagtg ctaggattac aggtgtgagc catggccccc agccgtatct ttgtcttaaa 210780
aagtaatctc tgtgcttggt aggccaagaa tttaaaatat aaaaaattta agaaagaaaa 210840
aaaataagta aagtaactat acaggttggt ctggccgtaa tggtgagtgt cattattttt 210900
cttccctagg tattttggct ctgttgctca gagcagtgca ggcgaaatgg tcattagggc 210960
atcgtcatgg tgcctgggga tgcctggctc agccagttta ttttctgtct gcctctctcc 211020
ttggtccttt tcctccactt tcattcatga aattctagtc aagagctggg tccagtggtt 211080
ttcaatccaa gggctttgga agcctctggg gtctattttg gtcattgcag tcactgggct 211140
gctgctcctg gcatttaggt tggcagggt ctgggctggg aagcaggaat gttcagtggc 211200
cataaatgta agggttggtc ttacatttac ataagggaga caatgaaaac ttaactcctc 211260
cacagtagtg gagtagtgcc gttgggtact cacagtcagt agtgccgttg ggtactcaca 211320
tgtacaacat ggatcaggac attgactttc tgtggatacc ttttaatagt ttattagatg 211380
tgttaggctg ttttgcactg ctctaaagga atatctgagt ctaggtaatt tataaagaca 211440
agaggtttaa ttggctcatg gttctgaagg ctgtacaagc atggctccag catctgcttc 211500
tggtgagggc ctcaggaagc ttccggtcat agtggaaggc aaaaggaggg cagacgatca 211560
catggccgga gtggtggcaa gggtggggtg ggagccacgc tcttttttta attttatttt 211620
aatttgagac agtgtctcac tcttttgccc agcctggagt gcagtggcgt gatctcagct 211680
cactgcagcc tctgcctccc aggttcaagc aattctcctg cctcagcctc ctgagtagtt 211740
gggactacag gcgcgcatca caatgcccag ctgattttg tatttttagc agagacaggg 211800
tttcaccatg ttggccaggc tggtctcgga ctcctgatct caagtaatcc gcctgcctcg 211860
gcctcccaaa gtgctgggat tacaggcatg agccactgcg cacggccacc acactgtttt 211920
aaacaaccag attgcacgtg aacttagagt gagaactcac tgtgaggatg gcaccaaaac 211980
```

```
attcatgaag gatccaccac cttcctttag gccccacctc caacactgga ggtcatattt    212040
caacttgaga tttggagggg acagacatcc aaaccgtatc attaaattta atagttttat    212100 gcagttttt  tggctctaga tctgtttaga ctcctgcagt caggtgtctg taactagcct    212160
ctggtccttt ttgagagttc acagtttggt gcaaacccctt tggatgtatt atttgggaaa   212220
atgggatatc tggcagcctg tgtccctgct ttacattatc cttttttgctg cctgccccaa   212280 gcctcctcat tagcatccct gccaaggcca gtggagaagg atggagatgc ggtgacattc    212340
agcttgacag gtcattagca gcttttgtgc cctagggact gctggtggga gggaggttgt    212400
ggaagataaa ccctgacagg aatgtattct cctcgagggc agggtttatt tgatattttt    212460
ctggagctta gaaccataag cctggtgctg gggaggaagc gcccttagca tttggtagcc    212520
tctgtgggca gagcatggaa agtcacaact tctgaattgt ttgtattttc agtctcactc    212580
tagatggatg gcatcttctg ctatgggaaa tgaaatatgt ttaggcaact tgagtcccag    212640
gtgcagatga ggctgggcta attggtgcac tagggaagga gccgggggag agatgtgctg    212700
ttagctatta tcaatctgtg acaactgtca gctgctggca gttagcaccc acctgagcct    212760
gggatgcagg ggtgcctctc ctgtcctctg tggaagcctc tggacccagc agccatcttg    212820
actgtgcact gttcaagccc caagtccgcc tggaagaggt gattgagaac ttactgcagg    212880
ataaggaaag cgcaggacag gtgcagtggc tcacgcctgt aatctcagtg ctttgggagg    212940
ctgaggccgg aggagggctg gagtccttga gtgcgagacc agcctgggca acatagtgag    213000
accctgtctt tacaaaaagg aaaagaatta gccagatgtg gtggtgcgtg cctgtagtcc    213060
cagccactca agaggctgag gtgcgaggat cacttgagcc caggagtttg aggttacagt    213120
gagctatgat cataccactg cattccagcc tgggtgagag agcatgactc tgtcccaaca    213180
acaaaaaaaa agattaaggg aagcctctgg cagacctgat gatgggtggc ccagccaaaa    213240
tgagtattga tgaggatttc cctggtctgg aactctgaat ttagtctggc aaagtattcc    213300 cttttgtgttg tgagatgatt cttggtgtta ccccatcacg gtaggtaaga tgaattagca    213360
aatgagaaag gctttctctt tttcatcctt atctagtccg tagatgaagc ctgaagaagg    213420
tctccatatg gtagtagtaa gtgtttaaca tctacctcta acacttgcct gtgtcttttt    213480
ttttttgcaa agcctcagga atgccccagt atctaggtag aatttgataa tatttcattt    213540
ttgttatatt cccttttctg tttaccttct atatacagca aaatgaaaaa attttaaaa    213600 tttgtgcaag taagggcaat ttctttttt  tttttctttt tttttgagac agggtcttgc    213660
tctggcaccc aggctggagt gcagtgacac aatctcggct cactgcaacc tctgcttcct    213720
gggtttaagc gattctcctg cctcaggctt ccaagtagct gggattacag gtgcctgcca    213780
ccactcccag ctaattttca tatttttagt agagaccagg ttttgccatg ttgactgggc    213840
tggtcttgaa ctcctgacct caggtgatcc atccaccttg gcctcccaaa gtgctgggat    213900
tataggcttg agccactggg cctggctgag gcagtttctt tttgaaatat attttgtgaa    213960
ggagaaaaag aggagttcag tttaaagaaa caaatgacat aagaggtggt atgcagagat    214020
gccaaagcat cttgaaggtg cttttttttt tggaaacaga gtcttgcttc attgcccagt    214080
ctggtctgca gtggtgcaat catggttccc tgcagccttg accttctggg ctcaagtaat    214140
cctcccacct cagcctctca gtagctggg  actacagatg catgccacta tgtctggcta    214200
atctttaaat ttttgtaga agccagctct caccatattg cccaggctgg tcttgacctc    214260
ctgtcctcga gcaaaaatac cgattttgat taagtctggg gtaggacctg gggctgggat    214320
tctaaccagc tcccaggtgg tgctaatgct gctggtctac agaccacacg tggagtagcc    214380
```

```
agtgtagagt tcatgtagca atagtgatgt catagaaata gccagtatct gtatacttgc   214440
tttgttgtat gtcacgcact gtatagtgat gtacatgcat ctcatttgac cctcaccccg   214500
cccctttggg ggtagaaagg attgtgctca tttcacactc aaggaaactg aggcacagac   214560
aggcaaagta gcttggcgaa acagaaagga acttagaggc aggccctgat tagctcagag   214620
actagaaggc cttgtgcgtc atcctgaaca gcttggactt gatcttgaag gtggagggag   214680
aaattgaagg gtaattaaac aggaactgta ggaaattcac cttgcatagt gattgctttg   214740
gccacgtgtg ccctgccacc gcccccccac ctcagtgaag tgtcatgcga agtgggttc    214800
gtaaatgaag gcccgaatgc tttcctgaca agtttgtttt aaatcaagct gctaattagt   214860
cccagtcccc ctcccccggt atgtattttt ttgttgatgt cgtttcactt catttagttg   214920
aagtgattga ttcagttcag tgtttgaact tcttttgaa cctcacctta ataacctgtc    214980
taaacatcaa ggttaaacct tcttgctaac acagcagtat tgcttggtaa gactggctca   215040
cagtccaagg aaatgcttgc ccagagaggg caaactgcct taactcctta acctgagctc   215100
attaaaaaaa attcaaatga ctgattcctt gtcacagttc tacctacatt gttttatttt   215160
ttgtccaggt ttcagctagt taaatgcttt tgtgatgagc ttatgtccag gctgaaggtt   215220
gcattttgaa actgagcgtc aaataccaat ttaaagtcca gacctttaca cttgtgaaat   215280
tcagataaat gaaatggaaa taaaacaggg ctgctgtgtt gtgaaatatg actgtgtttt   215340
tccttgtagg actctttgag ggtagccatt ttggcatttt atatataaat tttcttttct   215400
tagcctacct tttactttct tgatttgcct atttgtgatt tcccattaaa cactaggctt   215460
tttgtaaacc aattatccct tgaaattgac tttttttttt tttgagacag gatcttgttt   215520
tgccacacag gctggagtgc cgtggctcca tcatatgata aacagaaaga gagagagaga   215580
gagagagaga gagagagaga gagaccctgt cttatttaaa acaaaaaaag aagaagaaaa   215640
aaagaatata gatcacagct gttatttgta tatgctacgc caatccttgt tgggtttcat   215700
tcttataat tgttattttt aaagattttt cttatgaata ttctattgtt tcattgtaga    215760
aaatttaagg gagaacacag tgggaaaaaa aaaacaagaa aaggacttca taatcctgct   215820
accctgggag aaaaaaaaaa tcaccattac ctatttggtt cttctcccac tttttttttt   215880
ttcgagatgg agtctccctt tgttacccag gctggagggc agggacgtga tcttggctct   215940
ctgcaacctc tgcctcctgg gttcaagcga ttctcgtgcc tcagcctccc gagtatctgg   216000
gattacaggt gtgtgccatc acacctggct aattttttgta ttttagtag agacggggt    216060
ttgtcatgtt ggccaggctg gtttgttggc catgtctggt ttttttgtcat attggccagt   216120
ctgtttgtca tgtcaggctg acatgttttg tcatgttggc caggctggtc tttaactcct   216180
gacttcaggt aatcctgaag tgctaggatt ataggcgtga gccattgcac ctggccttct   216240
gccttttttt taaagaaaaa aaattaaaac attttttttct ttttaagata gcgtctcatt   216300
ttgttgccca ggctggtctt gaactcctgg gctcaagtga tcctccagcc tcagcctctg   216360
gagtagctgg gactacagat gcacatcatg gtgtccttat gccatttctt ttgtacgtag   216420
gtgaatgcaa gtgtatgatt acatcatatg ctattttgga ggtttgactt tcttttcact   216480
ttcatcatct ttccaaggtg ttattttcct agtacatctt tttaaatgga catagaacat   216540
tcttttgtat gaacaaacaa tagttttatt taggcggtcc tttcctgttg gacatttata   216600
ttattttcag catttctcca cagttgttgc agcattcaga tgaaccttct ttttttttttt  216660
ttttgagacg gagtctcgct ctttcgccca ggctggagtg cagtggcaca atctctcctc   216720
```

```
aagtgattcc tgtgtcaccc tcccacgtag ctgggattac aggtgcccat gtctggctaa 216780
tttttgtgtt tttggtagag ctgtggtttt accatgttgg ccaggctggt ttcgaactcc 216840
tgccctgaag tgatctgccc acctcagcct cccaaagtgt ggggattaca ggtgtaagcc 216900
atcacgcctg acccagatga acattcttgt agctatcgca cacaattctg aacatttcct 216960
aggatgaatt ccttaaagaa gtaatgctga tccaggcttt tttcttttc tgtgactctt 217020 tgacacgtaa taatattgac ttttcttct ttccagacac tacaacaaca ggagtgcaaa 217080
cttctctaca gccgaaaaga gggtcaaagg caagaaaaca aaaacaaaaa tagatataaa 217140
aacatcctgc cctgtaagta tcaatattcc gctcagtaat agtcactctt ggagattttg 217200
attcctagca cctctgtacc tttcctcagg gtcgtgtgct cttgttagca catcggaggc 217260
cttagcttct ttaattgcaa gcagtttcca aaataatcaa ccatggtggg tgttgatgac 217320
ttcattcact gagctcccgt gatgctgatt actgagtaaa gttgccacta ggtggctttg 217380
tctgtggttg gttccttctg ttaattaatt ttctgtctgc ccaagataga tcatctcaag 217440
gcttgggatc tctcagtgtc agggaccta gggtgccaga tttgtgtctt gactcctcct 217500
cactgggcct gtgagtcctg ggtaaggcct gcctcctttc tgggactcag ttcccttaag 217560
tgggaaacag acaaacacct cctgagggct cctagaactg ttctgcttgc tgatcccctg 217620
agctcaagtt actggagaaa gggtatatac ctaaactgct cagaagaaga ctttgtgggc 217680
cgggcgcagt ggctcacacc tgtaatccca gcactttcgg aggccgaggc aagcggatca 217740
cctctgatca ggagttcaag accagcctgg ccaacatggt gaaacccat ctctactaaa 217800 aatacaaaaa ttagccatat gtggtggtgt gcgcctgtaa tcccagctac tcgggaggct 217860
gaggcgggaa attggttgaa cccaggagat ggaggttgca gtgagccgag atgtgccatt 217920
gcactccagc ctgggtgaca agagcaaaac tccgtctcaa aaaaaaaaa ggaagacttt 217980 gtgaatattc gcaaagctgt aaagctgtac ctttcaattt ttttttgaga catagtctca 218040
ctctgttgct cagggtgcag tcacagctca ctgtagcctc aacctcctgg gctcaagcga 218100
ttctcccacc tcagcctcct gattagctgg gacaataggc aggcaccagt acacctggtt 218160
gattttacag ttttttctgta ggccggcgca gtggcttacg cctgtaatcc cagcaccctg 218220
ggaggccgag gtgggcggat cacctgaggt taggagttcg agagtagcct ggccaacatg 218280
gtgaaacccc atctctatta aaaattacaa aaattagctg ggcgtggtgg tggatgcctg 218340
taatcccagc tacttgggag gctgaggctg aggcaggaga tcgcttgaa cctgggaggc 218400 ggaggttgca atgagccgga ggtgctatgt gcaccactgc actccaggct gggcgacaga 218460
gtgagactct gtctcaaaac aaaaaacgat ttaaaaaata ataaaatttt ttctagggcg 218520
gggtctccct atgttgccca ggctggtctt gaactcctgg gctcaagtag tcctcctgcc 218580
tcagcctccc aaactgttgg gattaccagt gcaagccatt gtgcctggct gtaccttctg 218640
taacacccaa atgccacctg gcaaagccca agttgaatca tgaggaaaaa aggcctgaa 218700 ggatgtagac cttccttttt tctacttatt tatttattta ttttgagat agggtcttac 218760 tctgttgccc aggctggagt gcagtggcat gatcatgggt cactgcagcc tcaacctccc 218820
gggctcaagt ggtccttccc accccagcct gcaatgtagc tgggactaca gcatgtgct 218880 accatgccca gctaattttt gtattttttg taattatttt ttttgtagag acagggtttc 218940
gtcatgttgc ctaggctggt ctcgaattcc tgggctcaaa cgatctgcct gcatcggcct 219000
cccaaagtgt tgggattaca ggtgtgaacc actgtgtctg gctatatctt ctgtaacacc 219060
caaatgccac caggcaaagc ccaagttgaa ccaggaggga aaaaggcctg gcaggatgta 219120
```

```
ggccttgcat gaggatctca gaaactgcac taaaccagtc acagttcctc tctcccgagg   219180
tctaactcta tgctgaactc tttgcatttt tatctcactt aatccatatc acatgcacag   219240
gaaggaagca ttcgtagtat cctggtttcc tagaccattt tagcaaggtt ataagtgaag   219300
gggagtgggt gggagaactg gcactagagc ccccaaagtc actgttctta gcaccactct   219360
aatgcatggg gttctccatt gatgtgctat gcaaggcagt gcactgagga gaaaggaagg   219420
aacatttaca acttctcttt atttatatcc tgtccctaaa aaaaaagaa aagaaaaat    219480 ttgtctgagg cctagattga ttgcagggag tgcataatgt tttattgatt gattgattga   219540
ttgtatatag agatgggggg tctcactata ttgcccaggc tgatctcgaa ctcctaggct   219600
caagcaatcc tcctgctttg gcttcccaaa gtgctgggat tacaggcatg agcgactgca   219660
cctggctatg catactatat ttatccaact tacaaataag gcttgcttgc ctgtagtgca   219720
tatgtgtata catttcagca tagaaaaact gtgtgattgg gggttgtgat caaatttgga   219780
gagcattgct ctcatgtctt atcaggtcag agtcattttg tcaaatcttg taaaccattc   219840
tttgtgtgtg tctatgcatg aaacatagtc tttctctttc tgcatgcata tgtacatata   219900
catggtatat atgtatatca tatctacatg gatattgtaa tgtatatgta tgaggatggg   219960
ggaaagtgga gacatttgta atactgagaa aaggcagtga ggaatttgca gagaagcagt   220020
ttgagctgta gcatggtact agtgaccttg aggaagcctt atccttttt  tttggaattt   220080 attttttcaa tttttagaaa tagacaagag tttctctatg ttgcccaggc tggtcttgac   220140
ctcctgggcc caaactatcc tcctgccttg gcttcccaaa gtgccaggat tacaggtgtg   220200
gaccaccatg cctggccacc ttgtcctttc tatgtctaag ttgtgacatc tgctcagggg   220260
tcaggtggta ttaaatggta taaatgtat gggaaagtga agggatcaat ggtatgcagt    220320
atctaaatag aatatcgctt tttcctccct taaaggtctc attcagatgt ttcctctgat   220380
gaacatctca tttccttaaa gatgaggagt ctgaagcaaa aaagacatta ttcttttaag   220440
acacatggct gtcttactaa ttcccattgc aaaatatgtt gtttaggtag agcactcaga   220500
tttttatacg aataatagac ttttgtacag aatttggaca gttgatacta tcagagcctt   220560
gtgatattcc actgcattat gcttcactaa aaaatacctg gctgggtgcg gtggctcaca   220620
actgtaatcc cagcactttg ggaggctgag gtgggcagat cacctgaggt caggagttca   220680
agatcagcct ggctaacatg gcaaaacccc atctctacta aaaatacaaa aattagccag   220740
atgtggtggc acgctcctgt aatcccagtt actcaggagg ctgaggtatg agaattgctt   220800
gagcccagga ggcagaggtt gcagagagcc gagatagtgc tattgcactc caacctgggt   220860
gacagaggaa aaccctgtct caaaaaataa atttaaaaca acaacaacaa caacaacaaa   220920
aacccctctt tattatggaa atttttcaaat atattcaaga gcataaagaa cccacatgta   220980
cccatcaccc agcttcaaca attatcaact catgcccagt cttggtttca tctatactct   221040
gatccacatc tcctctctcc ttgaattatt ttgaagccca tctcagacat catgtcatat   221100
atgtatactt caatcttctt tttttttaaa actcccctc cccttttctt ttttcttgag    221160
actgtgtctc actctgtcat ccaggctgga gtgatcttgg ctcactgcaa tgtccgcctc   221220
tcgggttcaa gcgattttg tacctcagcc tccctagtag ctaggattac agatgtggac    221280
caacatgcct ggctaatttt tgtattttta atagagacag gttttgtca  tgttggccag   221340 gctggtcttg acctcctgac ctcatatgat ccacctgcct tggcctccca aagtgctgaa   221400
attataggcc actgcgccca gcccaaaatt tcttggtttg aaataatttt ggaactcata   221460
```

```
agaagttaca catatagtag agagaatttt cttgtacctt ctctgagctt cctatatacc 221520
caatgataac atcctatata cccatagtat atgatcaaaa ctaggaaatt gtgaagatgg 221580
cattttgaga catcaggcag tgttcacgtt actgttttgc ttacctgggc tttaatttt 221640
atgtgttttt ttttcaatca ttgaatgaac aaaacttgga ctaggctggg gagtaactga 221700
tttgaactgt tttttcctga agcagtccag gacttatgtg accgtggtct ctttttcttc 221760
tagttgatca taccagggtt gtcctacacg atggtgatcc caatgagcct gtttcagatt 221820
acatcaatgc aaatatcatc atggtaagct tgcttttca cagtgttttc tgaccataca 221880
tttctagcct atttttgtat tttaaatcct tcctcatgtc ctgaaagtaa ctttaaggtg 221940
tttgaaggat ttcttccta aatttctagc ctgaatttga aaccaagtgc aacaattcaa 222000
agcccaaaaa gagttacatt gccacacaag gctgcctgca aaacacggtg aatgactttt 222060
ggcggatggt gttccaagaa aactcccgag tgattgtcat gacaacgaaa gaagtggaga 222120
gaggaaaggt aaatcacaga aacttctttt ctgctaaact gtttttaaag tatcagacat 222180
gtcagattgg ccatgtttag gaattgaata aatgaattaa gcttactgta actgattctc 222240
tggaaaaaag ggactaggag aaatttgatt atgttattcc ttggtgtagt tttctttatg 222300
ттттcттctgc ttgggatttg ttgagcttct tggctccatg gatttgtagt тттcстттaaa 222360
tttggataat gttcagtctt agtttcttca gatacatatc ctgggctggg catggtggct 222420
catgcctgta gtcccagcac tgtggggtgt tgaggtgggc ggatcacttg aggtcaggag 222480
tttgagacca gcctgggcaa tgtagtaaga ccccatctct taaaaaaaaa aaatgtaccc 222540
tgcacaacct tgtcctagga cagcagtcat acgtgtatta gactacttga agttgtctca 222600
tagcccactg atacttggtt tattttattc agttttttct ccccgtgтттт catttcgaat 222660
agcttctttt gctatgtctc caagttaatc ttctgcaata tgtcatccgc tcttaatcct 222720
atccagagta tttttcatca cagacattgt atttttcatc tctagaagtg ttaatgtcat 222780
ctatagcttt ccttttaaca tgtgtagcat тттcстттacc ttttgaatgt atggagtatt 222840
tctgttgttg тттттttgтттт tgtagagaca gggtctcggt ctgttgccca ggccggagtg 222900
cagtggcatg atctcagctc actgcagcct ctgcctcccg gttcaaatga ttctcatgcc 222960
tcagcctccc aagtagctgg gactacaggt gcgtgccacc acgcctgcct aatttttgta 223020
tttttagtag agatgggggтт ttgccatgtt ggccaggctg gttttggaac ccctgagctt 223080
aggtgatcca ccttccttga cctcccaaag tgttgggatt ataggtgtga gccaccatgc 223140
ctggccatgt tgtctgtttt aattaactct gcctaactgt cctcccaaat ggttgctgca 223200
gtgctcactc ccaccagcag cacctgccta ggactcatta ctccatactc ttcaagacac 223260
ttcagattaa aaaaataaat tgtaacaccc cacacctaca gaagagcgga cagatcttat 223320
tgagtgacag ccctctgtgt tatctcaaag tgagcccacc atggtggttt tttttttaaa 223380
tatgaaaaag тccтgтgтттт tgtttgtgt ctagtgaaa gttctttttt agatatcctt 223440
таaттggтттт atataagatt ttatgtggaa tgtagcagtc atacctataa attaaaccta 223500
aggcagatgc agaactttgg agttgagcct tcctactgta aтттттcatat tggatgtgaa 223560
gggcagtgtg aтттттcataa gactttcatt gttgtactcc tagttggtat acttctgaat 223620
acctttgagg ccagttctgg tcatcgtgaa acaaaggтттт ccttcagcaa atgcctgtgg 223680
taacattagg tgttcttgaa ttaatggacc aatgaaaaca tctttgtagt ttctgcttca 223740
ggcaaggggt ttttgcccta atgtggata ggaagaatga agcccttcat cctccтттттт 223800
gcctgattat agctatagga ggttcacctg ttctcagaag acatgaggat tgtgaagaga 223860
```

```
gggggtcttgt gttgcttcag aggaatcagt atcagtccct ttcagaagct ctcctggata  223920
gacaggcatt agggccaaat cactctgccc caccccctcac caccatgtcc tactctctgc  223980
tccctgtctc attcttcctc tttactttgg tggtgccgag aggatgacat gatgggtatt  224040
gattctctcc acagacctt ctgacatcct actttcagta tcccccccagt gcacagaaga  224100 caagccagac tgtggactgt gtttgattcc tgggctctat tttaaaagac agtgtattag  224160
ttctcacatt ttagaatttg tttgccaagg tttccacggg agtttagaaa ctaggggag   224220 ggctgatgtt taaagttagc taaaatgttc ttttcagggt catgatttaa ttttatattc  224280
tctggtgagt tccctatagt gactgggagc agtcctcagt cttgattggc cagtgacagc  224340
atagagtaca attaatatta ggagtgctca tttggggaaa ctaaaattttg catcaaatct  224400 gtcagaggtg tttggatcta caaaataccg gagggaaagc tgaattgaga atcataataa  224460
ataaaagacc acatcgttct tttttttttt tttttttggg actgtatctt gctctgtcac  224520
tcaggctgca gtgcagtggc actatcttgg atcactgcag gctccgcctc ccggattcaa  224580
gcgattttcc tgcctcagtg cctgagtagc tgggattaca ggcgtgtgcc actacacctg  224640 gctaatttt gtaattttag tagagacagg tttcaccatg ttggccaggc tggtctcaaa  224700
ctcctggcct caagtgatcc acccggcttc ccaaagtgct gggattacag gcgtgagcca  224760
ctgcgcccaa ccaagaccac atcctttat tgaacgttcc tcctaccatg ttttcttttt  224820
tctttcaatt aatcattgac tcattgactc tcactgttga tgtctgtagc tgctctctta  224880
tttccagttt tatagctgta aatttctctg tcttcctaag atacaaggta aatttctctt  224940
gctgatattg gtggttttgg aaagtgagtg gtgtggatga ctgcccagaa acaacagaa   225000 cacaaaagca ttctctgccc agaacacatc accaaataga tacaaactca tctcttactg  225060
agtgaaatag cttccttttt ggcagcaaga atgattttct tggtgccata ttttcaatc   225120 cgcctgctct tgaagccagc agctattgca gacttggcat tcccaggcac ccagttaagg  225180
gaaagtgacg tgtagaggag gtatcagatg ggtctggata tagaaaaagc agctggttca  225240
aaaccccatg ggctgccttt ctgtgataga gttattcaca cttgggttag ataaggcaca  225300
gagtcctcct acactggtgc ggaaatgaaa cagacagtct ggctcgttgg gcagcctagc  225360
ctcctccaga atctgtgctt gccttcccta tggagtgact ggtagatctt agaattcaga  225420
cctcagtggt tgctagccag cactctcaca ttggttggtc cttctctctg catctttgat  225480
tctttagaga tagataaacc aagcaccgac tctcctttga catgtgcttg aacagacac   225540 ctgcacgagc tgcctttctc ctcccacttc tgcctggtct tccaaacacc tgcttttctt  225600
gtttgaactc ttcctttttt tttgagacag aacctctctc tgtcacccag gctggagtgc  225660
agtggcatga tctcagctca ctgcaacctc tgcctcccag gttcaaataa ttctcctgcc  225720
tcagcctccc aagtagctgg gattacaggt gcctgctatc acgcctggct aattttttgta  225780 ttttagtag agacacggtt tcaccatttg gccaggttgg tctcaaacct ctggtctcaa  225840
gtgatctgcc cgcctcggcc acccgaactg ctgggattac aggcatgagc cactgcgccc  225900
cagctgattc tttacagata aacaaacatt gactctgctt tgacatgtgc ttggatcagg  225960
taactgcacc agctgccttt ctcctcccac ttctgcctgg tcctccgaat gcctgctttt  226020
cttatttgaa ctcttctgtc cttttctgaa aacctaacag atgcgaaaca ggccattttc  226080
catgttggtg gttattaagc aagacttgaa catttgtttg ttgcttgttt aggcttttat  226140
ttcagagttc acagaattaa ctttctttt ttctgatctc ttccagagta aatgtgtcaa   226200
```

-continued

```
atactggcct gatgagtatg ctctaaaaga atatggcgtc atgcgtgtta ggaacgtcaa    226260
agaaagcgcc gctcatgact atacgctaag agaacttaaa ctttcaaagg ttggacaagt    226320
aagtatattg tcgtattcta gagactttgg gaactgttga tggtgtgtag gaattcaggg    226380
tcttgccgtt actcatgttt gcatacatgc atgcattcgc tcactcattg attcagtagc    226440
catttattag cttccttcta tgtgccaggt acagtttaag cagtactggt acattgtgaa    226500
caaggcaggt agtgttcctg ccctcatcga gcctagggag atagacaatt taaaaacaaa    226560
taactggcca ggcgccgtgg ctcaggcctg taatcccagc actttgggag gctgaggtgg    226620
gtggatcgct tgagccgggg agttcgagac cagccctggg tgggagactg ggatagggtg    226680
acctgagtgg ctacaaggtc tgttaggagg cctccgcagg ggcctatgtt gatggcctcc    226740
tctccaagta tccacagact tcagcagttg ttcttttttg ttccttcctt tggaatggaa    226800
tattatataa aatggcagaa taaactggaa gagaagcagt agatgtgaga ggtgccgggg    226860
ggtgaagtct gcaggatgtg gggattgttt ggcttttgga ggaggaagga gggattcaag    226920
acacattgta gaggtttgag tctgagcgga cagtggtgct gtggcagaca ccacaaaagc    226980
tggaaggaga actgatgtgg gcagtgattt gttttcttct ggatgtgttc agctgggcat    227040
ctgaacagtc atgtggacat tcatctattc attcagagat atttgttcaa tgacctcttg    227100
gttcctggca ccatgctgct tgctggagat agagctgggg aacaaaacag atggaatccc    227160
tgcactccca agtgtacact atactggcca gtaatctacc agcccagtaa ttgcacatat    227220
aaatatatca ttataaactg taatcagggc tagaaagaaa aaatgcagga gtttagggtt    227280
catttggagg gggaagggac tttttttttt tttttttga aacagaatct tgttctgtca    227340
cccagactgg agtgcactgg tgcattcacg gctcactgca gccacaacct cctaagctca    227400
agtgatcctc tcacctcagc ctcccatgta gctgggggct acaggtgtgt gccaccatgc    227460
ccacccaatt gttaaatttt ttatagagac ggttgtctca ttatgttgcc caggctggtc    227520
ttgaactcct gggcttaagc gatcctgctg ccacatgcag cctcccaagg tgctggaatt    227580
acaggcgtga gccagcgcac ccggccaagg gagggaggt tcttaaggca tagggaacaa    227640
tgtgtttgag tcagcaaagg aggttgtggg ggtttgtcct aagtgtggta agcagccaga    227700
gttggattta agttttaaag agattcccct ccaccctgta gagactggag ggggcaggag    227760
ttgttctagg gattaggacc aatttggagg tagtgcagcc gtcagagtaa aaaataatag    227820
ggattgaact aggccagtgc ccagggtgcc tgaaagaaga ggacccagta gagctgactg    227880
gaggcagaca tgcagggatt cagtgaagga gtgtaccaag ggcgagggtg gtgtgcaggg    227940
tgactggcaa ttttctagct tgagaaaggt ccggggggat ggcagtggag ttgaggaagc    228000
tgggaggatc aaggaccttt ttgtgaacac acaaagtttg agatgccttg gacacattga    228060
agtggagcgg tcaggaggc aagggtggag gtgggatgcg gaggggaggt gggatgcaga    228120
gcgtcgtgga tggatcagtt ttgctcgata gagggacatg ttttttctgtg gcaacaggag    228180
ggcaaaagga gaaggtggcc acagatgccg gtagatgagc tgagagtgat tgtattccct    228240
atcctctcgg aagcttgagg caaggccatc aacagacaat cagagggaat aagaagagat    228300
agaatatatg aagaaaggga gaaaagatga aatcgtaatt gtgtagcagg gcaagaagtc    228360
cagaaatttc tgtgctgtgc caagttccca gttgaggcgg tgaacatgaa aatatactga    228420
tacccattgc ctggtttttc tccaaggaca cttggctcct agggcacaaa acagaaagta    228480
cgtggtttgt ccaggccgag ggctttgcat agttgcagtg gatggagagg aggtcaagga    228540
atggaggcac atggtagaga gagactgtcc ccagagcacg gggactcctg gccggatgag    228600
```

```
ggggacaggg gcaggaggag gcaggtggaa agtagaggga gggctcagtg gtctggaggc   228660
tacaggaagt gacgggggga ccagaaggag ctggaaacca gtgtggttgt ggcccagggt   228720
gggatgtttg gatttctgat gtcagagagg gtccagtcct tctgatgatg gggaggggtg   228780
gaggctgaat ctatggtaga gatagtgaga ggaactggaa caatgtagct gtcaagtgga   228840
aatgggagaa agggctgggc gtggtggctc acgcctgtaa tcccagcata ttggaggct   228900 gaggcaagag gatcgtgtta gctcaggagt tctgggctgc attgagctgt gattgtgcca   228960
ctgcactcca gccttggcaa cagagtgccc agttaaaaat aaaaataaaa taaaataaaa   229020
aaattaaaaa aaaagaaga agaaaaaaga gaaagtgtc cttttacatc ccttttaaaa    229080
atgtcactta aggctgggca aagtggctca tgcctgtaat ccctgcactt tgggaggctg   229140
aagtgggtgg attacttgag gtcaggagta caagaccagc ctggccaaca tggcgaaact   229200
ccttctctac taaaattagc tggatgtggt acatgcctgt agtcccagct actcgggagt   229260
cgagtctgag gcccaagaat tgcttgaatc ggggaggcgt aggttgcagt gagctgtgat   229320
caggtcactg tgcaccagcc tggatgacag agtgagactc tgtctcaaaa aaaaaagtca   229380
cttagcttag attgtctcta catatatagg aagaagatgt aggaatgaat ggtgctgcta   229440
caattacgtc atctggatag acccagaaac atgatacttt ttggttttct gtagccttgg   229500
tgccattgtt gatctttatt aattatcatt atcctcaaaa tagccataat gtgctgagtc   229560
tcttcctatt tgctgggcag aggctgagta tttcagcgag ctcactgagt ccttaaaatt   229620
gcattatgat agagagaaag agattattat ttgcattttg caaaatgaag aaattgaggt   229680
ttagagatac ccaagggcca cgtgagtgtg agtgcctgga attggagcct aaatctagtc   229740
atctgatagc aaagcctgtt ttcttatctg ctttgcatta aatataagtt taaaatagaa   229800
caatactggc caggctgggt ggctcacgcc tgtaatccca gcactttggg aggtcgaggc   229860
aggcagatca cctgaggtca ggagtttgca accagcctgg ccaatatggc gaaagaaacc   229920
ccatcgctac taaaaataca aaaattagcc aggcatggtg atgtgtgcct gtaatcccag   229980
ctacttggga ggctgaggca ggagaatggc ttgaacccgg gaggcagagg ttgcagtgag   230040
ccaagatcac gccactgcac tccagcctgg gcaacagagt aagactctgt cttggaaaaa   230100 aaaaaaaaa agaatgatac tatagtctgt gtttatatgg tggggaaggt tgagtatcaa     230160
aaaaataaca agaggaatg aatgtcttaa gtgaatgcct gtttccccat ctgcttcctc    230220
ttctgctggg aggagagacc tggatcccta gaggtttcag ttgcctccag agctgagtgc   230280
cacagggatg cagggaata gggatgttac ctgtcgctgg taattcagag agatgattca   230340
gggtatagtt acctgaaaga acaaattgcc atgccgacg tcttggttct tatgacagag    230400
gcaaagagtt gcctccagga ttgcccaaaa ggagacgagt tctgggaacc tcacgaagag   230460
gacctttcag tggaacctgg ggagattctc ttcctctcca ttggatttag gaaagcttag   230520
aaccgggtga ttcctcaacc tcttgattta tttaattctt ttctggtttt tcttggctct   230580
actccagggg aatacggaga gaacggtctg gcaataccac tttcggacct ggccggacca   230640
cggcgtgccc agcgaccctg ggggcgtgct ggacttcctg gaggaggtgc accataagca   230700
ggagagcatc atggatgcag ggccggtcgt ggtgcactgc aggtgacagc tcctgctgcc   230760
cctctaggcc acagcctgtc cctgtctcct agcgcccagg gcttgctttt acctacccac   230820
tcctagctct ttaactgtag gaagaattta atatctgttt gaggcataga gcaactgcat   230880
tgagggacat tttgatccca aggcatattt ctcctagacc ctacagcact gccattggcc   230940
```

```
atggccatgg caacatgctc agttaaaaca gcaaagacta agtcagcatt atctctgagt  231000
ccaccagaag ttgtgcatta aacaacttca tcctggctct gcagtttctc cttattcttc  231060
atgatgtttg cttgtagct gttgactgct ttgtaggtat tgaggtggtg ggggtgtggt  231120
ggaaataggc ctgactcttg aggatccctt aagtcatttt tgcttggttc tcttttcct   231180
tcttttcttc tactcttcta tgattcatct ctttgattgt gattctgttc tctctctctc  231240
tctctctttt ttttttttcg ttttttgagac agagtcttgt tttgttgccc aggctagagt  231300
gcagtggtgc catcttggct cactgcaacc tccgcctccc gggttcaggc cattctcctg   231360
cctcagcctc ccaagtagct gggattacag gcatctgaca ctacgcccgg ctaattttg    231420
tattttaata gagacaaggt tttgtcatgt tggccaggct ggtctcgaac ccttgacctc   231480
aggtgatcca cctgccttgt ccttccaaag tgctgggatt acaggtatga gctaccatgc   231540
ccggcccatt ctgttctctt ctaccataaa tatatttctc ccctaacact atatttgttt   231600
gcttcacaag attccagctg cttttccacc aaggcctttg atggaagctg tgctgtgacc   231660
tctgtaatga gtctgtgggc tgctgattct ccagtttggg cttcatgatt atactgggga   231720
atattgggtt tcctaaatct cattcatttc ttgggcaagt agatatatgt gaaagtgttt   231780
atttgtccag ttgttaaaga agctaccatt tattgagcca gcctctgagc acaatgtttt   231840
ttgttttgtt ttgtttttaa tttttaaaat tatttacttc ttctatttca ataacttat    231900
tattattatt tttgagaca gagtctcact ctgtcaccca ggctagagtg caattgagcg    231960
atcttagctc actgcaacct ctgctttctg ggttcaagca attctcatgt ctcagcctcc   232020
cgagtagctg ggattactgg tacgtgacaa catgcctggc taatttttgt gttttagta    232080
gagacgaggt tttgctatgt tggccaggct ggtctggaac tcctggcccc aagtgatcct   232140
cctgcctcgg cctcccaaag tgctggtatt ataggtgaga gccactgcgc ccggccctct   232200
ttcagtaatt ttgatgtatt ttttttgtata tgattcctgt ttcattctgt ccaaccagca   232260
ctctgtatgg tatgtgctgt tgtccccatt tcacagatgc agaaattaag ggtcagagag   232320
gttaagggac ttacctcagg cacgttgtac tggagaagct gaactccaag agcaggtttg   232380
ggctgactcc aaagccctat gcttttgcc aacatatttt caaacataaa tagacaattt   232440
tataaatagc tccaaagagt agacattgtt tctgttgata ttaatggctt ggttttgagt   232500
ctgaaacccc catgaatgat tctgttgtcc ctgcttttg tccttctgcc cgcagtgctg    232560
gaattggccg gacagggacg ttcattgtga ttgatattct tattgacatc atcagagaga   232620
aaggtgggtc atctggtggg caagaagcga cagtttctgt ttttagttta tggaaggaaa   232680
gtgctcacga aaacagtctg gggaagagag gttgaatggg aaaattcttt cacaaaaatc   232740
tgggctgaag acttcagtgt gtctgcctga gaacagaagt gacactattt gagcttttgg   232800
cataaaatga agtctaggag ctgcagaacc cactgccatg gccttttgtt gcatacacag   232860
tggtggtctc tatccagcca cctgaccttg tttacagtat ggggtgattt gttggcaagt   232920
gagggaatcc tgacttctgc cacttcgtta tttatgtagt cttctgggat cattggtatt   232980
ggtcagaagt tcaacactgt agccattgca acatgctcag ttaaaacagc aaagactaaa   233040
ttagcattgt ctctgagtcc actaaaagtt gtgcattaaa caacttcatc ctggctctgc   233100
agtttctctt tattcttcat gatgtttcct tcgtaggtgt tgactgcgat attgacgttc   233160
ccaaaaccat ccagatggtg cggtctcaga ggtcagggat ggtccagaca gaagcacagt   233220
accgatttat ctatatggcg gtccagcatt atattgaaac actacagcgc aggattgaag   233280
aagagcaggt accagcctga gggctggcat gcggattctc attctcttgc taggcctctt   233340
```

```
ggatacgctc tcctttgag caggaggaca ggctctgata gacaactgtt tgatttcgga 233400
atgggaaaca aactcccaac taaaagggcc tctggaaact gtcaattatt ctccacttct 233460
cagctctgat ttttcactgc agaggagctt agggaagggc accatcctat cagcctggcc 233520
tgccagattg aagaactgcc atgcagaaag gttctgatgt tctcaggctc atgtggcaag 233580
cgtaaaactc aaagcttga agtttctagc ctgttccagc cttgatccag gccatgttta 233640
tcctgattcc atcctttaaa acgaatgcct cactcttaat agcgcacggc agtttgaacc 233700
actaatttgg tcgagttgga aacagtgaaa tttcaatttt aataagctgt gcataatgaa 233760
gaggaatgtg gaattggagc cttcccatct gaagctattc ataacaggca caaagctgag 233820
ttaattagga atatgctgag atgaaggaaa tgaggagagc tgctcttttg ggggctgtgc 233880
ttctctcccc aaccctcaa ccccattgcc atgctgcaga tggggtggtg tctaaacatc 233940
agtggcgagt gcctgcatta ctctgctcgt tgccttccag agaactcagc ttctccaaat 234000
gctgagctct tttcagaatg ggacctgcca ccagtatttg aaagatttct agcctagcag 234060
aacagcagcc acgttatcaa agtttggttg gccaaaggaa ggtacttgct aattagttta 234120
gtaggttttc agtccgcaca gacatacggg attgttttat tgtacataga catcttcaga 234180
aacagtgtat gtatagaaat gtaaggtcaa aatttgaacc tcagtgcttt aaatctgaat 234240
ttgtattaac tgatatgaaa tatttagacg gttactttat tttatatctg tcttccatta 234300
tacttaattt ggctcaagaa tagttaggca aaaagttgcc caagagaag gatctcctag 234360 taaatacaaa gagaatgtaa catagttgct acaagttgga gcatgttcag ggatgtcttt 234420
tttttttttt tttttgaga gagaggtctc tctctgttgc ccaggctgga gtgcagtggt 234480
gtaatcatgg ctcactgcag cctcaatctc ccaggcttaa gcgatcctcc cacctcagcc 234540
tcccaagtag ctgggactat aggcatgcgc caccacacct agctaatttt cgcattttt 234600 gtagtgtcac agtttcgcca tgttgcccag gctagtctcg aattcctagg ctcaagcagt 234660
gcttctgcct cagcctctct gagtagttag gactacaaat tgtggctcc atgcccggct 234720 aattttttta tctttatttt gtagagacaa ggtctcactg tgttgcccag gctagtcttg 234780
aactcctggg ctcaaacaac cctcccactt tgggtttcca agtgctggg attacaagtg 234840 tgagccactg agcccagtga cctctgggtt taaaaatgt gtaggcttca attatttatt 234900
ttaaaaaatg aaatcctgca atatatagtt ttctgcgttg tgtggtttga atcaatctgg 234960
gaactggctt gctggctgat tgtggtaaag taagaagtac ttaatttagt agaaagttta 235020
aatggcagac ataacattaa acccagctga tttataaatg aagcaaaaga acaaaactca 235080
ttcaggataa ttggttattc taaaatacag tcatttctaa aattatgaag tgttcaggac 235140
ctttgggagt gaaagaattt gctaaagaag gatcagtgaa aaaaggaat gatgggtgaa 235200 gagctgtgga gaaggaagag aagaaacagc acaaggaagg aagaatataa atcagatgtt 235260
gggaatccag gggaaagtgc aaacgaagca agattgagaa aattctcaag tttttataaa 235320
cagttctcac actctgccag ttccttggag gtagactttt tgttaacttt ccaactacag 235380
tagtgaaaaa aaaaaaaaaa ccctcaaatt tgcaaagca gtctgtggaa ttttcttac 235440 ccagctttcc tgactgttaa cttttagca cacttaactt tatcattcgt ttattctctc 235500
tgtttaaaat taaaaatgta aattttaaaa agtaaatgt ttgttggtta caaacattta 235560 taccccttg tctctaaata tcatttcatt ttaaaaaatg aataatctaa gcctacacat 235620
tctaaaatgt gtatattttc taaaaataag ggcattctct tacataacca atgtcacaat 235680
```

```
tatttgatac agtgatcaaa atcaggaaac taacattgat ataacactat tatctaacct   235740
acagaccatc ttcaaatttt gtcctgctag tatcttttat gggtccaggg tcacacagtg   235800
catttggcta taatgtatct ttttctctt tttttgagac agggtctcac tttgttgccc   235860
aggttggagt gcagtggtgc aattatggct cacggcagcc ttgacctcct tgggctcagg   235920
tgatcctccc acctcagcct ctcgagtagc tggagaccac aggtgtgcac caccatgcct   235980
ggctaagttt tgtatttttt gtagagatgg agcttcgccg tgttgccccg gctggccttg   236040
aactcctggg ctcaagtgac cctcccgcct tggcctccca aagtgctggg attacaggcg   236100
tgagtcacca cacctggcca gttattagta tgtttagtct ctttaatctg aacagtttc   236160
tcagtcattc tttattttc atgacctgga tgttttgaa gagtttaggc cagctattta   236220
gcagaatgcc tttcagtttg gatttgtcca gtgttttctc ttgactatat tctagtcatg   236280
cattttggc aggactgtca cagaaatgtt gttgtagtct tcttagtaca tcacatcagg   236340
tacacactgt tgatctgatt cattactagt ggtgttaact ttgatcactt gaataaggtg   236400
gtgtctgtca aatttgtcca ccgtaaagtt acttgagcaa acgtagctg ggactacagg   236460
cgtagcaaaa aatgtagcaa aaagtagtat ttttgctaca tttttttttt aggaacaaag   236520
tatttttccc ttttaagtta atctcttgtc cataaagtta ttatttttcc cttttaagtt   236580
aatatcttgt gggtagatac tggagactgc gtaaattacc tatttctcat aatacttttt   236640
ttttttttga gatggagtct cgcaccgtct cccaggctgg agtgcagtgg tgcaatctcg   236700
ggtcactgca agctccacct cccggggttga cgccattctc ctgcctcagc ctcccaagta   236760
gttgggacta caggcgcccg ccatcacacc tggctaattt tttgtatttt tagtagagac   236820
ggggtctcac cgtgttagcc aggatggtct tgatctcctg accttgtgat ctgcccgcct   236880
tggcctccca aagtgctggg attacagatg tgagtcactg cgcccggctc tcataatact   236940
ttttgcctac taatttata ttcattgatt aaattcttgc ctgaaaaaat tattactgtg   237000
gtatttgcca aatggcaatt ttctgttcc atcattgcct ttcccccgct tttaaaagta   237060
taagtgacaa agaaaaactg tatataaagt gtacaccatg atattttgat atatgtatac   237120
tttgtgaaat gattatcaaa attgagttaa ataatgcatc caacatctca gttactttt   237180
ttttttttg agacagagtc ttggtttgtc actaaggctg gagtgcagtg ccacaatctc   237240
ggctcattac aacctccacc tcccaggttc aagtgattct cctgccttgg cctccccagt   237300
agctgggatt acaggtgccc accatcacac ccggctaatt tttgtatttt tagtagaggt   237360
ggggtttcac tacgttggcc aggctggtct cgaactcctg acctcaaatg atcctcccgt   237420
ctcagctttc caaagtggtg ggattacagg cgtgagccac tgtgcccggc cactcttagt   237480
aaatttaag tgtacatttt tttttttttt ttttgagat ggagtctcac tttgtcaccc   237540
tggctggagt gcagtggcat gatcttgcca cactggaacc tctgcctcct gggttcattc   237600
aggtgcttct cccacctcag cctcccaagt agctgagact acaggtaccc gccaccatgc   237660
ctggctaatt attgtatttt tagtagagat gggggttcac catgttagcc aggctggcct   237720
caaactcctg acctcaggtg atctacccac ctcggcctcc caaagtactg agattacagg   237780
catgagccac cacacccagc cacattacgt tagtattaac tataatcacc atgctgtaca   237840
ttagatctcc aaaatgtatt catcttatgt aacttcaagt ttgtaccctt tgaccaaagt   237900
ctccttgttt tccctacccc caaccctgg taatcactgc tttaatctca gttttatga   237960
gtttgactgg tttagattcc acatacaaat gagatcaggc agtgatggtt tatttcactt   238020
agcataatgt catccatgtt cttgcaaatg acaggatttt cttctttta aaactaatat   238080
```

```
ccatgctgga cacggtggct catgcctgta atcccagcac tttggaaggc tgaggagggt 238140
ggatcacttg aggtcaggag ttcgagacca gcctggccaa catggtgaaa ccccatctct 238200
accaaaaata taaaaaatta gctggatgtg gtggcgcaca cctgtgatcc cagctacttg 238260
ggacactgag gcaggaggat cgcttgaacc cgggaggcgg aggttgcagt gagccaagat 238320
ggtgccactg cactttagcc tggatgttga tgttgttcca cttgtttatt tttattttgt 238380
tccctgtgct tttggtatca aatcctaaaa accattgcca tgaccattgt catgttactt 238440
tccccatatg ctttcttcta gaacttttaa ggttcatcat tccctttttct gttttttagtt 238500 gcaagcctac tataaggaag ggcttttctt tcttccttat ttatttattc atgtctatca 238560
gaatgggcac cttactacta ttttttgttgt tattgcttga attgacttga atttggctag 238620
tggaaacctt ttcagatcgg gtactctgtc cttttgatct ctttccattt tcaagcactt 238680
ctttagactt aagatggtct aggctcatct tctcctttcc cagccatttt tcaaaggaac 238740
ctgattcctt ttagtgaaga gcagtatttt gaaaccaaga tctgggcact gggtctactt 238800
gtttgtactg gtacagtgtt ctttgaattg ctaattagct gatcaattac tgctctattt 238860
gagttccctc tttctaaaac ctcacatatg tgtacagacg gtccctgact tatgatggtt 238920
cgacttatga ttttgatttt tatgatggtt tgagagcaat acatccattc tgttttcac 238980 ttttcattca acactttatt ttaaaatagg gattgtgaga tgatattgcc cacgtgtagg 239040
ctaatgtaag tgttctgagc acgtttaaag taggctaggc taagctgtgg tgtttggtag 239100
gttagatatg ttaaatgcat tttcgactag tgatattttc aacttatgat gagtttattg 239160
ggatgtatcc ccataaagtc gaggagcatt atacatatct ctgtataaca gagtgagttc 239220
cttatacctt tcatccactt tcccctgaag ttaacatttt acctaaccat gatacattta 239280
tcaaaactaa aacattaaca tcaatacatt gctattaact aaactagagt ttaattggat 239340
tttgccagtt ttccaatgaa tatccttttt ctgttccttg atccaattca tggtcacaca 239400
ctgagtttgg tcacttgtca ctgtagtctt ctccaatctg cgacagcttc ttaggctttc 239460 cttgttttttc atgtactctt gacgattttt aagagtactg gtcagatatc ttgtaggata 239520
tcccacaact tgtgtttaat cttatgtttt ctcatgatta gacttgagta atggattttt 239580
gggaagaata ccacagaggt atattgttaa gtgttctcat cacttggagg taaatgttat 239640
caacatggcc tggtgatgtt aaacttgtca gtttgtttag ttagtatctg ccagattttt 239700
ctcactgcat aattacaaat cctccttaac ttatgatggg gttacagcct gataagccca 239760
tcataaattg aaaatatcat aagtcaaaaa tgcatttaat gcatctaaac tactaaacat 239820
cacagcttag cctagcctgc cttgaacgta ttcaggacac ttacattagc ctacagttgg 239880
gcaaaatcat ctcatgggaa gcctgttta taatgtgttg catatcttat gtaatgtgtt 239940
gagtactgta ctcagaatga aaacagaag ggttgtattg cttttgcacc atcataaaat 240000
caaaaaaacc ataaggcaaa ccatcatgaa gttggggact gcctgtactt ttttcctctt 240060
tccctgttca attccttgga agaaagtcat ttagttcaga ccatactcaa gaaaagggaa 240120
ataaagctcc atctcttgga gcttaattga aactggaatg actagtttct atatacatta 240180 tttgaatcc ttttgtaaga aagatttgtt ccttctctcc attttattat tccattattt 240240
atattgatag agacgcatgt acatttattt tatactttgg gttataatct attttttcttg 240300 ctcaaattgt tacagctttg gtcactggga ggttcttcag attggctcct gtgtcatttg 240360
acatgtcccc acctctcgt ttctgagtac ttctctactt tggcattaca aaagatgttc 240420
```

```
caggctcctc ttatattttt ccctgccgca gccctagaat catccatttt tctatggtgc    240480
cctggttcct tttactttag atgggggttt agaaaccaat ctgggtgttg ggtgtgctca    240540
ttgctactgg aatcactgct tctaggccct ctcagcagat agagctagaa aacatatggc    240600
tgtatatgaa tccatggatt catatatatc tataattgtt ttctgtatct ggccatctat    240660
atatatatta agctaaacat gaattcatac tgatgtctca gactcgaatc cattgccgca    240720
gggctcattc ttgccttcct cttgcttatt tgtgacttct ttctctaaca gggagaaacc    240780
ccagtctcat tatcaccaac ctatctactc atttgttcaa ccctggtata ggtgtaaagt    240840
agtttcagaa ttactaacct atacccatgt gagaattgta tttgcacttc ttgtttgaag    240900
gaaatacata caacacaggt agcgtctcta cacttcagta tacagagatc tgaacagtgt    240960
tctctctgag tgaatcatat tgcaggacag aaattacttt taaaaattct gtaatgggtc    241020
aggcctataa tcctagcact ttgggaggct gaggtgggca gatcacctga ggtcaggagt    241080
tcgagaccag cctggccaaa atggtaaaac cccatctcta caaaaatac aaaaattagc    241140
caggcgtagt ggtgtgtgcc tgtaatccca gctactcagg aggctgaggc acgagaatca    241200
cttgaacctg ggaggcagag cttgcagtga gctgagattg agccactgca ctccagtctg    241260
ggcgacagag cgagactctg tctcaaaaaa aaaaaaaaa aaaaattcca taatgatagc    241320
agagctggaa tagaaatggg attgcacagg ctgaatctga gttgttgcaa cagtaaacga    241380
gcaagattta aactggcctt gtgtagcact tgctatttgg ctcctcatat tttattagac    241440
gcttattctt ttttgtttgg tgtcattcct ttgagaaata tttgagtgcc ttttctgttg    241500
cagacattga ttagatgctg aggttgtaac aatgaagaag atagccatcg ctgttgcctc    241560
atggaactga agttttacta gatgtaaaat ttgagttaac atgaggccgt gcccctatgt    241620
gccctattgt ttcttcacac agctcccttc atctccttgg tccaatgaaa aggttttttc    241680
atacttgttc attcattcct gcattaatta agtaggttg tactgtgcca ggcactggga    241740
atatttaagt agttgtgttc ctgaattgga aatgaatcca gcatggttgg agtagaagga    241800
gctgggggc aatgtggagt gtgatgggga gattggaaaa gtaagctgag accagatttt    241860
tcagtttgga gggagaggtg ggccttgtag gccatattac agattgtaga ctttatttgg    241920
agggacatgg aagtcattga ggagtctgaa gcagggaat gacataaaaa gatcctcatt    241980
ttaggccgga tgtggtggct cacgcctgta atcccagcac tttgggaggt tgaagtgggt    242040
ggattgcttg aggccaagag tttgagacta gcctgggcaa catggtgaaa ccctgtctct    242100
atcaaaaata caaaaattag ctgggcatgg tggctcacac ctgtagtccc agctacttgg    242160
gaggctgagg catgagaatc gcttgaaccc gggaggcaga gattgcagtg agccgagatt    242220
gtgccactgc attccagcct gggtgacaga gtgagacttc gtgtcaaaaa aaaaacaaaa    242280
aaccccctcat tttgaaaggg aaccctggct tgagggtgaa gaatgggtgg gcactaggct    242340
agagcagctg cagggtcagt gaggagctgc cgcagtgctg cacgtgagaa cccgtcatgg    242400
tttggtcagg gtgggcagga ctgacagtga gcacagagcg aagtaaaacc agcaaaattt    242460
catgattgga tagtggaagg aatcatggtg tttgtagtct tcaaatgtga acccagagtg    242520
cactggacaa gtagtctagg ctgctctgta accaaggcaa gtgttttcat tttaccctct    242580
cttcctgctc ttggccttg gatttttgt aatttaaggt ttatgaatgt aatcagttac    242640
ttaacatgga aagatactta ataccagatg attttggagt cttgtgatca ataccttctc    242700
tcaatcttgg gtgtgtgtca gttggcaagg ccataaaatt tgttataaac attgcagaag    242760
gcttggttac tgtgctgtga cgttgaattt gggtggagat agatcaattt cagttgattt    242820
```

```
tctaggcttc agaaacacat taccctctac tccacaaaca caaatcaaaa caaaacaatc    242880
cctattccct gagcatttct cttgatctat aacacagcct gggctgtcac agtactaaga    242940
caagcccatc tgatttgtga gtcagtttta tttcttggtc ttctacataa gctaaaaagt    243000
ttcaacattt taatgctttt ccttggattc ctttgagtca ttgaagtaat tcctgtttca    243060
tttgtactaa ttattccaca ctagaaaatt ctgttgtaat cactttatgt attaatagaa    243120
atactgattt ttattttcaa ggaagtattg agtagggagg gggaaatagg gatttgctgt    243180
tcaatgggta tagagtttca gtaatacaag acaaaaaact tcagagatct tctatacagc    243240
agtgggtata tagttaacaa tactgcacat ctaacagttt gttaagaggg tagatctcat    243300
gtcatgtgtt tttaaaaatt gcttttaaaa aaagtatcga gtaaaaaagc agttttactc    243360
ctcagtttct atttatattt aaaatttta tttaaaaagt gagttgagat ttttaaacct    243420
caggataagt tttattttt aaaaaattta tttttatta tttttgaga tggagtctca     243480 ctccatctca agtcacccag gctggagtgc agtggtgtct tggctcactg cgacctctat    243540
ctcccaggtt caagtgtttc tgctgcttca gcctcctgag tagctgggat tacaggtctg    243600
caccaccacg cctggctaat ttttgtattt ttagtagaga tggggtgtca ccatgttggc    243660
caggtttgtc ttgaactcct aacctcaagt gaccacctgc cttggcctct caaagtgctg    243720
ggattacagg tatgagccac agtgcccggc gggataagtt ttaaaataat attctctgct    243780
ggctgggcat ggtggctcat gcctgtaaac ccagcacttt gggaggctga ggcaggagca    243840
tcactcgagg ccaagagttt gagaccagtc tgggcaacat aatgagaccc cctctctaca    243900
aaaaataaaa aaatttggc tgagtgtggc atgttcctgt agctatcggg aggctgagat     243960
gggaggattg cttgagccca ggagtttgag gctgcagtga gctatgattg caccactgcg    244020
ctctagtctg ggtgacagtg tgagaccctg tctcttaaaa aaaaaaaaa aaaaggccag     244080 gcacagtggc tcaggcctgt aaccccagca ctttgggagg ccgaggcggg tggatcactt    244140
gaggccagga atttgagacc aggctggcca acatgatgaa accccgtctc tactaaaaat    244200
acaaaaataa gctgggtgtt gtggtgcaca cctgtaatcc cagctacttg ggaggctgag    244260
ggagagaatt gcttgaacct gggaggcaga ggctacagtg agccgagatc acaccactgc    244320
actccagcct gggtgacaga gcaagactcc atctcaaaaa caacaacaac aaaaaaacca    244380
aatgttcttg ccaattcttc catttaatat ttaatttga attatattgt atctttctaa     244440
ggattgtttc ttatataagc aaagattttt cagtgctaaa catttacgac tgctattcag    244500
aaatggttat ttacaagtct ttttgtttta agaaaatggc tgttcaaaaa attaaaatag    244560
tatataaacc aaacaaaata ttttgcttt ggatgtctgt tttgcagctt cttccctaca     244620
ctataagttc ttactgactg ctttatcact taataaattg gtttggctac tttaacagag    244680
gcaaatagta tcaggcaaaa aattattttt tatttttatt ttttgagaca gtctcactcc    244740
atcacccagg ctgcagtgca gtggcctgat cttggctcac tgcaacctcc acctcccagg    244800
ttcaagcgat tctcatgcct cagcctcctg agtagctgga attataggca tgcaccacca    244860
cactcagcta attttgtat ttttagtaga cagggtttt tgccatgttg accaggctag     244920
tcttgaactc ctgacctcaa gtgatccatc tgctttggcc tcccaaagtg ctgggataac    244980
aggcatgagc caccatgccc agccctattt tttattttt agagatgggt ctcgcttttt     245040
agagatgggt cttgttgccc aggccagagt gcagtggtgc gatcatagct tactgcagcc    245100
ttgaattcct gggctcaagc aattctcctg cctcagcctc ccgagtagct gggactacag    245160
```

```
gcctgtgcca ccaggcctgg cttgtacatt agtatttgat atggctaccc taagggcaat    245220
cctatagtga agtcaacatt agataatgat gctcatctga tggattagat tttcagagtt    245280
ggctgtttcc aggtgcctat aggagtagaa aagggtgaca aacctcctaa ctagatgtcc    245340
taccaaatat agttcactcc acatctgaga tgagactgca tgactgctgg ttttctttgc    245400
cttttccccc ccagggtatc atcagaacca aaaataaagt tttaaaggtg ggtcaggtgt    245460
gtgttggctc atgcctgtaa tcctagcact ttgggaggct gaggcaggtg gatcatctga    245520
gctcaggagt tcaagaccag cctggctaat aacatggtta agcccatctc ctactaaaat    245580
acaaaaagtt agctgggcat ggtggtgggc acctgtaatc ccagctactc aggaggctga    245640
ggcatgaaaa tcgcttgaac cccagaggcg ggggttgcag tgagccgaga tcatgccact    245700
gcacactagc ctgaacaaca gagcaaggct ctgtctccaa acaaacaaaa atggtgccag    245760
agtcttttcc agggctgagg ggagatacaa tgaagtgtgt tattttttct gataagagtg    245820
ctaccatctt tcattcttgt gtgccatttc tagttggggt gaatttgttt tcggagttcc    245880
tttcccagct gtttgcctga aaaaccatga aatgtgttcc acatgaacta tgaaatgatt    245940
agatgctaat gtggcaaaga aagtgtgaat tctcttgtag aaacagggac atttggttcg    246000
gtacagtaag ttgttaatgc gtgactctgt gctttcaaat tctgtggttc aaaagtactt    246060
ttcactccta ctgtgtattt accttgagaa ggtgaatccc ctaacaattt ggtcaatgta    246120
tcagtattct caacccgtct atcaattttt ttttctttct ccctcttttt tcttttttg    246180 ggcaaaatac cttttttgct ttttatcccc ttaaaataac cattgtccct cacatgtgca    246240
ctcttccaaa tttcagaaaa gcaagaggaa agggcacgaa tatacaaata ttaagtattc    246300
tctagcggac cagacgagtg gagatcagag ccctctcccg ccttgtactc caacgccacc    246360
ctgtgcagag taagtagtgc tgaaggaaat tcttttttacc tggtcatggt ggtttaaaaa    246420
ggtttaaaaa acaaaaacaa aaacaaaaca caagtttgta gcacatgcct ttcactggtg    246480
cacgttcctg ttgccctact gttagtgtat ctgtgactgg tgatatctat tgattgtgtt    246540
aatgctatct caaccacgtt ttaattttcc taagctggcc aggcacggtg gctaacgcct    246600
gtaatcccag tgctttggga ggccgaggtt catggattac tttgaagtca ggagttcgag    246660
accagcctgg ccaacatggt gaaaccctgt ctctactaaa aatacaaaaa ttagccgggc    246720
atggtggcgc atgcctgtaa tcccagctac tcaggaggct gaggcaggag aatcgcttga    246780
acccaggaaa cggatgttgc agtgagccga gatcatgcca ctgcactcca gcctgggcga    246840
tagagtgagc ctctgtctaa aaataaaata aaataaaata aattcctaaa ctgaaggctg    246900
actgctatgc tagctaggat tatatgggat tttaagtata tcaagtggtg gttctccaag    246960
aagaatctaa ttttctttt gatgggctgg ggattgtaac aaaggaaggt catatgtctt    247020
aatgatgtgt taaggctctt tgcaaaatca aagtaaataa attgaccact aatgtgtcag    247080
cccagccatg ttctgctcat ttgccaccag tcaacagaaa tctactttgg gtgtttaaac    247140
caggagtcag caaactacag ctcacaaggc cagatgtggg ccatggcctg ttactgtatg    247200
gcctgttaat ggttttaaag ggttgtaaaa caaaagaaca caaacaaag acccaataac    247260 aaaacaaagc ccgaagaata atatgcgaca gagaccatgt atggcatata gagcctaaaa    247320
tactgactct caagcccttc ccagaaatcc ttcccgactc cttgttgaaa acacggtagg    247380
aaagcatttg tcaaattgag gatatgaata gcaattgtaa gttattattt ttctatatat    247440
tcgaaagtca cttgctagta taacatttac ctttttatttt tccctaagaa tcttctctct    247500
gtttgctttc gacatggatt tttaaacccc tgcagatttt aatattctat ataaatgttt    247560
```

```
taggtggcat atatgaggtt tgtattaaca tttgctttct atttaacatt gaaatgaaat 247620
tatacagcag aggtattttc tcgtccaagt tgccacttct ttctatcttt tttcttttct 247680
ttcccagtgg actgcctggg aaaattgata ttttaaattg ctctctgcaa taatttgcaa 247740
tggaactgga atgccagggt tctgagtcct tgccagacag ctcgtccctc ctgttggcat 247800
gactgagtca gctgtcatga ttccctcagt accagtggca tgcctgtgac agacagcctg 247860
tctgcctttc attcccgtcg tctcccttgt agggttcaga tccaggatac actggtcctg 247920
gagcccctct cagcctggca cccacagctg ctgggttcct tactctcctg gactgctctg 247980
atgtcatctc cctgctcagc agaaagaagt ctgggatctt gatgctttgg ccctctgtcc 248040
taggccctaa accacccatt gcccttcaca taacctgagc tggggctaaa tagatctctc 248100
atcactgcct gcctgctcct gtattttccc ttcttggagc ttttgcctgt tcagatccct 248160
ctactgaaaa ttaataggat ttcattctat gtgtgcattt ccaacctttc ttcacagtgc 248220
gatccaaatg cctcatccta caggcctcct taaaacaacc tgctttctgc cagacccag 248280
ggagcaccag gacttgaggc ttttattgca cttctgttgt ttttttgaga tggagtctcg 248340
ctctgtcgcc caggctggag tgcagtggca cgatctctgc tcactgcaac ctccatctcc 248400
cgagttcaag agattcttct gcctcagcct ctcaagcagc tgggactaca ggcatgtgcc 248460
atgacacccg gataattttt gtattttag tagagacggg gttcaccata ttggccaggc 248520
tggtctcaaa ctcctgacct cgtgatccac ccacctgggc tcccaaagt tctgggatta 248580
caggcgtgag ccaccatgcc cagcgttatt tcacttctgc ctctgtaatt atattgctgt 248640
atggctatct cttctctccc tgggaatgtc aggtcctagg cacaggaact gtgtctgtac 248700
catatctggt gcccaaagaa tgtagtatgt gtttttataga tatcatgtaa gcttaaacag 248760
cgtggtctac attttgtaa atgtctttct ttttcttttc tctccagaat gagagaagac 248820
agtgctagag tctatgaaaa cgtgggcctg atgcaacagc agaaaagttt cagatgagaa 248880
aacctgccaa aacttcagca cagaaatagg tatttaaatg caagtgctct attggttaat 248940
tgtttatata attggcagta ttttaagca ggcaagcaat tgggaatgt tttagcaaag 249000
tgtaccataa ttgagttta caaccaggc tccttttcc tctccctgta cttctttc 249060
caagatggtt ttagtttaga gttcattaaa cattaaaatc aaacacagaa ttaattctgc 249120
atgaggcaag gctagcactt attccagaga aatggctgat actggtggta gagtgcaggt 249180
atcactgttc ctgcaatttt tattagagtt ggttagccca ggctgtgctg ggggatgatc 249240
tgtagggatc tgggaagcat cgggactcag cactgggtgg ttgggagtca ggaagcctga 249300
gttctcattt cagtcagtct ctgaccaact gtgtggcatg gggtgctaga ccacttggct 249360
gccgactggg tcaccgacat cccttccagc tctgctgctg gaaattcatc tctcccatat 249420
gttgcctccc catcaattac gttttttaag tgtgacccaa gtatatgatg tatgttttca 249480
tgataaatta gaaacttatc tgggcatggt ggctcatacc tgtaatccca gcactttggg 249540
aggctgaggt gggcggatca cctgaggtca ggagttcgag accagcctga ccaactaaaa 249600
tagtagagac caacccgtct ctactaaaaa tagaaaatta gctgagcatg gtggtgcatg 249660
cctataatcc cagctactca ggaggctgag gcaggagagg cagcggttgc agtgtgccaa 249720
gatcgcgcca ttgcactcca cctgggccac aagagtgaaa ctccatctca aaaaaaaaa 249780
aaaaaaaaaa aaaactcagt gtcagtattt catgtcgaaa ttcccacttca atgggtagtg 249840
tagttaaaag ctctaagtct accttaaaat cacctaatgc tttgttaagc ttttagatat 249900
```

```
atgttcctta aaaactctta acttatttct tccccagatg tggactttca ccctctccct 249960
aaaaagatca agaacagacg caagaaagtt tatgtgaaga cagaatttgg atttggaagg 250020
cttgcaatgt ggttgactac cttttgataa gcaaaatttg aaaccattta aagaccactg 250080
tattttaact caacaatacc tgcttcccaa ttactcattt cctcagataa gaagaaatca 250140
tctctacaat gtagacaaca ttatatttta tagaatttgt ttgaaattga ggaagcagtt 250200
aaattgtgcg ctgtattttg cagattatgg ggattcaaat tctagtaata ggcttttta 250260
tttttatttt tataccctta accagtttaa tttttttttt cctcattgtt ggggatgatg 250320
agaagaaatg atttgggaaa attaagtaac aacgacctag aaaagtgaga acaatctcat 250380
ttaccatcat gtatccagta gtggataatt cattttgatg gcttctattt ttggccaaat 250440
gagaattaag ccagtgcctg agactgtcag aagttgacct tgcactggc attaaagagt 250500
catagaaaaa gaatcatgga tatttatgaa ttaaggtaag aggtgtggct ttttttttt 250560
tcttttttcc agccgttgac caattatagt tcggctgttg actgagaagt ttgtggtggg 250620
aaaacgtttg ccatattttc tttgcatttg ataattgtc ttgtacttag aaaaaaggcg 250680
tctatgaatg accagtgttt ttggtcgcca aatgttgctg acaaacttat cccaaaactt 250740
tagtggctta aaaaaacctg cccccaactg ttagtcaatc tgagctgggc tcagctgggc 250800
tgttcttctg ccagcctgca ggtggccact catgtggtca gcaggtcggc ggagagactg 250860
ggatggctgg gcttctctct ctgcctgcag tcctgagtct ctccttcttc gtgtagtctc 250920
tttcagtggc ctggctggca gggtagctag acctctcaca tgcagctcag agctcccaag 250980
agctcaaaag cagaaatggc caggccttct gaaaacttaa gtccagaatt gtcacagtgt 251040
cccttctact tccctctatt gatgatgatg atgatgatga tgatgatgat gatgatgatg 251100
atgatggttt tttctaatca gaagaaagct ggggtatgcc ctctacttac taaacaagtc 251160
acaagcccag ctcagattca agaaaagggg gtgaagtaga ggtgcagtta agtgggggggc 251220
cactagtcta acagacggtc acaaccagtg ccatggaaaa ccaaggatat tagcaaaagc 251280
agaagttgct agtgaccttg ggaagccgaa gctgcttaca gtagctggga caagctgaaa 251340
gtcagactaa gaaataaaga gagggccttc aagaagcttc ctgaatgatt tctgctagcc 251400
ctgagcctat ttttgaacc agcacttggg gaaactgatc ttgtgaggat ggatgtgttt 251460
agggacacag ggcttttgag agcagcacca ccccactggg gcatcccag acttgggaaa 251520
cgtgactctt tcttaatgcc actgggtttt agtcaggcca cagtgagaag gaacagccct 251580
aacaggcctc cagccaggtt gaatgagctc attttgttg tagccaacca gtaagatttg 251640
ctaatgttct acattaagtg ccttctccaa agacatccct cttgcctca tatgttgaat 251700
catccagtgc ggatattca atgaaaatat cattggttga cttttgtgat ggtaataatg 251760
ctatggcatc tttgccatga agttgtggcc tccttggatt cttctgactt tggcttctga 251820
aaggaaggcc tagatccagc cctggtggta gttccttct gaggtctctc agtcccttga 251880
gactttgggg tagtttggct gccattctca ctgacaaaat gtatatcagc ccccacctcc 251940
accccccaat attccttgaa ctttgaattg cttcagaaca caggtgtggc ctgaaggtat 252000
tcccttatta gggaagtgtc actgctgtct tctagtcaaa cttgtaaaga aaaagattcc 252060
agttcagtat ttgcagcaag aagcttgaat gctgttcttt ttatcgcatt gttacatcga 252120
ctcattctcc attttgcttt ggttttgtct tgacttgact tgactttggg ggtaaagtct 252180
ttcaccagca cacaagagtt tgattgtaca aatatatctt ctgcattaac atctctgcct 252240
gttgcttaag atcagttgct tttatactca gaatggaaat acctgatctt ggctagtttt 252300
```

```
gttataagat attgatttca tttagatttc cctccacgag gtcagcaaac tatcatgttc 252360
ttatgtaaac ttaggccaag gccagagtta tcatagtccc taggttgcta cggcttatca 252420
tgtgcttggt aaaaggtgat cgcaggttct cagacgagtt tactttacat gagatggaat 252480
caggcagaga ggctgggatg atggagaaag ctcgaggtga agttttaaaa aaaaagttgt 252540
ggaaaggaaa gttccaaaga ggtggttttct gaggaagtca gagcgcccag ggccagagca 252600
gtcagtaatg ggtgaatgag gttgtttgga aagtcggtgt gacagacaca tggatgccat 252660
ctacttctag gttgctggtg ggtattaaat atgcacaata ttccatagct cactgaggat 252720
tttaaaatta taagcatagg attttatatt ttggggtgaa agaattatct ggcacattag 252780
gtattggagt ttaaaaaaaa agccaaattt cacagtctta ataactttt ttaaaaaaaa 252840
ctaaaaggcg cttcatgtcc agtgtgtggc ccttctgaaa cttatggtca tctctcccac 252900
tgaaaccaag gtcttttcaa atgtggctaa atggggatga ggagacacgg gtaggacttt 252960
cttggtgtgt gtgcattctt taaagagcca agttgcttcg gggaaacagc caggaaaatg 253020
gtcaagatta tttttagagg ttattttatt ggggatttta agaactaata acatcttgag 253080
ttattttaa ttcaggggga tgtggaaagg tttgcaattg tcaagtgttt tgttgtagct 253140
tagtatccat aagggaaact tagactatag acataactac aaagccagtg cagcttttgt 253200
tttctgtatg ttgttggggg atcaactttc acacatagca agcacatggc ctccctgatg 253260
tcaggatgcc tttgttagga tctgtatttg cccttaattt tgttgaaatc ttttttcctt 253320
cttcctcttg aaaagttcca aaatatagtt tattgtatct ttcatcacta aaaatttgtt 253380
ccttttcac tatgggcagt tcacacaagg caaaaactat tgaacagttg gttttagtgt 253440
gttgtataac tttgctgtat atcaaactaa ttttgacaag ttttcatcct aagcctcaaa 253500
tcatgtaatt aataatttgc ctgtttattt atgacctaat tgtgattctt ttattaataa 253560
aagctaatgg gaaaaggatc cctgattaag ctgatgacta gacctacaat taattttcct 253620
gcagtatatg aagtattgta ccagagtatt aaaagatatg taatatttta ttgataaatc 253680
tatccttaa aaggaatacg ttttaggatg tcatcatttt gatgtgaatc atgtaaatgt 253740
tgataatatg ctgtttatta tacatttagt gtttcaagag attcacttaa ttgcctttt 253800
gcccacgtat attatgtagt ctatttgcaa ctgttcttaa aaaaatgaca ttaaaagaat 253860
agtttatgta gagaaacatt agtggatgtt aattgtctcc ccacctatat ttatgggtgt 253920
tagcgcaact gctttgctag ttgcaaagct gtattatcag agtaaaagtg tatttgtaaa 253980
ctgtatggga actaaaaatt aggaataaaa ccattttctt tatgatggc atttgtcgtt 254040
tgcttcatca gaaatgtcca ggaaaaaat gggattattg gtcactccac ctctcacact 254100
ggcaaaatac tgacatttag cagctcttat ctagaagtga cttggaacat agaataaagg 254160
catgagttcc tgaagaattc attgagtgtt tcctgtagaa atagctttag gagatgggaa 254220
gttctatctg ggagaacata tgagtaactc aagagtaaaa agtatagtct gtgtaaacta 254280
tagaagaaat gctgggcatg gtggcgcgcc cctgtaatct cagctacttg gaggctgaga 254340
cgggaggatt ccttgaaccc aggagcccag gagttttaga ccagtctggg taacatagtg 254400
agacccttt tcacctactc tcactgcatg cccccccaaaa atatatatgt gcgcgcacgc 254460
gcgcgcacac acacatacac acacacacac acacacacac acacagagga aattgttaga 254520
aaacacacag aactgaatgt aaatagtatt aggtgggaat aagaagtaaa gggatggtaa 254580
ggaggcttgg aggaggagta aattatctgc tatgggacat cagctcttcc tttagagtag 254640
```

```
gtttaggtca cataccaaca gggccacttt gttctgacaa cagtgtgcac tgacatgggc 254700
agaaagaaac cattttatag atagcaaaac aggtggttat tctttattag aaatataagg 254760
aatgatttgg attacttatt tacactgtaa aatactatga ccccctctc agtctcattt 254820 gaattgttta atgcatctaa tcaaatctag ctggtttagt ttgttagtcc tgtcacctgt 254880
ccattcagaa atacagagca tgggccaggc acagtgactc atgcctgtaa tcccagcact 254940
ttgggaagcc aagacgggcg gatcacttga ggccaggggt tcgataccag cctggccgac 255000
atggcgaaac cccgcctcta ttaaagatac taaaattagt tggccatggt ggcgcatgct 255060
tgtaatccca gctactcggg aggctgaggc atgagacttg cttgagccca ggaggtggag 255120
gttgcagtga gccaaaattg cgccactgca ctctagccct ctagcctagg cgacagagtg 255180
agactctctc tcaaaagaat aaataaataa aaataacaga gcaccttcaa aatactaggc 255240
actacacctg tgccctgggg aggaacgctg cccgaaacaa cctgatagg tgcctgtcta 255300 ccagggagct aggccttgca ccgtcagaag gcagttcctg aagctgccca gagccaagac 255360
aaaagacaga agtgagacga ctagttccaa acaagataag agccatgaag aggggctaag 255420
agtgtgtatc gcaccggagg attactacgg ggttttcaaa ccatggtact gtttggtgat 255480
tacccttggg tttcagaaga ggtgctgtac acaatattgc ttggagacac ctcattccac 255540
ataatccttc ttgaggtcct ggattgcatg ttagagggca gtgacaatat cttgtccttg 255600
gccatgccat gaaatgacct tctgtttgtg tagttcctac tcacaagaag agttcccaag 255660
aaaatgagta cattaaaggc agagccggaa tccctgcaat aaatcctgcg gacagagatg 255720
aggaattatt caacgtggtc accttgtgaa tgaaaaagct tctggtgtga gggtctactg 255780
ttggctcata tgacatgtat gctttcatcc acctcttctc ttcgcctcta cgagggggta 255840
gcaaaagggg gactgtgatc tcaagtgaat ggtttgattt tgcaggtgct gttattttc 255900 ccctaggaac tagctaagtt tccaaacact gaatttgcaa atgggatgag ccagaaatag 255960
agatttgcta ttttgtcagt ggtgacagtt accagtgagc tggtaatatt caagtcactg 256020
gaggtcagat catttaaatc ctcaaatacc atcatgatag aaaatatagc tactgaaata 256080
agggttacaa gaaagcaata ccatactgcc aagatctgtg agcagtttac ggacaaagga 256140
attgtatgtg atgcgcagac atgatgtcat ttctacctgt tacactgaac taaacagagt 256200
ttgtttggga tccaaatttt ccatttggca aagattaaat ccccaataac agttaggcat 256260
cgggaagcag atgaataaaa tagttcatgc atctgaggag ctatgcatgg agtcatagtc 256320
agggagacat atatattcaa atatttgtca tttgactaga atagacaatg ataagattat 256380
taacttaaat tgatggttgc atagaggagt gaattatagt gaggttagaa ttcagagaag 256440
gggtcacctg agcttactct gtcccccagg ctggaatgca gtggtgagat ctcagctcac 256500
tgcaacctct gcctcccagg ttcaagtgat tctcctgcct cagcctcctg agtagctgga 256560
attacaggca tgtaccacca catcaggcta atttttgtat ttttattaga gattgggttt 256620
caccatgttg gccaggctgg tctcgaactc ctgacctcag gtgatccacc cacctcagcc 256680
acccaaagtg ctgggattac aggcgcgaac cagtgagcca ctgcgcccag ctccctgtct 256740 ctttttttt tttttttttt tgacacaagg tctcactgtg ttgcccaggc tggagtgtag 256800
tggcacaatc ttggctctgc aacctctccc tcccaggttc aagcaatttt catgcctcag 256860
cctcccgagt agctgagatt gcaggcgcaa accaccacgt ctggctattt tttgtatatt 256920
ttgtagaggg gagggttttg ccatgctgga caggctggtc tcgaacttct gagctcaagt 256980
gatctgccca ccttggcctc ccaaagtgtt gggattatag acgtgagtca ctgcacccag 257040
```

```
cagcatttct ctttaaagtg aggctgagcg tctttccatg tggttttcat gtgattttct   257100
gggaattctt catgtctctt ggcattttg cctattgaat tctggttctg tcttgctttg    257160
agtttaggaa taaagatatt ttattattat tattattatt tcagacaggg tctcactccg   257220
ttgcttaggc tggaatgcag tggtgtgatc ttggctcact gcaacctcta tttgccaggc   257280
tcaagtgatc ctcccacttc agcctcctga gtagctggga ctataggcat gcgcgaccaa   257340
acccagctaa tttttttaaa tttttgtgt agatggtgtc ccactatatt ctccaggctg    257400
gttttgcact cctgggctca aacaaacctc ctgtcttggt tcatcaaagt gctgggatta   257460
caagtgtgag tcactgtgcc cagccaagat atttaattct ttacaacgga ctgccatgac   257520
tggagttatt gaatcagtag gatcaatttc aatcaaatgc cttttatag gtgcatgtgg    257580 gatagctacc cctatgtgtg agttgcagtt ttggccttgc tgtgattata attctcagtg   257640
cggatgggga gaacagcctg ggaaatgcat tctcagcact cccaagatgg tgaaaccttg   257700
tctcagctgc catgtgagac cagtcttaat tatcctggtg agtgagttga gaattatttc   257760 agatttctt tcatattcaa aaccaccaag cagtatgcat gcatgcaccc attcaagcac    257820
tttttaatga gtacaatgaa ccaggcattg ggctaggtgc tttggggaat acaaaataaa   257880
tacttgtctt aatccctgtc tgaacggact ttatggcaat ggcccattta gggagaggag   257940
acacacacag gctgaataca agatggaaaa caaaacagct atggagggag cctggatcaa   258000
gaccttaaga tgaaggattg aaggaaatga taattccttt aatttactga caattaggtg    258060
ccaaacactg tcagcgggtt tatataatga tatggtttgg ctctgtgtcc ccacccaaat   258120
ctcatcttga cttgtaatcc ccacacgctg agagaatgac ctggtgggag gtgattggat   258180 caaggggca gtttccttca tgctgttttc atgatagtga gtaagttctc ctgagatcag    258240
atggtttaaa agtgtggcac tggccaggcg cagtggctca cgcctgcaat cccagcactt   258300
tgggaggcca aggtggttgg atcacctgag gtcaggagtt cgagaccagc ctgaccaata   258360
tggcgaaacc ccgtctctac taaaaatatg aaaattagct gggcgtggtg gcaggcacct   258420
gtaatcccag ctacttggga ggctgaggca ggaggattgc ttgaaccagg gagatggagg   258480
ttgcagtgag ccaagattgc gccactgcac tccaacctgg gtgacagagc gagactctgt   258540
ctcaaaacaa aaacaaaaac aaaaacaaaa aacacagagg ttggccttga ctccttcctt   258600
cccgctccca ttccagaccc tgcttgttca gcccccagcc acttctgctc atggtccttc   258660
caaaatatat atccacggtt tgtcgcctct ccctagctct gctaccacca caatggggag   258720
cctctgttat ctctgaaaga caagaaggta gggcaccagt cttcctggaa cctggttaga   258780 ttttttctc ccccactgga gacatggtct tgctctgtca cccaggctgg agtgcagtgg    258840
ccccatcata actcactgca gcctcctacc cctggattca agggatcccc ccaacctcag   258900
cctctttaat agctgggact acaggcgcag gccaccatac cggctaagtt ttttaatttt   258960
ttaatttatt attattattt tttgagacag agtctcactc tgtcacccag gctgcagtgc   259020
agtggcatga tctccactca ctgcagcctc cgcccccca ggtttaagca attttcatgc    259080
ctcagcctct tgaatagctg agattacagc tgtgcgccac catgaccggc taattttta   259140 atatttttag cagagacggg gttttacaat gttggccagg ctggtctcaa actcctggcc   259200
tcaagtgacc ttcctgcctt ggcctcctgc atcgctggga ttacaggtgt gagccactgc   259260
acccagctcc gatctgctaa gatcttatgt ggcctcccca tctccactca gaccccactt   259320
ctgccattct ccccacagag ccatctgtta aacatgcaca tgggattctg ctgccctcct   259380
```

```
gttccccagt ggcctcccat cacattcaga ataaaagcca aattctttac tggccttttg  259440
gagtgggcag aactttactg catcagactc tctggtatat tttaggattt tttgcttcct  259500
gggcctccac ccagtaaatg tcaatagtgt tcatagttac tgtgacaacc acacacgtcc  259560
cacacattac caaattcccc cggaggccct tagtgtttcc cctgatggag aagcattgcg  259620
tgattctgtg gcctcttcca tgcctcctac ctcaccatgc catcattcac ccaacaatat  259680
atatcaaaca cttttttttt ttgtgagata gagtctcact ctgtagccca ggctggagtg  259740
cagtggcagg atctcagctc actgcagcct gcctcctggg ttcaagtgat tctcatgcct  259800
cagcctcctg agtagctgag accagaggca cacgccacca cgcccggcta atttttgtat  259860
ttttagtaga gatgggcagg gctggtctcg aactcctgac ctcaagagat ccacccgcct  259920
cagcctcccc atgtgccggg attacaggca tgagccacca cgcacggcct attctgctct  259980
ttttatttgt tgatggggttg tctgtcttct ccatgagaat gccagctcca agaggacagg  260040
gagttggcct tgtttattgc agtatcccca gtgcctacaa cagtgcctgg cccagggtag  260100
gtatgaatgg gtgattgaac aaacgagtga atgacatcat tctagagaag tcagccacgt  260160
gaggatctgg agggagagca tttcaggaaa gaggatgtgt acgtgcaaat gtcctgctgc  260220
aggaatcagc ttgggcacgt ttgaggacta gacagctaaa aggaagagca gatttgggga  260280
aaaggtgctg ggttcagtct tgaacatttt acagttgtat ctgaggtgcc atatatctgc  260340
caggatctgg gaagaaaacg aagttcactc acaagggttg aactgaagag aattttaaga  260400
agggactgtt tgtgtaagta agcagggttc agggttgcaa cgtgggaggg tgaaacacca  260460
gggacctaca tcaggaggga gctccttaca cctacattag cagggatgct ttccttctgg  260520
gggctctagg ggagaatctg ctctcttgcc ttttccagct tttcgaggct gcccacattc  260580
cttagcttgt gacgcctctg tccatcttca aagccggcga tggccggtca agcctttctc  260640
acattacatt tctcattttg gacattcctg cctcttctcc cacttattaa cacccctgatg  260700 atgaaatccg atccaccaga taatccagaa taatcttccc acctcaagat ccttgaccta  260760
atactatctg caaagtccct tttgccatgt aaagtaacat attcacaggt tccagggatg  260820
aggatgagga catctttggg ggcccattct gcttatcaca gtaccttgg gtcttaagga  260880 tataaggatg gtaggccagg catggtggct catgcctgta atcccagcac tttgggaggc  260940
cgaggcgggc agatcacctt gaccaacatg gtgtaacccc acctctacta aaaatacaga  261000
aattagccag gcgtggtggc acgtgcctgt aatcctagct acttgggagg ctgaggcagg  261060
agaatagctt gaacccagga ggtggaggtt gtagtgagct gagatagcgc tactgcactc  261120
caacctggac gatagagcga gactacattt cacacacaca cacacacaca cacacacaca  261180
cacacacaca cgctactgca ctccaacctg gacgatagag cgagactaca tttcacacac  261240
acacacacac acacacacac acacacacac acacacacac aaaaggatac agggatggaa  261300
gaacaggaac agtattcctg gaatctggaa agacctggag ccatggagaa ggactcccct  261360
gctggagctg cagccccaga agggctgagt gaggaagggc caaatgcact gaactctctc  261420
tcctgcctcc ctttgatctc cagggctgcc tctcattgtt ccagcctatc tgcaggccag  261480
gtggccaagc tgtgcaggtg ctgcagcctg cagggcttag cgtccccggc ccagagcagg  261540
gcaaataatg gatctggggt ggagatgggg ggcaaatgga gagtaacact taaggtgtgg  261600
cctgtgcatc agcagcctca gcctggtctg taactgttgg aaatgcagag tctcggatcc  261660
cacccaagcc ccactggatc agaatctgca ttttatccac gagatctcta ggggattcat  261720
aggtgcattt gcagtttgag acaagctgca ctggaggact attgatttat tcttagagac  261780
```

-continued

```
gggaccttgc tctgtctccc agactggagt gcagcagtgt aatcatagct cactacagcc 261840
tcgaactcct ggctcaggct atccccctgc ctcagcctcc caagtagctg ggaccacagg 261900
tgcacatcac cacatccagc taattaaaaa aaaaaatttt tttttaaata gagacatgat 261960
ttcactatgt tgcccacatt ggtcttgaac tcatggactc aagcgatcct cccactttgg 262020
tctcccaaag tgctgggatt acagatatga gccaccatgc gccgctgcac tgaggattt 262080 ccacgtggag ataaaggctg ttggaaatta tgcccatgct tgggtcagct catctcttga 262140
gaatcatttg atatcacaag agaagccacg aagtctaggc tatggagtaa gaagaaatcc 262200
aaagactaga tttcaaagaa caagacaagc attatcacaa aatgtcttga aaatagcttc 262260
agatattctt agacattaca cctaccaaaa ctgaatttgt gaaatcctaa gcatatgtta 262320
catccatcta accataggaa gagaagagaa aaaaaaaatg taaggaagc aaactctaaa 262380 attaaaatct gttcaggagg tgacggatgt ctgggtcttg acggatttct agacttgtaa 262440
aaagtagttg tttttttcat cttcattcat ccatgtttga ttgttgcttt ctcaggacca 262500
ttattttttt tttctcatag gaaaattaat ttctttcttt ctaaagtgtt gattctcccg 262560
tgttgctttg tatgaaggct ttagaaaatg tctaacaatg gtttgagtga tagacggaaa 262620
aaactccagt gcctcagcta cacaaaagac tctctagcga ggtcctattg tgcattgatt 262680
tactgtgttg aataactttt ccacattcga aaatgcatta aagctcttat ttaggaccat 262740
ctaattcctg tctttagagt taacaatcaa ccatcaggtt tctgcttagg gtaagttaaa 262800
acaggcgttt tggttgagga cgataaatac ctctgcgttt taggctgcag gtgcagatgg 262860
agcattctgt tctaggcatg ttgatttagg aggaaaatcg gagttttgga actttacagg 262920
cttgggttac tttcctggtt ttgccattta ctagctgtgc gaccttgggc ttgtcagtaa 262980
aggccttcgg tctgcccatc ctctttagaa aaatggagct acttttccta ctttgttggg 263040
aagggttgtt gagaagttta atattaatgg atggcctggc acatagtggg tgctcagtaa 263100
acagctgtgt ttttcctatg gggctaggga atgtctttca ggcttttgac atagcctgtt 263160
gctggggtcg tattgtgtcc ggaattggtg ggttcttgtt ctcactgact tcaagaatga 263220
agctgcggac cctcgcgatg agtgttacag ttcttaaagg cggcgtgtcc ggagtttgtt 263280
ccttctgacg ttcggatgtg ttcagtttct tccttctggt gggttcgtgg tctcactggc 263340
tcaggagtga agctgcagac tttcacggtg aatgttacag ctcttaaggc cgcgcgtctg 263400
gagttgttcc ttcctcccgg tgggctggtg ggctcgtggt ctcgctggct tcagaagtga 263460
agctgcagac cttcgcggtg agtgtttcag ctcataaagg cagtgtggac ccaaagagtg 263520
agcagtagca agattattg caaagagcaa aagaacaaag cttccacagt gtggaagagg 263580
accccagtgg gttgccactg ctggctcggg cagcctgctt ttattctctt atctggcccc 263640
acccacatcc tgctgattgg tagagcggag tggtctgttt tgccagggca ctgattggtg 263700
cgtttacaat ccctgagcta gacacaaagg ttctccaagt cccccccaga ttagctagat 263760
acagagtgtg gacacaaagg ttctccaagt cccaccagga gtagctagat acagagtgtc 263820
gattggtgca ttcacaaacc cagagctaga cacagggtgc tgattggtgt gtttacaaac 263880
cttgagctag atacagagtg ccagttggtg tatttataat ccctgagtta gacacaaagg 263940
ttctccacgt ccccaccaga ctcaggagcc cagctggctt cacccagtag atcctgcacc 264000
agggctgcag gtggagctgc ctgccagtcc catgcagtgc gactgcactc ctcagcccct 264060
gggtggtcga tgggactggg caccctggag cagagggcgg tgctcgtagg cgaggctctg 264120
```

```
gccgcacagg agcctatgga ggtgggggga ggctcaggca tggcgggctg caggtcccaa    264180
gccctgctcc acgggaaggc agctaaggcc ctgcgagaaa ttgagcacag cagctgctgg    264240
cccaggtgct aagcccctca ctgcccgggg ccggtggggc cggcctgccg ctccaagtgt    264300
ggggtccgct gagcccacgc ccaccaggaa ctcgcgctgg cccgcaagca ccgcgcacag    264360
ccccggttcc tgcccgcgcc tctccctcca cacctcccg caagctgagg gagccggctc    264420
cggccttggc cagcccagaa aggggctccc acagtgcagt ggcgggctga agggctcctc    264480
aagtgccgcc aaaatgggag cccaggcaga ggaggcgcct agagcgaggg agggctgtta    264540
agggctgcca gcatgctgtc acctctcagt atgaatttac cagttggtaa cgcatagcag    264600
ggagaatcag tgcacaatat tcacagattg cattagggtt tagatagctc ttccaagagg    264660
taattgttaa gcaaaaacct tttacttttta ttgcagtcta ttattagtat tggaagtcct    264720
cagttagatt ttctccctgg tatggaatga aacttaatt caaacacaca caggagaggc    264780
aaacatgtta ttatttgcta atggcttttta atcttgggaa gagagataga ttgattatca    264840
cctctgcctt ggataattgg gggaagtgct tccattttgg agagggtgat ttttaaagag    264900
ttgagagtgg gggaaggctg agagtcaaga gctggttagg agtcgtgcct gtgtgatttt    264960
ggtaacttaa gcttctagag cctcagtttc ctcactgaag aatgtggctg acaattgtac    265020
cgtactgccc atgccactgt gaggattaaa tgagctaata gacatcatgg gaacaattgt    265080 tggtttttttt ttttttttttt tttgagactg agattagctc tgtcgcctag gctggactgc    265140
agtggcacga tctcagctca ctgcaacctc tgcctcccgg gttcaagtga ttctcgtgcc    265200
tcagcctccc aagtagctgg gattacaggc acctgccacc acgtttggct aattttttgta    265260 tttttagtag agacagggtt tcaccatgtt gtccaggctg gtctcaaact cctgacctca    265320
ggtgatctgc ccttcttggc ctcccaaagt attgagatta taggcatgag ccaccacgca    265380
tggcctgttt ttgaggcagg gtctcgctct gttgcttagg ctggagtaca gtggtgggat    265440
cttagcttac tgcaatctcc gcctcctggg ctcaagccat cctcctgtct cagcctcctg    265500
agtagctgga actacaggca cacaccacca cgctcggcta attttttgaat tttttgtaga    265560 gatgagggtc ttgctatgtt gcccaggctt gttttgaact cctgagctca agcgatccac    265620
ctgccttggc ctcccagagt gctgggatta caggcgtcag ccaccgcact ggcgagaatg    265680
attgtttatt tgtagtatcc cacaacagaa gtaccacccc ctgcaaatgt tcctttaaag    265740
aaaaatggtt atggtgtcag ttgtgctatt ttccatacac tgaagtctga tgcatcagtg    265800
gaaaggagtg gatcacatca acacagataa atcatacgaa gggttgaggg agacaagcca    265860
atcatagaat catatgaaca gaacgagacc atttattttg catgttcagc aacatgcaaa    265920
agcaaataat acaatgtttg cagaagaaaa attacaactg gcatggtgg ctcacgcctg    265980 taatcccagc actttgggtg gctgaggcag gtggatcact tgaaatcagg agatcgagac    266040
cagcctggcc aacatggtga aaccacatct ctactaaaaa tacaaaaatt agccaggcgt    266100
ggtagcgggc gcctgtagtc ccagctactc gggaggctga ggcacaagaa tcacttgaac    266160
ccaggaggtg gaggttgcag tgagcccaga tggtgccatt gtactccagc ctcagcaaca    266220
gagcaagact ccgtctcaaa caatcaaaca acaaacaac tgtgtatgga tctcaaagtt    266280
tttttgcacc aaaataaact catactaact tgttacaaca cgtctgaaca ggatctagtt    266340
tgaggcacta agaaggataa gacatctgtt tgaaaagaac ccctgtcaga gcaacatgaa    266400
ttctcctaaa actgaagtaa gaacaaacat caagtttatg gtgaagctcg ggtgaagga    266460 tggtgaaatc actaatgcct tatgaaaagt ttgtggggaa aatgtggtag ataaatcagc    266520
```

-continued

```
agtttacaaa tggatatctc attttaagaa gggacaagac aatattgact tgccaggcat 266580
ggtggcacac gcccgacatt ccagctactg tggaggctga ggtgggagaa ttgcttgagc 266640
ccaggaggtg gaggctgcac tgagtcaaga ttgcaccact gcactccagc ctgggtgaca 266700
gagtgagact ccatctcaaa aagaaaaaa aagacaatgt cgaaaatgag gtgcacagtg 266760
gcagatcatc cacatcaatt ttcgaggaga aaattatctt atttgtgccc taactgaaga 266820
ggactgatga ttaacagcag aaacaatagc cagcaccata gacatctcca ttggttctgc 266880
ttacaccatt ctgagtgaaa aattaaagtt gagcaatgcc actcatgagt gtaaaattat 266940
tacacccaga tcagctgcag acaaaagcag agttttcaat ggaaatttaa acaaatgaga 267000
tcaagatcct gaacatttat ttgaagaatt gtaacaggag atgaaacatt taccattatg 267060
atcctgaaaa ctaagcccaa gcgaagccat ggatactaag aggtagaagt agtccagtca 267120
aagcaaaagc agaccggtca agagcaaggt catggcaaca gttttcgggg atgctccagg 267180
cattttgctt gttgactttc tggagggcca aagaatgata acatctgctg attatgagag 267240
tgttttgaga gagctagcta aagctttaac cagaaaaaca cctgggaaac cttcaccaga 267300
aagtcctcct ccactatgac aacactactg ctcattcctc tcatcaaaca aggacgattt 267360
tgtaagagtt tttatgggaa attattaggc atccacttta cagttctgat tctgcacctt 267420
ctgacttctt tttgtttctt aatcttaaaa aaatcttcaa agggcccatt tttctactgt 267480
taataatgta aaaagactg cattgacagg gttcaattcc caggaccctc agttcttcag 267540
ggttggacta aatggctggt atcatgactt acaaagtgt catgatcttt gctgggcaca 267600
gtggttcatg cctataagtg agaggattgc ttgaacctag gagattgagg ctgcagtgag 267660
ccatgatcat ggcactgcac tccagcctgg gtgacagagc aacaccctgt gtcaaaaaaa 267720
aaaaaaaaaa aaaagtcat gatcttgatg gagcttatgt tgagaaataa aatttatatt 267780
ttatatttt atcttttact tcaatatcta tgaactttt gaagtcccct tgtatataca 267840
ggcactgtgc taaggtgcct gacatggatt ctcttattaa atccacaaaa caaccatact 267900
gggtaggtgc tatggttatc ttcattttac agatgtgtaa actgaggcct gatatcattt 267960
ggctctgtgt cccacccaaa tctcataatc taaaactgta atccccatgt gtcagaggag 268020
gggcctggca ggagctgatt ggatcatcgg ggtggatttc cccttgctg ttcttgtgat 268080
agtgagttct catgagatct tacggtttaa aagtgtggca gtccccttc actgtctcgc 268140
ctgccgccat ttaagatgtg ccttgcttct ccttcacttt gtgccataat tgtaagtttc 268200
ctgaggcctc cccacccatg tgagtcaatt aaacttctat cacccactct aagctatgtc 268260
tttatagcag tgtgagaacg gactaaccca aggctgttag ctgccatctg ttaattgagc 268320
atttattaag tgctatgtac catcttactg aagtaagatg catgatctta cttcacttcc 268380
agaaacctta ggaactatac tgaaaacaca actttagacc agggttggca aacttttcct 268440
ataaaggtcc agatagtaaa tatttgatgc ttttgtgagc cgtacgatga tctctgtcga 268500
gactgttcaa ctctgttgct gtggtgcaaa agcagccaga gatgattcat aaatggatga 268560
gcatgactgt gttccaataa aactttattg aggaacattg atgtttaaat tttatttcat 268620
tttcacttga aaacgatcac aaaatatcat ttttccttcc ttttttgttt tttttttga 268680
gacagagttt cactctgtca cccaggctgg agtgcagtgg gaggatcaca gcccactcaa 268740
agggatcctc ccaccctaac ttcctaagta gctgggacta caggcatgca ccaccatgcc 268800
cagctaattt ttctttttaat tttttccaac tatttaaaaa tgtaaaattg ttcctaattc 268860
```

```
acaagtcata tgaaaacaag cagtggggct ggaactggct tgtgggccgg gctgtggttt   268920
gccaagcctg gctttaggcc atcagttccc tgagggctgg aaacttgctg accctgctca   268980
gtgtggtatg cccagtttcc gactcaccac caggtggtca gaacaagttt gctgaatgaa   269040
tgagtaaatg tacgttgata tctcagaagg tgaaagtgat gtttctactt tgggcaacaa   269100
ctctgacata cctagcattt tttagggtgc aatattaata atcatgtcag attacaggtg   269160
tacactgggg ctgtctcagg caaaccagga tgcatggcta tgccaatgtt cttcaccagg   269220
aagatgattc tttgccataa tgacagtagg acaccaaccc ctgtgtgtgt gtgtgtgtgt   269280
gtgtgtttgc acacatgcct gagagtgctg aacaaaatta tgaattttc ttttttttgtt   269340 ttgttttgtt tttttaagtc aaggtcttgc aatgttgccc aggttggagt gcagtggcta   269400
tttatgagtg tgatcatagc atactgcagt ctctaattcg tagtctcaag caatgctctt   269460
gcttcagctt cctgaatagc tggaactata ggtgtgtgcc atcacgccca gcctcccaca   269520
agcctgcaga agagctgcaa aaataatata ctgattcgat gaacacccat gcccgtcacc   269580
ctaatgtggc catctttaac attgtgccac atgtgcgcta tccaccacct atcatcgtta   269640
gctatcaatc caactatctg ttctatctat ctatctatct atctatctat ctatctatct   269700
atctatctat ctatctgatc tacctgtatt catctatctg tatctatcat ctatcttgta   269760
tctatatctc tgtatctatc tatctatcta tcctatctat ctctatctta ttatttttc   269820 ctgggtacga agtgcagaca tcacggcatt tcacccttc catactgcaa tgtgcatctc   269880
ttaagaacac agacatcctt tttcataacc acaatatatt gttcatattt agaaaattta   269940
acattgatac aatactatca tatgagatac agtcagtatt tgaattttcc cagtaatgta   270000
ttttacagga cccaattaag gatcatgcat ggcatttatt agtcattttt attcagtctc   270060
ttggaatcca gaacagtccc ttccttcttt ttgtcttcca tggcgtgggt acttgaagag   270120
catagatcag gtgtttcgta cagagtctct caatgtggat ttgtttgatt gcttcctggt   270180
gattgcattg gagttaaata tttctggtaa aaatatgata ttggtgatgt tgtgttctta   270240
gtgcattcca tcaccaggca cgtaatgtca tttgtcccat tatcaatgac gttaaccttg   270300
attacctggt taaggtgata ttgtcagatt tctcccctgt aaaggaaact tttccattca   270360
taattaacaa ctgccatttt gtaactcagg agaaatatca ttcaggtgaa gaaatcattg   270420
aagagtgtaa gcaggaaaag acaaaacagg tgtaagaggc tctgtctggc agacactgtt   270480
ggcccagctt ccaggttctt acaagcttaa gggtgactgc atgcaaccag tgaaatagct   270540
gatggctttt tgctccgtgg ctgtatgtat gcaaaacagc gctcttgccc agcaactgta   270600
gatttattga ttgtgttaac tctccatgat tcagtaattc gggctgactg ccggggtgca   270660
gcaaatcttt cttgagaagt tgcattagtt ttcacatcat gtagctgcca aagtagagga   270720
cgtggccagc ttcccctcct ctctaccgtc tttccaaggg cagcagctca gacacatgct   270780
gttccagacc actatatctc tcacctgatg atgataatag tcccccacaa catccactct   270840
gctcgcctcc tcaccctggt gcattctcct tgaagcagcc tcagtgaact tgcaaaaac   270900 ttaaatcagg ctgggcatgg tggctcacgc ctgtaatccc aacactttgg gaggctgagg   270960
cgggtggatc acctgaggtg aggagttcga gaccagctgg ccaacgtggt gaaacccgt   271020 ctctactaaa aatacaaaaa ttagctgggt gtggtggtga cgcctgtag tcccgcctat   271080 tgggaggct gaggcaggag aatggcttga acccggtagg tggaggttgc agtgagccaa   271140
gattgtgcca ctgcactcca gcttgggtga cagagtaaga ctgtgtctta aaaaaaaaaa   271200
acccaaaaaa caaacacccc ccaccctcaa atcagatgat taaccctctc cttgaaactt   271260
```

```
ctcccattgc ccttagaata aagatctaaa tccttactgt gacctaccct ggatggcctg    271320
gcccttgcct ttctctcaga tctcattttc ttcctctctt gcctgttgct gctttctgaa    271380
ctcagccaca atgcctttct ttctgtttta caaaaatgct tctacctcag gcctttgca    271440 tatgcttaca attcttctgc cagagacact cctctttcat tctcccacta agataacagt    271500
ttgtgttgtg tgctcactag ggagggctcc agtttcaggt atgactggat cccaaggctc    271560
caataaagtt ggagggaatt tatctcttga ctcagtgttg gctttgtgga ggccatttct    271620
cttctcatgg tggcaagacg gctgccaata tctccaggct tacatcctac cttctctgta    271680
gctcctatga aaagagagcc ccttttttcct gatagttctt aaacggatta tgggattggc    271740
ttgaattgga tcaccacagg tcccatgtct actcctgagc caattcctat gggcaggagg    271800
atggaatgca ctcattggtc aggcctgggt cctgtgacca cccctaggaa gagggcgtgg    271860
attggccttt cctacacctc atggactaaa atgggggga ggcgaattcc cctaaagaaa    271920 acagggtgc tgttaccaga tgaggggag tgcatactgg ggggcagcaa aataaaacat    271980
gcccattatg ggatgtagta tggattcaag gaggcaaagc ttgaagcacc tttatctgga    272040
agatgctaac ttctttttttt ttaaacggag tctcgctgtg tcgcccaggc tggagtgcag    272100
tggcactatc gcggctcact gcaagctccg cctcccgggt tcgcgccatt ctcctgcctc    272160
agcctcccga gtagctggga ctacaggcgc ccaccaccat gcccagctaa ttttttttgta    272220 tttttagtag agacggggtt tcaccttgtt agccagcatg gtctcgatct cctgacctcg    272280
tgatccaccg gccttggcct cccaaagtgc tgggattaca ggcgtgagcc accgtgctcg    272340
gccctattta tttatttatt gagacagagt ctcgctctgt cacccaggct ggagtgcagt    272400
agtgcaatct cagctcactg tagtctccgc ctcctgggtt caagcgattc ttctgcctca    272460
gcctcctgag cagctgggat tacaggccac catggccggg taattttttgt atttttatta    272520 gagactgggt ttcaccatgt tggccaggct tgtctgaaac tactggcctc aggtgatctg    272580
cccaactcat cctcccaaag tgttgggatt ataggtgtga ccaccgtgc ccggcccagg    272640 ctgtctttta aattgtgcct ggcttttatt taccettact gttttctcaa caggtcaagg    272700
acagaactga cacccccttta caacaaatct ccacaccttg gccactttaa gtaattggta    272760
ttttatttta attttttaag agacagggtc tcactctgtc atcctggctg agggcagtgg    272820
aaagatcatg gctcactgca gcctcaaact cctgggctca attgatcttc ctgcatctgc    272880
ctcttgagta gtggggactg taggcatgca ccaccatgcg ctgccaacca agatactaa    272940 cattgtaact acaggtgtgc accaccatgc tcagcttatt tttttgtttt tgttttttgtt    273000 tttgagacag agtctcattc tgtcactgag gctggagtgc agtgactcaa tctcggctca    273060
ctgcaacctc tgcctcccag gttcaaatga ttctcttgcc tgagccaccc gagtagctgg    273120
gatgacaggt gcctgccacc atgcctggct aagttttgta ttttagtag agattgggtt    273180 tctccatgtt ggccaggctg gtctcgaact cctgacctca ggtgatccac ctgccttggc    273240
ctcccaaagt gttaggatta caggcgtgag ccactgcgcc cggccagcta ttttttat    273300 gttttatttt ttgtagagac agggtttat catgttgccc gggctggtct tgaactccta    273360
gactcatgca atccatctgc cttggcctct caaagtgctg gaattacagg cgtcagccac    273420
catgcccagc catgtgtttt tatttaaaaa ttttttatat taggccgggt gtgatggttt    273480
gtgcctgtga tcccagcact tcacgaggtc aaggtgggcg gatcacctga ggtcaggagt    273540
tcaagaccag cctggccaac atggtgaaac ccaatctcta ctaaaaatac aaaaattagc    273600
```

```
tgggcatggt ggcacgtgcc tataatccca gctagtccgg aggctgaggc aggagaattg 273660
cttgaaccca agaggcagag gctgcactcc agcctgggca acacagtgag actctctctc 273720
ttgaaaaaag tatttatttt aggtcaggtg aagtgtccat gcctgtaatc ctagcacttt 273780
gggaggccaa ggtgggagga ttgcttaaag ccaggacttc aagtccagcc tgggaaacac 273840
agcaagacct tgtctctaca aacaattaaa aaaaattatc ctgtgttttt atttccttt 273900 tctccaggaa tgcaaacttg aattaatttc acaaccaaa ggagaacatt gcaggaattt 273960
ttatttattt attttattttt aattttttgt atttacatac attgtttcat ttatttttct 274020
aattaccagt cctcaaagta gatgttattc ccattttaca aggaaaagtt gaggcttaat 274080
gagtttaact ttcccaagga cacttaatta atgatagaag aatgaggaat cccaatatag 274140
gactgatggt aaacctatcc ttttggttat gttgctgttc tctctctctc tgtctctgtc 274200
tctctgtgtg tgtattgtcc atataaagaa cccagttgat tatgaaatgc aattagaagc 274260
tgttattttt gggactcttg ccatggctgg agtaggctta aatttaagag acacagctct 274320
tgccactgat tagtttctca cagcactctc atgcctggga agggcgtcat caaccagttg 274380
atcacgtcag ctggagtaac tagcagtcgc taatgaggac cttttcccaa gcatctatat 274440
ctgagaattt cagagattca caaatgcaat ttagaaatgt cattatgtag ttacataaat 274500 gtttaattt tccacccata tgtttacact ttgaatattt ttgaatattt gaatattttc 274560
tataagccat gtattgtttt attattatta ttattattat tattattatt attattatac 274620
tttaagtttt agggtacatg tgcacaatgt gcaggttagt tacatatgta tacatgtgcc 274680
atgctggtgc gctgcaccca ctaactcgtc accttgcatt aggtatatct cccaatgcta 274740
tccctccgcc ctccccccac cccacaacag tccattgcag gattttttaa tggcaaaaag 274800
aaaaaaaaaa atcaagttcc ctgaggctaa ctacaacatg gattgcaata taccagcatt 274860
caccacccct gggaggggttg ctaaagcttt cacttttatg gccgttttgt ttttgttttg 274920
ttttcttcat aaaggcagtt tggagaagat gaagatattt tagtctttgg caaatcattt 274980
tgtttaatgg ccactgactg cttctcaagt ttttataaaa ttttataaaa gccttcattt 275040
ttgggaggct tttcatgttg gatacctaag gagatgaacc catttaacag agatctagac 275100
tgaagtgtcc agtctttcct cctaggatag gctctgggag tcctgatgtg cagagaatct 275160
ccaggcagac tgagaatgac atctgtgtaa atagtgcctt tggtcaagct ttctctatct 275220
tctggacctc ggtttgcctc tgtaattgga gggggaaacc acagagaaat gcagtgtatg 275280
gtactaagga tgactgtaga tcatgcaagg atagaacttt aaatacccct gaatcagctg 275340
gttagaaagt tctcccttt ctcagttctc ttttggtctt tctgaaaact tcagctttgt 275400
gctaataggg ttcgttacca cagactgaat gttttgtgcac cccacacccc caaaattca 275460 tagcttcag cttaaccct ccagtggcat agtattagga ggtgaggcct ttgggaggtg 275520
attaggttta atggggttat gagggtaggg ggccttatga tggaattagt gcccttataa 275580
gaccaccaga gcttcatttc ttgccactga ggagacagca agaaggctgc tgtctacaag 275640
ccaggaaggg agtcctcacc agaactcaat catgatcttg gacttccag cctccaaaac 275700 tgtgagaaga aaacacctgt tgtttaagcc actcagtcta tggtagtttg ctagagcagt 275760
tgaagttgac tacgacaatg gctttcacgc cagatgtttg ctgatctctc tttataacaa 275820
agaaaatgta ataacatcac ttttaatttt gtatttatgt ttttcccctta acttctaatt 275880 ttttttgttttt gttttggag atggaatctc actctgttgc ccaggctgca gtgcagtggc 275940
acgatctcgg ctcactgcaa cctctgcctc ctgagttcaa gcgattctcc tacctcaggc 276000
```

```
tcttgagtag ctgggactac aggtgcacgg caccacaccc ggctaatttt tgtatttttt 276060
agtagagatg gggtttcatc atattggcca ggctggtctt gaactcctga cctcaggtca 276120
tccaccgttc tcggcctccc aaagtgttgg gattacaggc gtgagccact gcacccagcc 276180
tccccttaac ttctatgtag ccagtgctaa gtggttttc aattaaaaca acaacaacca 276240
ctaccatcac ttatgctact aattccaggt acttttctaa aggttttac atgtatagct 276300 catttaatcc tcttaagggg taagatactg tcattattac cgttttatag atgagaaaac 276360
caaatcagag aggtgaaagc acttgcctaa ggtcacacag ctagtaagta ccagagctgg 276420
ggtctggact caggaaatct gcttccagag cctgtgctgt aaaccattct actttgctaa 276480
tgcatgacat aatgtttcct tttaaaatgt atttgcacac acacacacag aggatggggg 276540
agaggccatt aaaaaattaa tagaaaataa agtatctgta atagggaaat gggaaaatgg 276600
tgactgtagt tctgaacaac tgaaacatgg gaaacactgg acactcttgg tatctagaat 276660
tctatttttt aaattaatta attgattaat ttgacacaga gtctcactct gttttccagg 276720
ctggagtgca atggtgcaat ctcggctcac tgcaacttct gcctcccaga ttcaagcgat 276780
tctcctgcct cagtctcctg agtagctggg attacaggcc accacctg gctaattttt 276840 ttgtatttta tgtatttttt tttttttgta tgtggtggct aaaaaattag ccaccacacc 276900
tggctaattt ttttgtattt taagtagaga caggatttca ccatgttggc caggctagtc 276960
ttgaactcct gacctcaggt gatctgcccg cctcggcctc gtaaagtgct aggattacag 277020
gcgtgagcca ccgtgcctgg cctatttttt attttttga gatggagtct ctctctgtca 277080
cccagactgg agtgcagtgg catgatcttg gctcactgca acctcagcct ctggggttca 277140
agtgattctc ctgcctcagc ctcctgtgta gctgggatta caggcatgcg ccaccacacc 277200
tggctaattt ttgtattttt agtagagacg gggttttgcc atgttggcca ggctggtctt 277260
gaactcctga cttcaagtgg tccacctgcc tcagcctccc aaagtgctgg gattacagac 277320
gtgagccact gtgcctgccc aaggtatcta gaattctata cattacaaac atgcctgcac 277380
tggacacagg aggaagccag atggaagcac ctgagtatat gctaaacaac agtactgggt 277440
agtttaaaaa aaactgctta tttggctggg tgtggtggtt cacacctgtg gtgggaggat 277500
cacttgagac cagaagtttg aggctgcagt gagctatgat cgtgccactg cactccagcc 277560
tgggtgacaa agcaagacct tgtctctaag atagaataaa atgagataaa atcgcttatc 277620
taaagggaga aatgtcttcc tttcatagcc acagagcccg gtgccttcct ttaagggat 277680 ggggagagct ggacttcttg catctgacct tgctcgaggc tggggtctga tgtcctttag 277740
tcgtgatgcc cgcacctcat cattgggtgg gtggttaaaa tgtactgtct gtggagtgag 277800
tgtgggtgtg ggagctgacc tccagccagc gtaattaatg ggcttttgc atcggacagg 277860 cacctcccat tctacaggca gcagagacgg atggaggagt cttaatgctg catcagggac 277920
agctgtgggc agctcacctg gattttttt tcttcctgtt tttcaagaga caggctcttg 277980
ctctgtcacc caggctggag tgcaggggtg taatcttggc tcactgtgcc ctgggactcc 278040
tgggttcaag tcatcctcct gcctcagcct cctgtgtagc tgggactaca ggcgtgcacc 278100
accacatctg gctcattttt tatttattta tttatttatt tatttatttt ttgagatgga 278160
gtctcactct gtcgtccagg ctgtggtgca gtggtgcgat ctcggctcac tgcaagctcc 278220
gcctcccggg ttcacgccat tctcctgcct cagcctccca gtagctggg actacaggtg 278280 cccgccacca cgcctggcta atttttttgta tttttagtag agatggggtc tcaccatgtt 278340
```

```
caccaggatg gtctcgatct cctgacctcg agatccgcct gcctcggcct cccaaagtgc 278400
tgggattaca ggtgtgagtc actgcgcccg gccatctggc tcattttaa aaacttgttt 278460 gtagagatgg ggggtgggg tatctcacta tgttgcccag ctggtctcga actcctggcc 278520
tcaagcaatc ctcctacctt ggcttcccaa agtgttgaga ttacaggtgt gagccactgt 278580
gtccatcctt cacctggact tctgtgtcat cctgtctccc tctgctttgt aaacagatcc 278640
aaattctagt ttttacctta atcctaccct aaccctaacc ccatgtcaac acctacccta 278700
actttaacct ttatcctaac ccttatctat atcctaatcc taatcttacc tgtcccctcg 278760
tcctaagctt tgccataaac ttaaccctta tccctaacct ttttcttaac tgtaacccttt 278820 atctgtccct aacacttaac cctaatcctt ccctaatcct ccatttctcc tctgtagcca 278880
cacatttatt tgtttactta ttcatttatt tttcacccat atttattgag catctgctct 278940
gtcagtgagg gttccaccag gagagagaag gcacaattta actacgtaat tgaggcgaat 279000
ttgataaaag gacggtttac catgaggtgg gtgaggtcaa aggaactgaa gagtatactg 279060
aggcactgag ctggggcta gcctggtgag gagcagttac cacccgtggg gtgaagggag 279120
tgttggggga acccagtgac aggcagtgct ctagaggagg ggctgctggc aggcactgtt 279180
gtcagggagg tgtattgtcg cagttttgc cataaaacag cccagatcgg aaggggggcg 279240
agaagggagt acctggacct cctcctcctc ttgccttcct ggcctctgtg agtactagtt 279300
gctggacctg cccctatag gctggacctg cctggaacca gagtgcagaa gtccgtgggg 279360
gtcagctcct ggcccaggac ataggcaggg tggaggatgg ctccgagtgg ggagcggaca 279420
ggaatgaggg taaccagcat gtatactgtg tgtcaggcac tgttctgggc ccagagtaac 279480
agcaagtgaa caaggcacac aaaaattccc accctctagc tgggcatgga gtctcacacc 279540
tataatccca gcacttgggt ggccgaggcg ggtgaatcac ctgaggtcag gagttcgtga 279600
ccagcctggc caacatggcg aaaccccgtc tctactaaaa atacaaaaat tagccaggtg 279660
tggaggcagg tgcctgtaac ccagctactc gggaggctga ggctggaaaa tcacttgaac 279720
ccggcaggca gaggttgcag tgagctgaga ttatgccatt gcgttccagc ctgggtgaca 279780
gagcgagact cggtctcaaa aaacaaaaca aaacaaaaca aaaacccac cctcatgaaa 279840 tttgccttgt agtgggagaa gagagcccaa gtagcaagtt aacaaatgac aatttcaaac 279900
agtgagaaat gctgtgaaaa taagaagga taacagaccg agcagagtca gcatattttt 279960
tttctgtaaa gggttggatg ttagatattt tggttttatg agccctagga tctttgtcac 280020
aactgttcaa ctctgtcatt gtagcacaaa agcagccaca aatgatctgc aaatggatgg 280080
gcacggctgt gttcaaataa aactttattt acagactggt acagtgtaat ctcagcactt 280140
tgggaagcta aggcaggagg aattacttga gcccagtgat cttgagtttg agaccaactt 280200
gggccacata gcaagacccc atctctccaa gaaaaaaaa aattagctga catggtggtg 280260
tgtgcctata atcctggcta cttgggaggc tgaggtggga ggattgcttg agcccaagag 280320
tccgaggctg cagtgagcta tgatggtgcc actgaactgc agcctgggca acagagcaag 280380
accctgtctc aaaaaacaaa acaaaaaca aaacaaaac aaaaagcag gcagtgggct 280440 ggatttggct tgctgatctc caggctagag aatgacttgg tggtagaggt ggagggctg 280500 cggtaggcag tggttagata gggtggtcaa ggaaggcctc tctgaggagg tgacgttgac 280560
ctgaggcctg aaagacaaga gggcttgtca tgaaccaggc cggcaaagac ctggatctga 280620
gtcttagaga gggaacagca ttcatgcagc agcagatatt caccaagcca ggtaaatatc 280680
tctctgtgct aggtattatt gtaggcccgg gggtgctcag cagcaaacaa agcagacaaa 280740
```

```
acgcctgtcc tggtagaagt gacagtccag acaaaggcca tgagggtgca gtggtgggtt  280800 gggcatggt gcggcaagag ttgagcatct tccaggattt gaggatctta aaggatttaa  280860
tagaacctaa gagaccagaa gacatggggt gggagggagg aatgggcaag gatacaggac  280920
ttgtggagag cagtttgcag gaaaaagctt atgtttagag atgatctttt tcaccctgct  280980
ctgcagtgcg ggtgcatcca ggcgcaagaa atgccaagtg ctggaggcag aggctgggtg  281040
aggccaagcc accagcgctg gttggaattg gcaggacaac tcggggaggg tggccctggc  281100
tatctctggc atggctttca ggggaatgaa acacacttca tatccccact tttagggaac  281160
acaaatggca ttgtttatgt acctgtctcc catgggatgc tgtactggag tgcccaggct  281220
gtcttccatt catggaacca gagctgggag gcttggtcca gggatcccat tcaacaaccc  281280
tcaggtggcc tctggcccat agatccatag ctgcatcttt tttttttttt ttttttgag   281340 acagagtctt acactgtcgc cgaggctgga ctgtagtggc atgataatag ctcactgcag  281400
cctccattcc ccaggctcaa gcaattctcc cacctcagcc tctggagttg ctgggaccac  281460
acatacgcac caccatgcct ggctaatttt ttaaattttt ttgtagagat gcggtctcct  281520
tatgttgccc aggctggtct caaacttctg ggctccagca atcctcctac ctcggcctcc  281580
caaggtgctg gaattacagg tgtgagccac cacatctgcc tagatgcatc ttatttgatc  281640
ccagacagga ttttttttgt ttttgtttct tttaaattga ggtgaaattc acataacata  281700
aaatgaagag tttagcgag taccattcaa ggcatttcgt acattgtggt gcaaccataa    281760
cccctattta gttccaaaac attttcgtca ccccaaaaga aaatcctgtt tatcatacag  281820
tgacttccca ttttctcctc ccagacggga ttttaaaaat atgcaaatta gttaacatga  281880
agaggaaaag gagattttt catttaaatt agatttcagc tttcttttc tccttccttc    281940 tttccctcct tccttccttc cttcattcct ttcttccctt cctctctcct tccttccttc  282000
cttccttcct tccttccttc cttccttcct tccttccttc cttccttcct tccttctctc  282060
cttccctcct tctgagacag ggtctcactt tgttgtatag gctgaagtgc aatggcatga  282120
tcatagctca cttcagcctc gacctctagg gctcaagcaa ttctcctgtc tcagcctccc  282180
aagtacctgg gactgcaggc agatgtcacc acacccagcc cagatttcag ctttctcttg  282240
aaaaacagga ctgcctggca ataacaggtc tgcattcttc cctggcaaca aatggcagcc  282300 acccccttc caggggccc aagcattcct ttcgccagag tccttaccac ttcctgtgtc     282360
tgtgacatgt tggttgagtg ccacttgttg tcatgtatca gcacattcct gttgttacag  282420
tagagttagg agaaaagtga agtatttctt ttaaccagtg ccactttgaa aggggaagaa  282480
caaaaggtgg attgagaggg ctgtgtgatc aaagtcgatg agaaatgagc atttttcttt  282540
tttctttttt tttttttttt tgagatggag tcttgctctg tcgcccaggc tgaagtgcag  282600
tggcacaatc tcggctcact gcaacctctg ccttctggtt tcaagtgatt ctcctgcctc  282660
agcctcccga gtagctggga ttacaggcac ccgtcaccag gcccagctaa ttttgtatt   282720 ttttttagt agagacgggg tttcaccatg ttggccaggc tggtctcgaa ctcctgacct   282780
cgtgatccgc ccaccttggc ctcccaaagt gctgggacaa gacatgagca tttttctttg  282840
tagaaataat gctcttctta caggcttaat gtgcaaagtg tgtctgtgac aaaaaaaaaa  282900
aatacaatct cagaaattac tggagacaaa ccttttgat ttcactccct attataccta    282960
gcttctgtaa agcagacctc actcactcta ttcactgtaa ctcattctca ctgaggctca  283020
gagagggcaa gtggcttgct caaggacaca cagcatcttt gtcaatgcag agctggggct  283080
```

```
ggagctcaga ctgcttgctt cctcatcgtg tgcttgtttt actttgtcat catctgtgaa   283140
actgtctgca attgccacct ctctctgggg acacacctga gtcctcacag tctctggaag   283200
aaagtgcagt gggattcttt aatctctccg gctgcatttc atctttccca agtgttaatg   283260
gaaaaaaaaa aaacaaaaaa aaaaacacct gggttatctc cctggcattt tgccatctca   283320
gagagatgtt tttaaaaatg atgatttctt tatctttccc cgaatacaaa ttttcattct   283380
agcaacctct gctaaaggca gcttggccag acctgaccca gccatctctc cttgctctgg   283440
ccccacagcc cagccttcct atttatcagg ggtgacatca tatatccagg ctcccaggct   283500
gtccaacctt ggattgacac atttttgaat ttttctttt ttattcccgc tatccaagta   283560
gttatgaact cctttggtga atgcactgat ttttgccatc tagtggttaa aaaaaaaaa   283620
aaagaaaaaa gggagtcggg agacatgggc atcagacagt cctgggttct gctcctgact   283680
ctgccagttt ttgtgtatga gctctgggca gtttggtaa tgtcatcaaa acctcagttc   283740
caagacccct ttcaatggag cacttgctgc cccaactgct gggggtgctg acagcagatg   283800
gctctcagct gttaaccccct ttagcaatcc cttcagctgc agagccacct cgttcaaggt   283860
tattccactt cctgggacag ttcacagccc aagatagatc aagatggggc ataaaggctt   283920
gtccatctgg acccaactgg agacatcacc aatttagctc caggactctc ggtagggtag   283980
gctaggatgg ggtcggccct gcatcacagc tcaacttccc cctatgccca ttcctgcttc   284040
cttcctcaat cttccccagg gattgattcc aagggacctc cttaatatgt caactggatg   284100
ctaaacttga tctcaaagac agcttgctgg ggaatgtcac ttgggatagt gggtggtaac   284160
cacacctaca ccactgcctt gtttcgggga tcaatgaggc agtcgtggta gctggcacat   284220
agtaagtgtt cagatagtgt cattaattat tagcatattt attcactaag tgccaggcat   284280
tgttcagggc acatgagaca caagtgggca ttatcagctc cggttcacag ttgagaagcc   284340
aagacttgcc aaaggtcaca cggttcattc atggtccagc tgaatctcag cttggggca   284400
atcagctcct aaagagactg ggcttttcag aggagcctac ctggctggca ccagtcccaa   284460
ccctggactg cttgtctgtg tggtctctgg cacatcagga ctctctctga gcgccaagtt   284520
ccacaactgt aaaatgggat gaaacagagc ccgactttga gaattgttgt ggggatttga   284580
tgagtgaatc cttgtaaata aagtgcttag tgtggtgcct gccatacagt atatgctcaa   284640
tgaatgacag ttatcactat caccatttat gataattact cattattatt attcggcata   284700
ctctctgagc cccaggagct tgtatgatag ctagagggct aaaccataca tagtaaattt   284760
ttttttttcg agtctgggtc tcactctgtc accgctggag tgcagtggtg aggtcttggc   284820
ttactgcaac ttccgcctct tgggctcaag caatgctccc acctcagcct cccgagtagc   284880
tgggactata ggcatgcacc actaaaccca gctaattttt gcatttttg tacagaaaga   284940
gttttgccac atttgccagg ctggtcttga actcctgggc tcaagagatc ttcccgcctt   285000
ggccttctga agtgctgtga ttacaggcat gcgccactgt gtctgttcca tacatagttt   285060
tttttttttt tttttttttt tttgagacag tctcactctg ttgcccacgc tggagtgcag   285120
tggtgtgatc tcgggtcact gcaacctctg cctcctgggt tcaagcaatt ctcatgccac   285180
agcctcccga gtacttagga ttataggcac gtgccaccat gcctggctaa gttttgtgtg   285240
tgtgtgtgta tatatatata tatatgtata taaatatatg tatatatgta tatataaata   285300
tatgtatata tacatataat tatatacata tacatataaa taaatatata tatatatatt   285360
tattttagta gagatggggt gtcaccatgt tggccaggct agtctcgaac tcctgacctg   285420
aagtgatcca ccagcctggg cctcccaaag tgctgggatt acaggcgtga actgccatgc   285480
```

```
ccaaccccgt taattccttg tgaattgcct gctcaccatg tgccaggcac tgtgctaggt   285540
gctgcaactt cggctgtgaa caagatggac acgatctcta ccttgttgaa gtttataacc   285600
tggtggggaa acagatgaaa aaataaataa agacacaaat aagtatataa ttgcatcttg   285660
tgaaggaaaa atggcagcat gggtggatgg tgggaaggt ggttggaggc atccatttta    285720
ggaggtcagg cagggtctct ctgaagaggg gacacttaaa aagaaacctg aagcatgaga   285780
aggaagcagc caactaagga atggggagaa gagctttcct ggcagagaaa acagcacagg   285840
caacagtcct ggataggaag gagtcatgcc tattctagga gttaaaggta tgactgcagg   285900
aggtgaggga ggaggctagc cgcctgggaa aaggctgtgt cagaggcgtt ggaaccagag   285960
agactccatc ttgaataggg gctgggtaaa atgaggctga acctgctgg gctgcattcc    286020 ctggaggtta ggcattctta gtgacaggat gagataggtg gttggcacaa gatgcaggtc   286080
acaaagacct tgttgataga acagttttcc ataaagaagt cagctaaaac ccaccaaaac   286140
caagaaggcg atgaaagtga cctcggattg tcctcgctgc tcattacacg ctaattagaa   286200
tacattagca tgcgaagaga cactcccacg agcgtcatga cagttcacaa atgccatggc   286260
aacgtcagga agttacccta tatggtctaa aaggggaagg aacccaccga tccaggaatt   286320
gcccaccctg ttcccagaaa actcatgaat aatacacctc ttgtttagca tgtaatcacg   286380
aaataactat aagtataccc agctgagcag tccatgctgc tgctctgccc atggaatagc   286440
cattctttat tccttcactt ccttttttt ttgagacaga gtctctctct gtcgcccagg     286500
ctggggtgca gtggcgccat ctcagctcac tgcaagctcc gcctcctggg ttcacgccat   286560
tctcctgcct cagcctcctg agtagctggg actaacgccc gccaccgtgc ccagcaagtt   286620
ttttgtattt ttagtagaga cggggtttca ctgtggtctt gatctcctga cctcgtgatc   286680
ctcccacctc ggcctcccaa agtgctggga ttacaggcgt gagccaccgc gcccggccta   286740
ttccttcact ttcttaataa acttactttc actttactct atggactcac cccgaattct   286800
ttcttgcgtg agatccaaga accctctctt ggggcctgga ttgggaccgc tttctgataa   286860
cagctggaga agtagaaaga agccccatca tgcgaggggt acaggggtgg cggctcttag   286920
gcctcagcat gagggctttg attgtacttt aggtagaacg ggaagccgct aaaagccttt   286980
aaacaggtaa aagtcacaat acaatttttct taaaaaaaaa aaaaaaagaa aggaaaaaac   287040
tctggcaaat gaatgaggtt attattagca gtattaacat ccacactgaa aataacagac   287100
gctggtctct gttgtgcaaa acgtctgtca tttctctcat ttaccctgaa aactgaactt    287160 ttttccagg ttgtctcaca tctataagac cttctgctcg gaaggaatcc cattcttccc    287220 aatcttttg gaatatttgg agctgctgtt acaagtattc ttgatctaca gccacaacat    287280
ctgaaggatt taattactgt aatttaaggg gaatgactaa gattttttgca tattttcttt   287340 ctctttcttt ctttctttct tttttcttcc ttccttcctt tccttctttc tttccttcct   287400
tcccttccct tccctccccc ctccctccct ccctccccc tccctccctc ccttccttcc     287460
tttcttcctt ccttccttct ctctctctct ctctctctct ctctctctct ctttctttat    287520
gagacagagt ctctctctgt tgcccaggct ggagtgcaat ggcgcaatct cagttcactg    287580
caacctctgc ttcccggatt caagcaattc tcctgcctca gcctcctgag tagttgggac    287640
tacaggcacc caccaccatg cttggctaat ttttgcattt ttagtagaga tggagtttca    287700
ccatgttggc caggctggcc tcgaactcct gacctcaagt gatctgccca cctcagcctc   287760
ccaaagtgct ggattatagg catgagccac caagcccgac tgaaattttt gcatatttca   287820
```

```
agtgagaaat tgacgcagga gcaaacttac tgcacaaaga ccgacctctt ccgtgggccg   287880
ttcccagcct ccagtatcct ccacccactc tagtgtctca taatctctct tcctccctcc   287940
caatctctct tcctccctcc caatctctct tcctccctcc tgctgccccg cagagaatgg   288000
tcggctccca gctggagcaa gttcatccag ttgagaggat gatgtttgca taatttgaat   288060
aataattttg cataatagag gctctctttg aaatgatgta aatcagccct cagttctctc   288120
ttcagattat tattcattca ttcagtgaga tcacttttag gggatgagat agaaatattt   288180
acagaagaca gaggatcaag tgtggaggct ttgatgattt ctagtgaaaa aaatgttttt   288240
gtcttgtctg gtttgatgca tttgagggtg gagactggag ctgaatgtgc aacattttta   288300
tgcaacgcag tggatctttt ttttgagaca tggtctcact ctgttgctca gggtggagtg   288360
caatggtgcc atcttggctc actgcaacct caacctcctg gcttaagag attctcctgg    288420 cttggcctcc caagtagctg ggactacagg tgcgtgccac catgcctggc tgattttaa    288480 attcttttgt agagacaggg cctcccacag tgttgggatt atgagcatga gctcccacca   288540
tgcctggcct catgactcag tggatcttaa tgcgaaattt gccctgggtc agtggggta    288600 ggggaaagag gggtagagga tggggataag aagtaggtct aagggtaggg aggaaggagt   288660
gggaccaact cagtctctgg cacctcctc ctgagatata cctgaggatg ccttcccatc    288720 ctctcttct ccctctctgt atcctctatc tttaatggat acagacctag tatgtattta    288780
cccccgcttt aaaaaaaatt ttttttttg agacggagtt tcactcttgt tgcccaggct    288840
ggagagcaat ggcacgatct cggctcatcg caaactctgc ctcctgggtt caagcggttc   288900
tcctgcctca gcctcctgag tagctgggat tacaggcatg caccaccacg ctcggctaat   288960
tttgtatttt tagtacagac ggggtttcac catgttggtc aggctggtct cgaactcccg   289020
accttaggtg atcagcccac ttcagcctcc caaagtgctg ggattacagg cgtgagccac   289080
cacgtccagc ccctccttt ctaatggaaa gaaaatggg cttggggct gagcagacct      289140 gttagtgttc tttggttgca agcaacggaa acctgttcac ttttggttaa gccaaaggtt   289200
taggaagtag attgtaggca gggggcatcc aattggccaa gcttgggttc catgcctgct   289260
tcttgccctg gggtggtgga ggtaccttgc agccgcaccc ccctcatttg tggcactcag   289320
agcaagagta caaaaggaag cctttacacc acttgtctac aagtgataaa gcaaccagat   289380
aaactattag atgaagtatg atctgtcatc ctaccttggc acatatacgt gaataaggac   289440
ctggaaggcc aggtttgaat tagaatcttg gagtcctcag agttatcgac cagcatgtgg   289500
tgacttggga ggggccagcc ttggtttatg gtccactctg cttctcttct aaccctttggc  289560 tctgtcctac actctgagag gctggggtgt ggacccccag cccctgtgtt caagctctgt   289620
tttctaactc cccaaatggc tgtcccttgg ccacttctca ggtcttaaga tgcccacagt   289680
ggtggcatgg ttcactcttt ggaggacgac ctgggaaagg ggcccaggct ggccctgaag   289740
caggagccct gggtacctgg atgagctcta aaggaggg catggactca gggtgggcgc     289800
atccctggga ccccacaaac gctttaccca catggccaga ggccaagcag gacccttta    289860 agagcagtcc ccagggcagg gtgggcctgg caccaaaatt gacagcctgc tcgtctgtag   289920 caaaagggc agggcaattc ctcaaatcaa aaggaaatg gaagctgcgt agagaggaga     289980
caaatatcaa ccccacctga ggtcttatct aggcttttct gcagctaggg gtcttttggt   290040
agcaagaaag aaaaacccag ccgggcacgg tggctcactc ctgtaatccc agcactttgg   290100
gaggctaagc cgggcagatc acctgaggtc aggagttcaa gaccagcctg ccaacatgg    290160 tgaaacccca tctctactaa aaatataaaa attagctggg catgttgatg gcacctgca    290220
```

```
atctcagcta ctcgagaggc tgaggcaggg agaattgctt gaactgagga ggcggaggtt   290280
gcagtgagcc aagattgctc actgcactct agcctgggtg acagagcaag actccgtctc   290340
aaaaaaaaaa aaaagagaaa ctcactctga cactggcttg agcccaagga gtctctgtgg   290400
tggtggtggt ggtatccata ggggtggctc acggacccag gaaggtggaa gtatggccag   290460
tcctcttgag gaacaggagt caggactgag aagctgctga ggatcagggc gtctctcctc   290520
tctatctcta ctcttctatg catctaacag cagagtggct tcacgggctt tcctcaagga   290580
ctcgaaagag atacaacatg gggatctcaa acttagaacc tttgtcaggc aggtgatgtc   290640
aatgggaaca acagtggagg gaaactcaca gggccttctc agttcccttt tcttttcttt   290700
taagagacaa gatctcgctc tgttatccag tctggaatgc agtggcacga tcatagctca   290760
ctgcagcctt gacctcctgg gcttaagcga tcttcccacc tcagcctcct gagtagctgg   290820
aactacagat gtgcaccacc atgcccagct aatttttaag attttttgta gagacagggg   290880
cccaccatgt tgcccaggct ggtcttgaac tcctgggctc aaaagatcct cctgccttgg   290940
cctcccaaag tgaggggatt agaggcatga gccactgtgg ctgacccgtc ccctttctt    291000 gataggaaca tggcatatca gtcaggaaac agatgacaaa tcctcattag gatgcccga    291060 ggaggcaggg ttaacacagg gactgtttac taaggtatgg atcagctgtg gaagccaca    291120 gggccagtac cccagggcta gttctgaaag agctgtcacc attcctatgc ccaaaaggat   291180
agggatggga gtggttctgg aatccagaag ccgtgggtgg ttggagaggg ctgcctggac   291240
agcagatgtg gccttccttg gagagttgca gtcagtcctc agcaacccca ctgggagcca   291300
gtcaaataaa taacctgaca gcacactctt catgccctgg atctcctgct ggcattgccc   291360
attggccaaa cccaactgaa atcctgagag cccattcatg cagtccttgg gcaggatggg   291420
gaagccagag aggggtgtgg aggggcaaag ggaagacagc tgccacgtgt gggtataaga   291480
gacatttccc tgctgaaagg cataccatag cttaaacctg agggacgatg ttcatggata   291540
ctgggtcttg ggaagcgaat gagatgttgt ggttcatggg accaagagga aagtacaaac   291600
ccccttttaa ccactcagct ctggccaatt attgccatgc aggagtgtgg gctcctagtg   291660 gcagggctc tgaacttgga agagaagtag gcaatccaga atctgaaatt atgaaatttc    291720
aagattaaat catattggca actagttaaa acaaacaaaa atagttttaa aatgctgtat   291780
gagtccagta aatcccattc acaagccaga tttggcccga ggatgctcta aacagaaact   291840
catttggggc ttttgtctca attccaaatt ccccaggaag gagagatgct gtttgatgtt   291900
tttttttttg tttttgtttt tttttgagat ggagtcttgt tctgtcaccc aggctggagt   291960
gtagtggtgt gattttggct cactgcaatc tctgcctttt gggttcaagt gattctcctg   292020
cctcagcctc cctagtagct gcgactacag gtgcatgcca ccacgcctgg ctatttttt    292080 attttttagag acgaggtttt cctgtgttgg ccaggttggt tttgaactcc tgacctcaag   292140
tgatcagcct gcctcagcct cccaaagtgc tgggattaca ggcgtgagct actgagcctg   292200
gcctatttga cctattttgg tttggctgtc cctcccaggt gcaatcagtc gtggccagga   292260
ggggtcatgt ccctgctgct cactcagctc gggacaggat agtccctctg agagctgagc   292320
atgtgccctt ggaaagcagt caatgatctg tgggtctaat cgcaatcact tactcctctg   292380
tgatggggaa gtgtgtgctt gtcttccatg gctgctgtaa tgaatgacca caaactcggg   292440
cttaaaaacc acagattcat tatctgacag ttctgaaagt cagaactgca atgggctaaa   292500
ggcaataggc aaaaatcaag gtgtcaaaaa gctgcattgc ttttgggagt cttttttttt   292560
```

```
tttttttttt tttttttgaga cagagtctcg ctctgttgcc taggctggag tacagtggtg   292620
tgatctcagt tcactgcaac ctctgcctcc caggttcaag ggattctcct gcctcagctg   292680
taatcccagg tagctgggat tacaggtgtg tgccaccatg cctggctaat tttgtatttt   292740
ttagtagaga cagggtttca ccatgttggt caggctggtc tcaaacctga cctcaggtga   292800
tccacccacc ttgtcctccc aaagtgctag gattacaggc acgagccact gcgcccggcc   292860
cacttttggg aggcttaggg ggagaatctg tttccttgc cttcttcagc ttcttagagc    292920
agtggtcccc aacctttttg gcaccaggga ctggtttcat ggaagacagt ttttccgcgg   292980
gatggtgatg gtgtagggga tggtttcagg atgattcaag tatatcacat ttattgtgca   293040
ctttatttct attattatta cattgtaatg tataatgaaa taattataca actcaccata   293100
atgtagaatc agtgggagcc ctgagcttgt ttttctgcaa gtagatggtc ccatctggga   293160
gtgatgggag acagtgacag atcatcaggc atttgatttt cataaggagt gcacaagcta   293220
gatcccttgc atgagcagtt cacgataggt tcgtgctcc tatgagaatc taatgccgca    293280
gctgatctga caggaggcgg agctcaggtg gtaatgtgag agatggggag tggctataaa   293340
tacagatgaa gctttgctca cttgcctgct gcttgcctcc tgctgtgtgg cctggttcct   293400
aagaggccac agacagtacc aaccggtggc ctgggggttg gggacccctg tcttagagga   293460
tgcctgcatt ctttggctca tggccccttc aaccttcaaa gccagtaaca gctggtttag   293520
tctttctcat gttgcattcc tttgactctg cctccctcat atatatatat atatatatat   293580
gtgtgtgtgt gtgtgtgtgt gtgtgtgtgt gtgtgtgtgt gtattttgag acacagtctc   293640
actctgttgc ccaggctgga gtgcagtggc atgatcatgg ttcactgcag cctcgacctc   293700
ctgggctcaa gtgatcttcc catctcagcc tcccaagtgc tcttcaatct ttaaaggacc   293760
cttgtgatta cattgagtcc acccagataa tccaggataa tttctttatt ttaaggttag   293820
caaacttaat tctgtttaat ttttaaaaag ttcttttgtt tcactctgtc gcccaggctg   293880
gagtgcagtg gtacaatcat ggctcacggc agcctccatt tcctttgctc aagcgatgct   293940
cttgcctcag ccgcccaagt agctgggact acaggtgtgc aaaatcaagc ctggctaatt   294000
tttttgtttg tttgttgttg ttgttcttgt tgttgttttg tagagacggg gtttctctgt   294060
gttgcccagg ctggtctcaa actcctgggc tcaagtgatc ctcccacctt ggcctcccaa   294120
agtgctgaga ttacaggtat aagtcactgc atccagccaa caaacttaat tctatctgca   294180
accataatta ccctttgcac catgtaaagt aacatattca caggttccaa ggattaggat   294240
gtggatatct tgtgggggt ggggggggtg ttattctgtc taccacaagg cagtttctga   294300
actttgctag tcatccataa tatatgggta accctgactt cttcatgggt tgttaacggg   294360
ttcagatgag agaacctatg caatacacct ggcgcagtcc gtggcacaca gcaggcattc   294420
ctgttagtcc ctttcccttc tcctccttgg gctattggct tcagtgtggc tgagcgtgtt   294480
tcttcagctg ttaaatgacg tagatatatc agtcccgcct acctcaaagt gctgttcctt   294540
tcttccttca ttcactttct cattcactca tgcaacaaat atgtattgag ggcctacgat   294600
gcgtgagacg cttgtgctag gtgccggagc agagccgcag ataagggaga catgaggttt   294660
attttcaggt gaggaaggaa atagtgagaa acagataaa caatcctaat ttggtatagt    294720
aataagtaca agaagacaaa gtagggtaag agaacacaga agggtggaga tggtggaggg   294780
tgggcagtgg gatgctattt taaatagaga ggtcagaaag agcatgtcta ggctgggtgc   294840
ggtggctcac ccctataatc ccagcacttt gggaggctga ggtgggcgga tcacttgagt   294900
ccaggagttt gagaccagcc tggccaacaa ggtgaaaccc catctctact aaaaatacaa   294960
```

```
aaatttgccg ggtgtattgg cacatgcctg taatctcagc tactcgggag gttgaggcaa 295020
gataatcgct tgaacctggg aggcagaagt tgcagtgagc tacactccat cctgggtgac 295080
agagtgagac tctatctcaa aaaaaaaaaa aaagaaaag aaagaaagaa agaaagagca 295140
tgtctgagtg acatgagaaa tgacagtgag tgtttgttga tcgcctgaat gacatgatgc 295200
tgatttccag cttgattgtg gcagaagtgg ataagctgat tgctggtaat cagtttaatt 295260
atgtaagatt cctttcacaa cattttaaga ttttctggct tctcttttct gtgttgcatt 295320
ttactagcat tgaaagaagt gacccaaagc atagattcat ttttccttt ggaactggac 295380 agatatttct cagatttagc tgctattcct cctggaggcc tctcaaaggc agcaggaaga 295440
gagaccctga cagctctgtc cccagctctg tttgtgacct gctccacttg cttggcagct 295500
gggaacctca gcagcctcat taacgttgga aagcactttg ggtctcttgc tgaaagacgc 295560
taggaaaggc aggtcataat tattttgttt ttcctacatc ttcaaggccg tcagatgcag 295620
cttgaacctt ctccatcaag aacaagaggc tggccgggcg cagtggctca tgcctgtaat 295680
cccaggactt tgggaggccg aggcaggaga attgcttgaa tctgggagct ggaggttgca 295740
gtgagccaag atcgcgccac tgcactccag cctgggcaac agagctaggc tctgtctatt 295800
aaaaaaaaaa aagaacaaga ggctgcagtt agtgcaggga ggagaggaga tgggcaagga 295860
agagagaggc tgaggctgga aagtgggaag gaagacaggc agtgactgct cctggcctct 295920
ggctgaggat gggtcatagg caggccagtc ccctcccatg cctgtgatgc gtgtttgcat 295980
gttgctggtg acatcagcat cttagagtcc atctccaatc agacccattt cccttccac 296040 actagaacat agctccatga cccctggtgg cctctgaaag tcgttgtggg gtggtttgca 296100
gagccactgg gagagggaca ttggctgagg cagacgataa aaatgataat agcagccagt 296160
cgagttagct gacgcctgta atcccagcaa tttgggaggc caaggtggga gaatcacttg 296220
aggtcaggag ttcaagacaa gcctggacaa aatggtgaaa ccccatctct actaaaaata 296280
caaaaattag ctgggtgtgg tggtgtgcgc ctatagtccc agctactggg gaggctgagg 296340
tgggaggatc acctgagccc aggaggtgga gattgcagtg agctatgatc gcgccactgc 296400
actccagctt aggcaacaga gcgagaccct gtcttaaaat aaataaataa ataactacta 296460
ctactgccac taatagcagc tttgattcac tgtgcaccag ctcacttgcc ttctcatcca 296520
tagccctgtt gggaatgatt atccccattt tacaggtgag gaaactgagg ctcaccaaag 296580
gtaggtgata tgcctatgag ctgggattcg aactcagttt tatttggagt cagtatagtc 296640
tattgattct acttttattt agttaattaa ttaattaatt aattttatta tactttaagt 296700
tctggggtac atgtgtagaa cgtgcagttt tgttacatag gtatacacaa gccatggtgg 296760
tttgctgcac acatcaatcc gtcatctaca ttaggttttt ctcctaatgg tatccctccc 296820
ctagacccca cccccgacag gccccagtgt atgatgttcc cctccctgtg tccgtgtgtt 296880
ctcattgttc agctcccact tatgagtgag aacatgcgat gtttggtttt ctgttcttgt 296940
gttagtttcc tgagaatgat gatttccagc ttcatccatg tctctgcaaa ggacatgaac 297000
tcatgctttt taatggccgc atagtattcc atggtgtcta cgtgtcactg attctacttt 297060
taaaatatac ttagtacctc ccttctcttc cccatgcctg ctggggagcc cgctgctccc 297120
acctggtcca tgcaccatca ccttttacct ggactattgc aatagcctct tcctgggtct 297180
ccctgattat gtcctcccca ctcccttcca ccttatagtc tgttctcaaa ccagcagcct 297240
gaggaatgct actcaaagtt ctcctgtgac tcccctacgg taaaagccaa aagtcttact 297300
```

```
ctggttataa gccccagatg ttctctctct gtcctgcaat tcatctcctt gctcactgta 297360
gttgagttat acaggccccc tgactcttcc ttaagcagac cagacacgct cttaccacag 297420
ggtctttgca ctggctgttg ttccccctgc ctggaatact cttcctcaaa tatccacata 297480
ggcttgtttc cttttaaagt ctctacccag gagccatctc attgacccTT CTCTGACAGC 297540
cctgttgaca cttgcaatta tttcctagta ccctaattgc tccttctttc cttctttttc 297600
tctctagcac ctctcattat ctaacatact cttTGACTTA cttattttgt gtgtggttca 297660
cgcttatcca tgagaacatc agctccatgg caaggcattt tgtctgtctt actctctgct 297720
gcattcccag caccaagaat agcgcctggc acctagtagg cgctcaataa atatttgttg 297780
aatgaatgac tctgaagcca tcattctgtc caccacacaa actgccacct tcctacaccg 297840
acttcttgtc tataagaatt ccacatcctt gccaacactt gctatggtca tgtttccatt 297900
ttctctaact tatggctgta aatggtatc tgattgtggt tttaacatgc atttcttgag 297960
atgcctgggc actcaggtac tgacatgtct gagggacaga gagtgggtct ttgtctccct 298020
ctggctggaa gtccagagct ccaaaataga ccatctccca gcattttttg agaaaatggg 298080
aaatgagtct ttgttttggg ttataataag ataagcaact catgtacaac aaaagttagc 298140
atctgctctg cacacaaggt ttaatattta gagataattt aaaaccaagg aaaaggcaga 298200
gttattaata acacttgggg ggaggtgtg aagagagagt atgaaaatct ccatttgaaa 298260
aagctactgt agttagcatc caaaataaga ccttacttag cattcggttc tgctcatttg 298320
caaattaaga gatgtattgt tttaaaaata attaagtcta atttgcatg tttgggagat 298380 ggctctccac tggcttttaaa aatctttatt tatcagtaat gttctgaata cagatttttt 298440 ttcttttcg agacagaatc ttgctctgtc gtccaggcta gagtgcagtg gcacaatctc 298500
agctcactgc aacctctgcc tcccaggctc aagcaatctt cccacctcag cctcccaagt 298560
agctgggact acaggcatgt gccaccacac ctggctaatt tttgtgtttt ttttttggta 298620
gagatggtgg ggttctgtca tgtttcccag gctggtcttg aactcctggg ctgaagcgat 298680
cctcctgcct tggcctccca agtggtgtg attataggca tgaaccactg cgcctgactc 298740
tgaatacaga ttaatctcca tcgctaagct aagtgtttgc tgttctaggt agtcacaaat 298800
gttcactaag gcaagccaca gttgaagctg aagtcgctac aggagtgatg tctgggtcc 298860 ccaggaatta ctttggggtt ctatagatcc ccagaattcc tgtcatttac agcagggatc 298920
ttagcaacca ctgagcccag ttttcttcat ttttacaggt aaagacatag aagctcagag 298980
agatgaagag gcttttctga ggtcacacag tagggcagtg gaagaactca gattagaata 299040
caggcctttt ctagccttat aaatggtatt ttcagctggg tatggtggct cacacctgta 299100
ataccaacac tttaggaggc caagacggga ggattgcttg aaactaggag tttgagacca 299160
gcctgggaag caaagtgaga ccccacctct acaaaaataa aataaaaat aaattagctg 299220 ggtgtggtgg catgcacctg tagtcccagc tactcaggtg gctgaggcag gaagatagct 299280
tgagctcagg agttcaaggc gacagtgagc tacgatggca ccactgcact ccagcctggg 299340
tgacagagca agaccttgtc tctaaagata taaaaacaga caaaaataaa taataaaatt 299400
gtattttcca tcaaacctgt gtatctcata tttcagttac gcttttaaca tatccctgta 299460
ccacccatac tattgtttag tgaactcttt ttccccttaa atcaattca cttttaaaaa 299520 tgtaaagaca tttatttaaa aggaaaaatg tcacaaatat aaatggaaaa tcctattgct 299580
tgccaaatag aaagtaaatg acaataaata tgaggcaaac aaaacaacgt tattaagctc 299640
tagtaaggca acttgcttga taaaacgtca actcttgtga aacaaaagtt agcatctgct 299700
```

-continued

```
ccgacaccag gtttaatacc gagggatatc tagggatgct taaagccctg ggccgagacc    299760
tgctccctct ttgttaaaag gagacattag caaaggcagg agaggtttca gaaccctgta    299820
gcaccaacct gagactttct cctcctcata agcagaagga ttggaaggga atggaaaagg    299880
gaatgaattt ctcccaaggt gattgcgtgc aatctcaaca accaccacaa gtcctcgctc    299940
tagatgaatc tggacagcga gaacttcttt tgaaaccatg ctccaaagag ttaaagagac    300000

<210> SEQ ID NO 34
<211> LENGTH: 16
<212> TYPE: DNA
<213> ORGANISM: Artificial Sequence
<220> FEATURE:
<223> OTHER INFORMATION: forward PCR primer - with GC clamps added at
      the 5' end for DHPLC analysis

<400> SEQUENCE: 34
cccgccgccc ccgccg                                                          16

<210> SEQ ID NO 35
<211> LENGTH: 15
<212> TYPE: DNA
<213> ORGANISM: Artificial Sequence
<220> FEATURE:
<223> OTHER INFORMATION: reverse PCR primer - with GC clamps added at
      the 5' end for DHPLC analysis

<400> SEQUENCE: 35
ccgcgccccc gcccg                                                           15
```

US 7,335,469 B2

METHODS FOR DIAGNOSING NOONAN SYNDROME

This application claims priority from U.S. Provisional Application Ser. No. 60/326,532, filed Oct. 1, 2001, which is hereby incorporated by reference in its entirety.

FIELD OF THE INVENTION

The present invention relates to diagnostic and therapeutic applications for Noonan Syndrome. In particular, diagnostic and therapeutic applications based on certain mutations in the protein tyrosine phosphatase gene PTPN11 or its expression product are contemplated.

BACKGROUND OF THE INVENTION

Noonan syndrome (NS) is an autosomal dominant disorder characterized by dysmorphic facial features, proportionate short stature, and heart disease, i.e., pulmonic stenosis and hypertrophic cardiomyopathy most commonly (Noonan, Am. J. Dis. Child. 1968, 116:373-380; Allanson, J. Med. Genet. 1987, 24:9-13). Webbed neck, chest deformity, cryptorchidism, mental retardation, and bleeding diatheses constitute other frequently associated findings. NS is a relatively common syndrome with an estimated incidence of 1:1000 to 1:2500 live births.

At present there is no blood test for diagnosing Noonan syndrome, or any other conclusive genetic test for this disease. The diagnosis depends on recognition of the symptoms by a knowledgeable doctor. However, substantial phenotypic variations, including mild or subtle cases, make the diagnosis difficult. Furthermore, the facial characteristics become less apparent with progressing age, and so the condition sometimes remains undiagnosed. In addition, whereas the disorder may be suspected in utero when fetal ultrasound show excess fetal fluid, such as nuchal edema, there is no reliable test for Noonan syndrome during pregnancy.

A number of therapeutic or surgical treatments are available to alleviate various symptoms of Noonan syndrome. Such symptoms include heart defects, undescended testicles, or excessively short stature. However, no therapeutic treatment of the underlying disorder has been proposed so far, absent identification of the causative gene of the Noonan syndrome.

Physical mapping of the genetic region involved in Noonan syndrome has been described. A 5-cM region (NS1) on chromosome 12q24.1 has been disclosed, and genetic heterogeneity has also been documented (Jamieson et al., Nat Genet 1994;8:357-360; Brady et al., Eur J Hum Genet 1997;5:336-337; Legius et al, Eur J Hum Genet 1998;6:32-37; van Der Burgt, and Brunner, Am J Med Genet 2000;94: 46-51). However no specific gene has been identified.

Therefore, there remains a need to identify a specific gene involved in Noonan syndrome. Such identification would immediately provide strategies for diagnosis, in particular early diagnosis, and treatment of this disorder.

SUMMARY OF THE INVENTION

The present invention provides methods of diagnosing and treating Noonan syndrome (NS). By identifying mutations in protein tyrosine phosphatase gene PTPN11 in subjects with Noonan syndrome, the inventors provide tools for developing diagnostic and therapeutic applications.

Thus, the invention provides a method for diagnosing Noonan syndrome in a subject, which method comprises detecting a mutation in a protein tyrosine phosphatase 11 (PTPN11) gene in the subject, wherein the mutation results in increased PTPN11 expression or activity as compared to a control. The mutation can be a missense mutation, a deletion, an insertion, and both a deletion and an insertion. Preferably, the mutation is in a coding region of the gene, and results in a mutation in the PTPN11 protein. For example, in one embodiment, the mutation in the PTPN11 protein is in an src-homology 2 (SH2) domain, including, but not limited to amino acid substitutions selected from the following residues of SEQ ID NO:2: a G to A substitution at position 60; a D to N substitution at position 61; a D to G substitution at position 61; a Y to D substitution at position 62; a Y to C substitution at position 63; an A to S substitution at position 72; an A to G substitution at position 72; an E to D substitution at position 76; and a Q to R substitution at position 79. In another embodiment, the mutation is an amino acid substitution selected from the following residues of SEQ ID NO:2: a T to A substitution at position 42; a G to V substitution at position 60; a T to I substitution at position 73; and an E to D substitution at position 139. In a particular embodiment, the PTPN11 protein further comprises a deletion of D at positon 61 of SEQ ID NO:2.

Regarding PTPN11 gene mutations in the region encoding for an SH2 domain, they may be selected from nucleotide substitutions at the following residues of SEQ ID NO:1: a G to C substitution at position 179; a G to A substitution at position 181; an A to G substitution at position 182; a T to G substitution at position 184; an A to G substitution at position 188; a G to T substitution at position 214; a C to G substitution at position 215; a G to C substitution at position 228; and an A to G substitution at position 236. Alternatively, the mutation may be selected from an A to G substitution at position 124; a G to T substitution at position 179 of SEQ ID NO:1; a C to T substitution at position 218; a G to C substitution at position 417; and a G to T substitution at position 417. In a particular embodiment, the PTPN11 gene further comprises a deletion of positions 180-182 of SEQ ID NO:1.

In a further embodiment, the mutation in the PTPN11 protein is in a linker domain connecting a first SH2 domain to a second SH2 domain (See FIG. 1). For example, the mutation can be a D to A amino acid substitution at position 106 of SEQ ID NO:2, preferably corresponding to an A to C substitution at position 317 of SEQ ID NO:1.

In yet a further embodiment, the mutation in the PTPN11 protein is in a protein tyrosine phosphatase (PTP) domain. For example, the mutation can be an amino acid substitution selected from the following residues of SEQ ID NO:2: a Y to C substitution at position 279; an I to V substitution at position 282; an F to L substitution at position 285; an F to S substitution at position 285; an N to D substitution at position 308; an N to S substitution at position 308; an I to V substitution at position 309; an R to K substitution at position 501 of SEQ ID NO:2; and an M to V substitution at position 504. Alternatively, the mutation can be an amino acid substitution selected from the following amino acid residues of SEQ ID NO:2: a G to S substitution at position 268; an N to T substitution at position 308; a P to S substitution at position 491; and an S to L substitution at position 502.

Regarding PTPN11 gene mutations in the region encoding for a PTP domain, they may be selected from nucleotide substitutions at the following residues of SEQ ID NO:1: an A to G substitution at position 836; an A to G substitution at position 844; a T to C substitution at position 853; a T to C substitution at position 854; an A to G substitution at position 922; an A to G substitution at position 923; an A to G substitution at position 925; a G to A substitution at position 1502; and an A to G substitution at position 1510. Alternatively, the gene mutations may be selected from a G to A substitution at position 802; an A to C substitution at position 923; a C to T substitution at position 1471; and a C to T substitution at position 1505 of SEQ ID NO:1.

In addition, the invention provides for a method of diagnosing Noonan syndrome in a subject, which method comprises assessing the level of activity of a PTPN11 signal transduction pathway in a test subject and comparing it to the level of activity in a control subject, wherein increased activity of the pathway in the test subject compared to the control subject is indicative of Noonan syndrome. The level of activity of the pathway can, for example, be assessed by assessing an increase in the level of expression or activity of a PTPN11 protein. Alternatively, the level of activity of the pathway can be assessed by assessing an increase in the level of expression or activity of an ERK protein, such as, e.g., ERK2. The level of expression or activity of the ERK protein may be assessed by assessing kinase activity, as described herein.

The invention also provides for a kit for diagnosing Noonan syndrome, comprising an oligonucleotide that specifically hybridizes to or adjacent to a site of mutation of a PTPN11 gene that results in increased activity of a PTPN11 protein encoded by the gene, and instructions for use. The site of mutation may, for example, comprise a nucleotide selected from the group consisting of nucleotides 179, 181, 182, 184, 188, 214, 215, 228, 236, 317, 836, 844, 853, 854, 922, 923, 925, 1502, and 1510 of SEQ ID NO:1. In another embodiment, the site of mutation comprises a nucleotide selected from the group consisting of nucleotides 124, 180, 218, 417, 802, 1403, 1471, and 1505 of SEQ ID NO:1. In one preferred embodiment, the kit comprises at least one probe comprising the site of mutation. In another preferred embodiment, the kit comprises a first oligonucleotide primer comprising at least 15 consecutive nucleotides of SEQ ID NO:33, and a second oligonucleotide primer comprising at least 15 consecutive nucleotides of a sequence complementary to SEQ ID NO:33. Such primer pairs may be selected from, for example, a first primer comprising a nucleotide sequence selected from the group consisting of SEQ ID NOS: 3, 5, 7, 9, 11, 13, 15, 17, 19, 21, 23, 25, 27, 29 and 31, and a second primer selected from the group consisting of SEQ ID NOS: 4, 6, 8, 10, 12, 14, 16, 18, 20, 22, 24, 26, 28, 30, 32.

The invention further provides for a kit for diagnosing Noonan syndrome, comprising an antibody that specifically recognizes a mutation in a PTPN11 protein, and instructions for use. Optionally, the mutation results in an increased activity as compared to a PTPN11 protein having the amino acid sequence of a wild-type PTPN11, such as that of SEQ ID NO:2. The mutation may be in an SH2 domain, and is preferably selected from the following amino acid substitutions in SEQ ID NO:2: a G to A substitution at position 60; a D to N substitution at position 61; a D to G substitution at position 61; a Y to D substitution at position 62; a Y to C substitution at position 63; an A to S substitution at position 72; an A to G substitution at position 72; an E to D substitution at position 76; and a Q to R substitution at position 79. Alternatively, the mutation may be selected from a T to A substitution at position 42; a G to V substitution at position 60 and a deletion of position 61 of SEQ ID NO:2 a T to I substitution at position 73; and an E to D substitution at position 139 of SEQ ID NO:2.

The mutation may also be in a linker domain connecting a first SH2 domain to a second SH2 domain. For example, the mutation can be a D to A substitution at position 106 of SEQ ID NO:2.

In addition, the mutation can be in a PTP domain, and is preferably selected from the following amino acid substitutions in SEQ ID NO:2: an Y to C substitution at position 279; an I to V substitution at position 282; an F to L substitution at position 285; an F to S substitution at position 285; an N to D substitution at position 308; an N to S substitution at position 308; an I to V substitution at position 309; an R to K substitution at position 501; and an M to V substitution at position 504. Alternatively, the mutation can be selected from the following: a G to S substitution at position 268; an N to T substitution at position 308; a P to S substitution at position 491; and an S to L substitution at position 502 of SEQ ID NO:2.

The invention also provides for a method for diagnosing Noonan syndrome in a subject, which method comprises assessing the level of expression or activity of a PTPN11 protein in the test subject and comparing it to the level of expression or activity in a control subject, wherein an increased expression or basal activity of the PTPN11 protein in the test subject compared to the control subject is indicative of Noonan syndrome. The level of expression may, for example, be assessed by determining the amount of mRNA that encodes the PTPN11 protein in a biological sample or by determining the concentration of PTPN11 protein in a biological sample. The level of activity may, for example, be assessed by determining the level of PTPN11 phosphatase activity in the test subject.

The invention further provides for a method for treating Noonan syndrome in a patient, which method comprises administering to the patient in need of such treatment an effective amount of an agent that modulates the expression or activity of a PTPN11 protein, in association with a pharmaceutically acceptable carrier. Preferably, although not necessarily, the PTPN11 protein comprises the amino acid sequence of SEQ ID NO:2.

In one embodiment, the agent is a PTPN11 antisense nucleic acid, preferably an antisense nucleic acid hybridizing to a segment of SEQ ID NO:1 comprising at least one nucleotide substitution selected from a G to C substitution at position 179; a G to A substitution at position 181; an A to G substitution at position 182; a T to G substitution at position 184; an A to G substitution at position 188; a G to T substitution at position 214; a C to G substitution at position 215; an G to C substitution at position 228; an A to G substitution at position 236 of SEQ ID NO:1; and complementary segments thereof. Alternatively, the antisense nucleic acid can hybridize to a segment of SEQ ID NO:1 comprising at least one nucleotide substitution selected from an A to G substitution at position 124; a G to T substitution at position 179; a C to T substitution at position 218; a G to C substitution at position 417; a G to T substitution at position 417 of SEQ ID NO:1; and complementary segments thereof. In a particular embodiment, the segment of the PTPN11 gene further comprises a deletion of positions 180-182 of SEQ ID NO:1.

In a further embodiment, the antisense nucleic acid hybridizes to a segment of SEQ ID NO:1 comprising at least one nucleotide substitution selected from: an A to G substitution at position 836; an A to G substitution at position 844; a T to C substitution at position 853; a T to C substitution at position 854; an A to G substitution at position 922; an A to G substitution at position 923; an A to G substitution at position 925; a G to A substitution at position 1502; an A to G substitution at position 1510 of SEQ ID NO:1; and complementary sequences thereof. Alternatively, the antisense nucleic acid hybridizes to a segment of SEQ ID NO:1 comprising at least one nucleotide substitution selected from an G to A substitution at position 802; an A to C substitution at position 923; a C to T substitution at position 1471; and a C to T substitution at position 1505 of SEQ ID NO:1; and complementary segments thereof.

In a specific embodiment, the agent inhibits PTPN11 activity by blocking a PTP domain. For example, the agent can be an anti-PTPN11 inhibitory antibody. Such an antibody could specifically recognize a PTPN11 amino acid sequence comprising mutation selected from the following residues of SEQ ID NO:2: a G to A substitution at position 60; a D to N substitution at position 61; a D to G substitution at position 61; a Y to D substitution at position 62; a Y to C substitution at position 63; an A to S substitution at position 72; an A to G substitution at position 72; an E to D substitution at position 76; a Q to R substitution at position 79; a D to A substitution at position 106; an Y to C substitution at position 279; an I to V substitution at position 282; an F to L substitution at position 285; an F to S substitution at position 285; an N to D substitution at position 308; an N to S substitution at position 308; an I to V substitution at position 309; an R to K substitution at position 501; and an M to V substitution at position 504. Alternatively, the antibody may specifically recognize a PTPN11 mutation in SEQ ID NO:2 selected from the following: a T to A substitution at position 42; a G to V substitution at position 60 and a deletion of position 61; a T to I substitution at position 73; an E to D substitution at position 139; a G to S substitution at position 268 of SEQ ID NO:2; an N to T substitution at position 308; an P to S substitution at position 491; and an S to L substitution at position 502.

The invention also provides for an isolated PTPN11 variant comprising a mutation resulting in increased level of PTPN11 activity. In particular embodiments, the isolated PTPN11 variant comprises an amino acid substitution in an N-SH2 domain, C-SH2 domain, or PTP domain, or in a region between an N-SH2 and a C-SH2 domain. The amino acid substitution may be selected from the following group, referring to residues in SEQ ID NO:2: a G to A substitution at position 60; a D to N substitution at position 61; a D to G substitution at position 61; a Y to D substitution at position 62; a Y to C substitution at position 63; an A to S substitution at position 72; an A to G substitution at position 72; an E to D substitution at position 76; a Q to R substitution at position 79; a D to A substitution at position 106; an Y to C substitution at position 279; an I to V substitution at position 282; an F to L substitution at position 285; an F to S substitution at position 285; an N to D substitution at position 308; an N to S substitution at position 308; an I to V substitution at position 309; an R to K substitution at position 501; and an M to V substitution at position 504. Alternatively, the amino acid mutation can be selected from the following: a T to A substitution at position 42; a G to V substitution at position 60 and a deletion of position 61; a T to I substitution at position 73 of SEQ ID NO:2; an E to D substitution at position 139; a G to S substitution at position 268; an N to T substitution at position 308; an P to S substitution at position 491; and an S to L substitution at position 502 of SEQ ID NO:2.

The invention further provides for an isolated cell comprising a vector, which vector comprises a nucleic acid encoding any PTPN11 variant described above, the nucleic acid operatively associated with an expression control sequence. The cell can be, for example, a prokaryotic cell or an eukaryotic cell.

The invention also provides for an isolated nucleic acid encoding any of the PTPN11 variants described above, as well as isolated oligonucleotides which specifically hybridizes to such nucleic acids.

BRIEF DESCRIPTION OF THE DRAWINGS

FIG. 3A shows a G-to-T transversion at nt (nucleotide) 214 in an affected individual from NS-C. FIG. 3B shows an A-to-G transition at nt 236 in an individual from NS-L. Wild-type exonic sequences and the amino acid residues for which they encode are shown below the electrophoregrams. Bases that were mutated are shown in bold with arrows indicating the position of the heterozygous sequences.

DETAILED DESCRIPTION OF THE INVENTION

Figure 1:
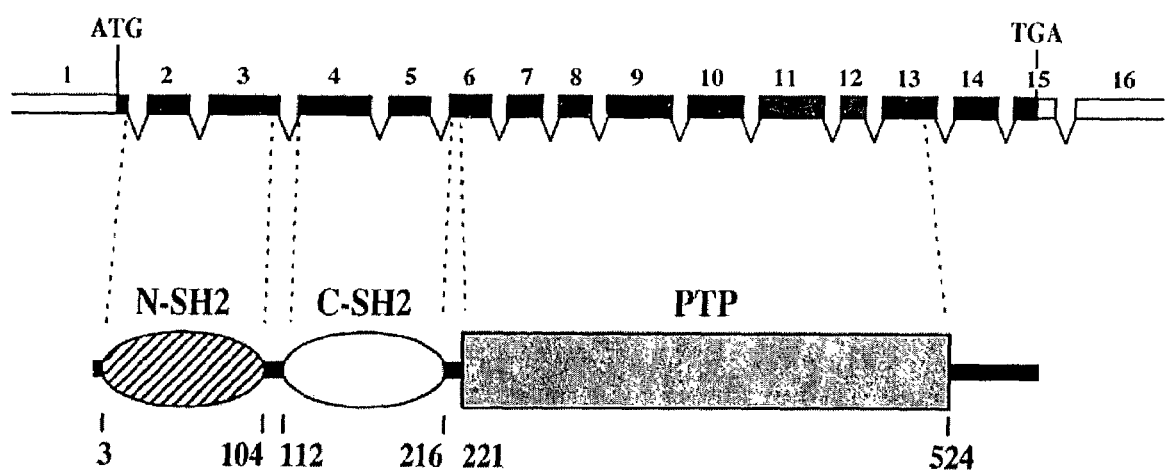
FIG. 1 is a schematic drawing showing PTPN11 gene organization and domain structure. The numbered, filled boxes at the top indicate the coding exons; the positions of the ATG and TGA codons are shown. The functional domains of the PTPN11 protein, consisting of two tandemly arranged src-homology 2(SH2) domains at the N-terminus (N-SH2 and C-SH2) followed by a protein tyrosine phosphatase (PTP) domain, are shown below. The numbers below that cartoon indicate the amino acid boundaries of those domains.

The present invention is, in part, based on the identification of mutations in the protein tyrosine phosphatase gene, PTPN11, that are causative for, or associate closely with, Noonan Syndrome (NS). In particular, the invention provides mutant PTPN11 coding and non-coding nucleotide sequences associated with NS. The invention further provides PTPN11 polypeptides that are encoded by such variant nucleic acids and/or comprise one or more amino acid residue substitutions, insertions or deletions. Preferably, the PTPN11 or PTPN11 variants are characterized by an increased PTPN11 activity, i.e., gain-of-function in PTPN11 activity; or by higher PTPN11 expression levels, as compared to controls.

The invention also provides antibodies that specifically bind to these variant PTPN11 polypeptides, as well as nucleic acids which may be used in the methods of the invention to detect a variant PTPN11 nucleic acid or PTPN11 gene. For example, in one embodiment, the invention provides oligonucleotides sequences which may be used, e.g., to detect a mutation in a PTPN11 gene, or to amplify a PTPN11 nucleic acid (for example, a specific locus on a PTPN11 gene) having or suspected of having a mutation that correlates to NS.

Methods are also provided, as part of the present invention, which use the nucleic acids, polypeptides and antibodies described herein to diagnose or treat NS. For example, the invention provides methods to evaluate individuals for NS by detecting a variant PTPN11 nucleic acid or polypeptide, such as one of the variants described herein, that statistically correlates to NS. The invention further provides methods to evaluate individuals for NS by detecting an increased activity in the PTPN11 signalling pathway, for example, by comparing PTPN11 or ERK2 activity to controls. In addition, the invention provides therapeutic methods for treating NS by administering a compound that modulates (e.g., enhances or inhibits) the expression or activity of either a PTPN11 nucleic acid (e.g., a PTPN11 gene) or a PTPN11 gene product (e.g., a PTPN11 polypeptide). In one preferred embodiment, the compound modulates the expression or activity of a variant PTPN11 nucleic acid or expression product, such as one of the variants described herein.

PTPN11 was considered as a candidate gene for Noonan syndrome because it mapped to chromosome 12q24.1 between D12S84 and D12S79. This region has previously been identified to be associated with Noonan syndrome. In addition, its protein product occupies a critical role in several intracellular signal transduction pathways controlling diverse developmental processes, including cardiac semilunar valvulogenesis (Dechert, et al, Hum. Genet., 1995, 96: 609-615; Feng, Exp. Cell Res., 1999, 253: 47-54; Chen, et al, Nature Genet., 2000, 24:296-299).

Briefly, as described in the Examples, the PTPN11 gene organization and intron boundary sequence were established using cDNA (Genbank Accession Nos. NM_002834; nucleotide and amino acid sequences represented herein as SEQ ID NOS: 1 and 2, respectively) and genomic sequences (GenBank Accession No. NT_009770, residues 3,000,001-3,300,000 of which represented herein as SEQ ID NO:33; Bacterial Artificial Chromosome (BAC) clone RP3-329E11). Example 1 describes mutation screening with two moderate-sized families, in which the NS phenotype co-segregated with haplotypes defined by D12S84, D12S105, D12S354 and D12S2070. Bi-directional sequencing of the fifteen PTPN11 exons and their intron boundaries for the two families revealed mutations in one exon, predicting a substitution in the N-SH2 domain. These sequence changes were confirmed in all affected individuals in the families, but was absent in unaffected family members and controls. Example 2 describes the molecular consequences of the mutations. Example 3 describes analysis of the protein mutants. Example 4 describes the identification of additional mutations and further characterization of the role of the mutations in Noonans syndrome. Taken together, these findings established PTPN11 as an NS disease gene.

DEFINITIONS a) Noonan Syndrome:

As used herein the term "Noonan syndrome" (NS) encompasses all forms of the disorder as described under the accession No. MIM 163950 in the Online Mendelian Inheritance in Man (OMIM) as well as disorders similar or related to NS. Such disorders include, but are not limited to, the Watson (MIM 193520) and LEOPARD (MIM 151100) Syndromes, essentially indistinguishable from NS (Mendez and Opitz, Am J Med Genet 1985;21:493-506); male Turner and female pseudo-Turner Syndrome, as well as Turner phenotype with normal karyotype (see MIM 163950); Noonan syndrome with multiple giant-cell lesions (MIM 163955; Tartaglia et al., Am J Hum Genet 2002;70:1555-1563) and/or Noonan syndrome with multiple café-au-lait spots (also known as LEOPARD syndrome, MIM 151100; Digilio et al, Am J Hum Genet 2002;71:389-394; Legius et al, J Med Genet 2002;39:571-574); valvular sclerosis (Snellen et al, Circulation 1968;38(1 Suppl):93-101); and idiopathic short stature (Attie K M, Curr Opin Pediatr 2000;12:400-404).

NS encompasses familial or sporadic forms, including NS1, whose locus has been identified on chromosome 12. The present invention takes into consideration, however, that NS and its related disorders are genetically heterogeneous, but share phenotypical features. The features of NS have been well described and a clinical scoring system devised. See, Mendez and Opitz, Am J Med Genet 1985; 21:493-506; Noonan, Clin Pediatr (Phila) 1994;33:548-555; Sharland et al., Arch Dis Child 1992;67:178-183; Duncan et al., Am J Med Genet 1981;10:37-50).

The subject to whom the diagnostic or therapeutic applications of the invention are directed may be any human or animal, more particularly a mammal, preferably a primate or a rodent, but including, without limitation, monkeys, dogs, cats, horses, cows, pigs, sheep, goats, rabbits, guinea pigs, hamsters, mice and rats.

The subject may be of any age, e.g., an adult, a child, an infant. Prenatal diagnostics and therapeutics interventions are also encompassed.

b) PTPN11:

PTPN11, also known as SHP-2, Syp, SHPTP2, PTP2C, PTP1D and BPTP3, is a member of the family of non-membrane tyrosine phosphatases and is ubiquitously expressed in all tissues examined, with higher levels of expression in the heart and the brain (Ahmad et al, Proc Natl Acad Sci USA 1993;90:2197-2201; Bastien et al, Biochem Biophys Res Commun 1993 ;196:124-133; Freeman et al, Proc Natl Acad Sci USA, 1992;89:11239-11243). The function of the SH2 domain is to specifically recognize the phosphorylated state of tyrosine residues, thereby allowing PTPN11 to localize to tyrosine-phosphorylated sites.

The genomic sequence of PTPN11, is organized as follows (residues referring to SEQ ID NO:33): Exon 1, residues 123211-123604; Exon 2, residues 136831-136953; Exon 3, residues 194431-194625; Exon 4, residues 197308-197500; Exon 5, residues 198677-198793; Exon 6, residues 200063-200176; Exon 7, residues 217057-217153; Exon 8, residues 221764-221843; Exon 9, residues 221970-222128; Exon 10, residues 226187-226318; Exon 11, residues 230588-230742; Exon 12, residues 232556-232623; Exon 13, residues 233137-233288; Exon 14, residues 246257-246369; Exon 15, 248808-248909; Exon 16, residues 249938-250510. The adenine nucleotide of the start codon "ATG" is located at residue No. 123591 of SEQ ID NO:33. A partial genomic sequence is also provided by GenBank Accession No. AC004086.

In the context of the present invention, the PTPN11 gene encompasses a gene of human origin, comprising a coding nucleotide sequence set forth in SEQ ID NO:1, or homologs, including allelic variants and orthologs. The PTPN11 protein encompasses a PTPN11 protein of human origin having the amino acid sequence set forth in SEQ ID NO:2, or homologs, including orthologs thereof. As used herein, the term "PTPN11" in italicized form refers to a nucleotide sequence (genomic, cDNA, etc.), whereas the non-italicized form refers to a peptide or protein sequence.

FIG. 1 shows the organization of the PTPN11 gene and the functional domains of the PTPN11 protein. The PTPN11 protein comprises two SH2 (src-homology 2) domains, one from amino acid 3 to amino acid 104, the other from amino acid 112 to amino acid 216, and one PTP (protein tyrosine phosphatase) domain, from amino acid 221 to amino acid 524.

"PTPN11 variants" nucleic acids are PTPN11 genomic DNA, cDNA, or mRNA comprising at least one mutation, preferably a nucleotide substitution. The nucleotide substitution may be in a coding or non-coding region. Preferred PTPN11 variants are those resulting in the expression of higher levels of PTPN11 as compared to a control, and those encoding PTPN11 variants characterized by increased PTPN11 activity (i.e., "gain-of function variants").

Figure 2:
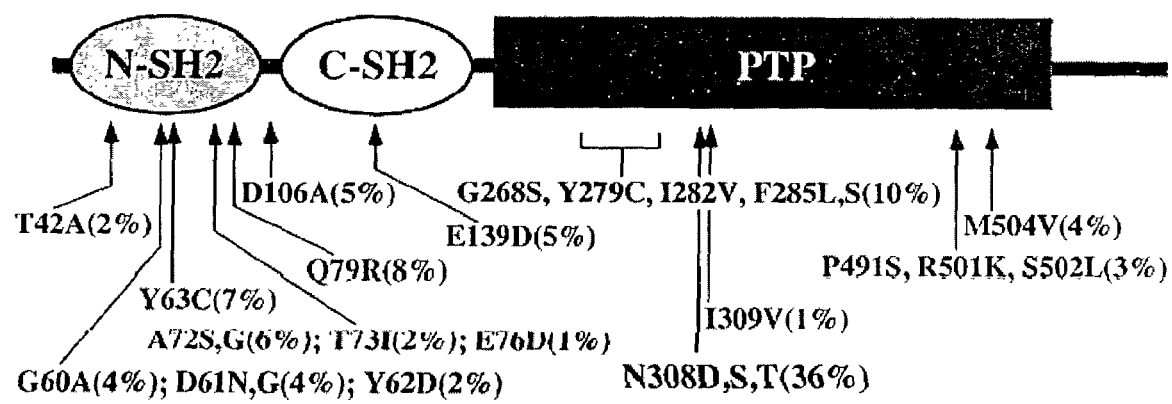
FIG. 2 shows the distribution of PTPN11 (SHP-2) mutations and their relative prevalence in Noonan syndrome.
Figure 3A:
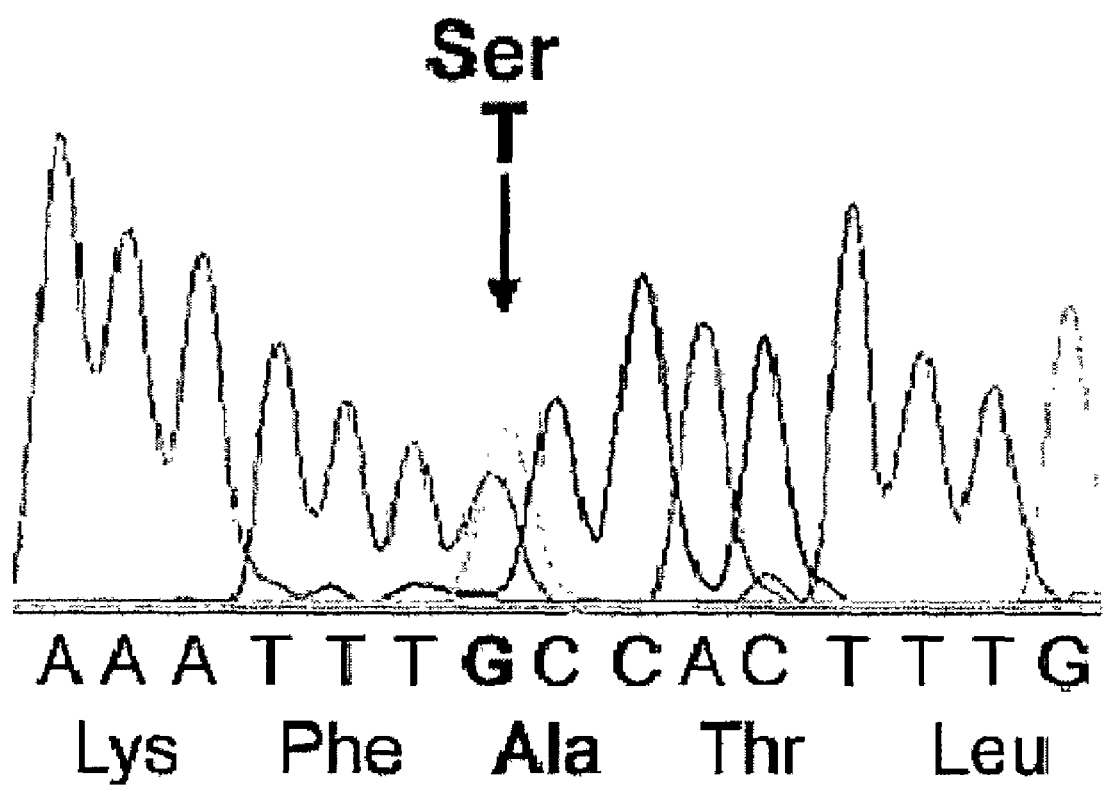
FIGS. 3A and 3B show sequence analysis of amplified DNA containing the PTPN11 exon 3 and flanking intronic boundaries, which revealed heterozygous changes in the NS-C and NS-L families.
Figure 3B:
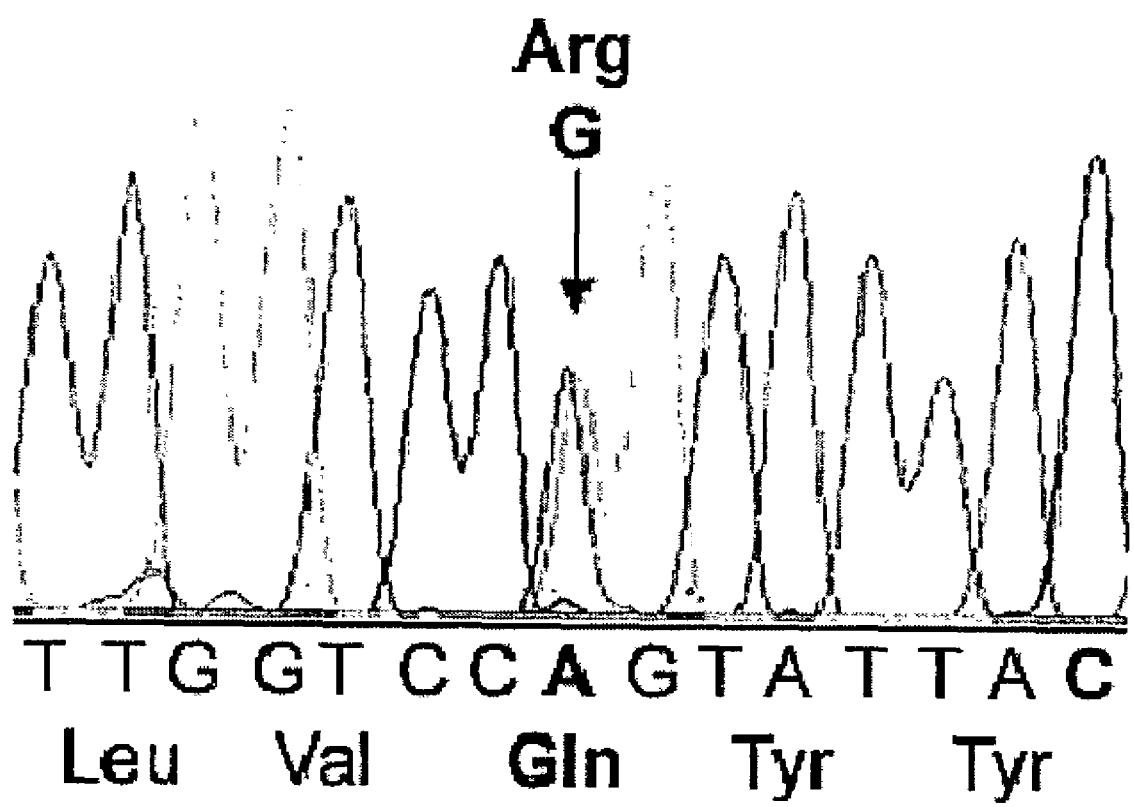
Figure 4A:
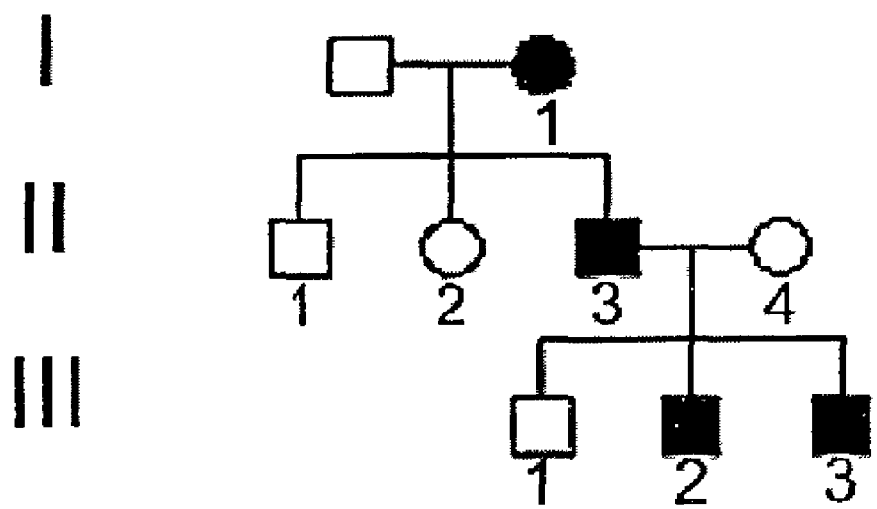
FIGS. 4A and 4B show segregation of the G214T (FIG. 4A) and A236G (FIG. 4B) mutations in NS-C and NS-L families, respectively. Family trees for these two families are shown above. A single BglI site was present in the wild-type amplified product so that this digestion resulted in 164- and 374-bp (base pair) products. The G214T change obliterated that BglI site so that the heterozygotes have undigested 538-bp product as well. The A236G mutation introduced a novel BsaWI restriction site, resulting in 177- and 361-bp products, whereas wild type alleles remained undigested at 538 bp.
Figure 4A:
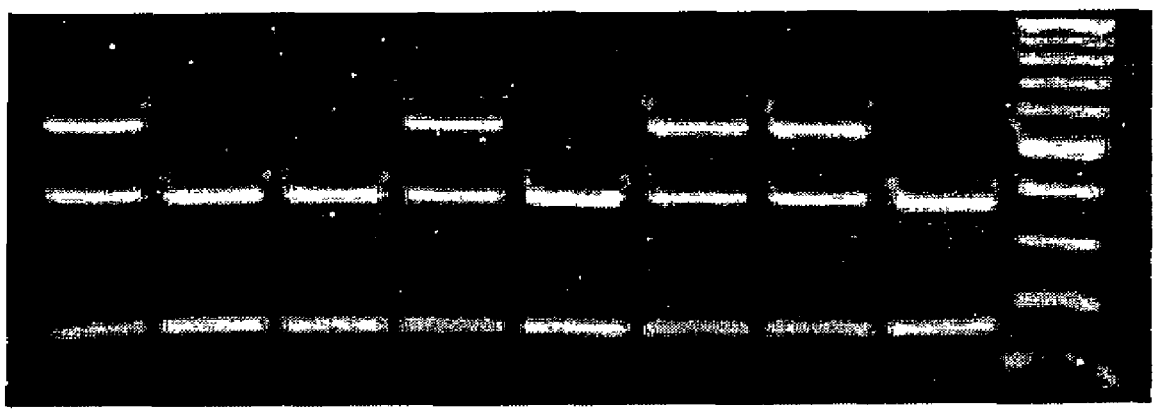
Figure 4B:
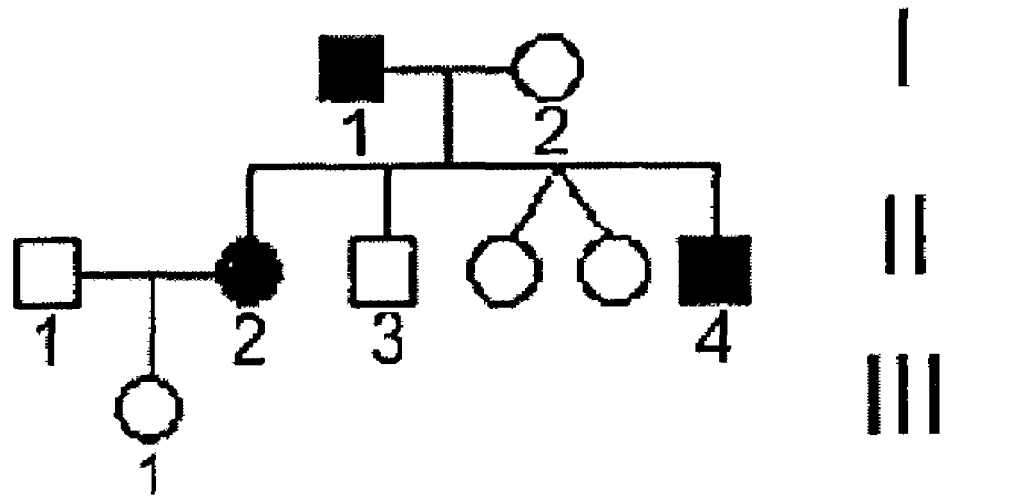
Figure 4B:
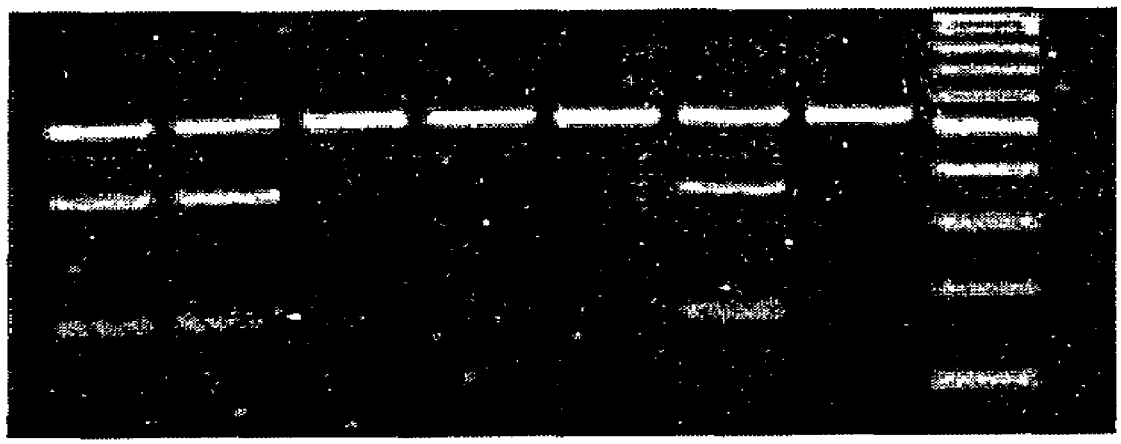

"PTPN11 variants" are PTPN11 proteins or polypeptides comprising at least one mutation. The PTPN11 variants can be function-conservative variants, including gain-of-function-variants, i.e., variants capable of increased PTPN11 activity, such as higher tyrosine phosphatase activity. The increase in PTPN11 activity includes, for example, increased phosphatase activity, prolonged activity of PTPN11, and a higher proportion of PTPN11 remaining in an active state (see below). This may be assessed either by direct measurement of PTPN11 activity or by measuring the activity of components regulated by PTPN11 activity (see, Example 4). Preferred mutations are amino acid substitutions and/or deletions, in particular those described in FIG. 2 and Table 1.

PTPN11 plays a role in modulating cellular proliferation, differentiation and migration. Following ligand-induced receptor activation, PTPN11 is recruited through its SH2 domains directly by the receptor or indirectly via docking proteins. The C-terminal tail of PTPN11 also has tyrosine residues that can become phosphorylated, providing SH2 binding sites for other proteins. Thus, PTPN11 may act as a phosphatase and as an adapter molecule with docking function, both functions being relevant in signal transduction. Depending on the specific signaling pathway, PTPN11 can act as either a positive or negative regulator of ERK, Jnk kinase, Jak/STAT, and NF-κB cascades (Saxton, et al, EMBO J.,1997;16:2352-2364; Shi et al, J. Biol. Chem., 1998;273:4904-4908; You et al, Mol. Cell. Biol., 1999;19:2416-2424; Maroun et al, Mol. Cell. Biol., 2000;20:8513-8525; You et al, J. Exp. Med., 2001;193:101-110). These various roles of PTPN11, as described herein, are also referred to as "functions" or "activities" of the protein.

An "increased activity" of PTPN11 in a test subject or a biological sample refers to a higher total PTPN11 activity in the test subject or biological sample in comparison with a control, e.g., a healthy subject or a standard sample. Preferably, although not necessarily, the activity is at least 10%, more preferably at least 50%, even more preferably at least 100%, and still more preferably at least 150% higher in the test subject or sample than in the control. The increased activity may results from increased basal PTPN11 activity, prolonged stimulation of a downstream component (e.g., ERK2) of a PTPN11-associated pathway, and a higher PTPN11 expression level. (See Examples).

Basal level of PTPN11 activity is dependent on the conformation of the protein. Wild-type PTPN11 exists in an inactive (I) or an active (A) conformation, with the N-SH2 domain acting as a molecular switch. In the I state, N-SH2 assumes a conformation that blocks the PTP active site and disrupts its own, separate phosphopeptide-binding cleft. On binding of phosphopeptide, the N-SH2 domain assumes the A conformation that disrupts its PTP recognition surface.

Without being bound to any specific theory, it is believed that mutations in PTPN11 observed in Noonan syndrome could result in destabilization of the I state, favoring the A state.

A higher expression level of wild-type or variant PTPN11 may result from, for example, a mutation in a non-coding region of a PTPN11 gene or a mutation in a coding or non-coding gene involved in PTPN11 transcription or translation. The expression level of PTPN11 can be determined, for example, comparing PTPN11 mRNA or level of PTPN11 protein in a test subject as compared to a control.

c) PTPN11 Signaling Pathway

PTPN11 participates in signaling cascades elicited by a number of growth factors, cytokines and hormones (Feng, Exp. Cell Res. 1999;253:47-54; Stein-Gerlach et al, Int. J. Biochem. Cell. Biol. 1998;30:559-566; Tamir, et al, Curr. Opin. Immunol., 2000; 12:307-315). Much of what is known of the PTPN11 pathway in humans derives from studies of its *Drosophila* homologue, "corkscrew" (csw), as well as from transgenic mice studies (Van Vactor et al., Curr Opin Genetics Development 1998;8:112-126). For example, PTPN11 (SHP-2) has been implicated in regulating fibroblast growth factor receptor (FGFR) and platelet-derived growth factor receptor (PDGFR) signaling and Dos-like scaffolding proteins in several mammalian signaling pathways, including the insulin and IGF1R pathways.

A preferred "PTPN11 signaling pathway" is the RAS-MAP kinase pathway (ERK1/2). Briefly, transmission of the stimulatory signals from Ras to nuclear targets involves regulation of the family of kinases known as MAPKs ("mitogen-activated protein kinases") or ERKs ("extracellular signal regulated kinases"). This pathway includes, but is not limited to, components such as PTPN11 and ERK2. Additional components of this pathway have been identified and described (see, e.g., Lee and McCubrey, Leukemia 2002; 16:486-507).

An "upregulation" or "increased activity" of a PTPN11 signaling pathway such as the RAS-MAPK pathway herein means a detectable change in signaling flux or output of the pathway that could also result from a gain-of-function PTPN11 mutant. Preferred examples of output signals include, but are not limited to, an increased PTPN11 phosphatase activity or increased ERK2 kinase activity. See Example 2 (section C), and FIG. 9.

d) Molecular Biology Terms:

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

The terms "polypeptide" and "protein" may be used herein interchangeably to refer to the gene product (or corresponding synthetic product) of a PTPN11 gene. The term "protein" may also refer specifically to the polypeptide as expressed in cells.

A "PTPN11 gene" is used herein to refer to a portion of a DNA molecule that includes a PTPN11 polypeptide coding sequence operatively associated with expression control sequences. Thus, a gene includes both transcribed and untranscribed regions. The transcribed region may include introns, which are spliced out of the mRNA, and 5'- and 3'-untranslated (UTR) sequences along with protein coding sequences. In one embodiment, the gene can be a genomic or partial genomic sequence, in that it contains one or more introns. In another embodiment, the term gene may refer to a cDNA molecule (i.e., the coding sequence lacking introns). In yet another embodiment, the term gene may refer to expression control sequences, such as the promoter or the enhancer sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide.

Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "variant" also includes a polypeptide or enzyme which has at least 60% amino acid identity as determined by BLAST or FASTA algorithms, preferably at least 75%, most preferably at least 85%, and even more preferably at least 90%, and still more preferably at least 95%, and which has the same or substantially similar properties or functions as the native or parent protein or enzyme to which it is compared. A particular variant is a "gain-of-function" variant, meaning a polypeptide variant in which the change of at least one given amino acid residue in a protein or enzyme improves a specific function of the polypeptide, including, but not limited to, protein activity. The change in amino acid residue can be replacement of an amino acid with one having similar properties (such as, for example, polarity, hydrogen bonding potential, acidic, basic, hydrophobic, aromatic, and the like), or different properties.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987,Cell 50:667). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or at least 95%) of the nucleotides match over the defined length of the DNA sequences, as determined by sequence comparison algorithms, such as BLAST, FASTA, DNA Strider, etc. An example of such a sequence is an allelic or species variant of the PTPN11 gene. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% or 95% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

The terms "mutant" and "mutation" mean any detectable change in genetic material, e.g., DNA, or any process, mechanism, or result of such a change. When compared to a control material, such change may be referred to as an "abnormality". This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Amplification" of DNA as used herein encompasses the use of polymerase chain reaction (PCR) to increase the concentration of a particular DNA sequence within a mixture of DNA sequences. For a description of PCR see Saiki et al., Science 1988, 239:487.

"Sequencing" of a nucleic acid includes chemical or enzymatic sequencing. "Chemical sequencing" of DNA denotes methods such as that of Maxam and Gilbert (Maxam-Gilbert sequencing, Maxam and Gilbert, Proc. Natl. Acad. Sci. USA 1977 74:560), in which DNA is randomly cleaved using individual base-specific reactions. "Enzymatic sequencing" of DNA denotes methods such as that of Sanger (Sanger et al., Proc. Natl. Acad. Sci. USA 1977, 74:5463), in which a single-stranded DNA is copied and randomly terminated using DNA polymerase, including variations thereof, which are well-known in the art. Preferably, oligonucleotide sequencing is conducted using automatic, computerized equipment in a high-throughput setting, for example, microarray technology, as described herein. Such high-throughput equipment are commercially available, and techniques well known in the art.

The term "polymorphism" refers, generally, to the coexistence of more than one form of a gene (e.g., more than one allele) within a population of individuals. The different alleles may differ at one or more positions of their nucleic acid sequences, which are referred to herein as "polymorphic locuses". When used herein to describe polypeptides that are encoded by different alleles of a gene, the term "polymorphic locus" also refers to the positions in an amino acid sequence that differ among variant polypeptides encoded by different alleles. Polymorphisms include "single nucleotide polymorphisms" (SNPs), referring to a polymorphic site occupied by a single nucleotide, which is the site of variation between allelic sequences. Typically, the polymorphic site of an SNP is flanked by highly conserved sequences (e.g., sequences that vary in less than 1/100 and, more preferably, in less than 1/1000 individuals in a population). The polymorphic locus of an SNP may be a single base deletion, a single base insertion, or a single base substitution. Single base substitutions are particularly preferred.

As used herein, "sequence-specific oligonucleotides" refers to related sets of oligonucleotides that can be used to detect variations or mutations in the PTPN11 gene.

A "probe" refers to a nucleic acid or oligonucleotide that forms a hybrid structure with a sequence in a target region due to complementarity of at least one sequence in the probe with a sequence in the target protein.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of PTPN11, or to detect the presence of nucleic acids encoding PTPN11. In a further embodiment, an oligonucleotide of the invention can form a triple helix with a PTPN11 DNA molecule. In still another embodiment, a library of oligonucleotides arranged on a solid support, such as a silicon wafer or chip, can be used to detect various mutations of interest. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Specific non-limiting examples of synthetic oligonucleotides envisioned for this invention include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—$N(CH)_3$—O—$CH_2$, $CH_2$—O—$N(CH)_3$—$CH_2$, $CH_2$—$N(CH)_3$—$N(CH)_3$—$CH_2$ and O—$N(CH)_3$—$CH_2$—$CH_2$ backbones (where the phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. No. 5,792,844 and U.S. Pat. No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_n NH_2$ or $O(CH_2)_n CH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$;$NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

The present invention provides antisense nucleic acids (including ribozymes), which may be used to inhibit expression of PTPN11. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607). Synthetic oligonucleotides are suitable for antisense use.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.

The term "linkage" refers to the tendency of genes, alleles, loci or genetic markers to be inherited together as a result of their location on the same chromosome. Linkage may be measured, e.g., by the percent recombination between two genes, alleles, loci or genetic markers.

Expression of PTPN11 Polypeptides

A nucleotide sequence coding for PTPN11, for an antigenic fragment, derivative or analog of PTPN11, of for a functionally active derivative of PTPN11 (including a chimeric protein) may be inserted into an appropriate expression vector, i.e., a vector which contains the necessary elements for the transcription and translation of the inserted protein-coding sequence. Thus, a nucleic acid encoding a PTPN11 polypeptide of the invention can be operationally associated with a promoter in an expression vector of the invention. Both cDNA and genomic sequences can be cloned and expressed under control of such regulatory sequences. Such vectors can be used to express functional or functionally inactivated PTPN11 polypeptides. In particular, the PTPN11 nucleic acids which may be cloned and expressed according to these methods include, not only wild-type PTPN11 nucleic acids, but also mutant or variant PTPN11 nucleic acids. These include, for example, a PTPN11 nucleic acid having one or more of the mutations or polymorphisms set forth in Tables 1 and 6. In addition, nucleic acids that encode a variant PTPN11 polypeptide, for example a variant PTPN11 polypeptide comprising one or more of the amino acid substitutions listed in Table 1 may be cloned and expressed according to the methods described here.

The necessary transcriptional and translational signals can be provided on a recombinant expression vector. Potential host-vector systems include but are not limited to mammalian cell systems transfected with expression plasmids or infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Expression of a PTPN11 protein may be controlled by any promoter/enhancer element known in the art, but these regulatory elements must be functional in the host selected for expression. Promoters which may be used to control PTPN11 gene expression include, but are not limited to, cytomegalovirus (CMV) promoter (U.S. Pat. Nos. 5,385,839 and 5,168,062), the SV40 early promoter region (Benoist and Chambon, Nature 1981, 290:304-310), the promoter contained in the 3' long terminal repeat of Rous sarcoma virus (Yamamoto, et al., Cell 1980, 22:787-797), the herpes thymidine kinase promoter (Wagner et al., Proc. Natl. Acad. Sci. U.S.A. 1981, 78:1441-1445), the regulatory sequences of the metallothionein gene (Brinster et al., Nature 1982, 296:39 42); prokaryotic expression vectors such as the b-lactamase promoter (Villa-Komaroff, et al., Proc. Natl. Acad. Sci. U.S.A. 1978, 75:3727-3731), or the tac promoter (DeBoer, et al., Proc. Natl. Acad. Sci. U.S.A. 1983, 80:21-25, 1983); see also "Useful proteins from recombinant bacteria" in Scientific American 1980, 242:74-94. Still other useful promoter elements which may be used include promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 1985, 315:338-340; Kollias et al., Cell 1986, 46:89-94), hematopoietic stem cell differentiation factor promoters, erythropoietin receptor promoter (Maouche et al., Blood 1991, 15:2557), etc.

Soluble forms of the protein can be obtained by collecting culture fluid, or solubilizing-inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2 dimensional gel electrophoresis, chromatography (e.g., ion exchange, affinity, immunoaffinity, and sizing column chromatography), centrifugation, differential solubility, immunoprecipitation, or by any other standard technique for the purification of proteins.

A wide variety of host/expression vector combinations may be employed in expressing the DNA sequences of this invention. Useful expression vectors, for example, may consist of segments of chromosomal, non chromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., Gene 1988, 67:31-40), pCR2.1 and pcDNA 3.1+ (Invitrogen, Carlsbad, Calif.), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Preferred vectors are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant PTPN11 protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures (see below), as well as in vitro expression, are DNA-based vectors and retroviral vectors. Methods for constructing and using viral vectors are known in the art (see, e.g., Miller and Rosman, BioTechniques 1992, 7:980-990). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), or can be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), baculovirus, and the like. RNA viral vectors include, for example, retroviruses, lentiviruses, and alphaviruses (e.g., Sindbis virus and Venezuelan Equine Encephalitis virus), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 1991, 2:320-330), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. 1992, 90:626-630; see also La Salle et al., Science 1993, 259:988-990); and a defective adeno-associated virus vector (Samulski et al., J. Virol. 1987, 61:3096-3101; Samulski et al., J. Virol. 1989, 63:3822-3828; Lebkowski et al., Mol. Cell. Biol. 1988, 8:3988-3996).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), Transgene (Strasbourg, France; adenoviral, vaccinia, retroviral, and lentiviral vectors) and Invitrogen (Carlbad, Calif.).

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner et al., Proc. Natl. Acad. Sci. U.S.A. 1987, 84:7413-7417; Felgner and Ringold, Science 1989, 337:387-388; Mackey et al., Proc. Natl. Acad. Sci. U.S.A. 1988, 85:8027-8031; Ulmer et al., Science 1993, 259:1745-1748). Useful lipid compounds and compositions for transfer of nucleic acids are described in International Patent Publications WO 95/18863 and WO 96/17823, and in U.S. Pat. No. 5,459,127. Lipids may be chemically coupled to other molecules for the purpose of targeting (see, Mackey et al., Proc. Natl. Acad. Sci. U.S.A. 1988, 85:8027-8031). Targeted peptides, and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce the vector in vivo as a naked DNA plasmid. Naked DNA vectors for gene therapy can be introduced into the desired host cells by methods known in the art; e.g., electroporation, microinjection, cell fusion, DEAE dextran, calcium phosphate precipitation, use of a gene gun, or use of a DNA vector transporter (see, e.g., Wu et al., J. Biol. Chem. 1992, 267:963-967; Wu and Wu, J. Biol. Chem. 1988, 263:14621-14624; Hartmut et al., Canadian Patent Application No. 2,012,311, filed Mar. 15, 1990; Williams et al., Proc. Natl. Acad. Sci. U.S.A. 1991, 88:2726-2730). Receptor-mediated DNA delivery approaches can also be used (Curiel et al., Hum. Gene Ther. 1992, 3:147-154; Wu and Wu, J. Biol. Chem. 1987, 262: 4429-4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C.P. Acad. Sci. 1998, 321:893; WO 99/01157; WO 99/01158; WO 99/01175).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nat. Med. 1995, 1:887-889). In that regard, it is advantageous to employ a viral vector that is engineered to express a minimal number of antigens.

Diagnostic Methods

According to the present invention, mutated forms of PTPN11 can be detected to diagnose Noonan syndrome.

Accordingly, diagnostic methods may comprise, for example, detecting a mutation in a PTPN11 gene, wherein the mutation results in increased PTPN11 activity. The mutation may especially affect a coding region of the gene, such as a region of the PTPN11 gene that encodes a SH2 (src-homology 2) domain of the PTPN11 protein, or a region of the PTPN11 gene that encodes a PTP (phosphotyrosine phosphatase) domain of the PTPN11 protein. The mutation may be a missense mutation, preferably a missense mutation resulting in nucleic acid substitution, or a deletion, or a combination of both. Preferably, the mutation results in one or more of the amino acid substitutions or deletions set forth in Table 1. Most preferably, the nucleotide substitutions or deletions are selected from the ones described in Table 1.

The diagnostic methods of the invention also encompass detecting a mutation in PTPN11 protein, in particular a mutation that results in increased activity of the PTPN11 protein. The mutation is preferably an amino acid substitution. More preferably, the mutation is in the SH2 (src-homology 2) domain of the PTPN11 protein, including the N-SH2 and C-SH2 domains, the domain between the N-SH2 and C-SH2 domain, or the PTP (phosphotyrosine phosphatase) domain of the PTPN11 protein. Preferred amino acid substitutions and deletions are set forth in Table 1.

In a further embodiment, the diagnosis of Noonan syndrome in a subject comprises assessing the level of expression or activity of PTPN11 protein in the test subject and comparing it to the level of expression or activity in a control subject, wherein an increased expression and/or activity of the PTPN11 protein in the test subject compared to the control subject is indicative of Noonan syndrome.

The level of expression of PTPN11 may be assessed by determining the amount of mRNA that encodes the PTPN11 protein in a biological sample, or by determining the concentration of PTPN11 protein in a biological sample. The level of PTPN11 protein or activity may be assessed by determining the level of phosphatase activity in a sample or subject, and the level of activity in a PTPN11 signaling pathway may be assessed by determining the pathway signaling flux, e.g., by measuring PTPN11 or ERK activity in a sample or subject, as described herein.

The invention also provides kits for performing these diagnostic methods. A particular subject of the invention is a kit for diagnosing Noonan syndrome, comprising an oligonucleotide that specifically hybridizes to a site harboring a mutation of the PTPN11 gene, or an adjacent site, wherein the mutation results in increased basal activity of the PTPN11 protein. The site of mutation may particularly comprise a nucleotide selected from the group consisting of nucleotides 214, 215, 236, 844, 922, and 1510 of SEQ ID NO:1, or any nucleotide recited in Table 1, as described below. A further subject of the invention is a kit for diagnosing Noonan syndrome, comprising an antibody that specifically recognizes a mutated form of PTPN11 protein that results in increased basal activity of the protein.

As used herein, the term "diagnosis" refers to the identification of the disease at any stage of its development, and also includes the determination of a predisposition of a subject to develop the disease. Importantly, the invention permits genetic counseling of prospective parents and in utero genetic testing for Noonan syndrome. Families with one affected parent or with advanced paternal age are of particular concern. The diagnostic method of the invention also allows confirmation of a questionable NS diagnosis based on phenotype (appearance and symptomology). The diagnostic method of the invention may also be envisioned in the case of fetal abnormalities whose cause may not be obvious, or in the case of fetal loss, to evaluate viability of future pregnancies.

The term "biological sample" refers to any cell source from which DNA may be obtained. Non-limiting examples of cell sources available in clinical practice include without limitation blood cells, buccal cells, cervicovaginal cells, epithelial cells from urine, fetal cells, or any cells present in tissue obtained by biopsy. Cells may also be obtained from body fluids, including without limitation blood, plasma, serum, lymph, milk, cerebrospinal fluid, saliva, sweat, urine, feces, and tissue exudates (e.g., pus) at a site of infection or inflammation. For prenatal testing, genetic material can be obtained from fetal cells, e.g., from amniotic fluid (through amniocentesis), chronic villi, blood, or any tissue of a pregnant woman. DNA is extracted using any of the numerous methods that are standard in the art. It will be understood that the particular method used to extract DNA will depend on the nature of the source. Generally, the minimum amount of DNA to be extracted for use in the present invention is about 25 pg (corresponding to about 5 cell equivalents of a genome size of $4 \times 10^9$ base pairs).

Various methods for detecting such mutated forms of PTPN11 are described herein.

The present invention especially contemplates detecting abnormalities, i.e., mutations in the PTPN11 gene that result in an increased basal activity of the PTPN11 protein, render the protein in a constitutively active conformation, provides prolonged increased PTPN11 activity, or increases the level of expressed PTPN11 protein.

Mutations may include an insertion in the gene, a truncation of or deletion in the gene, a nonsense mutation, a frameshift mutation, a splice-site mutation, and a missense mutation. Such mutations can occur in the coding region of the PTPN11 gene, more particularly in any of the functional domains, as well as in the untranslated regions, more particularly in the promoter or enhancer regions. Preferred mutations are those in any of exons 2, 3, 4, 7, 8, or 13. Even more preferred are mutations resulting in amino acid substitutions. Specific mutations are listed in Table 1:

TABLE 1

Mutations in PTPN11 Gene (n = 91). Nucleotide and amino acid substitutions are numbered as set forth in SEQ ID NO:1 and 2, respectively.

| Nucleotide Substitution | Exon | Predicted Amino Acid Substitution | Functional Domain | Relative Prevalence |
|---|---|---|---|---|
| A(124)G | 2 | Thr(42)Ala | N-SH2 | 2% |
| G(179)C | 3 | Gly(60)Ala | N-SH2 | 4% |
| GTGA-del (179-182) + T-ins (179)[a] | 3 | Gly(60)Val + Asp(61)del | N-SH2 | 1% |
| G(181)A | 3 | Asp(61)Asn | N-SH2 | 4% |
| A(182)G | 3 | Asp(61)Gly | N-SH2 | |
| T(184)G | 3 | Tyr(62)Asp | N-SH2 | 2% |
| A(188)G | 3 | Tyr(63)Cys | N-SH2 | 7% |
| G(214)T | 3 | Ala(72)Ser | N-SH2 | 6% |
| C(215)G | 3 | Ala(72)Gly | N-SH2 | |
| C(218)T | 3 | Thr(73)Ile | N-SH2 | 2% |

TABLE 1-continued

Mutations in PTPN11 Gene (n = 91). Nucleotide and amino acid substitutions are numbered as set forth in SEQ ID NO:1 and 2, respectively.

| Nucleotide Substitution | Exon | Predicted Amino Acid Substitution | Functional Domain | Relative Prevalence |
|---|---|---|---|---|
| G(228)C | 3 | Glu(76)Asp | N-SH2 | 1% |
| A(236)G | 3 | Gln(79)Arg | N-SH2 | 8% |
| A(317)C | 3 | Asp(106)Ala | N-SH2/C-SH2 linker | 5% |
| G(417)C | 4 | Gly(139)Asp | C-SH2 | 5% |
| G(417)T | | | | |
| G(802)A | 4 | Gly(268)Ser | PTP | 10% |
| A(836)G | 7 | Tyr(279)Cys | PTP | |
| A(844)G | 7 | Ile(282)Val | PTP | |
| T(853)C | 7 | Phe(285)Leu | PTP | |
| T(854)C | 8 | Phe(285)Ser | PTP | |
| A(922)G | 8 | Asn(308)Asp | PTP | 36% |
| A(923)G | 8 | Asn(308)Ser | PTP | |
| A(923)C | 8 | Asn(308)Thr | PTP | |
| A(925)G | 8 | Ile(309)Val | PTP | 1% |
| C(1471)T | 13 | Pro(491)Ser | PTP | 3% |
| G(1502)A | 13 | Arg(501)Lys | PTP | |
| C(1505)T | 13 | Ser(502)Leu | PTP | |
| A(1510)G | 13 | Met(504)Val | PTP | 4% |

[a]This means "deletion of nucleotides 179-182 (GTGA) and insertion of a T at position 179.

Nucleic Acid Based Assays

According to the invention, mutated forms of PTPN11 nucleic acids, i.e. in the PTPN11 DNA or in its transcripts, as well as a deregulated expression, e.g. overexpression, of PTPN11 or other components of a PTPN11 pathway (e.g., ERK2) can be detected by a variety of suitable methods.

Standard methods for analyzing the nucleic acid contained in a biological sample and for diagnosing a genetic disorder can be employed, and many strategies for genotypic analysis are known to those of skilled in the art.

In a preferred embodiment, the determination of mutations in the PTPN11 gene encompasses the use of nucleic acid sequences such as specific oligonucleotides, to detect mutations in PTPN11 genomic DNA or mRNA in a biological sample. Such oligonucleotides may be specifically hybridize to a site of mutation, or to a region adjacent to this site of mutation present in a PTPN11 nucleic acid. One may also employ primers that permit amplification of all or part of PTPN11. Alternatively, or in combination with such techniques, oligonucleotide sequencing described herein or known to the skilled artisan can be applied to detect the PTPN11 mutations.

One skilled in the art may use hybridization probes in solution and in embodiments employing solid-phase procedures. In embodiments involving solid-phase procedures, the test nucleic acid is adsorbed or otherwise affixed to a selected matrix or surface. The fixed, single-stranded nucleic acid is then subjected to specific hybridization with selected probes.

In another embodiment, one skilled in the art may use oligonucleotide primers in an amplification technique, such as PCR or reverse-PCR ("reverse polymerase chain reaction"), to specifically amplify the target DNA or mRNA, respectively, that is potentially present in the biological sample.

Useful oligonucleotides include primers that permit amplification of PTPN11 exons, such as:

Exon 1:
Forward primer:
5'-GCTGACGGGAAGCAGGAAGTGG-3' (SEQ ID NO:3)
Reverse primer:
5'-CTGGCACCCGTGGTTCCCTC-3' (SEQ ID NO:4)

Exon 2:
Forward primer:
5'-ACTGAATCCCAGGTCTCTACCAAG-3' (SEQ ID NO:5)
Reverse primer:
5'-CAGCAAGCTATCCAAGCATGGT-3' (SEQ ID NO:6)

Exon 3:
Forward primer:
5'-CGACGTGGAAGATGAGATCTGA-3' (SEQ ID NO:7)
Reverse primer:
5'-CAGTCACAAGCCTTTGGAGTCAG-3' (SEQ ID NO:8)

Exon 4:
Forward primer:
5'-GATTGATCAATCCCTTGGAGGAATG-3' (SEQ ID NO:9)
Reverse primer:
5'-GTCACCAGACCCAACGTGGTG-3' (SEQ ID NO:10)

Exon 5:
Forward primer:
5'-CTGCAGTGAACATGAGAGTGCTTG-3' (SEQ ID NO:11)
Reverse primer:
5'-GTTGAAGCTGCAATGGGTACATG-3 (SEQ ID NO:12)

Exon 6:
Forward primer:
5'-TGCATTAACACCGTTTTCTGT-3' (SEQ ID NO:13)
Reverse primer:
5'-GTCAGTTTCAAGTCTCTCAGGTC-3' (SEQ ID NO:14)

Exon 7:
Forward primer:
5'-GAACATTTCCTAGGATGAATTCC-3' (SEQ ID NO:15)
Reverse primer:
5'-GGTACAGAGGTGCTAGGAATCA-3' (SEQ ID NO:16)

Exon 8:
Forward primer:
5'-GACATCAGGCAGTGTTCACGTTAC-3' (SEQ ID NO:17)
Reverse primer:
5'-CCTTAAAGTTACTTTCAGGACATG-3' (SEQ ID NO:18)

Exon 9:
Forward primer:
5'-GTAAGCTTTGCTTTTCACAGTG-3' (SEQ ID NO:19)
Reverse primer:
5'-CTAAACATGGCCAATCTGACATGTC-3' (SEQ ID NO:20)

Exon 10:
Forward primer:
5'-GCAAGACTTGAACATTTGTTTGTTGC-3' (SEQ ID NO:21)
Reverse primer:
5'-GACCCTGAATTCCTACACACCATC-3' (SEQ ID NO:22)

Exon 11:
Forward primer:
5'-CAAAAGGAGACGAGTTCTGGGAAC-3' (SEQ ID NO:23)
Reverse primer:
5'-GCAGTTGCTCTATGCCTCAAACAG-3' (SEQ ID NO:24)

Exon 12:
Forward primer:
5'-GCTCCAAAGAGTAGACATTGTTTC-3' (SEQ ID NO:25)
Reverse primer:
5'-GACTGTTTTCGTGAGCACTTTC-3' (SEQ ID NO:26)

Exon 13:
Forward primer:
5'-CAACACTGTAGCCATTGCAACA-3' (SEQ ID NO:27)
Reverse primer:
5'-CGTATCCAAGAGGCCTAGCAAG-3' (SEQ ID NO:28)

-continued

Exon 14:
Forward primer:
5'-ACCATTGTCCCTCACATGTGC-3' (SEQ ID NO:29)
Reverse primer:
5'-CAGTGAAAGGCATGTGCTACAAAC-3' (SEQ ID NO:30)

Exon 15:
Forward primer:
5'-CAGGTCCTAGGCACAGGAACTG-3' (SEQ ID NO:31)
Reverse primer:
5'-ACATTCCCAAATTGCTTGCCT-3' (SEQ ID NO:32)

The present invention is more particularly directed to a method of in vitro diagnosis of NS comprising the steps of:

a) contacting a biological sample containing DNA with specific oligonucleotides permitting the amplification of all or part of the PTPN11 gene, the DNA contained in the sample having being rendered accessible, where appropriate, to hybridization, and under conditions permitting a hybridization of the primers with the DNA contained in the biological sample;

b) amplifying said DNA;

c) detecting the amplification products;

d) comparing the amplified products as obtained to the amplified products obtained with a normal control biological sample, and thereby detecting a possible abnormality in the PTPN11 gene.

The method of the invention can also be applied to the detection of an abnormality in the transcript of the PTPN11 gene, e.g. by amplifying the mRNAs contained in a biological sample, for example by RT-PCR.

Thus another subject of the present invention is a method of in vitro diagnosis of NS, as previously defined comprising the steps of:

a) producing cDNA from mRNA contained in a biological sample;

b) contacting said cDNA with specific oligonucleotides permitting the amplification of all or part of the transcript of the PTPN11 gene, under conditions permitting a hybridization of the primers with said cDNA;

c) amplifying said cDNA;

d) detecting the amplification products;

e) comparing the amplified products as obtained to the amplified products obtained with a normal control biological sample, and thereby detecting a possible abnormality in the transcript of the PTPN11 gene.

For RNA analysis, the biological sample may be any cell source, as described above, such as a biopsy tissue, from which RNA is isolated using standard methods well known to those of ordinary skill in the art such as guanidium thiocyanate-phenol-chloroform extraction (Chomocyznski et al., Anal. Biochem., 1987, 162:156). The isolated RNA is then subjected to coupled reverse transcription and amplification by polymerase chain reaction (RT-PCR), using specific oligonucleotide primers that are specific for a selected site. Conditions for primer annealing are chosen to ensure specific reverse transcription and amplification; thus, the appearance of an amplification product is diagnostic of the presence of a particular genetic variation. In another embodiment, RNA is reverse-transcribed and amplified, after which the amplified sequences are identified by, e.g., direct sequencing. In still another embodiment, cDNA obtained from the RNA can be cloned and sequenced to identify a mutation.

The PTPN11 nucleic acids of the invention can also be used as probes, e.g., in therapeutic and diagnostic assays. For instance, the present invention provides a probe comprising a substantially purified oligonucleotide, which oligonucleotide comprises a region having a nucleotide sequence that is capable of hybridizing specifically to a region of a PTPN11 gene which differs from that of the wild-type gene (SEQ ID NO: 33), e.g., a mutant or polymorphic region. Such probes can then be used to specifically detect which mutation of the PTPN11 gene is present in a sample taken from a subject. The mutant or polymorphic region can be located in the promoter, exon, or intron sequences of the PTPN11 gene.

For example, preferred probes of the invention include one or more of the nucleotide substitutions listed in Table 1, as well as the wild-type flanking regions (see, e.g., SEQ ID NOS: 1 or 33). For each such probe, the complement of that probe is also included in the Table as a preferred probe of the invention. Particularly preferred probes of the invention have a number of nucleotides sufficient to allow specific hybridization to the target nucleotide sequence. Thus, probes of suitable lengths based on SEQ ID NO:1 or 33 and complementary to the mutant sequences provided herein can be constructed and tested by the skilled artisan for appropriate level of specificity depending on the application intended. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of the PTPN11 gene may first be amplified and thus isolated from the rest of the chromosomal DNA and then hybridized to a probe. In such a situation, a shorter probe will likely provide sufficient specificity of hybridization. For example, a probe having a nucleotide sequence of about 10 nucleotides may be sufficient, although probes of about 15 nucleotides, even more preferably 20 nucleotides, are preferred.

In a preferred embodiment, the probe or primer further comprises a label attached thereto, which preferably is capable of being detected. The label can, for example, be selected from radioisotopes, fluorescent compounds, enzymes, and enzyme co-factors.

In another preferred embodiment of the invention, the isolated nucleic acid, which is used, e.g., as a probe or a primer, is modified, such as to become more stable. Exemplary nucleic acid molecules which are modified include phosphoramidate, phosphothioate and methylphosphonate analogs of DNA (see also U.S. Pat. Nos. 5,176,996; 5,264,564; and 5,256,775).

In yet another embodiment, one may use HPLC or denaturing HPLC (DHPLC) techniques to analyze the PTPN11 nucleic acids. DHPLC was developed when observing that, when HPLC analyses are carried out at a partially denaturing temperature, i.e., a temperature sufficient to denature a heteroduplex at the site of base pair mismatch, homoduplexes can be separated from heteroduplexes having the same base pair length (Hayward-Lester, et al., Genome Research, 1995, 5:494; Underhill, et al., Proc. Natl. Acad. Sci. USA,1996, 93:193; Doris, et al., DHPLC Workshop, 1997, Stanford University). Thus, the use of DHPLC was applied to mutation detection (Underhill, et al., Genome Research,1997, 7:996; Liu, et al., Nucleic Acid Res., 1998, 26;1396). DHPLC can separate heteroduplexes that differ by as little as one base pair. "Matched Ion Polynucleotide Chromatography" (MIPC), or Denaturing "Matched Ion Polynucleotide Chromatography" (DMIPC) as described in U.S. Pat. Nos. 6,287,822 or 6,024,878, are separation methods that can also be useful in connection with the present invention.

Alternatively, one can use the DGGE method (Denaturing Gradient Gel Electrophoresis), or the SSCP method (Single Strand Conformation Polymorphism) for detecting an abnormality in the PTPN11 gene. DGGE is a method for resolving two DNA fragments of identical length on the basis of sequence differences as small as a single base pair change, using electrophoresis through a gel containing varying concentrations of denaturant (Guldberg et al., Nuc. Acids Res. 1994, 22:880). SSCP is a method for detecting sequence differences between two DNAs, comprising hybridization of the two species with subsequent mismatch detection by gel electrophoresis (Ravnik-Glavac et al., Hum. Mol. Genet. 1994, 3:801). "HOT cleavage", a method for detecting sequence differences between two DNAs, comprising hybridization of the two species with subsequent mismatch detection by chemical cleavage (Cotton, et al., Proc. Natl. Acad. Sci. USA 1988, 85:4397), can also be used. Such methods are preferably followed by direct sequencing. Advantageously, the RT-PCR method may be used for detecting abnormalities in the PTPN11 transcript, as it allows to visualize the consequences of a splicing mutation such as exon skipping or aberrant splicing due to the activation of a cryptic site. Preferably this method is followed by direct sequencing as well.

More recently developed techniques using microarrays, preferably microarray techniques allowing for high-throughput screening, can also be advantageously implemented for detecting an abnormality in the PTPN11 gene or for assaying expression of the PTPN11 gene or the gene of another component in the PTPN11 pathway resulting in increased signaling as described herein. Microarrays may be designed so that the same set of identical oligonucleotides is attached to at least two selected discrete regions of the array, so that one can easily compare a normal sample, contacted with one of said selected regions of the array, against a test sample, contacted with another of said selected regions. These arrays avoid the mixture of normal sample and test sample, using microfluidic conduits. Useful microarray techniques include those developed by Nanogen, Inc (San Diego,Calif.) and those developed by Affymetrix. However, all types of microarrays, also called "gene chips" or "DNA chips", may be adapted for the identification of mutations. Such microarrays are well known in the art (see for example the following: U.S. Pat Nos. 6,045,996; 6,040,138; 6,027,880;6,020, 135; 5,968,740; 5,959,098; 5,945,334; 5,885,837; 5,874, 219; 5,861,242; 5,843,655; 5,837,832; 5,677,195 and 5,593, 839).

The solid support on which oligonucleotides are attached may be made from glass, silicon, plastic (e.g., polypropylene, nylon), polyacrylamide, nitrocellulose, or other materials. One method for attaching the nucleic acids to a surface is by printing on glass plates, as is described generally by Schena et al., Science 1995, 270:467-470. This method is especially useful for preparing microarrays of cDNA. See also DeRisi et al., Nature Genetics 1996, 14:457-460, ; Shalon et al., Genome Res. 1996, 6:639-645; and Schena et al., Proc. Natl. Acad. Sci. USA 1995, 93:10539-11286. Another method of making microarrays is by use of an inkjet printing process to bind genes or oligonucleotides directly on a solid phase, as described, e.g., in U.S. Pat. No. 5,965,352.

Other methods for making microarrays, e.g., by masking (Maskos and Southern, Nuc. Acids Res. 1992, 20:1679-1684), may also be used. In principal, any type of array, for example, dot blots on a nylon hybridization membrane (see Sambrook et al., Molecular Cloning A Laboratory Manual (2nd Ed.), Vol. 1-3, Cold Spring Harbor Laboratory, Cold Spring Harbor, N.Y., 1989) could be used, although, as will be recognized by those of skill in the art, very small arrays will be preferred because hybridization volumes will be smaller. For these assays nucleic acid hybridization and wash conditions are chosen so that the attached oligonucleotides "specifically bind" or "specifically hybridize" to at least a portion of the PTPN11 gene present in the tested sample, i.e., the probe hybridizes, duplexes or binds to the PTPN11 locus with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., Science 1996, 274:610-614).

A variety of methods are available for detection and analysis of the hybridization events. Depending on the reporter group (fluorophore, enzyme, radioisotope, etc.) used to label the DNA probe, detection and analysis are carried out fluorimetrically, colorimetrically or by autoradiography. By observing and measuring emitted radiation, such as fluorescent radiation or a particle emission, information may be obtained about the hybridization events.

When fluorescently labeled probes are used, the fluorescence emissions at each site of transcript array can, preferably be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. Genome Res. 1996, 6:639-695).

Protein Based Assays

As an alternative to analyzing PTPN11 nucleic acids, one can evaluate PTPN11 on the basis of mutations in the protein, or dysregulated production, e.g. overproduction, of the protein. In addition, PTPN11 phosphatase and/or ERK kinase activity can be evaluated to determine increased activity of a PTPN11 signaling pathway such as the RAS-MAPK pathway.

In preferred embodiments, PTPN11 or ERK2 are detected by immunoassay. For example, Western blotting permits detection of a specific variant, or the presence or absence of PTPN11 or ERK2. In particular, an immunoassay can detect a specific (wild-type or mutant) amino acid sequence in a PTPN11 protein. Other immunoassay formats can also be used in place of Western blotting, as described below for the production of antibodies. One of these is ELISA assay.

In ELISA assays, an antibody against PTPN11, an epitopic fragment of PTPN11, or ERK2, is immobilized onto a selected surface, for example, a surface capable of binding proteins such as the wells of a polystyrene microtiter plate. After washing to remove incompletely adsorbed polypeptides, a nonspecific protein such as a solution of bovine serum albumin (BSA) may be bound to the selected surface. This allows for blocking of nonspecific adsorption sites on the immobilizing surface and thus reduces the background caused by nonspecific bindings of antisera onto the surface. The immobilizing surface is then contacted with a sample, to be tested in a manner conductive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures between about 25° to 37° C. Following incubation, the sample-contacted surface is washed to remove non-immunocomplexed material. The washing procedure may include washing with a solution, such as PBS/Tween or borate buffer. Following formation of specific immunocomplexes between the test sample and the bound antibody, and subsequent washing, the occurrence, and an even amount of immunocomplex formation may be determined by subjecting the immunocomplex to a second antibody against PTPN11 or ERK2, that recognizes a different epitope on the protein. To provide detecting means, the second antibody may have an associated activity such as an enzymatic activity that will generate, for example, a color development upon incubating with an appropriate chromogenic substrate. Quantification may then be achieved by measuring the degree of color generation using, for example, a visible spectra spectrophotometer.

Typically the detection antibody is conjugated to an enzyme such as peroxidase and the protein is detected by the addition of a soluble chromophore peroxidase substrate such as tetramethylbenzidine followed by 1 M sulfuric acid. The test protein concentration is determined by comparison with standard curves.

These protocols are detailed in Current Protocols in Molecular Biology, V. 2 Ch. 11 and Antibodies, a Laboratory Manual, Ed Harlow, David Lane, Cold Spring Harbor Laboratory (1988) pp 579-593.

Alternatively, a biochemical assay can be used to detect expression, or accumulation of PTPN11 or ERK2, e.g., by detecting the presence or absence of a band in samples analyzed by polyacrylamide gel electrophoresis; by the presence or absence of a chromatographic peak in samples analyzed by any of the various methods of high performance liquid chromatography, including reverse phase, ion exchange, and gel permeation; by the presence or absence of PTPN11 or ERK2 in analytical capillary electrophoresis chromatography, or any other quantitative or qualitative biochemical technique known in the art.

The immunoassays discussed above involve using antibodies directed against the PTPN11 protein or fragments thereof. The production of such antibodies is described below. Production of anti-ERK2 antibodies, or other components of a PTPN11 pathway, can be prepared in a similar manner.

Anti-PTPN11 Antibodies

Such antibodies include but are not limited to polyclonal, monoclonal, chimeric, single chain, Fab fragments, and Fab expression library.

Various procedures known in the art may be used for the production of polyclonal antibodies to PTPN11 polypeptides or derivative or analog thereof. For the production of antibody, various host animals can be immunized by injection with the antigenic polypeptide, including but not limited to rabbits, mice, rats, sheep, goats, etc.

For preparation of monoclonal antibodies directed toward the PTPN11 polypeptides, any technique that provides for the production of antibody molecules by continuous cell lines in culture may be used. These include but are not limited to the hybridoma technique originally developed by Kohler and Milstein (Nature 256:495-497, 1975), as well as the trioma technique, the human B-cell hybridoma technique (Kozbor et al., Immunology Today 4:72, 1983; Cote et al., Proc. Natl. Acad. Sci. U.S.A. 80:2026-2030, 1983), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published Dec. 28, 1989).

According to the invention, techniques described for the production of single chain antibodies (U.S. Pat. Nos. 5,476,786 and 5,132,405 to Huston; U.S. Pat. No. 4,946,778) can be adapted to produce the PTPN11 polypeptide-specific single chain antibodies. Indeed, these genes can be delivered for expression in vivo. An additional embodiment of the invention utilizes the techniques described for the construction of Fab expression libraries (Huse et al., Science 246: 1275-1281, 1989) to allow rapid and easy identification of monoclonal Fab fragments with the desired specificity for a PTPN11 polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

PTPN11 and ERK2 Activity Assays

As described herein, increased activity or level of PTPN11 or other components in a PTPN11 signaling pathway is indicative of NS.

In one embodiment one may assess the activity of the PTPN11 protein in a test subject or biological sample taken from the subject and compare it with a control. An increased activity of the PTPN11 protein in the test subject or biological sample compared with the control is indicative of NS in the test subject.

The activity of PTPN11 may be indirectly assayed by evaluating the level of expression, accumulation or activity of down-stream effectors, as described above. Preferred target are MAP kinases, such as ERK1 or ERK2. The nucleic acid-based assays or protein-based assays as described above may be readily adapted for that purpose.

Since PTPN11 is a phosphatase, the basal activity of PTPN11 in a test subject may be easily determined by assessing the phosphorylation level of peptides or proteins contacted with the test PTPN11 protein. For example, phosphorylation of PTPN11 docking partners such as Gab1, Gab2, Grb2, or gp130, as well as peptides such as src, may be assessed. The levels of phosphorylation of proteins can be assessed by various methods, including immunoassays or radiolabelling. Kits for assessing phosphorylation activity are commercially available, e.g., from from Upstate Biotechnology, Inc. (Lake Placid, N.Y.) under the name "PTP Assay Kit 1", and from Calbiochem (San Diego, Calif.) under the name "Fluorometric Protein Tyrosine Phosphatase Assay Kit."

One example of a PTPase activity assay is as follows: To activate PTPase activity, a synthesized phosphotyrosine peptide (Genemed Synthesis), PY627PY659, is used over a concentration range of 0-20 µM. PTPase reactions are carried out in 25 µl mixtures at 30° C. for 5 min in 50 mM Hepes (pH 7.2), 0.2% BSA, 1 mM EDTA, and 1 mM DTT, and the reactions stopped by addition of 20 µl Malachite Green/Tween-20 solution. After 30 min at RT, absorbance at 620 nm is determined with a microplate reader. A standard curve of free phosphate concentrations is prepared using $KH_2PO_4$, treated identically to the PTPase conditions. All conditions are repeated in triplicate.

In one embodiment, the level of phosphorylation of a peptide or protein is assessed by utilizing a binding partner, which should preferably be highly specific for the phospho-epitope on the target protein. It is preferred that the binding partner is an antibody. The antibody is preferably generated against a unique epitope of the substrate. In an alternative embodiment, the binding partner should be specific for the phosphorylated form of the target protein. The detection procedure used to assess the phosphorylation state of the protein may for instance employ an antibody or a peptide that recognizes and binds to phosphorylated serines, threonines or tyrosines. The detection antibody is preferably a polyclonal antibody, to maximize the signal, but may also be specific monoclonal antibodies which have been optimized for signal generation.

An exemplary PTPase assay based on immunoprecipitation is as follows:

Step I: Immunoprecipitation of Phosphatase

To maximize Phosphatase activity, all reactions should be carried out on ice, and pulse spinning should be carried out in a centrifuge equilibrated at 4° C.

1. Add 4 µl-5 µl of an anti-Phosphatase antibody to a microcentrifuge tube.

2. Add 100 µl (50 µl packed beads) of Protein A or G agarose bead slurry, (which has been washed free of phosphate) and suspended in a cell lysis buffer optimized for phosphatases.

3. Add 100 µl of ice-cold phosphatase cell lysis buffer (optionally containing protease inhibitors, but must be free of phosphatase inhibitors).

4. Incubate for 30 minutes to 1 hour at 4° C. on a rotator to thoroughly mix the components during the incubation.

5. Pellet the agarose beads at 14,000 rpm for 15 seconds.

6. Remove the supernatant. Wash the protein A or G agarose beads in cell lysis buffer to remove weakly bound antibodies. This wash removes any form of antibody that does not bind to the protein A or G agarose, but which may bind to a tissue extract or cell lysate.

7. Resuspend the washed beads pellet in 100 µl of phosphatase cell lysis buffer.
8. Add whole cell/tissue extracts (about 500 µg-1 mg) containing active phosphatase to the beads.
9. Incubate for 2 hours on a rotator at 4° C. to immunoprecipitate active phosphatase.
10. Wash the protein A or G agarose/enzyme immunocomplex two to three times with 500 µl of phosphatase cell lysis buffer.
11. Wash the protein A or G agarose/enzyme immunocomplex twice with 100 µl of 1×phosphatase assay dilution buffer found to be suitable (e.g., HEPES, glycerol and EDTA buffer can be used as a start, and modified as necessary).
12. Pellet the immunocomplex at 14,000 rpm for 15 minutes and remove the supernatant fraction from the immunocomplex. Place on ice and proceed to Step II.

Step II: Malachite Green Phosphatase Assay of the Enzyme Immunocomplex

1. Add 50 µl of a 1×phosphatase buffer containing phosphothreonine peptide (KRµTIRR) to the immunocomplex.
2. Incubate overnight at 37° C. or, if preferred, for 30 minutes in a 30° C. shaking incubator. After the incubation, pulse spin to pellet the protein A or G-Agarose/enzyme immunocomplex. Note: the assay mixture must be thoroughly mixed throughout the reaction time to ensure that the peptide substrate and the enzyme immunocomplex achieve maximum interaction.
3. Add a suitable amount (e.g., 1, 2, 5, or 10 µl) of the supernatant into a 96 well plate and add Malachite Green solution (Van Veldhoven et al., Anal Biochem 1987;161:45-48) to assess for the liberation of phosphate measured in picomoles from the standard curve.

To assess for specific phosphatase activity, the phosphate levels detected with protein A or G-agarose beads incubated with cell lysates in the absence of antibody can be used as a control. Any buffer components should be checked for free phosphate, and the assay optimized as to not inhibit phosphatase activity. In addition, because the assay measures free phosphate, phosphate buffers are not compatible with this system. Thus, reaction components that contain phosphate (i.e., glycerol phosphate) may interfere with the analysis, depending on their concentration, purity and stability in strong acid. Also, high concentrations of reductants may bleach the dye color over time resulting in lower sensitivity. A final concentration of 0.02% p-mercaptoethanol has no effect on sensitivity; 0.05% p-mercaptoethanol has only a slight effect, and 0.1% p-mercaptoethanol results in an approximate 20% reduction in sensitivity. Many detergents at or below 0.1% can be used, but higher concentrations may generate high backgrounds. If high concentrations of detergent are required in the reaction, the background can be determined by including the corresponding concentration of the detergent in the Phosphate Standard curve.

ERK activity, in particular ERK2 activity, can be assessed by measuring kinase activity, i.e., transfer of phosphate from ATP to a second substrate. Many such assays are known in the art, and an exemplary ERK2 assay is provided in Example 2.

Alternatively, immunoassays may be replaced by the detection of radiolabeled phosphate according to a standard technique. This involves incubating cells with the test substances and radiolabeled phosphate, lysing the cells, separating cellular protein components of the lysate using as SDS-polyacrylamide gel (SDS-PAGE) technique, in either one or two dimensions, and detecting the presence of phosphorylated proteins by exposing X-ray film.

The phosphorylation of a protein may also be conveniently detected by migration on gel subject to electrophoresis, followed by Western blotting. Phosphorylation is detected by a shift of the molecular weight of the protein occurs, a phosphorylated protein being heavier than the corresponding non-phosphorylated form.

Diagnostic Kits

The present invention further provides kits for the determination of the sequence within the PTPN11 gene in an individual. The kits comprise a means for determining the sequence at the variant positions, and may optionally include data for analysis of mutations. The means for sequence determination may comprise suitable nucleic acid-based and immunological reagents. Preferably, the kits also comprise suitable buffers, control reagents where appropriate, and directions for determining the sequence at a variant position.

Nucleic Acid Based Diagnostic Kits

The invention provides nucleic acid-based methods for detecting genetic variations of PTPN11 in a biological sample. The sequence at particular positions in the PTPN11 gene is determined using any suitable means known in the art, including without limitation one or more of hybridization with specific probes for PCR amplification (e.g., primer pairs selected from SEQ ID NOS: 3-32), restriction fragmentation, direct sequencing, SSCP, and other techniques known in the art.

The present invention also provides kits suitable for nucleic acid-based diagnostic applications. In one embodiment, diagnostic kits include the following components:

a) Probe DNA: The probe DNA may be pre-labeled; alternatively, the probe DNA may be unlabeled and the ingredients for labeling may be included in the kit in separate containers; and b) Hybridization reagents: The kit may also contain other suitably packaged reagents and materials needed for the particular hybridization protocol, including solid-phase matrices, if applicable, and standards.

In another embodiment, diagnostic kits include:

a) Sequence determination primers: Sequencing primers may be pre-labeled or may contain an affinity purification or attachment moiety; and b) Sequence determination reagents: The kit may also contain other suitably packaged reagents and materials needed for the particular sequencing protocol.

In one preferred embodiment, the kit comprises a panel of sequencing primers, whose sequences correspond to sequences adjacent to variant positions.

Antibody Based Diagnostic Kits

The invention also provides antibody-based methods for detecting mutant (or wild type) PTPN11 proteins in a biological sample. The methods comprise the steps of: (i) contacting a sample with one or more antibody preparations, wherein each of the antibody preparations is specific for mutant (or wild type) PTPN11 under conditions in which a stable antigen-antibody complex can form between the antibody and PTPN11 in the sample; and (ii) detecting any antigen-antibody complex formed in step (i) using any suitable means known in the art, wherein the detection of a complex indicates the presence of mutant (or wild type) PTPN11.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labeled immunoassays, such as ELISA assays.

The present invention also provides kits suitable for antibody-based diagnostic applications. Diagnostic kits typically include one or more of the following components:

(i) PTPN11-specific antibodies: The antibodies may be pre-labeled; alternatively, the antibody may be unlabeled and the ingredients for labeling may be included in the kit in separate containers, or a secondary, labeled antibody is provided; and (ii) Reaction components: The kit may also contain other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput and/or automated operation.

Therapeutics

The present invention further provides a method for the treatment of NS, which method comprises modulating PTPN11 activity in a subject or patient. The method comprises administering to a patient in need of such treatment an effective amount of an agent that modulates PTPN11 expression or activity, with a pharmaceutically acceptable carrier. For example, the therapeutic agent may be a PTPN11 antisense nucleic acid, or an anti-PTPN1 intracellular inhibitory antibody. Agents that block either the N-SH2, C-SH2, or PTP domains of the PTPN11 proteins are of particular interest. Preferably, although not necessarily, the agent blocks the PTP domain so that PTPase activity is inhibited.

A "subject" or "patient" is a human or an animal likely to develop NS, more particularly a mammal, preferably a rodent or a primate, as described above in connection with diagnostic applications. Prenatal treatment is particularly envisioned.

The term "treatment" means to therapeutically intervene in the development of a disease in a subject showing a symptom of this disease. The term "treatment" also encompasses prevention, which means to prophylactically interfere with a pathological mechanism that results in the disease.

The term "modulating PTPN11 activity" in a subject means modifying it so that it is rendered as close as possible to the normal PTPN11 activity of a control subject. It especially encompasses inhibiting, or blocking the activity of the PTPN11 protein in the NS patient. Preferred modulators block any of the functional domains of the PTPN11 of the protein, especially the consitutively active PTP domain. "Modulating PTPN11 activity" also encompasses restoring SH2 domain activity.

The modulation activity may be achieved by various methods, as described hereafter.

In one embodiment, the modulatory agent may be a substance that is known or has been identified to modulate, especially inhibit, whether fully or partially, PTPN11 activity. Such compounds can include any compound(s) described in, for example, the International Patent Publication WO99/46267 and in Ann Rev Pharmocol Toxicol 2002;42:209-234; Exp Mol Med 2002;31:211-223; Biochem 2002;41:10700-10709; and J Immunol 167:3391-3397, 2001, as well as other compounds shown to inhibit PTPN1 activity as described herein. For example, this modulatory agent may be a candidate drug as identified by a screening method. It may also be an inhibitory antibody directed against PTPN11. In a further embodiment, it may be an antisense nucleic acid. All these embodiments are described in greater detail below.

The term "therapeutically effective amount" is used herein to mean an amount or dose sufficient to modulate, e.g., decrease the level of PTPN11 activity e.g., by about 10 percent, preferably by about 50 percent, and more preferably by about 90 percent. Preferably, a therapeutically effective amount can ameliorate or present a clinically significant deficit in the activity, function and response of the subject. Alternatively, a therapeutically effective amount is sufficient to cause an improvement in a clinically significant condition in the host.

The substance that modulates or inhibits PTPN11 activity is advantageously formulated in a pharmaceutical composition, with a pharmaceutically acceptable carrier. This substance may be then called active ingredient or therapeutic agent against NS.

The concentration or amount of the active ingredient depends on the desired dosage and administration regimen, as discussed below. Suitable dose ranges may include from about 0.01 mg/kg to about 100 mg/kg of body weight per day.

The pharmaceutical compositions may also include other biologically active compounds.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

According to the invention, the pharmaceutical composition of the invention can be introduced parenterally, transmucosally, e.g., orally (per os), nasally, or rectally, or transdermally. Parental routes include intravenous, intra-arteriole, intramuscular, intradermal, subcutaneous, intraperitoneal, intraventricular, and intracranial administration. Targeting heart, e.g. by direct administration to heart muscle or cavities, may be advantageous.

The pharmaceutical compositions may be added to a retained physiological fluid such as blood or synovial fluid.

In another embodiment, the active ingredient can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the therapeutic compound can be delivered in a controlled release system. For example, a polypeptide may be administered using intravenous infusion with a continuous pump, in a polymer matrix such as polylactic/glutamic acid (PLGA), a pellet containing a mixture of cholesterol and the active ingredient (SilasticR™; Dow Coming, Midland, Mich.; see U.S. Pat. No. 5,554,601) implanted subcutaneously, an implantable osmotic pump, a transdermal patch, liposomes, or other modes of administration.

Screening Methods

A "test substance" is a chemically defined compound or mixture of compounds (as in the case of a natural extract or tissue culture supernatant), whose ability to modulate PTPN11 activity may be defined by various assays. A "test substance" is also referred to as a "candidate drug" in the present description.

Test substances may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech 1996, 14:60).

A modulatory effect may be determined by an in vitro method using a recombinant PTPN11-reporter gene promoter activity system.

Reporter genes for use in the invention encode detectable proteins, include, but are by no means limited to, chloramphenicol transferase (CAT), β-galactosidase (β-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

A screen according to the invention involves detecting expression of the reporter gene by the host cell when contacted with a test substance. If there is no change in expression of the reporter gene, the test substance is not an effective modulator. If reporter gene expression is modified, in particular reduced or eliminated, the test substance has modulated, e.g., inhibited, PTPN11-mediated gene expression, and is thus a candidate for development of an NS therapeutic.

The reporter gene assay system described here may be used in a high-throughput primary screen for antagonists, or it may be used as a secondary functional screen for candidate compounds identified by a different primary screen, e.g., a binding assay screen that identifies compounds that modulate PTPN11 transcription activity.

Potential drugs may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679, 582, and 6,020,141). Such high-throughput screening methods are particularly preferred. Alternatively, simple reporter-gene based cell assays such as the one described here are also highly desirable.

Intact cells or whole animals expressing a gene encoding PTPN11 can be used in screening methods to identify candidate drugs.

In one series of embodiments, a permanent cell line is established. Alternatively, cells are transiently programmed to express a PTPN11 gene by introduction of appropriate DNA or mRNA.

Identification of candidate substances can be achieved using any suitable assay, including without limitation (i) assays that measure selective binding of test compounds to PTPN11 (ii) assays that measure the ability of a test substance to modify (i.e., inhibit) a measurable activity or function of PTPN11 and (iii) assays that measure the ability of a substance to modify (i.e., inhibit) the transcriptional activity of sequences derived from the promoter (i.e., regulatory) regions of the PTPN11 gene.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways, e.g. to enhance their proteolytic stability.

Inhibitory Antibodies

The modulatory substance may also be an antibody that is directed against PTPN11. Antibodies that block the activity of PTPN11 may be produced and selected according to any standard method well-known by one skilled in the art, such as those described above in the context of diagnostic applications.

Intracellular antibodies (sometime referred to as "intrabodies") have been used to regulate the activity of intracellular proteins in a number of systems (see, Marasco, Gene Ther. 1997, 4:11; Chen et al., Hum. Gene Ther. 1994, 5:595), e.g., viral infections (Marasco et al., Hum. Gene Ther. 1998, 9:1627) and other infectious diseases (Rondon et al., Annu. Rev. Microbiol. 1997, 51:257), and oncogenes, such as p21 (Cardinale et al., FEBS Lett. 1998, 439:197-202; Cochet et al., Cancer Res. 1998, 58:1170-6), myb (Kasono et al., Biochem Biophys Res Commun. 1998, 251:124-30), erbB-2 (Graus-Porta et al., Mol Cell Biol. 1995, 15:1182-91), etc. This technology can be adapted to inhibit PTPN11 activity by expression of an anti-PTPN11 intracellular antibody.

Antisense Therapy

In another embodiment, vectors comprising a sequence encoding an antisense nucleic acid according to the invention may be administered by any known methods, such as the methods for gene therapy available in the art. Exemplary methods are described below. For general reviews of the methods of gene therapy, see, Goldspiel et al., Clinical Pharmacy 1993, 12:488-505; Wu and Wu, Biotherapy 1991, 3:87-95; Tolstoshev, Ann. Rev. Pharmacol. Toxicol. 1993, 32:573-596; Mulligan, Science 1993, 260:926-932; and Morgan and Anderson, Ann. Rev. Biochem. 1993, 62:191-217; May, TIBTECH 1993, 11:155-215. Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al., (eds.), 1994, Current Protocols in Human Genetics, John Wiley & Sons, NY.

In one embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, Proc. Natl. Acad. Sci. USA 1989, 86:8932-8935; Zijlstra et aL., Nature 1989, 342:435-438).

Delivery of the vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

In a specific embodiment, the vector is directly administered in vivo, where it enters the cells of the organism and mediates expression of the construct. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-β-1-→4-N-acetylglucosamine polysaccharide; see , U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, J. Biol. Chem. 1987, 62:4429-4432), etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., Mol. Therapy 2000, 2:339-47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188).

Preferred examples of specific anti-PTPN11 antisense sequences are any of the sequences described in U.S. Pat. No. 6,200,807, owned by Isis Pharmaceuticals. Antisense compounds that are 8 to 30 nucleobases in length and are targeted to a region selected from the 5' untranslated region, the start codon, the region from nucleotides 298 through 1883 of the coding region, the stop codon, or the 3' untranslated region of human PTPN11, are of particular interest.

Examples of practicing the invention are provided, and are understood to be exemplary only, and do not limit the scope of the invention or the appended claims. A person of ordinary skill in the art will appreciate that the invention can be practiced in many forms according to the claims and disclosures here.

EXAMPLE 1

Detection of Mutations in PTPN11 Gene

Methods

Subject recruitment. Subjects with NS were recruited, primarily through a GeneTests listing, and informed consent was obtained from all subjects. The diagnosis of NS was assigned based on clinical evaluations from the referring clinical geneticists.

Molecular analysis. Genomic DNA was isolated from peripheral blood lymphocytes (Gentra). Genotyping was carried out using dye-labeled simple tandem repeat markers, D12S84, D12S105, D12S354 and D12S2070 (Research Genetics). PCR products were resolved by using the ABI Prism 377 DNA Sequencer (Perkin Elmer), and genotype determinations were conducted using the GeneScan v. 3.1 and Genotyper v. 2.1 software packages (Perkin Elmer).

Genomic and cDNA sequences for PTPN11 were compared using DNA analysis software (MacVector) and predictions of the gene organization were made using the NIX software package (UK HGMRP). Mutational screening of PTPN11 was carried out by direct sequencing of purified PCR products bi-directionally using the ABI BigDye terminator Sequencing Kit (Perkin Elmer) and the ABI 3700 Capillary Array Sequencer (Perkin Elmer). Sequences were analyzed using Sequencing Analysis v. 3.6.1 and AutoAssembler v. 1.4.0 software packages (Perkin Elmer). To confirm sequence changes in affected individuals and exclude them from unaffected family members and controls, the relevant exons were PCR amplified and then digested with restriction endonucleases (BglI for G214T and C215G, BsaWI for A236G and EcoRV for A922G) according to manufacturer's instructions (New England Biolabs), or analyzed by DHPLC (A844G and A1510G) using the Wave DNA Fragment Analysis System (Transgenomics) at column temperatures recommended by the WaveMaker version 4.0.28 software (Transgenomics).

Results

Mutation screening was initially conducted with two moderate-sized families (called NS-C and NS-L), in which the NS phenotype co-segregated with haplotypes defined by D12S84, D12S105, D12S354 and D12S2070. Bi-directional sequencing of the fifteen PTPN11 exons and their intron boundaries for family NS-C revealed a G-to-T transversion at position 214 in exon 3, predicting the substitution of Ala72 by a Ser residue (A72S) in the N-SH2 domain.

This sequence change was confirmed with a PCR-based RFLP assay that documented its presence in all affected family members and its absence among unaffected ones. This change was not observed in more than 200 control individuals. Sequence comparison of PTPN11 with its orthologues and other closely related PTPases revealed complete conservation of Ala$^{72}$. Analysis of family NS-L revealed an A-to-G transition at position 236 in exon 3. This change predicted the substitution of Gln79 by an Arg (Q79R), affecting another highly conserved residue in the N-SH2 domain. This sequence change was confirmed in all affected individuals in this family, but was absent in unaffected family members and controls.

Sequence analysis of amplified DNA containing the PTPN11 exon 3 and flanking intronic boundaries that revealed heterozygous changes in the NS-C and NS-L families is shown in FIGS. 3A, 3B, 4A and 4B.

Since NS is genetically heterogeneous, the relative importance of PTPN11 defects in the epidemiology of NS was considered. Mutation screening was performed with 14 unrelated individuals affected with NS, either sporadic cases or small kindreds for which linkage analysis would not have been informative. Among these 14, PTPN11 missense mutations were identified in seven (Table 2).

TABLE 2

PTPN11 and PTPN11 Mutations Among Familial And Sporadic Noonan Syndrome Cases

| Family ID | Nucleotide substitution | Exon | Amino acid substitution | Functional domain |
|---|---|---|---|---|
| NS-C | G214T | 3 | A72S | N-SH2 |
| NS-U | C215G | 3 | A72G | N-SH2 |
| NS-L, NS-D | A236G | 3 | Q79R | N-SH2 |
| NS-F | A844G | 7 | I282V | PTP |
| NS-A, NS-B, NS-V | A922G | 8 | N308D | PTP |
| NS-N | A1510G | 13 | M504V | PTP |

Ala$^{72}$ was altered by a second mutation, which was observed in family NS-U, a C-to-G transversion at nucleotide 215 that predicted its substitution with a Gly (A72G). The Q79R mutation was recurrent in sporadic case NS-D. Three missense mutations affecting the PTP domain were observed, one being recurrent. An A-to-G transition at nucleotide 922 in exon 8 was found in families NS-A and NS-V as well as sporadic case NS-B. This change predicted the substitution of Asn$^{308}$ with an Asp residue (N308D). Sporadic cases NS-F and NS-N had A-to-G transitions of nucleotides 844 and 1510, respectively, leading to substitutions of Ile$^{282}$ and Met$^{504}$ with Val residues (I282V and M504V, respectively). For familial cases, mutations co-segregated with the NS phenotype, and no mutation was found among greater than 200 controls. All amino acid substitutions affected highly conserved residues of PTPN11. The results of this small series, combined with those from the two chromosome 12-linked families, suggest that greater than 50% of NS cases can be attributed to PTPN11 mutations.

EXAMPLE 2

Molecular Consequences Of PTPN11 Mutations

To explore the molecular consequences of the amino acid substitutions, crystallographic information about PTPN11 was exploited (Lee, et al., Structure, 1994, 2:423-438; Eck et al, Nature, 1996, 379:277-280; Hof et al, Cell, 1998, 92:441-450).

Methods

Computational methods. Recently, a protocol was devised for calculating the (unknown) structure of segments connecting known elements of secondary structure in proteins. The approach consists of two steps where first Monte Carlo-simulated annealing is carried out to allow the segment to find all structures that are intrinsic to its sequence, while it remains tethered to the protein only at its amino terminus. In the second step, MC-SCV (Noguti et al Biopolymers, 1985, 24:527-546) is used to drive the carboxy terminus to its attachment point. The entire procedure has been programmed into the CHARMM suite of programs (Brooks, et al. J. Comput. Chem, 1983, 4:165-175) using the PAR22 all-atom force field (MacKerell, et al. J. Phys. Chem. B, 1998, 102:3586-3616). The method is fully described in Hassan, S. A., Mehler, E. L. & Weinstein, H. *Structure calculations of protein segments connecting domains with defined secondary structure: A simulated annealing Monte Carlo combined with biased scaled collective variables technique*. In Lecture Notes Series in Computational Science and Engineering, Vol. 24 (eds. T. Schlick and H. H. Gan), pp. 197-231 (Springer Verlag, New York, 2002).

In the present calculations, the first step of the general procedure was modified. Starting from the native conformation, the segment was cut between E76 and L77, and a long MC-SCV simulation was carried out on the nine residue segment Gly$^{68}$-Glu$^{76}$ at T=310K. In this step, only a few fixed residues at the amino and carboxy termini of the variable segment were included in the calculation. This step allowed the segment to relax and explore conformation space to find conformations intrinsic to its sequence and resulted in a large number of conformations that provide the starting structures for the second step. To reduce the calculation, the structures were first clustered (Shenkin, et al. J. Comput. Chem., 1994, 15:899-916).on the basis of structural similarity and a representative from each class (n=31) was used.

In the second step, MC-SCV (Noguti et al., Biopolymers, 1985, 24:527-546) was used to drive the segment back to its attachment point at Leu$^{77}$. This was achieved by attaching a dummy residue at the carboxy terminus identical with the target residue (Leu$^{77}$) to which the segment will attach. This dummy residue had no role in the energetics but served as a geometric reference for adding a harmonic term, $\Sigma k(r_i - r_i^\circ)^2$, to the energy that drove the segment to its target; $r_i$ and $r_i^\circ$ are the coordinates of atom i in the dummy and target residues, respectively, and the sum runs over the backbone and C$\beta$ atoms. Starting with k=0, an MC-SCV simulation was carried out at 310K on each coordinate set obtained from the first step to relax it in the field of the tertiary structure of the protein that had now been added to the system, as well as the aqueous solvent represented by the screened Coulomb potential-implicit solvent model (Hassan, et al, J. Phys. Chem. B, 2000, 104:6478-6489). Subsequently, k was increased in successive steps, with an MC-SCV simulation carried out at each step, to facilitate the movement of the carboxy terminus to its attachment point. A power schedule of $k_i = 10k_{i-1}$ was used, starting from $k_o = 10^{-6}$. Ten steps have been found sufficient to achieve closure.

Results

When the six residues affected by NS-causing mutations were identified in the three-dimensional structure of PTPN11 in the inactive (I) conformation, it became clear that all resided in and around the interactive surfaces of the N-SH2 and PTP domains. Most strikingly, Ala$^{72}$, which was affected by two mutations, resided in the loop between $\beta$F and $\alpha$B and interacted directly with PTP in the I conformation by forming a hydrogen bond with the PTP domain residue, Gln$^{506}$. These observations suggested that the A72S and A72G mutations might affect the intrinsic structural properties of the loop segment around Ala$^{72}$, shifting the equilibrium between the A (active) and I (inactive) states of PTPN11.

To determine the energetically accessible conformations of the segment Gly$^{68}$-Glu$^{76}$ in the context of N-SH2 in the A conformation, the technique of Monte Carlo (Allen, M. P. & Tildesley. *Computer simulation of liquids* (Clarendon Press, Oxford, 1987) with scaled collective variables (MC-SCV) (Noguti, T. & Go, N. Biopolymers, 1985, 24:527-546) was used. From this procedure, more than thirty structures were analyzed to relate their structure and energy. For the wild type, only three low-energy structures had Cα-root mean square distance (rmsd)≦2 Å. The lowest energy structure (rmsd=0.86 Å) was ~8 Kcal/mole below the other two states with small rmsd, supporting the observed stability of the active conformation of isolated N-SH2 (Lee, et al. Structure, 1994, 2:423-438). In addition to the two low-rmsd states around 8 Kcal/mole above the lowest energy conformation, several conformations were found at this energy with considerably larger rmsd values. Therefore, shuttling of wild-type PTPN11 between the A and I conformations becomes energetically plausible if, upon interacting with the PTP domain, the energy gap between the lowest energy conformation and the nearby states decreases. This would make those conformations accessible and confer the requisite flexibility to this segment of N-SH2. In contrast, both A72G and A72S had large populations with small rmsd and low energies. Even if the energies of these states shifted relative to each other upon binding of the PTP domain, there would still be several low-energy conformations available that were close to the A conformation, but none that would confer the flexibility required for transition to the I state. Consequently, the ability of these two mutants to shuttle between the A and I states is impaired, suggesting that the equilibrium is shifted toward the A state relative to the wild-type protein.

There are functional data supporting the conclusions of the foregoing energetics-based structural analyses. O'Reilly and co-workers (O'Reilly et al, Mol. Cell. Biol. 2000, 20, 299-311) created and characterized two PTPN11 mutants, D61A and E76A, which they postulated would be gain-of-function changes since both are N-SH2 residues that interact directly with the PTP domain. Both mutants showed increased basal phosphatase activity (E76A>>D61A>WT) and retained normal phosphopeptide binding properties. When expressed in Xenopus ectodermal explants, both mutants induced changes mimicking some aspects of development that are fibroblast growth factor-inducible, documenting basal stimulation of some signaling cascades in vivo. D61G, found in case N-17, was extremely similar to D61A, providing strong evidence that this mutation has gain-of-function effects. E76D, observed in case N-34, affected the same residue as the E76A, but was more a more conservative change. Glu$^{76}$, however, is invariant among the PTPN11 orthologues and homologues. The similarity in function of Asp$^{61}$, Ala$^{72}$ and Glu$^{76}$ in stabilizing the I state (Hof et al, Cell, 1998, 92, 441-450) provides further evidence that NS is caused by increased activity of PTPN11.

EXAMPLE 3

Characterization of Mutant PTPN11 Proteins

A. Analysis of Basal and Signal-Dependent Phosphatase Activity of Mutated PTPN11 In Vitro The full length PTPN11 cDNA was cloned into pRc/CMV vector (Invitrogen) and the cDNA was shuttled into pcDNA6/V5-his A vector (Introgen). Three separate mutations were introduced into the PTPN11-V5 fusion construct using site-directed mutagenesis (QuickChange Site-Directed Mutagenesis Kit, Stratagene): A72S (A$^{72}$ interacts directly with the PTP domain), I282V (I$^{282}$ interacts directly with the N-SH2 domain), and N308D (recurrent mutation). After sequence confirmation, the wild type and mutant PTPN11-V5 constructs were transfected into COS-7 cells using LipofectaminePlus (Invitrogen) according to the manufacturer's protocol. After growing the transfected cells in complete growth medium (DMEM supplemented with 10% fetal bovine serum (FBS)) for 24 h, they were starved for 20 h in DMEM with 0.1% FBS and then exposed to epidermal growth factor (EGF). Cells were lysed, and the fusion protein was purified by immunoprecipitation using anti-V5 (Invitrogen).

PTPase assays were determined by measuring the phosphate released from phosphopeptides using the Malachite Green assay (Harder et al, Biochem J, 1994;298:395-401). SrcPY 80 nM (Calbiochem), a phosphopeptide derived from the c-Src carboxyl-terminal region, was used as substrate.

After 30 min at RT, absorbance at 620 nm was determined with a microplate reader. A standard curve of free phosphate concentrations is prepared using KH$_2$PO$_4$, treated identically to the PTPase conditions. All conditions were repeated in triplicate.

Figure 7:
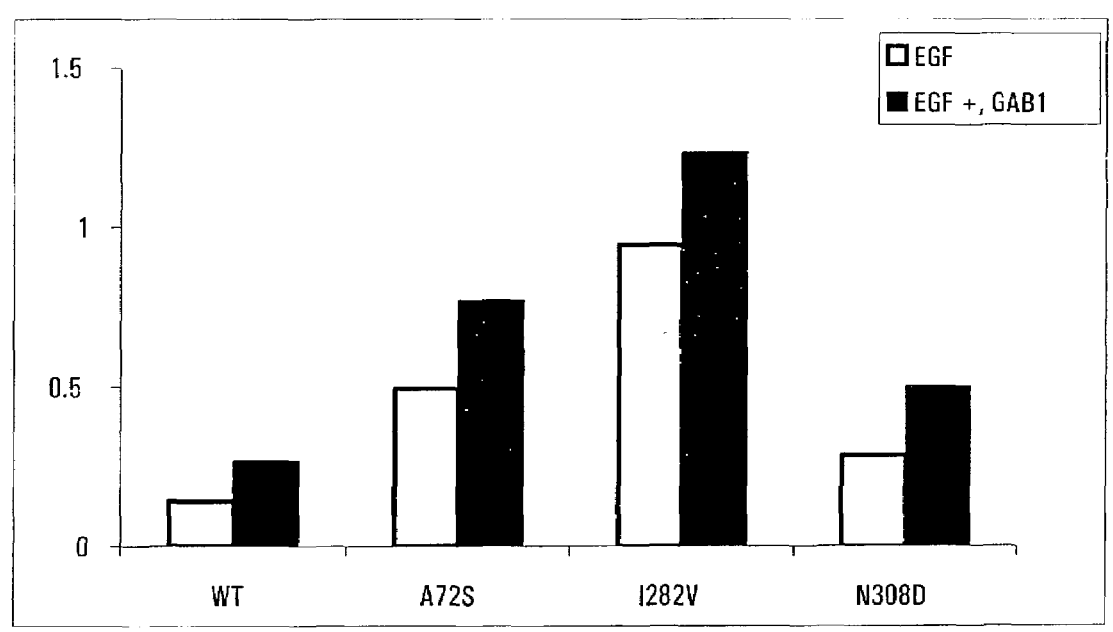
FIG. 7 shows the increased phosphatase activity observed in the mutant PTPN11 proteins. Wild type and mutant PTPN11-V5 proteins were immunoprecipitated using anti-V5 and the phosphatase activity measured with the malachite green assay. The absorbance at 620 nm is indicated on the y axis. A phosphate standard curve was performed, documenting linearity in this range of absorbance. The white bars indicate the phosphatase activities of wild type and mutant PTPN11 proteins isolated from starved, unstimulated COS-7 cells. The black bars indicate the phosphatase activities of wild type and mutant PTPN11 protein isolated from COS-7 cell that were stimulated for 5 min with EGF. See Example 3.

As shown in FIG. 7, the three mutant PTPN11 protein have significantly increased phosphatase activity, even without stimulation of the COS-7 cells with EGF. These results document that the PTPN11 mutations observed in NS result in a gain of function.

B. Analysis of the Docking Function of Mutated PTPN11

To evaluate the docking function of PTPN11, COS-7 cells were transfected with wild type and mutant PTPN11-V5 constructs as well as a FLAG-Gab1 construct. After starvation for 20 h, the cells were stimulated with EGF 0.25 ng/ml for 5 min and then lysed. Anti-FLAG monoclonal antibody (Sigma) was used for immunoprecipitation. Precipitated proteins were resolved by SDS-PAGE and transferred to nitrocellulose filters. Standard immunoblotting was carried out using anti-Gab1 (Upstate Biotechnology), anti-phosphotyrosine (Transduction Laboratories) and anti-PTPN11 (Santa Cruz) antibodies. Gab1 immunoblotting determined equivalence of Gab1 levels. Anti-phosphotyrosine immunoblotting documents that EGF stimulation results in Gab1 phosphorylation.

Figure 8A:
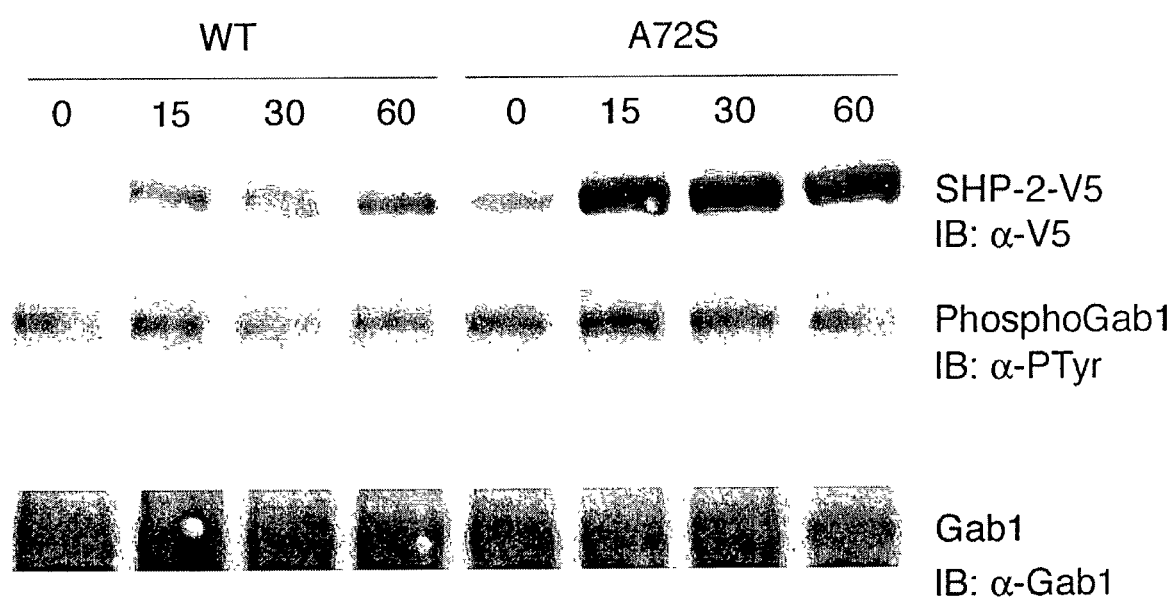
FIGS. 8A and 8B describe the results of immunoblotting experiments comparing docking activity of PTPN11 and PTPN11 variant V5-constructs to Gab1 (docking partner) under basal and activated conditions (i.e., with or without EGF-stimulation), showing increased docking function of PTPN11 variants. See Example 3. A. Comparison of the quantities of PTPN11 detected revealed that there was almost none docked to Gab1 prior to EGF stimulation and modest amounts thereafter. In contrast, the A72S PTPN11 mutant co-isolated with Gab1 without EGF stimulation and was present in much larger amounts compared to wild type PTPN11 after EGF stimulation. B. For the wild type, there was very little detectable Gab1 co-isolated prior to EGF stimulation, a brisk increase peaking around 5 min and then at taper nearly back to baseline by 60 min. In contract, high amounts of Gab1 were still co-localizing with N308D PTPN11 at 60 min.

As shown in FIG. 8A, anti-PTPN11 immunoblotting revealed that there was an increase in docking between Gab1 and mutant PTPN11 under basal and activated conditions compared to the wild type PTPN11. Briefly, COS-7 cells were transfected with constructs for FLAG-Gab1 and PTPN11-V5 (also referred to as SHP-2-V5). Gab1 was immunoprecipitated with anti-FLAG antibodies from cell lysates at 0, 15, 30, and 60 min after EGF stimulation. Proteins were separated with SDS-PAGE and immunoblotted. As shown in the bottom panel of FIG. 8A, the level of Gab1 was nearly equal for all conditions. Comparison of the quantities of PTPN11 detected revealed that there was almost none docked to Gab1 prior to EGF stimulation and modest amounts thereafter. By contrast, the A72S PTPN11 mutant co-isolated with Gab1 without EGF stimulation and was present in much larger amounts compared to wild type PTPN11 after EGF stimulation.

Figure 8B:
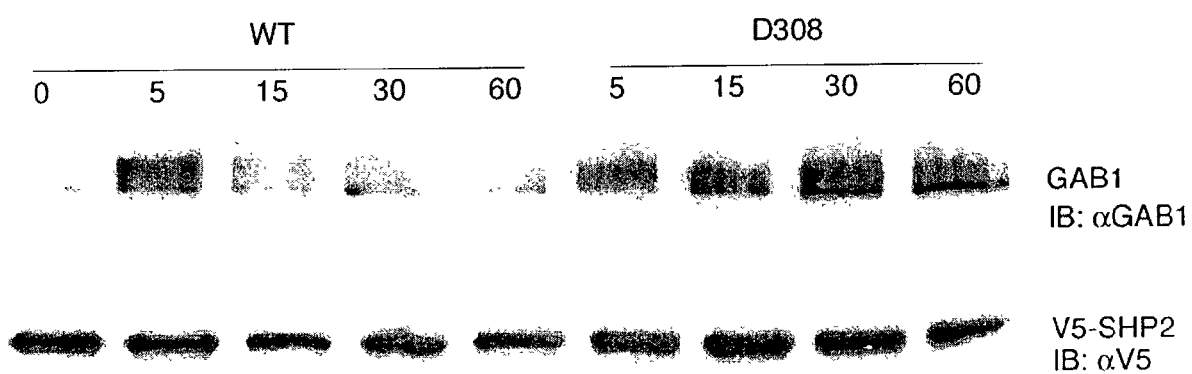

To correlate and expand those findings, COS-7 cells were transfected with the PTPN11-V5 fusion constructs for wild type or N308D (referred to as D308) PTPN11-V5. Lysates from starved or EGF-stimulated cells were obtained, and PTPN11-V5 proteins were immunoprecipitated with anti-V5 antibody at 0, 5, 15, 30, and 60 min after EGF stimulation. Proteins were separated with SDS-PAGE, and immuno-blotting performed with specific antibodies to measure PTPN11 levels as well as co-precipitation of Gab1. As shown in the bottom panel of FIG. 8B, roughly equivalent amount of the PTPN11 (referred to as V5-SH2) protein was obtained in all conditions. FIG. 8B further shows that there was increased docking of the mutant PTPN11-V5 with Gab1 under basal and activated conditions. These results provided confirmation that the NS mutations result in a gain of PTPN11's docking function.

C. Determination of the Effects of Mutated PTPN11 on the ERK MAP Kinase Cascade

Modulation of the extracellular signal-related kinase group (ERK1 and ERK2) of MAP kinases is a major feature of PTPN11 function for several intracellular transduction pathways (Bennett et al., Mol Cell Biol, 1996;16:1189-1202; Craddock et al., J Biol Chem, 2001;276:24274-24283; Cunnick et al., J Biol Chem 2000;275:13842-13848; Schaeper et al., J Cell Biol, 2000;149:1419-1432; and Xu et al., J Biol Chem, 2001;276:13049-13056).

To investigate the effects of NS PTPN11 mutations on this pathway, COS7 cells were transfected with a construct with hemagglutin-tagged ERK2 (HA-ERK2) as well as mutant or wild type PTPN11. Lysates were made from serum-starved and EGF-treat cells, and protein was immunoprecipitated from cell lysates from 0, 15, 30, and 60 min after EGF stimulation. PTPN11 levels were assessed by immunoblotting with aliquots of the lysates. Immunoprecipitation with anti-HA (Covance) was performed using the lysates. A portion of the immunoprecipitates was immunoblotted with anti-ERK2 (Jerry Wu). Another aliquot was used to assay ERK2 kinase activity by incubating at 30° C. for 5-10 min in 20 mM Hepes (pH 7.5), 10 mM $MgCl_2$, 1 mM DTT, 10 mM p-nitrophenyl phosphate, 40 µM ATP, 0.375 mg/ml myelin basic protein (Sigma), with 10 µCi of $[\alpha\text{-}^{32}P]ATP$. After terminating the reactions with SDS loading buffer and heating to 95° C. for 5 min, proteins were separated with SDS-PAGE. Gels were dried and autoradiography was performed.

Figure 9:
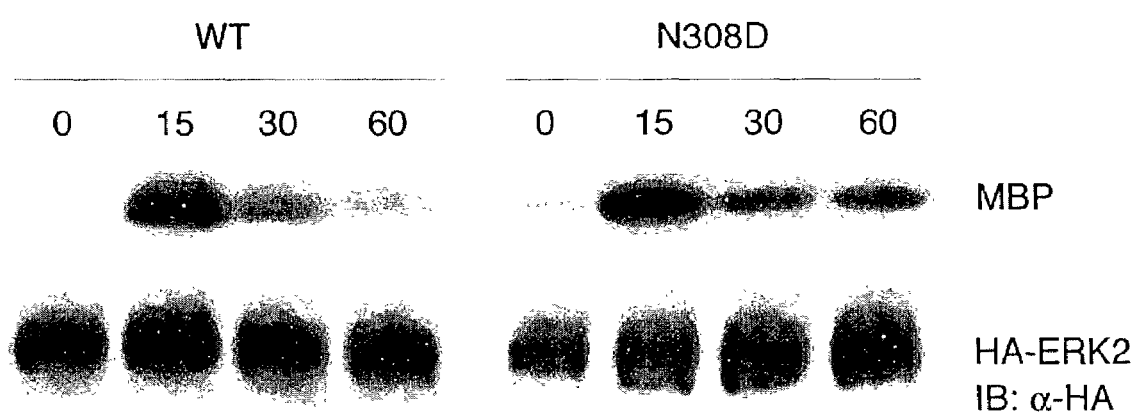
FIG. 9 shows a prolonged increase in ERK2 kinase activity after EGF stimulation of COS-7 cells expressing mutant PTPN11. Cells were co-transfected with a construct for HA-ERK2 and that protein was immunoprecipitated from cell lysates from 0, 15, 30, and 60 min after EGF stimulation. Kinase activity was assessed using myelin basic protein (MBP). The bottom panel indicates roughly equivalent amounts of HA-ERK2 in all conditions. There was no detectable ERK2 kinase activity prior to EGF stimulation for wild type PTPN11, but a small amount with N308D mutant (even though there was relatively less HA-ERK2 for this condition). For the wild type, the kinase activity increased briskly at 5 min and then tapered off dramatically by 60 min. For the N308D, there was a similar increase in ERK2 kinase activity at 5 min but the activity remained modestly elevated even at 60 min. See Example 3.

As shown in FIG. 9, the mutant PTPN11 proteins resulted in a prolonged increase in the kinase activity of ERK2 compared to wild type PTPN11. This result is consistent with increased signaling flux through the RAS-MAP kinase pathway. Since it has been shown that PTPN11 is a positive regulator of the EGF signal transduction pathway (Cunnick et al., J Biol Chem, 275:13842-13848, 2000), these results document another aspect of mutant PTPN11 gain-of-function.

EXAMPLE 4

PTPN11 Mutations in Noonans Syndrome: Molecular Spectrum, Genotype-Phenotype Correlation, and Phenotypic Heterogeneity This Example reports the screening for PTPN11 coding regions in a large, well-characterized cohort of individuals with sporadic or familial NS. The results provide a more extensive assessment of the range of PTPN11 lesions causing NS, evaluation of disease penetrance, establishment of genotype-phenotype correlation, and broadening of the phenotype associated with PTPN11 mutations to include NS with multiple giant-cell lesions.

Material and Methods

Clinical Evaluation. Subjects were examined by clinicians experienced with NS. Electrocardiograms, echocardiograms, and clinical photographs were obtained routinely for the probands, as well as for most of other affected family members in the kindreds segregating the disorder. NS was diagnosed on the basis of the presence of the following major characteristics: typical facial dysmorphia, pulmonic stenosis or HCM plus abnormal electrocardiogram pattern, pectus carinatum/excavatum, height>2 SD below the mean, and cryptorchidism in male subjects. To have a diagnosis of NS, individuals with typical facial dysmorphia had to have at least one additional major feature, whereas individuals with suggestive facial findings had to have at least two other major characteristics (van der Burgt et al. Am J Med Genet 1994;53:187-191). HCM was diagnosed when the left-ventricular maximal end diastolic wall thickness was >1.5 cm in adults (Shapiro and McKenna, J Am Coll Cardiol 1983;2:437-444) or >2 SD above the mean for a given age in children (Burch et al., J Am Coll Cardiol 1993;22:1189-1192). The clinical description of a kindred with Noonan-like/multiple giant-cell lesion syndrome was reported elsewhere (Bertola et al., Am J Med Genet 2001;98:230-234). Informed consent was obtained from all subjects included in the study.

Mutational Analysis. Genomic DNAs were isolated from peripheral blood lymphocytes (Gentra). The entire PTPN11 coding region (exons 1-15) was screened for mutations. For exons 2-15, PCRs were performed in a 25-µl reaction volume containing 20-80 ng genomic DNA, 1 U AmpliTaq Gold (Roche), 20 pmol each primer, 1.5 mM $MgCl_2$, 75 µM each dNTP, and 1×PCR Buffer II (Roche), through use of a GeneAmp PCR System 9700 (Applied Biosystems). Exon 1 amplifications were performed using the GC-rich PCR System (Roche), according to the manufacturer's specifications. Cycling parameters were as follows: 94° C. for 8 min (first denaturing step); 33 cycles of 94° C. for 45 s, 54-60° C. (see table 1) for 30 s, and 72° C. for 45 s; and 72° C. for 10 min (last extension step).

Primer pairs were designed to amplify exons, exon/intron boundaries, and short intron flanking stretches. Primer sequences, annealing temperatures, and sizes of PCR products are listed in Table 3. Mutational analysis of the amplimers was performed by means of denaturing high-performance liquid chromatography (DHPLC), through use of the Wave DNA Fragment Analysis System (Transgenomics) at column temperatures recommended by the WaveMaker version 4.1.31 software (Transgenomics). DHPLC buffers and run conditions were as follows: buffer A (0.1M triethylammonium acetate (TEAA), 0.025% acetonitrile (ACN)), buffer B (0.1M TEAA, 25% ACN); a flow rate of 0.9 ml/min; and a gradient duration of 3 min, with active clean (75% ACN). Buffer B gradients and temperatures are reported in table 4. Positive controls—that is, PCR products expected to result in variant elution profiles—were used in all DHPLC runs.

TABLE 3

Primer Pairs and Annealing Temperatures Used to Amplify the PTPN11 Coding Sequence and Sizes of PCR Products

| Exon | Primer Sequence Forward (SEQ ID NO) | Primer Sequence Reverse (SEQ ID NO) | Annealing Temp (° C.) | Product Length (bp) |
|---|---|---|---|---|
| 1 | 3 | 4 | 60 | 589 |
| 2 | 5 | 6 | 60 | 405 |
| 3 | 7 | 8 | 60 | 384 |
| 4 | 9 | 10 | 58 | 447 |
| 5 | 11 | 12 | 60 | 329 |
| 6 | 13 | 14 | 54 | 282 |

TABLE 3-continued

Primer Pairs and Annealing Temperatures Used to Amplify the PTPN11 Coding Sequence and Sizes of PCR Products

| Exon | Primer Sequence Forward (SEQ ID NO) | Reverse (SEQ ID NO) | Annealing Temp (° C.) | Product Length (bp) |
|---|---|---|---|---|
| 7 | 15 | 16 | 56 | 271 |
| 8 | 17 | 18 | 57 | 350 |
| 9 | 19 | 20 | 56 | 357 |
| 10 | 21 | 22 | 60 | 284 |
| 11 | 23 | 24 | 60 | 453 |
| 12 | 25 | 26 | 56 | 250 |
| 13 | 27 | 28 | 60 | 356 |
| 14[a] | 29 | 30 | 60 | 259 |
| 15 | 31 | 32 | 60 | 321 |

[a]GC clamps were added at the 5' end for DHPLC analysis: forward primer, 5'-CCCGCCGCCCCCGCCG-3' (SEQ ID NO:34); reverse primer, 5'-CCGCGCCCCCGCCCG-3' (SEQ ID NO:35) (product length = 290 bp).

TABLE 4

Percent Buffer B and Temperatures Used in DHPLC Analysis for PTPN11 Mutation Detection

| EXON | % BUFFER B[a] Loading | Initial | Final | TEMPERATURE(S) (° C.) |
|---|---|---|---|---|
| 1 | 56 | 61 | 67 | 67 |
| 2 | 55 | 60 | 66 | 56, 57 |
| 3 | 54 | 59 | 65 | 57, 58 |
| 4 | 53 | 58 | 64 | 56, 57 |
| 5 | 51 | 56 | 62 | 56, 58 |
| 6 | 50 | 55 | 61 | 56, 57 |
| 7 | 50 | 55 | 61 | 56, 57 |
| 8 | 51 | 56 | 62 | 57, 58 |
| 9 | 52 | 57 | 63 | 56, 57 |
| 10 | 50 | 55 | 61 | 57, 58 |
| 11 | 54 | 59 | 65 | 59 |
|  | 49 | 54 | 60 | 64 |
| 12 | 48 | 53 | 59 | 58, 59 |
| 13 | 51 | 56 | 62 | 59 |
|  | 50 | 55 | 61 | 60 |
| 14 | 52 | 57 | 63 | 57 |
|  | 49 | 54 | 60 | 60 |
| 15 | 51 | 56 | 62 | 56, 57 |

[a]% buffer A = 100 − % buffer B

Heterozygous templates with previously identified mutations or single-nucleotide polymorphisms (SNPs) were used as positive controls for exons 3, 4, 7, 8, and 13. For each of the remaining exons, a synthetic template containing a single nucleotide change was constructed using the overlap extension method in a two-step PCR procedure. Wild-type and mutated PCR products were denatured together at 94° C. for 5 min and were slowly cooled at room temperature, to allow heteroduplex formation. Bidirectional direct sequencing of purified PCR products (Qiagen) was performed using the ABI BigDye Terminator Sequencing Kit (Perkin Elmer) and an ABI 3700 Capillary Array Sequencer (Perkin Elmer). Sequences were analyzed by the Sequencing Analysis v.3.6.1 and AutoAssembler v.1.4.0 software packages (Perkin Elmer). Cosegregation analysis and exclusion of the mutations in control samples were performed by means of RFLP, (n=100) DHPLC, or direct sequencing.

Genotype-phenotype correlations were performed using 2×2 contingency-table analysis. The significance threshold was set at P<0.05.

Results

Spectrum of PTPN11 Mutations. The study population comprised 119 propositi with NS, including 70 with sporadic NS and 49 apparently unrelated families. Of the familial cases, the phenotype was linked to the NS1 locus in 11. Linkage exclusion for the NS1 locus was documented in four families. The small size of the remaining 34 families (typically, an affected parent and child) did not allow for linkage analysis. All subjects were of northern-European descent, except for two, one of Afro-Caribbean and one of Indian origin. DNAs from the 119 propositi with NS were screened for PTPN11 coding-region mutations. Exons 1-15 and flanking intron sequences were PCR amplified and were analyzed by means of DHPLC, and products with variant elution profiles were sequenced bidirectionally. PTPN11 mutations were identified in 54 subjects, comprising 22 different nucleotide changes (Table 5). All mutations were missense exonic changes, with the majority clustering in exons 3 and 8. The mutations cosegregated completely with the disease in all familial cases. None of the 22 different mutations was observed in at least 100 control Europeans or Americans of European descent. Parental DNAs were available for 43 of 52 (83%) individuals with sporadic NS who had PTPN11 mutations. Only one parent was identified as carrying a mutation—the 925A→G transition, predicting an Ile309Val substitution. The variant profile for this mutation was not observed in >400 control chromosomes.

TABLE 5

PTPN11 Mutations in NS

| Nucleotide Substitution | No. of Cases | Amino Acid Substitution | Domain |
|---|---|---|---|
| Exon 2: |  |  |  |
| 124A→G | 2 | Thr42Ala | N-SH2 |
| Exon 3: |  |  |  |
| 179G→C | 2 | Gly60Ala | N-SH2 |
| 181G→A | 1 | Asp61Asn | N-SH2 |
| 184T→G | 2 | Tyr62Asp | N-SH2 |
| 188A→G | 4 | Tyr63Cys | N-SH2 |
| 215C→G | 1 | Ala72Gly | N-SH2 |
| 218C→T | 1 | Thr73Ile | N-SH2 |
| 228G→C | 1 | Glu76Asp | N-SH2 |
| 236A→G | 5 | Gln79Arg |  |
| 317A→C | 3 | Asp106Ala | N-SH2/C-SH2 linker |
| Exon 4: |  |  |  |
| 417G→C | 1 | Glu139Asp | C-SH2 |
| 417G→T | 1 | Glu139Asp | C-SH2 |
| Exon 7: |  |  |  |
| 836A→G | 1 | Tyr279Cys | PTP |
| 844A→G | 1 | Ile282Val | PTP |
| 853T→C | 1 | Phe285Leu | PTP |
| Exon 8: |  |  |  |
| 854T→C | 1 | Phe285Ser | PTP |
| 922A→G | 17 | Asn308Asp | PTP |
| 923A→G[a] | 2 | Asn308Ser | PTP |
| 925A→G | 1 | Ile309Val | PTP |
| Exon 13: |  |  |  |
| 1502G→A | 1 | Arg501Lys | PTP |
| 1510A→G | 3 | Met504Val | PTP |

[a]Affected members of one family segregating the 923A→G change (Asn308Ser) exhibited the Noonan-like/multiple giant-cell lesion condition.

Figure 5:
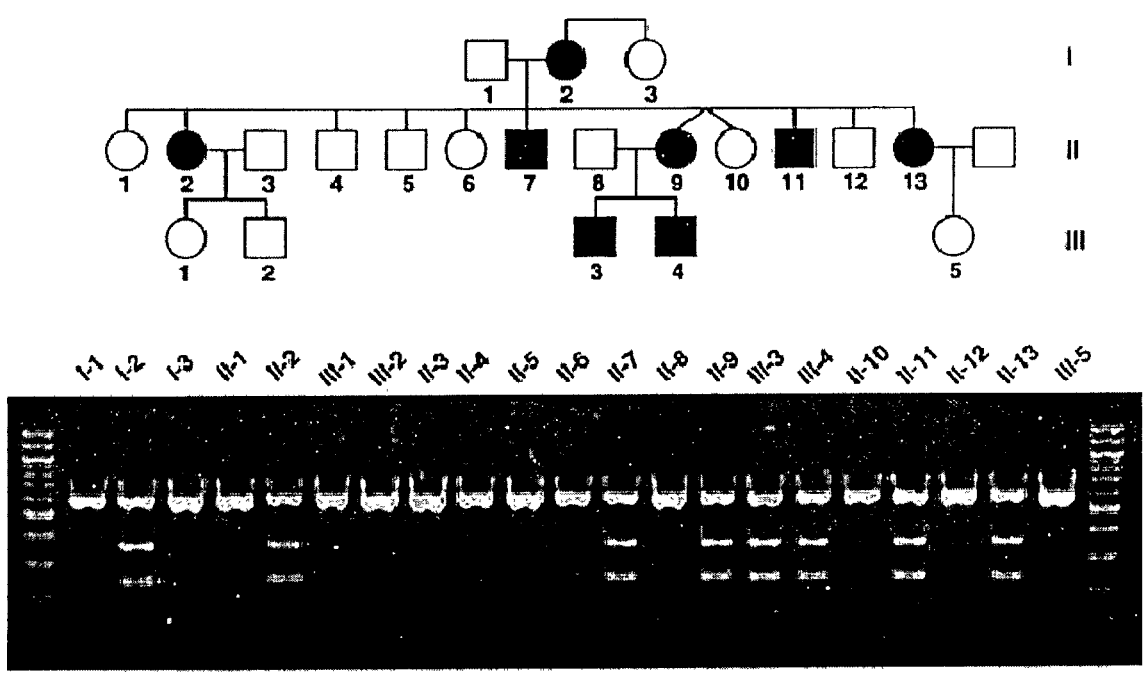
FIG. 5 shows a restriction analysis of PTPN11 PCR product containing exon 8, showing segregation of the 922A→G (A922G) mutation in the original large family with NS that shows linkage to 12q24 (Jamieson et al. Nat Genet 1994;8:357-360). The family tree is shown above. The mutation introduces an EcoRV restriction site, resulting in 246- and 366-bp products, whereas the wild-type allele remains undigested (612 bp).

The A→G transition at position 922 in exon 8, predicting the Asn308Asp substitution within the PTP domain, was the most common mutation, accounting for one-third of the total. Of note, the Asn308Asp mutation was identified in the large three-generation family that was used to originally establish linkage to the NS1 locus (Jamieson et al., Nat Genet 1994;8:357-360; van der Burgt et al., Am J Med Genet 1994;94:46-51) (FIG. 5). The two occurrences of the adjacent 923A→G mutation, predicting an Asn308Ser change, indicate that codon 308 represents a hotspot for NS. Eight additional mutations were found recurrently. Among them, the 182A→G (Asp61Gly), 188A→G (Tyr63Cys), and 236A→G (Gln79Arg) substitutions in exon 3, as well as the 1510A→G (Met504Val) change in exon 13, have previously been reported as disease-causing mutations (Tartaglia et al., Nat Genet 2001;29:465-468). Interestingly, 90% of mutational events involved amino acid residues located in the N-SH2 and PTP functional domains. The exceptions were the 317A→C transversion, observed in two individuals with sporadic NS and in one family, predicting an Asp106Ala substitution in the peptide linking the N-SH2 and C-SH2 domains, and the 417G→C and 417G→T changes, both predicting a Glu139Asp substitution within the C-SH2 domain.

On the basis of the secondary structure of PTPN11 in the inactive conformation determined by Hof et al. (Cell 1998: 92:441-450), the N-SH2 and PTP mutations were noted to cluster dramatically in specific regions of those domains. Of the 10 N-SH2 substitutions, 5 were positioned in the D'E loop and flanking βD' and βE strands (residues 57-65), and 4 were in the βF strand and αB helix (residues 69-84). The nine PTP mutations were restricted to the DB loop (residues 277-288; n=4), βC strand (residues 303-311; n=3), and HI loop (residues 499-507; n=2). Most strikingly, all N-SH2 and PTP mutations except the Thr42Ala substitution involved residues located in or close to the N-SH2/PTP interacting surface.

Fifteen sequence variants representing polymorphisms were observed in subjects with NS, unaffected family members, and control individuals (Table 6). These changes included 13 intronic SNPs, a single-base deletion within the 5'-UTR, and a synonymous change in exon 3.

TABLE 6

Polymorphisms in the PTPN11 Gene

| Location | Nucleotide Change | Position of SEQ ID NO:33 |
|---|---|---|
| Exon 1(5' UTR) | −140delG[a] | 3123451 |
| Intron 1 | +25G→C | 3123629 |
| Intron 1 | +54C→A | 3123658 |
| Exon 3 | 255C→T (His85) | 3194548 |
| Intron 4 | +12G→C | 3194637 |
| Intron 4 | +78A→G | 3194703 |
| Intron 7 | −21C→T | 3221743 |
| Intron 7 | −30T→C | 3221734 |
| Intron 7 | −32A→C | 3221732 |
| Intron 7 | −35A→C | 3221729 |
| Intron 7 | −132T→C | 3221632 |
| Intron 9 | −9C→A | 3229178 |
| Intron 10 | −63G→A | 3230525 |
| Intron 13 | +26G→A | 3233314 |
| Intron 15 | +40T→C | 3248949 |

[a]Position refers to the A of the ATG initiator codon of SEQ ID NO:1, corresponding to nucleotide 3123591 in SEQ ID NO:33.

Genetic Heterogeneity in NS. PTPN11 mutations were detected in the 11 families for which the disorder appeared to be linked to the NS1 locus, including the original large family described by Jamieson et al. (1994). As anticipated, no PTPN11 sequence change was observed in the four families for which linkage to NS1 had been excluded. For the entire study group of 119, PTPN11 mutations were observed in 45%, a slightly lower incidence than had been seen in a small cohort (Tartaglia et al., Nature Genet 2001;29:465-468). PTPN11 mutations were detected in 59% of individuals with familial NS, whereas such defects were observed in only 37% of individuals with sporadic NS. This statistically significant (P<0.02) difference in PTPN11 mutation prevalence suggests that the additional gene or genes responsible for NS engender incomplete penetrance or have greater adverse affects on fertility than does PTPN11.

Genotype-Phenotype Correlation. Because of the clinical heterogeneity observed in NS, we investigated possible associations between genotype and phenotype. The distribution of several major clinical features of NS, in subjects with and without mutations in PTPN11, is shown in Table 7. A statistically significant association with pulmonic stenosis was found in the group with PTPN11 mutations (70.6% vs. 46.2%; P=0.008). In contrast, a statistically significantly lower incidence of HCM was observed in this group (5.9% vs. 26.2%; p=0.004). There was no significant difference in the prevalence of atrial and/or ventricular septal defects or other congenital heart malformations between the groups with and without PTPN11 mutations. Similarly, there was no difference in the rates of short stature, pectus deformities, cryptorchidism, or enrollment in special education (as a marker of developmental delay).

TABLE 7

Clinical Features in Subjects with NS with and without PTPN11 Mutations

| | NO./TOTAL (%) OF SUBJECTS | | |
|---|---|---|---|
| Clinical Feature | With PTPN11 Mutation | Without PTPN11 Mutation | p[a] |
| Cardiac defects: | | | |
| HCM | 3/51 (5.9) | 17/65 (26.1) | .004 |
| Pulmonic stenosis | 36/51 (70.6) | 30/65 (46.2) | .008 |
| Septal defects | 6/50 (12.0) | 11/63 (17.5) | NS |
| Short stature | 39/51 (76.5) | 45/64 (70.3) | NS |
| Special education | 11/46 (23.9) | 21/59 (35.6) | NS |
| Pectus deformities | 39/50 (78.0) | 46/61 (75.4) | NS |
| Cryptorchidism | 26/31 (83.9) | 25/35 (71.4) | NS |

[a]"NS" indicates a difference that is not statistically significant.

The clinical manifestations of NS were compared between the cohort with N-SH2 mutations and the cohort with PTP mutations. Although this analysis had less statistical power, owing to sample size, no significant differences were identified. The phenotype observed in subjects with the common Asn308Asp substitution (n=17) was not qualitatively different from the phenotype in subjects with other mutations, except for the fact that no subject carrying the Asn308Asp change was enrolled in special education.

Figure 6:
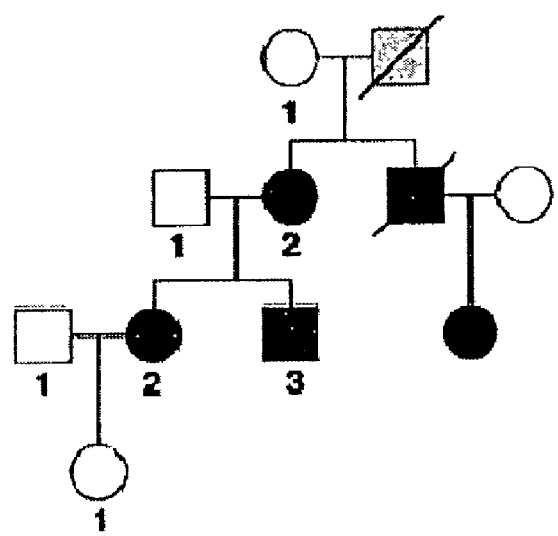
FIG. 6 shows DHPLC elution profiles of PTPN11 exon 8 PCR products, showing segregation of the 923A→G (A923G) change in a family inheriting Noonan-like/multiple giant-cell lesion syndrome (Bertola et al., Am J Med Genet 2001;98:230-234). A single peak characterizes the wild-type profile, and a variant profile, characterized by two peaks, is observed in all affected family members. The family tree is shown on the left. The gray-shaded symbol indicates an indeterminate phenotype.
Figure 6:
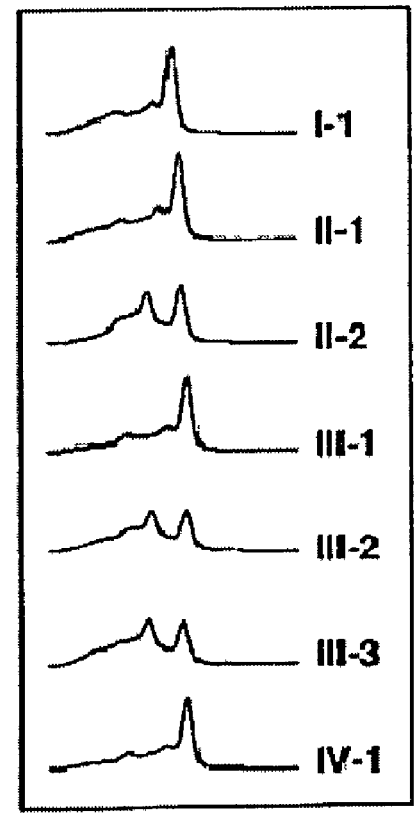

We identified an A→G transition at position 923 (Asn308Ser) in a family with typical features of NS associated with multiple giant-cell lesions in bone (Bertola et al., Am J Med Genet 2001,98:230-234). This mutation cosegregated perfectly with this phenotype (FIG. 6). One family member (III-3) had a typical NS phenotype (i.e., pulmonic stenosis, cryptorchidism, short stature, and distinctive face and chest deformity) and exhibited asymptomatic lesions in the right ramus of the mandible and in the maxilla, as well as osteolytic lesions in both humeri and in the left femur. Similarly, his affected sister (III-2) had multiple lesions in the mandible. Serum calcium, phosphate, and PTH levels were normal in both subjects. Their mother (II-2) had typical NS features but did not have any bone lesions. The same Asn308Ser mutation was observed in another family with NS that had no known bony involvement.

Discussion

In our present analysis of a large cohort with sporadic and familial cases of NS, we estimated the PTPN11 mutation prevalence to be 45%. This is quite similar to the rate of 50% observed in a small cohort with NS. In the present study, however, DHPLC was used to screen the PTPN11 coding exons. Since this method is purported to have a sensitivity of 96%-100% under ideal conditions (Xiao and Oefner, Hum Mut 2001;17:439-474), the true prevalence of point mutations in this cohort could be slightly higher. There may also be other types of molecular lesions that might cause NS, such as large intragenic deletions, changes in the 3'UTR, or promoter defects. Lastly, the prevalence detected in any NS cohort would be sensitive to the composition of sporadic and familial cases. With those issues stipulated, the contribution of PTPN11 mutations to the etiology of NS appears to be approximately 50%. When these results are combined with our previous work, we have now identified 78 unrelated individuals with NS who have mutations in PTPN11. All mutations are conserved among the vertebrate PTPN11 orthologs. Most altered residues are also conserved among the vertebrate SHP-1 proteins.

As described herein, we have found that the NS-causing PTPN11 defects result in gain-of-function effects on PTPN11. This was supported by energetics-based structural analysis of two mutants (Tartaglia et al., Nat Genet 2001; 29:456-468) and by the observation that two NS mutant alleles closely resembled two engineered PTPN11 mutants with increased phosphatase activity in vitro and inductive effects in Xenopus animal caps (O'Reilly et al., Mol Cell Biol 2000;20:299-311). Since we have not identified any nonsense, frameshift, or splicing defect among 78 PTPN11 mutations, it seems highly unlikely that PTPN11 haploinsufficiency results in the NS phenotype.

The distribution of the altered amino acid residues in PTPN11 has a nonrandom pattern (Table 7). The vast majority of the NS mutations clustered in the N-SH2 and PTP functional domains but were not restricted to those domains, as was seen previously. The N-SH2 domain interacts with the PTP domain and binds to phosphotyrosyl-containing targets on activated receptors or docking proteins, using two separate sites. These sites show negative cooperativity, so that N-SH2 can work as intramolecular switch to control PTPN11 catalytic activity. In the inactive state, the N-SH2 and PTP domains share a broad interaction surface. More precisely, the N-SH2 D'E loop and flanking βD' and βE strands closely interact with the catalytic cleft, blocking the PTP active site. Crystallographic data on PTPN11 in the inactive conformation revealed a complex interdomain hydrogen-bonding network-involving Asn58, Gly60, Asp61, Cys459, and Gln506—that stabilizes the protein (Hof et al., Cell 1998;92:441-450). Numerous polar interactions between N-SH2 residues located in strands βF and βA, helix αB, and residues of the PTP domain further stabilize the inactive conformation. Significantly, most of the residues mutated in NS are either directly involved in these interdomain interactions (i.e., Gly60, Asp61, Ala72, Glu76, and Gln79) or in close spatial proximity to them (i.e., Tyr62, Tyr63, Thr73, Tyr279, Ile282, Phe285, Asn308, Ile309, Arg501, and Met504). This distribution of molecular lesions suggests that the pathogenetic mechanism in NS involves altered N-SH2/PTP interactions that destabilize the inactive conformation without altering PTPN11's catalytic capability. Consistent with this view, no mutation altered Cys459 (the residue essential for nucleophilic attack), the PTP signature motif (positions 457-467), or the TrpProAsp loop (positions 423-425), which are all essential for phosphatase activity.

Three of the NS mutations affected residues outside of the interacting regions of the N-SH2 and PTP domains. One recurrent mutation affected Asp106, which is located in the linker stretch connecting the N-SH2 and C-SH2 domains. Although functional studies are required to understand the functional significance of the Asp-to-Ala substitution, we hypothesize that this mutation might alter the flexibility of the N-SH2 domain, thus inhibiting the N-SH2/PTP interaction. Two mutated residues, Thr42 (N-SH2 domain) and Glu139 (C-SH2 domain), are spatially far from the N-SH2/PTP interaction surfaces. In contrast to the other mutated residues, Thr42 and Glu139 are implicated in the intermolecular interactions of the SH2 domains with phosphotyrosyl-containing peptides (Lee et al., Structure 1994;2:423-438; Huyer and Ramachandran, Biochemistry 1998;37: 2741-2747). Specifically, Thr42 directly interacts with the tyrosine phosphate, and Glu139 is adjacent to Arg138 and Ser140, which form hydrogen bonds to that phosphate. The phenotype of the subjects bearing these mutations was typical for NS.

Previously, the penetrance of NS had not been addressed in a systematic fashion. Two lines of evidence now suggest that NS caused by PTPN11 mutations is almost completely penetrant. First, we analyzed 11 families, including the large kindred first described by van der Burgt et al. (Am J Med Genet 1994;94:46-51), for which significant or suggestive linkage to the NS1 locus had been established (Jamieson et al., Nat Genet 1994;8:357-360). In each instance, a PTPN11 mutation was identified that was inherited by all of the affected individuals in the family but by none of the unaffected ones. Analysis of small kindreds harboring PTPN11 mutations revealed the same consistent pattern. Second, we genotyped a high percentage (83%) of the unaffected parents for defects discovered in their offspring with apparently sporadic NS. In only one instance was a mutation identified. Although it is possible that inclusion of "milder" cases of NS might have uncovered some instances of incomplete penetrance, the strict criteria for NS employed in the present study identified a cohort with almost 100% penetrance.

We observed a statistically significantly higher incidence of pulmonic stenosis among subjects with NS inheriting PTPN11 mutations. Experimental evidence with mice indicates that epidermal growth factor (EGF) signaling is important for semilunar valve development and that PTPN11 is a component of the EGF-mediated signal transduction pathway (Qu et al., PNAS 1999;96:8528-8533; Chen et al., Nat Genet 2000;24:296-299). A proportion of mice that are homozygous for a hypomorphic Egfr allele exhibit thickened aortic and pulmonary valve leaflets because of an increased number of mesenchymal cells. Coinheritance of a Ptpn11 knock-out allele in heterozygosity results in a higher prevalence and increased severity of those valve abnormalities. These findings implicate PTPN11 in aspects of EGF-mediated semilunar valvulogenesis, such as mesenchymal transformation and proliferation, as well as leaflet remodeling.

Finally, we demonstrated the cosegregation of a 923A→G PTPN11 mutation in a family inheriting the Noonan-like/multiple giant-cell lesion syndrome. Since a 923A→G mutation was also identified in an unrelated kindred with classic NS, additional genetic factors or events may be necessary to result in the proliferation of these giant cells. Only a single family with this rare phenotype was available for genotyping. Although the Noonan-like/multiple giant-cell lesion syndrome was introduced as a distinct entity characterized by the association of some cardinal features of NS with giant-cell lesions of bone and soft tissues (Cohen et al., Syndrome Ident 1974;2:14-17; Cohen and Gorlin, Am J Med Genet 1991;40159-166), it is now a part of the NS spectrum.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

---

What is claimed is:

1. A method for diagnosing Noonan syndrome in a human subject, said method comprising the step of detecting a mutation in a protein tyrosine phosphatase 11 (PTPN11) nucleic acid molecule of SEQ ID NO: 1 from said subject, wherein said mutation results in an amino acid substitution in a PTPN11 protein tyrosine phosphatase (PTP) domain, and wherein said amino acid substitution is selected from the group consisting of:
   (a) a Y to C substitution at position 279 of SEQ ID NO: 2;
   (b) an I to V substitution at position 282 of SEQ ID NO:2;
   (c) an F to L substitution at position 285 of SEQ ID NO:2;
   (d) an F to S substitution at position 285 of SEQ ID NO:2;
   (e) an N to D substitution at position 308 of SEQ ID NO:2;
   (f) an N to S substitution at position 308 of SEQ ID NO:2;
   (g) an I to V substitution at position 309 of SEQ ID NO:2;
   (h) an R to K substitution at position 501 of SEQ ID NO:2; and
   (i) an M to V substitution at position 504 of SEQ ID NO:2,
wherein the presence of said mutation in said protein tyrosine phosphatase 11 (PTPN11) nucleic acid molecule is diagnostic of Noonan syndrome in said human subject.

2. A method for diagnosing Noonan syndrome in a human subject, said method comprising the step of detecting a mutation in a protein tyrosine phosphatase 11 (PTPN11) nucleic acid molecule of SEQ ID NO: 1 from said subject, wherein said mutation results in an amino acid substitution in a PTPN11 protein tyrosine phosphatase (PTP) domain, and wherein said mutation in the PTPN11 nucleic acid molecule is selected from the group consisting of:
   (a) an A to G substitution at position 836 of SEQ ID NO:1;
   (b) an A to G substitution at position 844 of SEQ ID NO:1;
   (c) a T to C substitution at position 853 of SEQ ID NO:1;
   (d) a T to C substitution at position 854 of SEQ ID NO:1;
   (e) an A to G substitution at position 922 of SEQ ID NO:1;
   (f) an A to G substitution at position 923 of SEQ ID NO:1;
   (g) an A to G substitution at position 925 of SEQ ID NO:1;
   (h) a G to A substitution at position 1502 of SEQ ID NO:1;
   (i) an A to G substitution at position 1510 of SEQ ID NO:1,
wherein the presence of said mutation in said protein tyrosine phosphatase 11 (PTPN11) nucleic acid molecule is diagnostic of Noonan syndrome in said human subject.

3. A method for diagnosing Noonan syndrome in a human subject, said method comprising the step of detecting a mutation in a protein tyrosine phosphatase 11 (PTPN11) nucleic acid molecule of SEQ ID NO: 1 from said subject, wherein said mutation results in an amino acid substitution in a PTPN11 src homology-2 (SH2) domain, and wherein said amino acid substitution is selected from the group consisting of:
   (a) a G to A substitution at position 60 of SEQ ID NO:2;
   (b) a D to N substitution at position 61 of SEQ ID NO:2;
   (c) a D to G substitution at position 61 of SEQ ID NO:2;
   (d) a Y to D substitution at position 62 of SEQ ID NO:2;
   (e) a Y to C substitution at position 63 of SEQ ID NO:2;
   (f) an A to S substitution at position 72 of SEQ ID NO:2;
   (g) an A to G substitution at position 72 of SEQ ID NO:2;
   (h) an E to D substitution at position 76 of SEQ ID NO:2; and (i) a Q to R substitution at position 79 of SEQ ID NO:2; wherein the presence of said mutation in said protein tyrosine phosphatase 11 (PTPN11) nucleic acid molecule is diagnostic of Noonan syndrome in said human subject.

4. A method for diagnosing Noonan syndrome in a human subject, said method comprising the step of detecting two or more mutations in a protein tyrosine phosphatase 11 (PTPN11) nucleic acid molecule of SEQ ID NO: 1 from said subject, wherein said mutation results in an amino acid substitution and a deletion in a PTPN11 src homology-2 (SH2) domain, and wherein said mutations results in a G to V amino acid substitution at position 60 and a deletion of amino acid D at position 61 of SEQ ID NO:2, wherein the presence of said two or more mutations in said protein tyrosine phosphatase 11 (PTPN11) nucleic acid molecule is diagnostic of Noonan syndrome in said human subject.

5. A method for diagnosing Noonan syndrome in a human subject, said method comprising the step of detecting a mutation in a protein tyrosine phosphatase 11 (PTPN11) nucleic acid molecule of SEQ ID NO: 1 from said subject, wherein said mutation results in an amino acid substitution in a PTPN11 src homology-2 (SH2) domain, and wherein said mutation in the PTPN11 nucleic acid molecule is selected from the group consisting of:
(a) a G to C substitution at position 179 of SEQ ID NO:1;
(c) a G to A substitution at position 181 of SEQ ID NO:1;
(d) an A to G substitution at position 182 of SEQ ID NO:1;
(e) a T to G substitution at position 184 of SEQ ID NO:1;
(f) an A to G substitution at position 188 of SEQ ID NO:1;
(g) a G to T substitution at position 214 of SEQ ID NO:1;
(h) a C to G substitution at position 215 of SEQ ID NO:1;
(j) an G to C substitution at position 228 of SEQ ID NO:1;
(k) an A to G substitution at position 236 of SEQ ID NO:1; and
wherein the presence of said mutation in said protein tyrosine phosphatase 11 (PTPN11) nucleic acid molecule is diagnostic of Noonan syndrome in said human subject.

6. A method for diagnosing Noonan syndrome in a human subject, said method comprising the step of detecting two or more mutations in a protein tyrosine phosphatase 11 (PTPN11) nucleic acid molecule of SEQ ID NO: 1 from said subject, wherein said mutation results in an amino acid substitution and a deletion in a PTPN11 src homology-2 (SH2) domain, and wherein said mutations in the PTPN11 nucleic acid molecule include a G to T substitution at position 179 and a deletion of positions 180-182 of SEQ ID NO:1, wherein the presence of said two or more mutations in said protein tyrosine phosphatase 11 (PTPN11) nucleic acid molecule is diagnostic of Noonan syndrome in said human subject.

7. A method for diagnosing Noonan syndrome in a human subject, said method comprising the step of detecting a mutation in a protein tyrosine phosphatase 11 (PTPN11) nucleic acid molecule of SEQ ID NO: 1 from said subject, wherein said mutation results in an amino acid substitution in a PTPN11 protein linker domain connecting a first SH2 domain to a second SH2 domain, and wherein said amino acid substitution is a D to A amino acid substitution at position 106 of SEQ ID NO:2, wherein the presence of said mutation in said protein tyrosine phosphatase 11 (PTPN11) nucleic acid molecule is diagnostic of Noonan syndrome in said human subject.

8. A method for diagnosing Noonan syndrome in a human subject, said method comprising the step of detecting a mutation in a protein tyrosine phosphatase 11 (PTPN11) nucleic acid molecule of SEQ ID NO: 1 from said subject, wherein said mutation results in an amino acid substitution in a PTPN11 protein linker domain connecting a first SH2 domain to a second SH2 domain, and wherein said mutation in the PTPN11 nucleic acid molecule is an A to C substitution at position 317 of SEQ ID NO:1, wherein the presence of said mutation in said protein tyrosine phosphatase 11 (PTPN11) nucleic acid molecule is diagnostic of Noonan syndrome in said human subject.

9. A method for diagnosing Noonan syndrome in a human subject, said method comprising the step of detecting a mutation in a protein tyrosine phosphatase 11 (PTPN11) nucleic acid molecule of SEQ ID NO: 1 from said subject, wherein said mutation results in an amino acid substitution in a PTPN 11 protein tyrosine phosphatase (PTP) domain, and wherein said amino acid substitution is selected from the group consisting of:
(a) a G to S substitution at position 268 of SEQ ID NO:2;
(b) an N to T substitution at position 308 of SEQ ID NO:2;
(c) an P to S substitution at position 491 of SEQ ID NO:2; and
(d) an S to L substitution at position 502 of SEQ ID NO:2, wherein the presence of said mutation in said protein tyrosine phosphatase 11 (PTPN11) nucleic acid molecule is diagnostic of Noonan syndrome in said human subject.

10. A method for diagnosing Noonan syndrome in a human subject, said method comprising the step of detecting a mutation in a protein tyrosine phosphatase 11 (PTPN11) nucleic acid molecule of SEQ ID NO: 1 from said subject, wherein said mutation results in an amino acid substitution in a PTPN11 protein tyrosine phosphatase (PTP) domain, and wherein said mutation in the PTPN11 nucleic acid molecule is selected from the group consisting of:
(a) a G to A substitution at position 802 of SEQ ID NO:1;
(b) an A to C substitution at position 923 of SEQ ID NO:1;
(c) a C to T substitution at position 1471 of SEQ ID NO:1; and
(d) a C to T substitution at position 1505 of SEQ ID NO:1, wherein the presence of said mutation in said protein tyrosine phosphatase 11 (PTPN11) nucleic acid molecule is diagnostic of Noonan syndrome in said human subject.

* * * * *